(12) United States Patent
Wu et al.

(10) Patent No.: US 11,098,062 B2
(45) Date of Patent: Aug. 24, 2021

(54) MONOCYCLIC AND BICYCLIC RING SYSTEM SUBSTITUTED CARBANUCLEOSIDE ANALOGUES FOR USE AS PRMT5 INHIBITORS

(71) Applicant: Janssen Pharmaceutica NV, Beerse (BE)

(72) Inventors: Tongfei Wu, Boortmeerbeek (BE); Dirk Brehmer, Freiburg (DE); Lijs Beke, Antwerp (BE); An Boeckx, Herentals (BE); Gaston Stanislas Marcella Diels, Turnhout (BE); Edward Charles Lawson, Pipersville, PA (US); Lieven Meerpoel, Beerse (BE); Vineet Pande, Vosselaar (BE); Marcus Cornelis Bernardus Catharina Paradé, Eindhoven (NL); Wim Bert Griet Schepens, Sint Katelijne Waver (BE); Weimei Sun, Lower Gwynedd, PA (US); Johannes Wilhelmus John F. Thuring, Antwerp (BE); Marcel Viellevoye, Breda (NL)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 16/336,934

(22) PCT Filed: Oct. 2, 2017

(86) PCT No.: PCT/EP2017/074983
§ 371 (c)(1),
(2) Date: Mar. 27, 2019

(87) PCT Pub. No.: WO2018/065365
PCT Pub. Date: Apr. 12, 2018

(65) Prior Publication Data
US 2019/0263833 A1 Aug. 29, 2019

Related U.S. Application Data

(60) Provisional application No. 62/403,336, filed on Oct. 3, 2016.

(30) Foreign Application Priority Data

Feb. 24, 2017 (EP) .................................. 17157785

(51) Int. Cl.
| | |
|---|---|
| *C07D 519/00* | (2006.01) |
| *C07D 487/04* | (2006.01) |
| *A61P 35/00* | (2006.01) |
| *A61K 9/00* | (2006.01) |
| *A61K 9/20* | (2006.01) |
| *A61K 9/06* | (2006.01) |
| *A61K 45/06* | (2006.01) |

(52) U.S. Cl.
CPC .......... *C07D 519/00* (2013.01); *A61K 9/0019* (2013.01); *A61K 9/0053* (2013.01); *A61K 9/0095* (2013.01); *A61K 9/06* (2013.01); *A61K 9/2059* (2013.01); *A61P 35/00* (2018.01); *C07D 487/04* (2013.01); *A61K 45/06* (2013.01)

(58) Field of Classification Search
CPC ............................ C07D 487/04; C07D 519/00
See application file for complete search history.

(56) References Cited

U.S. PATENT DOCUMENTS

| | | |
|---|---|---|
| 4,224,438 A | 9/1980 | Fauland et al. |
| 2003/0225205 A1 | 12/2003 | Epple et al. |
| 2004/0043959 A1 | 3/2004 | Bloom et al. |
| 2006/0167241 A1 | 7/2006 | Hayakawa |
| 2008/0132525 A1 | 6/2008 | Wahhab et al. |
| 2011/0159111 A1 | 6/2011 | Curry et al. |
| 2012/0035115 A1 | 2/2012 | Manoharan et al. |
| 2013/0023491 A1 | 1/2013 | Annes et al. |
| 2013/0310333 A1 | 11/2013 | Chesworth et al. |
| 2013/0310334 A1 | 11/2013 | Chesworth et al. |

(Continued)

FOREIGN PATENT DOCUMENTS

| | | |
|---|---|---|
| WO | WO 199640686 A1 | 12/1996 |
| WO | 03/39523 A2 | 5/2003 |

(Continued)

OTHER PUBLICATIONS

Andreu-Perez et al., "Protein Arginine Methyltransferase 5 Regulates ERK1/2 Signal Transduction Amplitude and Cell Fate Through CRAF.", *Sci Signal*, 2011, p. ra58, vol. 4(190).

(Continued)

*Primary Examiner* — Susanna Moore
(74) *Attorney, Agent, or Firm* — BakerHostetler

(57) ABSTRACT

The present invention relates to novel novel monocyclic and bicyclic ring system substituted carbanucleoside analogues of Formula (I)

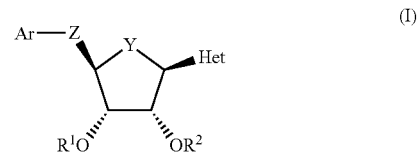

wherein the variables have the meaning defined in the claims. The compounds according to the present invention are useful as PRMT5 inhibitors. The invention further relates to pharmaceutical compositions comprising said compounds as an active ingredient as well as the use of said compounds as a medicament.

6 Claims, No Drawings

(56) References Cited

U.S. PATENT DOCUMENTS

| | | | |
|---|---|---|---|
| 2014/0100184 | A1 | 4/2014 | Song et al. |
| 2014/0221345 | A1 | 8/2014 | Duncan et al. |
| 2014/0228343 | A1 | 8/2014 | Duncan et al. |
| 2014/0329794 | A1 | 11/2014 | Duncan et al. |
| 2016/0009744 | A1 | 1/2016 | Duffey et al. |
| 2016/0244475 | A1 | 8/2016 | Tatlock et al. |
| 2017/0198006 | A1 | 7/2017 | Duncan et al. |
| 2018/0243328 | A1 | 8/2018 | Wu et al. |

FOREIGN PATENT DOCUMENTS

| | | |
|---|---|---|
| WO | WO 2003070739 A1 | 8/2003 |
| WO | WO 2003074083 A1 | 9/2003 |
| WO | 2004/022572 A1 | 3/2004 |
| WO | 2005/065150 A2 | 7/2005 |
| WO | 2006/078752 A2 | 7/2006 |
| WO | 2010/039548 A2 | 4/2010 |
| WO | 2011/075665 A2 | 6/2011 |
| WO | 2012/083170 A1 | 6/2012 |
| WO | WO 2012075500 A2 | 6/2012 |
| WO | WO 2012082436 A3 | 6/2012 |
| WO | 2012/138530 A1 | 10/2012 |
| WO | 2013/151975 A1 | 10/2013 |
| WO | WO 2014035140 A2 | 3/2014 |
| WO | WO 2014100695 A1 | 6/2014 |
| WO | WO 2014100719 A2 | 6/2014 |
| WO | WO 2014100730 A1 | 6/2014 |
| WO | 2015/106025 A1 | 7/2015 |
| WO | WO 2015200680 A1 | 12/2015 |
| WO | WO 2016135582 A1 | 9/2016 |
| WO | WO 2017032840 A1 | 3/2017 |
| WO | 2017/153186 A1 | 9/2017 |
| WO | 2018/065365 A1 | 4/2018 |
| WO | 2018/154104 A1 | 8/2018 |

OTHER PUBLICATIONS

Antonysamy et al., "Crystal structure of the human PRMT5:MEP50 complex.", *Proc Natl Acad Sci*, USA, 2012, pp. 17960-17965, vol. 109(44).
Bezzi et al., "Regulation of constitutive and alternative.", *Genes Dev*, 2013, pp. 1903-1916, vol. 27(17).
Chan-Penebre et al., "A selective inhibitor of PRMT PRMT5 with in vivo and in vitro potency in MCL models.", *Nat Chem Biol*, pp. 432-437, vol. 11(6).
Devkota et al., "Analogues of the Natural Product Sinefungin as Inhibitors of EHMT1 and EHMT2.", *ACS Med Chem Lett*, 2014, pp. 293-297, vol. 5.
Di Lorenzo et. al., "Histone Arginine Methylation.", FEBS Lett, 2011, pp. 2024-2031, vol. 585(13).
Friesen et al., "The Methylosome, a 20S Complex Containing JBP1 and plCln, Produces Dimethylarginine-Modified Sm Proteins.", *Mol Cell Biol*, 2001, pp. 8289-8300, vol. 21(24).
Geoghegan et al., "Comprehensive identification of arginine methylation in primary T cells reveals regulatory roles in cell signalling.", *Nat Commun*, 2015, vol. 6, Article No. 6758.
Gu et al., "Protein arginine methyltransferase 5 is essential for growth of lung cancer cells,.", *Biochem J*, 2012, pp. 235-241, vol. 446(2).
Hsu et al., "Crosstalk between Arg 1175 methylation and Tyr 1173 phosphorylation negatively modulates EGFR-mediated ERK activation.", Nat Cell Biol, 2011, pp. 174-181, vol. 13(2).
Jansson et al., "Arginine methylation regulates the p53 response.", *Nat Cell Biol.* 2008, pp. 1431-1439, vol. 10(12).
Karkhanis et al., "Versatility of PRMT5-induced methylation in growth control and development.", *Trends Biochem Sci*, 2011, pp. 633-641, vol. 36(12).
Kung et al, "Design, Synthesis, and biological evaluation of novel human 5'-deoxy-5'-methylthiadenosine phosphorylase (MTAP) substrates.", *Bioorg & Med Chem Letters*, Jun. 2, 2005, pp. 2829-2833, vol. 15(11).

Matsubara et al, "[2+1] Cycloaddition reaction of bis(iodozincio)methane with 1,2-diketones: face-to-face complex of bis(iodozincio)methane and 1,2-diketones as a reaction intermediate.", *Tetrahedron*, 2002, pp. 8255-8262, vol. 58.
Pal et al., "Low levels of miR-92b/96 induce PRMT5 translation and H3R8/H4R3 methylation in mantle cell lymphoma.", *EMBO J*, 2007, pp. 3558-3569, vol. 26(15).
Shilo et al., "Cellular localization of protein arginine methyltransferase-5 correlates with grade of lung tumors.", Diagn Pathol, 2013, 8: p. 201.
Stopa et al., "The PRMT5 arginine methyltransferase: many roles in development, cancer and beyond.", Cell Mol Life Sci, 2015, pp. 2041-2059, vol. 72(11).
Wang et al., "Protein Arginine Methyltransferase 5 Suppresses the Transcription of the RB Family of Tumor Suppressors in Leukemia and Lymphoma Cells.", *Mol Cell Biol*, 2008, pp. 6262-6277, vol. 28(20).
Wei et al., "PRMT5 dimethylates R30 of the p65 subunit to activate NF-κB.", *Proc Natl Acad Sci*, USA, 2013, pp. 13516-13521, vol. 110(33).
Wei et al., "Methylosome protein 50 promotes androgen- and estrogen-independent tumorigenesis.", *Cell Signal*, 2014, pp. 2940-2950, vol. 26(12).
Zhao et al., "PRMT5-mediated methylation of histone H4R3 recruits DNMT3A, coupling histone and DNA methylation in gene silencing.", *Nat Struct Mol Biol*, 2009, pp. 304-311, vol. 16(3).
International Search Report PCT/EP2017/074983, dated Nov. 16, 2017.
Written Opinion PCT/EP2017/074983, dated Nov. 16, 2017.
Alinari et al., "Selective inhibition of progen argrinine methyltransferase 5 blocks initiation and maintenance of B-cell transformation.", Blood, Apr. 16, 2015, pp. 2530-2543, vol. 125(16).
Barbash, O., et al., "Abstract LB-248: Protein arginine methyltransferase 5 (PRMT5) inhibition as a therapeutic strategy in B-cell lymphoma", Cancer Research, (2015), see Abstract.
Braun, C.J., et al., "Coordinated Splicing of Regulatory Detained Intrans within Oncogenic Transcripts Creates an Exploitable Vulnerability in Malignant Glioma", Cancer Cell, (2017), pp. 411-426, vol. 32, No. 4.
Bundegaard, H., "Design of Prodrugs", Elsevier, New York—Oxford, (1985), pp. 1-92.
Crane et al., Journal of Organic Chemistry, 45(19), 1980, pp. 3827-3831.
Deady, L.W., "Ring Nitrogen Oxidation of Amino Substituted Nitrogen Heterocycles with m-Chloroperbenzoic Acid", Synthetic Communications, (1977), pp. 509-514, vol. 7, No. 8.
European Search Report; EP Patent Application No. EP Patent Application No. 15184011.3; dated Oct. 22, 2015.
Guo, Fang, Yanxinig Han, Xuesen Zhao, Jianghua Wang, Fei Liu, Chunxiao Xu, Lai Wei et al. "STING agonists induce an innate antiviral Immune response against hepatitis B virus." Antimicrobial agents and chemotherapy 59, No. 2 (2015): 1273-1281.
Hu, H., et al., "Small Molecule Inhibitors of Protein Arginine Methyltransferase", Expert Opinion on Investigational Drugs, (2016), pp. 335-358, vol. 25, No. 3.
International Report on Patentability; International Patent Application No. PCT/EP2016/070097; Date of Issuance of Feb. 27, 2018.
International Search Report relating to International Patent Application No. PCT/EP2016/070097, filed on Aug. 25, 2016. dated Oct. 12, 2016.
International Search Report relating to International Patent Application No. PCT/EP2017/054324, filed on Feb. 24, 2017. dated May 2, 2017.
International Search Report relating to International Patent Application No. PCT/EP2018/054644, filed on Feb. 26, 2018. dated May 3, 2018.
International Search Report relating to International Patent Application PCT/EP2017/054324, filed Feb. 24, 2017. dated May 2, 2017.
International Search Report relating to International Patent Application PCT/EP2017/074983, filed Oct. 2, 2017. dated Nov. 16, 2017.

(56) References Cited

OTHER PUBLICATIONS

International Search Report relating to International Patent Application PCT/EP2018/054644, filed Feb. 26, 2018. dated May 3, 2018.
March, J., "Advanced Organic Chemistry—Reactions, Mechanisms, and Structure", John Wiley & Sons, Inc., (2002), 4th Edition, A Wiley-Interscience Publication, see Table of Contents.
Matsubara, S., et al., "[2+1] Cycloaddition reaction of bis(iodozincio)methane with 1,2-diketones: face-to-face complex of bis(iodozincio)methane and 1,2-diketones as a reaction intermediate", Tetrahedron, (2002), pp. 8255-8262, vol. 58.
Moukha-Chafiq, 0., et al., "Synthesis and General Biological Activity of a Small Adenosine-5'-(Carboxamide and Sulfanilamide) Library", Nucleosides, Nucleotides and Nucleic Acids, (2014), pp. 709-729, vol. 33, No. 11.
Penebre, E., et al., "Identification of a First-in-Class PRMT5 Inhibitor with Potent in Vitro and in Vivo Activity in Preclinical Models of Mantle Cell Lymphoma", Blood, (2014), see Abstract.
Prasad, R.N., et al., "Modification of the 5' Position of Purine Nucleosides. 2. Synthesis and Some Cardiovascular Properties of Adenosine-5'-(N-substituted)carboxamides1,2", J. Med. Chem., (1980), DD. 313-319, vol. 23, No. 3.
Schmidt, R.R., et al., "Synthese 5'-modifizierter Adenosinderivate", Chemische Berichte, (1968), pp. 590-594, vol. 101, No. 2.
Shendure, J., et al., "Next-generation DNA sequencing", Nature Biotechnolgoy, (2008), pp. 1135-1145, vol. 26, No. 10.
Stahl, P.H., et al., "Handbook of Pharmaceutical Salts: Properties, Selection, and Use", Journal of Medicinal Chemistry, Book Reviews, (2003), pp. 1277-1278, vol. 46, No. 7.
Stopa, N., et al., "The PRMT5 arginine methyltransferase: many roles in development, cancer and beyond", Cell. Mol. Life Sci., (2015), DD. 2041-2059, vol. 72, No. 11.
Tiwari et al. Nucleosides, Nucleotides and Nucleic Acids (2009), vol. 28, Nos. 5-7, pp. 657-677.
Vuilhorgne, M., et al., "New Synthetic S-Adenosyl-Homocysteine Analogues with Oncostatic and Antiviral Activity" Heterocylces, 1978, pp. 495-520, vol. 11, XP009112700.
Wang, Q., et al., "Identification of a Novel Protein Arginine Methyltransferase 5 Inhibitor in Non-small Cell Lung Cancer by Structure-Based Virtual Screening", Frontiers in Pharmacology, (2018), pp. 1-10, vol. 9, article 173.
Written Opinion of the International Search Authority relating to International Patent Application No. PCT/EP2017/054324, filed on Feb. 24, 2017. dated May 2, 2017.
Written Opinion relating to International Patent Application PCT/EP2016/070097, filed Aug. 25, 2016. dated Oct. 12, 2016.
Dermer, "Another Anniversary for the War on Cancer", Biotechnology, 1994, vol. 12, p. 320.
Evans, et al., "Pharmacogenomics: Translating Functional Genomics into Rational Therapeutics", Science, 1999, vol. 286, pp. 487-491.
Graubert, et al., "Recurrent mutations in the U2AF 1 splicing factor in myelodysplastic syndromes", Nature Genetics, Jan. 1, 2012, vol. 44, pp. 53-59.
HUGO Gene Nomenclature Committee (HGNC) reports for the Major Spliceosome found online at https;//www.genenames.org/data/genegroup/#!/group/1518 and accessed Apr. 20, 2021.
Li, et al., A patent review of arginine methyltransferase inhibitors, Expert Opinion on Therapeutic Patents, 2019, vol. 29, No. 2, pp. 97-114.
Xiong, et al., Driver Genes as Targets for Lung Cancer Prevention and Treatment Progress in Chemistry, Sep. 9, 2013, vol. 25, pp. 1517-1525.

MONOCYCLIC AND BICYCLIC RING SYSTEM SUBSTITUTED CARBANUCLEOSIDE ANALOGUES FOR USE AS PRMT5 INHIBITORS

CROSS-REFERENCE TO RELATED APPLICATIONS

This application is a U.S. national stage of PCT Application No. PCT/EP2017/074983, filed Oct. 2, 2017, which claims the benefit of priority of U.S. Patent Application No. 62/403,336, filed Oct. 3, 2016, and European Patent Application No. 17157785.1, filed Feb. 24, 2017, all of which are incorporated by reference herein, in their entireties and for all purposes.

FIELD OF THE INVENTION

The present invention relates to novel monocyclic and bicyclic ring system substituted carbanucleoside analogues useful as PRMT5 inhibitors. The invention further relates to pharmaceutical compositions comprising said compounds as an active ingredient as well as the use of said compounds as a medicament.

BACKGROUND OF THE INVENTION

PRMT5, also described as Hsl7, Jbp1, Skb1, Capsuleen or Dart5, is one of the major methyltransferases responsible for mono- and symmetric dimethylation of arginines. Post-translational arginine methylation on histones and non-histone proteins seems to be crucial for a variety of biological processes, like genome organisation, transcription, differentiation, spliceosome function, signal transduction and regulation of cell-cycle progression, stem cells and T-cell fate [Stopa, N. et al., Cell Mol Life Sci, 2015. 72(11): p. 2041-59] [Geoghegan, V. et al., Nat Commun, 2015. 6: p. 6758]. Metazoan PRMT5 forms a functional complex with the methylosome protein 50 (MEP50) also named as Wdr77, androgen receptor coactivator p44 and Valois. Both, elevated PRMT5-MEP50 protein level and cytoplasmic accumulation are implicated in cancer tumorigenesis and have recently been correlated with poor clinical outcome [Shilo, K. et al., Diagn Pathol, 2013. 8: p. 201]. Cellular rescue experiments that addressed both the catalytic and scaffold function of the PRMT5-MEP50 complex, beside comprehensive enzymological studies have substantiate the oncogenic link between protein level, localisation and enzymatic function [Gu, Z. et al., Biochem J, 2012. 446(2): p. 235-41] [Di Lorenzo, A. et. al., FEBS Lett, 2011. 585(13): p. 2024-31] [Chan-Penebre, E. et al., Nat Chem Biol, 2015. 11(6): p. 432-7]. This correlation turns PRMT5 into an essential small molecule drug target against cancer and other diseases [Stopa, N. et al., Cell Mol Life Sci, 2015. 72(11): p. 2041-59].

PRMT5 is a member of the type II PRMT subfamily that utilises S-adenosylmethionine (SAM) to generate symmetric dimethylated arginine on histones and non-histone protein substrates and S-adenosylhomocysteine (SAH). The crystal structure of the human hetereo-octameric complex $(PRMT5)_4(MEP50)_4$ co-crystalised with SAH and a histone H4 peptide substrate illustrated the mechanism of methylation and substrate recognition [Antonysamy, S. et al., Proc Natl Acad Sci USA, 2012. 109(44): p. 17960-5]. The regulation of PRMT5 activity occurs through a vast number of different binding partners, post-translational modification cross talk, miRNAs and subcellular localisation.

Methylation of histones H2A and H4 on Arg3 and histone H3 on Arg8 regulate chromatin organisation for specific repression of gene transcripts that are involved in differentiation, transformation, cell-cycle progression and tumour suppression [Karkhanis, V. et al., Trends Biochem Sci, 2011. 36(12): p. 633-41]. Furthermore, PRMT5-mediated methylation of histone H4 on Arg3 might recruit the DNA-methyltransferase DNMT3A to couple histone and DNA methylation for long-term gene silencing [Zhao, Q. et al., Nat Struct Mol Biol, 2009. 16(3): p. 304-11].

Non-histone methylation can occur either in the cytoplasm or nucleus dependent on the cellular localisation of PRMT5. The methylation of the Sm proteins D1 and D3, which are required for the assembly of the nuclear spliceosome, takes place in the cytoplasm as part of the PRMT5 containing "methylosome" [Friesen, W. J. et al., Mol Cell Biol, 2001. 21(24): p. 8289-300]. Further evidence for PRMT5 involved in splicing has been provided by the conditional PRMT5 knockout in mouse neural stem cells. Cells that lack PRMT5 showed a selective retention of introns and skipping of exons with weak 5' donor sites [Bezzi, M. et al., Genes Dev, 2013. 27(17): p. 1903-16].

In addition to a role in splicing, PRMT5 influences key pathways involved in cell fate and homeostasis by direct methylation of key signalling nodules like p53 [Jansson, M. et al., Nat Cell Biol, 2008. 10(12): p. 1431-9], EGFR [Hsu, J. M. et al., Nat Cell Biol, 2011. 13(2): p. 174-81], CRAF [Andreu-Perez, P. et al., Sci Signal, 2011. 4(190): p. ra58], PI3K/AKT [Wei, T. Y. et al., Cell Signal, 2014. 26(12): p. 2940-50], NFκB [Wei, H. et al., Proc Natl Acad Sci USA, 2013. 110(33): p. 13516-21].

Since PRMT5 is one of the major sym-Arg methyltransferases and involved in a multitude of cellular processes, an increased protein expression appears to be an important factor in its tumourigenicity. Interestingly, the translation of PRMT5 in mantle cell lymphoma (MCL) seems to be regulated by miRNAs. Although MCL cells show less mRNA and a slower transcription rate of PRMT5 than normal B lymphocytes, the PRMT5 level and the methylation of H3R8 and H4R3 are significantly increased [Pal, S. et al., EMBO J, 2007. 26(15): p. 3558-69]. Re-expression of miRNAs that binds the 3'UTR region of PRMT5 decreases PRMT5 protein level [Wang, L. et al., Mol Cell Biol, 2008. 28(20): p. 6262-77]. Strikingly, a prmt5 antisense RNA has been found within the human prmt5 gene that supports the hypothesis of a specific translational regulation rather than high mRNA expression level [Stopa, N. et al., Cell Mol Life Sci, 2015. 72(11): p. 2041-59].

Although PRMT5 is considered as a clinical relevant target, very few selective PRMT5 inhibitors have been published, yet. Very recently, a novel sub-nanomolar potent PRMT5 inhibitor (EPZ015666) with anti-tumour activity in multiple MCL xenograft models has been described to be the first chemical probe suitable for further validation of PRMT5's biology and role in cancer [Chan-Penebre, E. et al., Nat Chem Biol, 2015. 11(6): p. 432-7].

Further development of specific small molecule inhibitors of PRMT5 may lead to novel chemotherapeutic approaches for cancer.

WO2016135582 and US20160244475 describe substituted nucleoside derivatives useful as anticancer agents.

WO2014100695A1 discloses compounds useful for inhibiting PRMT5 activity; Methods of using the compounds for treating PRMT5-mediated disorders are also described.

WO2014100730A1 discloses PRMT5 inhibitors containing a dihydro- or tetrahydroisoquinoline and uses thereof.

Devkota, K. et al., ACS Med Chem Lett, 2014. 5: p. 293-297, describes the synthesis of a series of analogues of the natural product sinefungin and the ability of these analogues to inhibit EHMT1 and EHMT2.

WO2003070739 discloses partial and full agonists of A1 adenosine receptors, their preparation, and their therapeutic use.

WO2012082436 discloses compounds and compositions as modulators of histone methyltransferases, and for treating diseases influenced by modulation of histone methyltransferase activity.

WO2014100719 discloses PRMT5 inhibitors and uses thereof.

WO03074083 discloses combination therapies that selectively kill methylthioadenosine phosphorylase deficient cells. Analogs of MTA are described herein as anti-toxicity agents.

Kung, P.-P. et al., Bioorg Med Chem Lett, 2005. 15: p. 2829-2833, describes the design, synthesis, and biological evaluation of novel human 5'-deoxy-5'-methylthioadenosine phosphorylase (MTAP) substrates.

WO2012075500 discloses 7-deazapurine modulators of histone methyltransferase.

WO2014035140 discloses compounds and compositions for modulating histone methyltransferase activity.

WO2015200680 describes PRMT5 inhibitors and uses thereof.

WO9640686 describes heterocyclic substituted cyclopentane compounds and methods of using such compounds for inhibiting adenosine kinase.

WO2017032840 relates to novel 6-6 bicyclic aromatic ring substituted nucleoside analogues useful as PRMT5 inhibitors.

There is thus a strong need for novel PRMT5 inhibitors thereby opening new avenues for the treatment or prevention of cancer, such as e.g. mantle cell lymphoma. It is accordingly an object of the present invention to provide such compounds.

The compounds of the present invention are structurally different and may have improved properties such as for example improved potency, or improved pharmacokinetics (PK) and oral bioavailability, compared with compounds disclosed in the prior art.

SUMMARY OF THE INVENTION

It has been found that the compounds of the present invention are useful as PRMT5 inhibitors. The compounds according to the invention and compositions thereof, may be useful for the treatment or prevention, in particular for the treatment, of diseases such as a blood disorder, metabolic disorders, autoimmune disorders, cancer, inflammatory diseases, cardiovascular diseases, neurodegenerative diseases, pancreatitis, multiorgan failure, kidney diseases, platelet aggregation, sperm motility, transplantation rejection, graft rejection, lung injuries, and the like.

The present invention concerns novel compounds of Formula (I):

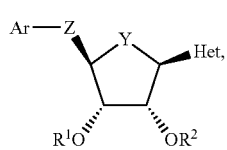

(I)

wherein
$R^1$ represents hydrogen or —C(=O)—$C_{1-4}$alkyl;
$R^2$ represents hydrogen or —C(=O)—$C_{1-4}$alkyl;
Y represents —$CH_2$— or —$CF_2$—;
Z represents —$CH_2$—, —$CHR^{5i}$—, —X—$CR^{5a}R^{5b}$—, —$CR^{5c}$=$CR^{5d}$—, —$CR^{5e}R^{5g}$—$CR^{5f}R^{5h}$—, —$CR^{5a}R^{5b}$—X—, —C≡C—, —$CR^{5c}R^{5d}$—$CR^{5e}R^{5g}$—$CR^{5f}R^{5h}$—, or —$CR^{5a}R^{5b}$—$CR^{5c}R^{5d}$—$CR^{5e}R^{5g}$—$CR^{5f}R^{5h}$—;
$R^{5a}$, $R^{5b}$, $R^{5c}$, $R^{5d}$, $R^{5e}$, $R^{5f}$, $R^{5g}$, $R^{5h}$, and $R^{5i}$ each independently represent hydrogen or $C_{1-4}$alkyl;
X represents —O—, —S—, or —$NR^{11}$—;
$R^{11}$ represents hydrogen, $C_{1-4}$alkyl, or $C_{1-4}$alkyl substituted with one substituent selected from the group consisting of —OH, —O—$C_{1-4}$alkyl, —$NH_2$, —NH—$C_{1-4}$alkyl, and —N($C_{1-4}$alkyl)$_2$;
Ar represents a monocyclic aromatic ring or a bicyclic ring system; wherein the monocyclic aromatic ring is selected from the group consisting of pyridinyl, pyrimidinyl, pyrazolyl, and imidazolyl;
wherein the bicyclic ring system is
(i) a 9-membered bicyclic aromatic ring system consisting of a 6-membered ring fused with a 5-membered ring, containing one, two or three heteroatoms each independently selected from O, S, and N, said 9-membered bicyclic aromatic ring being attached to the remainder of the molecule via a ring carbon atom of the 5- or 6-membered ring, or a ring nitrogen atom of the 5-membered ring; or
(ii) a 10-membered bicyclic aromatic ring system consisting of two fused 6-membered rings, wherein optionally 1 or 2 ring carbon atoms are replaced by a nitrogen atom; provided that when the nitrogen atom replaces one of the two fused carbon atoms, a carbonyl group is present in said bicyclic aromatic ring system;
provided that in case Ar represents a 10-membered bicyclic aromatic ring system, Z can only represent —$CR^{5c}R^{5d}$—$CR^{5e}R^{5g}$—$CR^{5f}R^{5h}$— or —$CR^{5a}R^{5b}$—$CR^{5c}R^{5d}$—$CR^{5e}R^{5g}$—$CR^{5f}R^{5h}$—; or
(iii) a fused bicyclic partially aromatic ring system which is attached with the aromatic ring to linker Z, wherein the fused bicyclic partially aromatic ring system is selected from (b-1), (b-2) and (b-3)

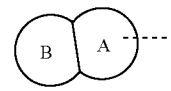

(b-1)

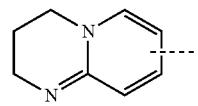

(b-2)

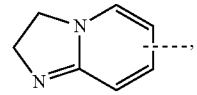

(b-3)

wherein ring A is a monocyclic aromatic ring is selected from the group consisting of pyridinyl, pyrimidinyl, pyrazolyl and imidazolyl;
wherein ring B is a $C_{5-6}$cycloalkyl or a 5- to 6-membered saturated heterocyclyl containing one or two heteroatoms each independently selected from O, S and N;

Ar is optionally substituted on the carbon atoms with in total one, two, three or four substituents each independently selected from the group consisting of halo, oxo, —OH, —NH$_2$, —NH—C$_{1-4}$alkyl, —NHR$^{10}$, cyano, —CF$_3$, C$_{1-4}$alkyloxy, C$_{3-6}$cycloalkyl, —O—C$_{3-6}$cycloalkyl, C$_{2-6}$alkenyl, C$_{1-4}$alkyl, and C$_{1-4}$alkyl substituted with one C$_{1-4}$alkyloxy; and where possible Ar is optionally substituted on one N-atom with one substituent selected from the group consisting of C$_{1-4}$alkyl; C$_{3-6}$cycloalkyl; C$_{1-4}$alkyl substituted with one, two or three halo atoms; and C$_{3-6}$cycloalkyl substituted with one, two or three halo atoms;

R$^{10}$ represents —(C=O)—C$_{1-4}$alkyl; C$_{3-6}$cycloalkyl; R$^{13}$; R$^{14}$; C$_{3-6}$cycloalkyl substituted with one, two or three substituents each independently selected from the group consisting of halo, —OH and —O—C$_{1-4}$alkyl; C$_{1-4}$alkyl substituted with one, two or three substituents each independently selected from the group consisting of halo, —OH and —O—C$_{1-4}$alkyl; or C$_{1-4}$alkyl substituted with one substituent selected from the group consisting of C$_{3-6}$cycloalkyl, R$^{13}$ and R$^{14}$;

R$^{13}$ represents a 4- to 7-membered monocyclic aromatic ring containing one, two or three heteroatoms each independently selected from O, S, S(=O)$_p$ and N; said 4- to 7-membered monocyclic aromatic ring is optionally substituted with one or two substituents selected from the group consisting of C$_{1-4}$alkyl;

p represents 1 or 2;

R$^{14}$ represents phenyl optionally substituted with one, two or three substituents each independently selected from the group consisting of halo;

Het represents a bicyclic aromatic heterocyclic ring system selected from the group consisting of (a-1), (a-2) and (a-3):

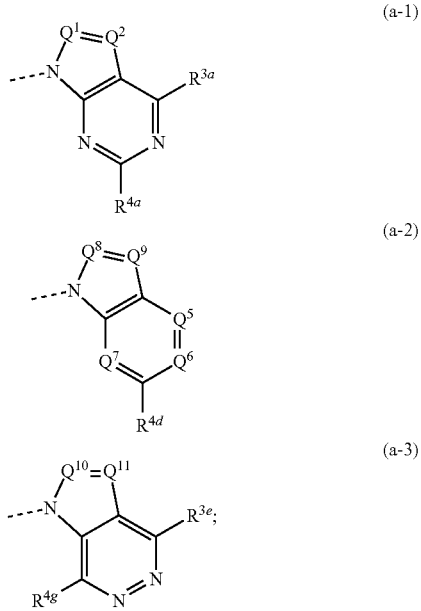

R$^{3a}$, R$^{3d}$ and R$^{3e}$ each independently represent hydrogen, halo, —NR$^{7a}$R$^{7b}$, C$_{1-4}$alkyl, C$_{2-4}$alkenyl, C$_{3-6}$cycloalkyl, —OH, or —O—C$_{1-4}$alkyl;

R$^{7a}$ represents hydrogen;

R$^{7b}$ represents hydrogen, C$_{3-6}$cycloalkyl, or C$_{1-4}$alkyl;

R$^{4a}$, R$^{4d}$, R$^{4e}$, R$^{4f}$ and R$^{4g}$ each independently represent hydrogen, halo, —NR$^{8a}$R$^{8b}$, or C$_{1-4}$alkyl;

R$^{8a}$ and R$^{8b}$ each independently represent hydrogen or C$_{1-4}$alkyl;

Q$^1$ represents N or CR$^{6a}$;
Q$^2$ represents N or CR$^{6b}$;
Q$^8$ represents N or CR$^{6g}$;
Q$^9$ represents N or CR$^{6h}$;
Q$^{10}$ represents N or CR$^{6i}$;
Q$^{11}$ represents N or CR$^{6j}$;
Q$^5$ represents CR$^{3d}$; Q$^6$ represents N; and Q$^7$ represents CR$^{4f}$; or
Q$^5$ represents CR$^{3d}$; Q$^6$ represents CR$^{4e}$; and Q$^7$ represents N; or
Q$^5$ represents N; Q$^6$ represents CR$^{4e}$; and Q$^7$ represents CR$^{4f}$; or
Q$^5$ represents N; Q$^6$ represents CR$^{4e}$; and Q$^7$ represents N; or
Q$^5$ represents N; Q$^6$ represents N; and Q$^7$ represents CR$^{4f}$; or
Q$^5$ represents N; Q$^6$ represents N; and Q$^7$ represents N;

R$^{6a}$, R$^{6b}$, R$^{6g}$, R$^{6h}$, R$^{6i}$ and R$^{6j}$ each independently represent hydrogen, halogen, C$_{1-4}$alkyl, —NR$^{9a}$R$^{9b}$, or C$_{1-4}$alkyl substituted with one, two or three halo atoms;

R$^{9a}$ and R$^{9b}$ each independently represent hydrogen or C$_{1-4}$alkyl;

and pharmaceutically acceptable addition salts, and solvates thereof.

The present invention also concerns methods for the preparation of compounds of the present invention and pharmaceutical compositions comprising them.

The compounds of the present invention were found to inhibit PRMT5 per se or can undergo metabolism to a (more) active form in vivo (prodrugs), and therefore may be useful in the treatment or prevention, in particular in the treatment, of diseases such as a blood disorder, metabolic disorders, autoimmune disorders, cancer, inflammatory diseases, cardiovascular diseases, neurodegenerative diseases, pancreatitis, multiorgan failure, kidney diseases, platelet aggregation, sperm motility, transplantation rejection, graft rejection, lung injuries, and the like.

In view of the aforementioned pharmacology of the compounds of Formula (I) and pharmaceutically acceptable addition salts, and solvates thereof, it follows that they may be suitable for use as a medicament.

In particular the compounds of Formula (I) and pharmaceutically acceptable addition salts, and solvates thereof, may be suitable in the treatment or prevention, in particular in the treatment, of any one of the diseases or conditions mentioned hereinbefore or hereinafter, in particular cancer.

The present invention also concerns the use of compounds of Formula (I) and pharmaceutically acceptable addition salts, and solvates thereof, for the manufacture of a medicament for the inhibition of PRMT5, for the treatment or prevention of any one of the diseases or conditions mentioned hereinbefore or hereinafter, in particular cancer.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

DETAILED DESCRIPTION

When describing the compounds of the invention, the terms used are to be construed in accordance with the following definitions, unless a context dictates otherwise.

When any variable occurs more than one time in any constituent or in any formula (e.g. Formula (I)), its definition in each occurence is independent of its definition at every other occurrence.

Whenever the term "substituted" is used in the present invention, it is meant, unless otherwise is indicated or is clear from the context, to indicate that one or more hydrogens, in particular from 1 to 3 hydrogens, preferably 1 or 2 hydrogens, more preferably 1 hydrogen, on the atom or radical indicated in the expression using "substituted" are replaced with a selection from the indicated group, provided that the normal valency is not exceeded, and that the substitution results in a chemically stable compound, i.e. a compound that is sufficiently robust to survive isolation to a useful degree of purity from a reaction mixture, and formulation into a therapeutic agent.

When two or more substituents are present on a moiety they may, unless otherwise is indicated or is clear from the context, replace hydrogens on the same atom or they may replace hydrogen atoms on different atoms in the moiety.

The prefix "$C_{x-y}$" (where x and y are integers) as used herein refers to the number of carbon atoms in a given group. Thus, a $C_{1-4}$alkyl group contains from 1 to 4 carbon atoms, a $C_{1-3}$alkyl group contains from 1 to 3 carbon atoms and so on.

The term "halo" as a group or part of a group is generic for fluoro, chloro, bromo, iodo unless otherwise is indicated or is clear from the context.

The term "$C_{1-4}$alkyl" as a group or part of a group refers to a hydrocarbyl radical of Formula $C_nH_{2n+1}$ wherein n is a number ranging from 1 to 4. $C_{1-4}$alkyl groups comprise from 1 to 4 carbon atoms, preferably from 1 to 3 carbon atoms, more preferably 1 to 2 carbon atoms. $C_{1-4}$alkyl groups may be linear or branched and may be substituted as indicated herein. When a subscript is used herein following a carbon atom, the subscript refers to the number of carbon atoms that the named group may contain. $C_{1-4}$alkyl includes all linear, or branched alkyl groups with between 1 and 4 carbon atoms, and thus includes methyl, ethyl, n-propyl, i-propyl, 2-methyl-ethyl, butyl and its isomers (e.g. n-butyl, isobutyl and tert-butyl), and the like.

The skilled person will realize that the term '$C_{1-4}$alkoxy' or '$C_{1-4}$alkyloxy' as a group or part of a group refers to a radical having the Formula $-OR^c$ wherein $R^c$ is $C_{1-4}$alkyl. Non-limiting examples of suitable $C_{1-4}$alkyloxy include methyloxy (also methoxy), ethyloxy (also ethoxy), propyloxy, isopropyloxy, butyloxy, isobutyloxy, sec-butyloxy and tert-butyloxy.

The term "$C_{2-4}$alkenyl" as used herein as a group or part of a group represents a straight or branched chain hydrocarbon group containing from 2 to 4 carbon atoms and containing a carbon carbon double bond such as, but not limited to, ethenyl, propenyl, butenyl, 1-propen-2-yl, and the like.

The term "$C_{2-6}$alkenyl" as used herein as a group or part of a group represents a straight or branched chain hydrocarbon group containing from 2 to 6 carbon atoms and containing a carbon carbon double bond such as, but not limited to, ethenyl, propenyl, butenyl, pentenyl, 1-propen-2-yl, hexenyl and the like.

The term '$C_{3-6}$cycloalkyl' as used herein as a group or part of a group represents cyclic saturated hydrocarbon radicals having from 3 to 6 carbon atoms such as cyclopropyl, cyclobutyl, cyclopentyl or cyclohexyl.

The term '$C_{5-6}$cycloalkyl' as used herein as a group or part of a group represents cyclic saturated hydrocarbon radicals having from 5 to 6 carbon atoms such as cyclopentyl or cyclohexyl.

The term "oxo" means the double-bonded group (=O) attached as a substituent.

In case Z is $-X-CR^{5a}R^{5b}-$, it is intended that X is attached to Ar.

In case Z is $-CR^{5c}=CR^{5d}-$, it is intended that the C-atom with the $R^{5c}$ substituent is attached to Ar.

In case Z is $-CR^{5e}R^{5g}-CR^{5f}R^{5h}-$, it is intended that the C-atom with the $R^{5e}$ and $R^{5g}$ substituents is attached to Ar.

In case Z is $-CR^{5a}R^{5b}-X-$, it is intended that the C-atom with the $R^{5a}$ and $R^{5b}$ substituents is attached to Ar.

It will be clear for the skilled person that, unless otherwise is indicated or is clear from the context, a substituent on a 4- to 7-membered monocyclic aromatic ring containing one, two or three heteroatoms (as in the definition of $R^{13}$) (non-limiting examples are pyrrolyl, pyridinyl, furanyl, and the like), may replace any hydrogen atom on a ring carbon atom or where possible on a ring nitrogen atom (in which case a hydrogen on a nitrogen atom may be replaced by a substituent).

A 4- to 7-membered monocyclic aromatic ring containing one, two or three heteroatoms (as in the definition of $R^{13}$), may be attached to the remainder of the molecule of Formula (I) through any available ring carbon or nitrogen atom as appropriate, if not otherwise specified.

The skilled person will realize that typical 4- to 7-membered monocyclic aromatic rings will be 5- or 6-membered monocyclic aromatic rings such as for example pyrrolyl, pyridinyl, furanyl, and the like.

In case Ar represents imidazolyl it may be attached to the remainder of the molecule via a ring carbon or ring nitrogen atom.

Non-limiting, examples of the Ar group being a 9-membered bicyclic aromatic ring system consisting of a 6-membered ring fused with a 5-membered ring, containing one, two or three heteroatoms each independently selected from O, S, and N, are

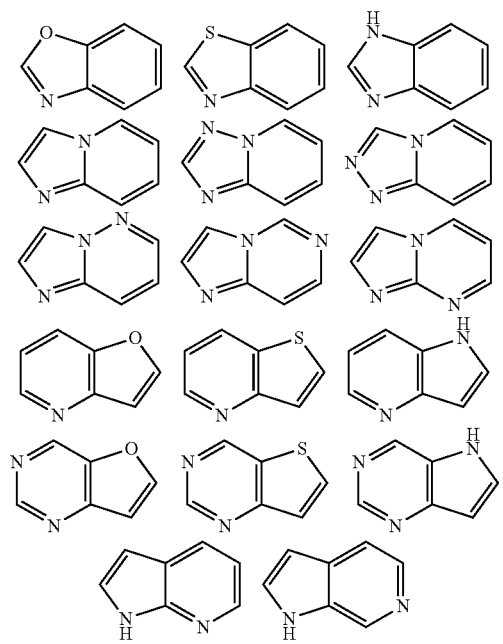

said 9-membered bicyclic aromatic ring being attached to the remainder of the molecule via a ring carbon atom of the 5- or 6-membered ring, or a ring nitrogen atom of the 5-membered ring;
each of which are optionally substituted according to any of the embodiments.

In case Ar represents a 10-membered bicyclic aromatic ring system consisting of two fused 6-membered rings, wherein a nitrogen atom replaces one of the two fused carbon atoms in the Ar group, a carbonyl group is present in said bicyclic aromatic ring system as exemplified by the structure shown below:

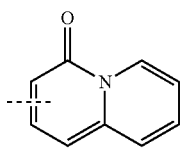

which is optionally substituted according to any of the embodiments. It will be clear this example is non-limiting.

Other, non-limiting, examples of the Ar group being a 10-membered bicyclic aromatic ring system consisting of two fused 6-membered rings, wherein optionally 1 or 2 ring carbon atoms are replaced by a nitrogen atom, are shown below:

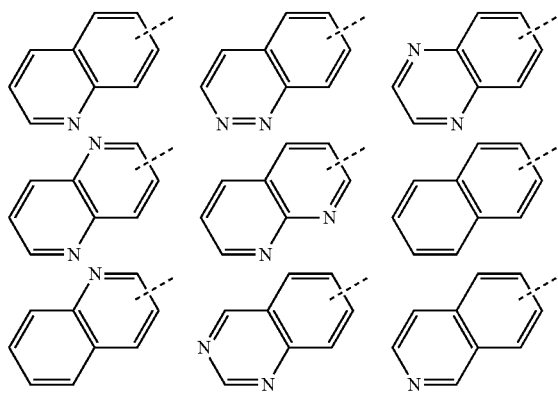

each of which are optionally substituted according to any of the embodiments.

Non-limiting examples of the Ar group being a fused bicyclic partially aromatic ring system which is attached with the aromatic ring to linker Z, are shown below:

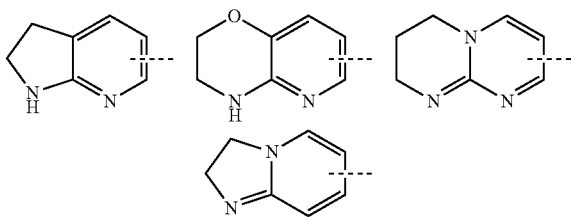

each of which are optionally substituted according to any of the embodiments.

Whenever substituents are represented by chemical structure, "---" represents the bond of attachment to the remainder of the molecule of Formula (I).

It will be clear that lines drawn from substituents into ring systems indicate that the bond may be attached to any of the suitable ring atoms, unless otherwise is indicated or is clear from the context.

The term "subject" as used herein, refers to an animal, preferably a mammal (e.g. cat, dog, primate or human), more preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medicinal doctor or other clinician, which includes alleviation or reversal of the symptoms of the disease or disorder being treated.

The term "composition" is intended to encompass a product comprising the specified ingredients in the specified amounts, as well as any product which results, directly or indirectly, from combinations of the specified ingredients in the specified amounts.

The term "treatment", as used herein, is intended to refer to all processes wherein there may be a slowing, interrupting, arresting or stopping of the progression of a disease, but does not necessarily indicate a total elimination of all symptoms.

The term "compounds of the (present) invention" as used herein, is meant to include the compounds of Formula (I) and pharmaceutically acceptable addition salts, and solvates thereof.

Some of the compounds of Formula (I) may also exist in their tautomeric form. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerisations. Valence tautomers include interconversions by reorganisation of some of the bonding electrons.

Such forms in so far as they may exist, although not explicitly indicated in the above Formula (I), are intended to be included within the scope of the present invention.

As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers. Where the stereochemistry of any particular chiral atom is not specified in the structures shown herein, then all stereoisomers are contemplated and included as the compounds of the invention, either as a pure stereoisomer or as a mixture of two or more stereoisomers.

Hereinbefore and hereinafter, the term "compound of Formula (I)" is meant to include the stereoisomers thereof and the tautomeric forms thereof. However where stereochemistry, as mentioned in the previous paragraph, is specified by bonds which are shown as solid wedged or hashed wedged bonds, or are otherwise indicated as having a particular configuration (e.g. R, S), then that stereoisomer is so specified and defined. It will be clear this also applies to subgroups of Formula (I).

It follows that a single compound may, where possible, exist in both stereoisomeric and tautomeric form.

The terms "stereoisomers", "stereoisomeric forms" or "stereochemically isomeric forms" hereinbefore or hereinafter are used interchangeably.

Enantiomers are stereoisomers that are non-superimposable mirror images of each other. A 1:1 mixture of a pair of enantiomers is a racemate or racemnic mixture.

Atropisomers (or atropoisomers) are stereoisomers which have a particular spatial configuration, resulting from a restricted rotation about a single bond, due to large steric hindrance. All atropisomeric forms of the compounds of Formula (I) are intended to be included within the scope of the present invention.

Diastereomers (or diastereoisomers) are stereoisomers that are not enantiomers, i.e. they are not related as mirror images. If a compound contains a double bond, the substituents may be in the E or the Z configuration. Substituents on bivalent cyclic (partially) saturated radicals may have either the cis- or trans-configuration; for example if a compound contains a disubstituted cycloalkyl group, the substituents may be in the cis or trans configuration. Therefore, the invention includes enantiomers, atropisomers, diastereomers, racemates, E isomers, Z isomers, cis isomers, trans isomers and mixtures thereof, whenever chemically possible.

The meaning of all those terms, i.e. enantiomers, atropisomers, diastereomers, racemates, E isomers, Z isomers, cis isomers, trans isomers and mixtures thereof are known to the skilled person.

The absolute configuration is specified according to the Cahn-Ingold-Prelog system. The configuration at an asymmetric atom is specified by either R or S. Resolved stereoisomers whose absolute configuration is not known can be designated by (+) or (−) depending on the direction in which they rotate plane polarized light. For instance, resolved enantiomers whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers. Thus, when a compound of Formula (I) is for instance specified as (R), this means that the compound is substantially free of the (S) isomer; when a compound of Formula (I) is for instance specified as E, this means that the compound is substantially free of the Z isomer; when a compound of Formula (I) is for instance specified as cis, this means that the compound is substantially free of the trans isomer.

For therapeutic use, salts of the compounds of Formula (I) and solvates thereof, are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

Pharmaceutically-acceptable salts include acid addition salts and base addition salts. Such salts may be formed by conventional means, for example by reaction of a free acid or a free base form with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin.

The pharmaceutically acceptable addition salts as mentioned hereinabove or hereinafter are meant to comprise the therapeutically active non-toxic acid and base addition salt forms which the compounds of Formula (I) and solvates thereof, are able to form.

Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of Formula (I) and solvates thereof containing an acidic proton may also be converted into their non-toxic metal or amine addition salt forms by treatment with appropriate organic and inorganic bases.

Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

For the purposes of this invention prodrugs are also included within the scope of the invention.

The term "prodrug" of a relevant compound of the invention includes any compound that, following oral or parenteral administration, in particular oral administration, is metabolised in vivo to a form that compound in an experimentally-detectable amount, and within a predetermined time (e.g. within a dosing interval of between 6 and 24 hours (i.e. once to four times daily)). For the avoidance of doubt, the term "parenteral" administration includes all forms of administration other than oral administration, in particular intravenous (IV), intramuscular (IM), and subcutaneous (SC) injection. Prodrugs may be prepared by modifying functional groups present on the compound in such a way that the modifications are cleaved, in vivo when such prodrug is administered to a mammalian subject. The modifications typically are achieved by synthesising the parent compound with a prodrug substituent. In general, prodrugs include compounds of the invention wherein a hydroxyl, amino, sulfhydryl, carboxy or carbonyl group in a compound of the invention is bonded to any group that may be cleaved in vivo to regenerate the free hydroxyl, amino, sulfhydryl, carboxy or carbonyl group, respectively; in particular wherein a hydroxyl group in a compound of the invention is bonded to any group (e.g. —C(=O)—$C_{1-4}$alkyl) that may be cleaved in vivo to regenerate the free hydroxyl. Within the context of this invention, prodrugs in particular are compounds of Formula (I) or subgroups thereof wherein $R^1$ and/or $R^2$ represent —C(=O)—$C_{1-4}$alkyl.

Examples of prodrugs include, but are not limited to, esters and carbamates of hydroxy functional groups, esters groups of carboxyl functional groups, N-acyl derivatives and N-Mannich bases. General information on prodrugs may be found e.g. in Bundegaard, H. "Design of Prodrugs" p. 1-92, Elesevier, New York-Oxford (1985).

The term solvate comprises the hydrates and solvent addition forms which the compounds of Formula (I) are able to form, as well as pharmaceutically acceptable addition salts thereof. Examples of such forms are e.g. hydrates, alcoholates and the like.

The compounds of the invention as prepared in the processes described below may be synthesized in the form of mixtures of enantiomers, in particular racemic mixtures of enantiomers, that can be separated from one another following art-known resolution procedures. A manner of separating the enantiomeric forms of the compounds of Formula (I), and pharmaceutically acceptable addition salts, and solvates thereof, involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

The present invention also embraces isotopically-labeled compounds of the present invention which are identical to those recited herein, but for the fact that one or more atoms are replaced by an atom having an atomic mass or mass number different from the atomic mass or mass number usually found in nature (or the most abundant one found in nature).

All isotopes and isotopic mixtures of any particular atom or element as specified herein are contemplated within the scope of the compounds of the invention, either naturally occurring or synthetically produced, either with natural abundance or in an isotopically enriched form. Exemplary isotopes that can be incorporated into compounds of the invention include isotopes of hydrogen, carbon, nitrogen, oxygen, phosphorus, sulfur, fluorine, chlorine and iodine, such as $^2$H, $^3$H, $^{11}$C, $^{13}$C, $^{14}$C, $^{13}$N, $^{15}$O, $^{17}$O, $^{18}$O, $^{32}$P, $^{33}$P, $^{35}$S, $^{18}$F, $^{36}$Cl, $^{122}$I, $^{123}$I, $^{125}$I, $^{131}$I, $^{75}$Br, $^{76}$Br, $^{77}$Br and $^{82}$Br. Preferably, the radioactive isotope is selected from the group of $^2$H, $^3$H, $^{11}$C and $^{18}$F. More preferably, the radioactive isotope is $^2$H. In particular, deuterated compounds are intended to be included within the scope of the present invention.

Certain isotopically-labeled compounds of the present invention (e.g., those labeled with $^3$H and $^{14}$C) are useful for substrate tissue distribution assays. Tritiated ($^3$H) and carbon-14 ($^{14}$C) isotopes are useful for their ease of preparation and detectability. Further, substitution with heavier isotopes such as deuterium (i.e., $^2$H may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C and $^{18}$F are useful for positron emission tomography (PET) studies to examine substrate receptor occupancy.

In an embodiment, the present invention concerns novel compounds of Formula (I), wherein
$R^1$ represents hydrogen or —C(=O)—$C_{1-4}$alkyl;
$R^2$ represents hydrogen or —C(=O)—$C_{1-4}$alkyl;
Y represents —CH$_2$— or —CF$_2$—;

Z represents —CH$_2$—, —CHR$^{5i}$—, —X—CR$^{5a}$R$^{5b}$—, —CR$^{5c}$=CR$^{5d}$—, —CR$^{5e}$R$^{5g}$—CR$^{5f}$R$^{5h}$—; —CR$^{5c}$R$^{5d}$—CR$^{5e}$R$^{5g}$—CR$^{5f}$R$^{5h}$—, or —CR$^{5a}$R$^{5b}$—CR$^{5c}$R$^{5d}$—CR$^{5e}$R$^{5g}$—CR$^{5f}$R$^{5h}$—;

$R^{5a}$, $R^{5b}$, $R^{5c}$, $R^{5d}$, $R^{5e}$, $R^{5f}$, $R^{5g}$, $R^{5h}$, and $R^{5i}$ each independently represent hydrogen or $C_{1-4}$alkyl;

X represents —O—;

$R^{11}$ represents hydrogen, $C_{1-4}$alkyl, or $C_{1-4}$alkyl substituted with one substituent selected from the group consisting of —OH, —O—$C_{1-4}$alkyl, —NH$_2$, —NH—$C_{1-4}$alkyl, and —N($C_{1-4}$alkyl)$_2$;

Ar represents a monocyclic aromatic ring or a bicyclic ring system; wherein the monocyclic aromatic ring is selected from the group consisting of pyridinyl, pyrimidinyl, pyrazolyl, and imidazolyl;

wherein the bicyclic ring system is
(i) a 9-membered bicyclic aromatic ring system consisting of a 6-membered ring fused with a 5-membered ring, containing one, two or three heteroatoms each independently selected from O, S, and N, said 9-membered bicyclic aromatic ring being attached to the remainder of the molecule via a ring carbon atom of the 5- or 6-membered ring, or a ring nitrogen atom of the 5-membered ring; or
(ii) a 10-membered bicyclic aromatic ring system consisting of two fused 6-membered rings, wherein optionally 1 or 2 ring carbon atoms are replaced by a nitrogen atom; provided that when the nitrogen atom replaces one of the two fused carbon atoms, a carbonyl group is present in said bicyclic aromatic ring system;
provided that in case Ar represents a 10-membered bicyclic aromatic ring system, Z can only represent —CR$^{5c}$R$^{5d}$—CR$^{5e}$R$^{5g}$—CR$^{5f}$R$^{5h}$— or —CR$^{5a}$R$^{5b}$—CR$^{5c}$R$^{5d}$—CR$^{5e}$R$^{5g}$—CR$^{5f}$R$^{5h}$—; or
(iii) a fused bicyclic partially aromatic ring system which is attached with the aromatic ring to linker Z, wherein the fused bicyclic partially aromatic ring system is selected from (b-1), (b-2) and (b-3)

(b-1)

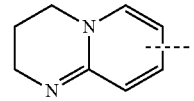

(b-2)

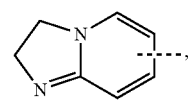

(b-3)

wherein ring A is a monocyclic aromatic ring is selected from the group consisting of pyridinyl, pyrimidinyl, pyrazolyl and imidazolyl;
wherein ring B is a $C_{5-6}$cycloalkyl or a 5- to 6-membered saturated heterocyclyl containing one or two heteroatoms each independently selected from O, S and N;

Ar is optionally substituted on the carbon atoms with in total one, two, three or four substituents each independently selected from the group consisting of halo, oxo, —OH, —NH$_2$, —NH—C$_{1-4}$alkyl, —NHR$^{10}$, cyano, —CF$_3$, C$_{1-4}$alkyloxy, C$_{3-6}$cycloalkyl, —O—C$_{3-6}$cycloalkyl, C$_{2-6}$alkenyl, C$_{1-4}$alkyl, and C$_{1-4}$alkyl substituted with one C$_{1-4}$alkyloxy; and where possible Ar is optionally substituted on one N-atom with one substituent selected from the group consisting of C$_{1-4}$alkyl; C$_{3-6}$cycloalkyl; C$_{1-4}$alkyl substituted with one, two or three halo atoms; and C$_{3-6}$cycloalkyl substituted with one, two or three halo atoms;

R$^{10}$ represents —(C═O)—C$_{1-4}$alkyl; C$_{3-6}$cycloalkyl; R$^{13}$; R$^{14}$; C$_{3-6}$cycloalkyl substituted with one, two or three substituents each independently selected from the group consisting of halo, —OH and —O—C$_{1-4}$alkyl; C$_{1-4}$alkyl substituted with one, two or three substituents each independently selected from the group consisting of halo, —OH and —O—C$_{1-4}$alkyl; or C$_{1-4}$alkyl substituted with one substituent selected from the group consisting of C$_{3-6}$cycloalkyl, R$^{13}$ and R$^{14}$;

R$^{13}$ represents a 4- to 7-membered monocyclic aromatic ring containing one, two or three heteroatoms each independently selected from O, S, S(═O)$_p$ and N; said 4- to 7-membered monocyclic aromatic ring is optionally substituted with one or two substituents selected from the group consisting of C$_{1-4}$alkyl;

p represents 1 or 2;

R$^{14}$ represents phenyl optionally substituted with one, two or three substituents each independently selected from the group consisting of halo;

Het represents a bicyclic aromatic heterocyclic ring system (a-1);

R$^{3a}$ represents halo, —NR$^{7a}$R$^{7b}$, or —O—C$_{1-4}$alkyl;

R$^{7a}$ represents hydrogen;

R$^{7b}$ represents hydrogen, C$_{3-6}$cycloalkyl, or C$_{1-4}$alkyl;

R$^{4a}$ represents hydrogen, halo, —NR$^{8a}$R$^{8b}$, or C$_{1-4}$alkyl;

R$^{8a}$ and R$^{8b}$ each independently represent hydrogen or C$_{1-4}$alkyl;

Q$^1$ represents CR$^{6a}$;

Q$^2$ represents CR$^{6b}$;

R$^{6a}$ and R$^{6b}$ each independently represent hydrogen, halogen, C$_{1-4}$alkyl, —NR$^{9a}$R$^{9b}$, or C$_{1-4}$alkyl substituted with one, two or three halo atoms;

R$^{9a}$ and R$^{9b}$ each independently represent hydrogen or C$_{1-4}$alkyl;

and pharmaceutically acceptable addition salts, and solvates thereof.

In an embodiment, the present invention concerns novel compounds of Formula (I), wherein R$^1$ represents hydrogen or —C(═O)—C$_{1-4}$alkyl;
R$^2$ represents hydrogen or —C(═O)—C$_{1-4}$alkyl;
Y represents —CH$_2$— or —CF$_2$—;
Z represents —CH$_2$—, —CHR$^{5i}$—, —CR$^{5c}$═CR$^{5d}$—, —CR$^{5e}$R$^{5g}$—CR$^{5f}$R$^{5h}$—, —CR$^{5c}$R$^{5d}$—CR$^{5e}$R$^{5g}$—CR$^{5f}$R$^{5h}$—, or —CR$^{5a}$R$^{5b}$—CR$^{5c}$R$^{5d}$—CR$^{5e}$R$^{5g}$—CR$^{5f}$R$^{5h}$—;

R$^{5a}$, R$^{5b}$, R$^{5c}$, R$^{5d}$, R$^{5e}$, R$^{5f}$, R$^{5g}$, R$^{5h}$, and R$^{5i}$ each independently represent hydrogen or C$_{1-4}$alkyl;

R$^{11}$ represents hydrogen, C$_{1-4}$alkyl, or C$_{1-4}$alkyl substituted with one substituent selected from the group consisting of —OH, —O—C$_{1-4}$alkyl, —NH$_2$, —NH—C$_{1-4}$alkyl, and —N(C$_{1-4}$alkyl)$_2$;

Ar represents a monocyclic aromatic ring or a bicyclic ring system; wherein the monocyclic aromatic ring is selected from the group consisting of pyridinyl, pyrimidinyl, pyrazolyl, and imidazolyl;

wherein the bicyclic ring system is
(i) a 9-membered bicyclic aromatic ring system consisting of a 6-membered ring fused with a 5-membered ring, containing one, two or three heteroatoms each independently selected from O, S, and N, said 9-membered bicyclic aromatic ring being attached to the remainder of the molecule via a ring carbon atom of the 5- or 6-membered ring, or a ring nitrogen atom of the 5-membered ring; or (ii) a 10-membered bicyclic aromatic ring system consisting of two fused 6-membered rings, wherein optionally 1 or 2 ring carbon atoms are replaced by a nitrogen atom; provided that when the nitrogen atom replaces one of the two fused carbon atoms, a carbonyl group is present in said bicyclic aromatic ring system;

provided that in case Ar represents a 10-membered bicyclic aromatic ring system, Z can only represent —CR$^{5c}$R$^{5d}$—CR$^{5e}$R$^{5g}$—CR$^{5f}$R$^{5h}$— or —CR$^{5a}$R$^{5b}$—CR$^{5c}$R$^{5d}$—CR$^{5e}$R$^{5g}$—CR$^{5f}$R$^{5h}$—; or (iii) a fused bicyclic partially aromatic ring system which is attached with the aromatic ring to linker Z, wherein the fused bicyclic partially aromatic ring system is selected from (b-1), (b-2) and (b-3)

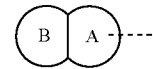
(b-1)

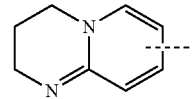
(b-2)

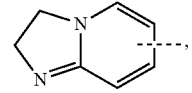
(b-3)

wherein ring A is a monocyclic aromatic ring is selected from the group consisting of pyridinyl, pyrimidinyl, pyrazolyl and imidazolyl;

wherein ring B is a C$_{5-6}$cycloalkyl or a 5- to 6-membered saturated heterocyclyl containing one or two heteroatoms each independently selected from O, S and N;

Ar is optionally substituted on the carbon atoms with in total one, two, three or four substituents each independently selected from the group consisting of halo, oxo, —OH, —NH$_2$, —NH—C$_{1-4}$alkyl, —NHR$^{10}$, cyano, —CF$_3$, C$_{1-4}$alkyloxy, C$_{3-6}$cycloalkyl, —O—C$_{3-6}$cycloalkyl, C$_{2-6}$alkenyl, C$_{1-4}$alkyl, and C$_{1-4}$alkyl substituted with one C$_{1-4}$alkyloxy; and where possible Ar is optionally substituted on one N-atom with one substituent selected from the group consisting of C$_{1-4}$alkyl; C$_{3-6}$cycloalkyl; C$_{1-4}$alkyl substituted with one, two or three halo atoms; and C$_{3-6}$cycloalkyl substituted with one, two or three halo atoms;

R$^{10}$ represents —(C═O)—C$_{1-4}$alkyl; C$_{3-6}$cycloalkyl; R$^{13}$; R$^{14}$; C$_{3-6}$cycloalkyl substituted with one, two or three substituents each independently selected from the group consisting of halo, —OH and —O—C$_{1-4}$alkyl; C$_{1-4}$alkyl substituted with one, two or three substituents each independently selected from the group consisting of halo, —OH and —O—C$_{1-4}$alkyl; or C$_{1-4}$alkyl substituted with one substituent selected from the group consisting of C$_{3-6}$cycloalkyl, R$^{13}$ and R$^{14}$;

R$^{13}$ represents a 4- to 7-membered monocyclic aromatic ring containing one, two or three heteroatoms each independently selected from O, S, S(═O)$_p$ and N; said 4- to 7-membered monocyclic aromatic ring is optionally substituted with one or two substituents selected from the group consisting of $C_{1-4}$alkyl;

p represents 1 or 2;

$R^{14}$ represents phenyl optionally substituted with one, two or three substituents each independently selected from the group consisting of halo;

Het represents a bicyclic aromatic heterocyclic ring system (a-1);

$R^{3a}$ represents halo, —$NR^{7a}R^{7b}$, or —O—$C_{1-4}$alkyl;

$R^{7a}$ represents hydrogen;

$R^{7b}$ represents hydrogen, $C_{3-6}$cycloalkyl, or $C_{1-4}$alkyl;

$R^{4a}$ represents hydrogen, halo, —$NR^{8a}R^{8b}$, or $C_{1-4}$alkyl;

$R^{8a}$ and $R^{8b}$ each independently represent hydrogen or $C_{1-4}$alkyl;

$Q^1$ represents $CR^{6a}$;

$Q^2$ represents $CR^{6b}$;

$R^{6a}$ and $R^{6b}$ each independently represent hydrogen, halogen, $C_{1-4}$alkyl, —$NR^{9a}R^{9b}$, or $C_{1-4}$alkyl substituted with one, two or three halo atoms;

$R^{9a}$ and $R^{9b}$ each independently represent hydrogen or $C_{1-4}$alkyl;

and pharmaceutically acceptable addition salts, and solvates thereof.

In an embodiment, the present invention concerns novel compounds of Formula (I), wherein $R^1$ represents hydrogen or —C(=O)—$C_{1-4}$alkyl;

$R^2$ represents hydrogen or —C(=O)—$C_{1-4}$alkyl;

Y represents —$CH_2$— or —$CF_2$—;

Z represents —$CH_2$—, —$X$—$CR^{5a}R^{5b}$—, —$CR^{5c}$=$CR^{5d}$—, —$CR^{5e}R^{5g}CR^{5f}R^{5h}$—, —$CR^{5a}R^{5b}$—X—, or —C≡C—;

$R^{5a}$, $R^{5b}$, $R^{5c}$, $R^{5d}$, $R^{5e}$, $R^{5f}$, $R^{5g}$, and $R^{5h}$ each independently represent hydrogen or $C_{1-4}$alkyl;

X represents —O—, —S—, or —$NR^{11}$—;

$R^{11}$ represents hydrogen, $C_{1-4}$alkyl, or $C_{1-4}$alkyl substituted with one substituent selected from the group consisting of —OH, —O—$C_{1-4}$alkyl, —$NH_2$, —NH—$C_{1-4}$alkyl, and —N($C_{1-4}$alkyl)$_2$;

Ar represents a monocyclic aromatic ring selected from pyridinyl and imidazolyl; or a 9-membered bicyclic aromatic ring system consisting of a 6-membered ring fused with a 5-membered ring, containing one, two or three heteroatoms each independently selected from O, S, and N;

said 9-membered bicyclic aromatic ring being attached to the remainder of the molecule via a ring carbon atom of the 5- or 6-membered ring, or a ring nitrogen atom of the 5-membered ring;

Ar is optionally substituted on the carbon atoms with in total one, two, three or four substituents each independently selected from the group consisting of halo, —OH, —$NH_2$, —NH—$C_{1-4}$alkyl, —$NHR^{10}$, cyano, —$CF_3$, $C_{1-4}$alkyloxy, $C_{3-6}$cycloalkyl, —O—$C_{3-6}$cycloalkyl, $C_{2-6}$alkenyl, $C_{1-4}$alkyl, and $C_{1-4}$alkyl substituted with one $C_{1-4}$alkyloxy; and where possible Ar is optionally substituted on one N-atom with one substituent selected from the group consisting of $C_{1-4}$alkyl; $C_{3-6}$cycloalkyl; $C_{1-4}$alkyl substituted with one, two or three halo atoms; and $C_{3-6}$cycloalkyl substituted with one, two or three halo atoms;

$R^{10}$ represents —C(=O)—$C_{1-4}$alkyl; $C_{3-6}$cycloalkyl; $R^{13}$; $R^{14}$; $C_{3-6}$cycloalkyl substituted with one, two or three substituents each independently selected from the group consisting of halo, —OH and —O—$C_{1-4}$alkyl; $C_{1-4}$alkyl substituted with one, two or three substituents each independently selected from the group consisting of halo, —OH and —O—$C_{1-4}$alkyl; or $C_{1-4}$alkyl substituted with one substituent selected from the group consisting of $C_{3-6}$cycloalkyl, $R^{13}$ and $R^{14}$;

$R^{13}$ represents a 4- to 7-membered monocyclic aromatic ring containing one, two or three heteroatoms each independently selected from O, S, S(=O)$_p$ and N; said 4- to 7-membered monocyclic aromatic ring is optionally substituted with one or two substituents selected from the group consisting of $C_{1-4}$alkyl;

p represents 1 or 2;

$R^{14}$ represents phenyl optionally substituted with one, two or three substituents each independently selected from the group consisting of halo;

Het represents a bicyclic aromatic heterocyclic ring system selected from the group consisting of (a-1), (a-2) and (a-3);

$R^{3a}$, $R^{3d}$ and $R^{3e}$ each independently represent hydrogen, halo, —$NR^{7a}R^{7b}$, $C_{1-4}$alkyl, $C_{2-4}$alkenyl, $C_{3-6}$cycloalkyl, —OH, or —O—$C_{1-4}$alkyl;

$R^{7a}$ represents hydrogen;

$R^{7b}$ represents hydrogen, $C_{3-6}$cycloalkyl, or $C_{1-4}$alkyl;

$R^{4a}$, $R^{4d}$, $R^{4e}$, $R^{4f}$ and $R^{4g}$ each independently represent hydrogen, halo, —$NR^{8a}R^{8b}$, or $C_{1-4}$alkyl;

$R^{8a}$ and $R^{8b}$ each independently represent hydrogen or $C_{1-4}$alkyl;

$Q^1$ represents N or $CR^{6a}$;

$Q^2$ represents N or $CR^{6b}$;

$Q^8$ represents N or $CR^{6g}$;

$Q^9$ represents N or $CR^{6h}$;

$Q^{10}$ represents N or $CR^{6i}$;

$Q^{11}$ represents N or $CR^{6j}$;

$Q^5$ represents $CR^{3d}$; $Q^6$ represents N; and $Q^7$ represents $CR^{4f}$; or $Q^5$ represents $CR^{3d}$; $Q^6$ represents $CR^{4e}$; and $Q^7$ represents N; or $Q^5$ represents N; $Q^6$ represents $CR^{4e}$; and $Q^7$ represents $CR^{4f}$; or $Q^5$ represents N; $Q^6$ represents $CR^{4e}$; and $Q^7$ represents N; or $Q^5$ represents N; $Q^6$ represents N; and $Q^7$ represents $CR^{4f}$; or $Q^5$ represents N; $Q^6$ represents N; and $Q^7$ represents N;

$R^{6a}$, $R^{6b}$, $R^{6g}$, $R^{6h}$, $R^{6i}$ and $R^{6j}$ each independently represent hydrogen, halogen, $C_{1-4}$alkyl, —$NR^{9a}R^{9b}$, or $C_{1-4}$alkyl substituted with one, two or three halo atoms;

$R^{9a}$ and $R^{9b}$ each independently represent hydrogen or $C_{1-4}$alkyl;

and pharmaceutically acceptable addition salts, and solvates thereof.

In an embodiment, the present invention concerns novel compounds of Formula (I), wherein $R^1$ represents hydrogen or —C(=O)—$C_{1-4}$alkyl;

$R^2$ represents hydrogen or —C(=O)—$C_{1-4}$alkyl;

Y represents —$CH_2$— or —$CF_2$—;

Z represents —$CH_2$—, —$CHR^{5i}$—, —$X$—$CR^{5a}R^{5b}$—, —$CR^{5c}$=$CR^{5d}$—, —$CR^{5e}R^{5g}$—$CR^{5f}R^{5h}$—, —$CR^{5a}R^{5b}$—X—, —C≡C—, —$CR^{5c}R^{5d}$—$CR^{5e}R^{5g}$—$CR^{5f}R^{5h}$—, or —$CR^{5a}R^{5b}$—$CR^{5c}R^{5d}$—$CR^{5e}R^{5g}$—$CR^{5f}R^{5h}$—;

$R^{5a}$, $R^{5b}$, $R^{5c}$, $R^{5d}$, $R^{5e}$, $R^{5f}$, $R^{5g}$, $R^{5h}$, and $R^{5i}$ each independently represent hydrogen or $C_{1-4}$alkyl;

X represents —O—, —S—, or —$NR^{11}$—;

$R^{11}$ represents hydrogen, $C_{1-4}$alkyl, or $C_{1-4}$alkyl substituted with one substituent selected from the group consisting of —OH, —O—$C_{1-4}$alkyl, —$NH_2$, —NH—$C_{1-4}$alkyl, and —N($C_{1-4}$alkyl)$_2$;

Ar represents a monocyclic aromatic ring or a bicyclic ring system;

wherein the monocyclic aromatic ring is selected from the group consisting of pyridinyl, pyrimidinyl, pyrazolyl, and imidazolyl;
wherein the bicyclic ring system is
(i) a 9-membered bicyclic aromatic ring system consisting of a 6-membered ring fused with a 5-membered ring, containing one, two or three heteroatoms each independently selected from O, S, and N, said 9-membered bicyclic aromatic ring being attached to the remainder of the molecule via a ring carbon atom of the 5- or 6-membered ring, or a ring nitrogen atom of the 5-membered ring; or
(ii) a 10-membered bicyclic aromatic ring system consisting of two fused 6-membered rings, wherein optionally 1 or 2 ring carbon atoms are replaced by a nitrogen atom; provided that when the nitrogen atom replaces one of the two fused carbon atoms, a carbonyl group is present in said bicyclic aromatic ring system;
provided that in case Ar represents a 10-membered bicyclic aromatic ring system, Z can only represent —$CR^{5c}R^{5d}CR^{5e}R^{5g}$—$CR^{5f}R^{5h}$— or —$CR^{5a}R^{5b}$—$CR^{5c}R^{5d}$—$CR^{5e}R^{5g}$—$CR^{5f}R^{5h}$—; or
(iii) a fused bicyclic partially aromatic ring system which is attached with the aromatic ring to linker Z, wherein the fused bicyclic partially aromatic ring system is selected from (b-1), (b-2) and (b-3)

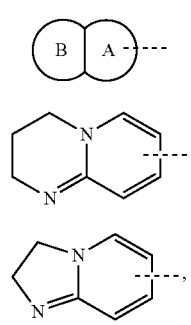

wherein ring A is a monocyclic aromatic ring is selected from the group consisting of pyridinyl, pyrimidinyl, pyrazolyl and imidazolyl;
wherein ring B is a $C_{5-6}$cycloalkyl or a 5- to 6-membered saturated heterocyclyl containing one or two heteroatoms each independently selected from O, S and N;
Ar is optionally substituted on the carbon atoms with in total one, two, three or four substituents each independently selected from the group consisting of halo, oxo, —OH, —$NH_2$, —NH—$C_{1-4}$alkyl, —$NHR^{10}$, cyano, —$CF_3$, $C_{1-4}$alkyloxy, $C_{3-6}$cycloalkyl, —O—$C_{3-6}$cycloalkyl, $C_{2-6}$alkenyl, $C_{1-4}$alkyl, and $C_{1-4}$alkyl substituted with one $C_{1-4}$alkyloxy; and
where possible Ar is optionally substituted on one N-atom with one substituent selected from the group consisting of $C_{1-4}$alkyl; $C_{3-6}$cycloalkyl; $C_{1-4}$alkyl substituted with one, two or three halo atoms; and $C_{3-6}$cycloalkyl substituted with one, two or three halo atoms;
$R^{10}$ represents —(C=O)—$C_{1-4}$alkyl; $C_{3-6}$cycloalkyl; $R^{14}$; $C_{3-6}$cycloalkyl substituted with one, two or three substituents each independently selected from the group consisting of halo, —OH and —O—$C_{1-4}$alkyl; $C_{1-4}$alkyl substituted with one, two or three substituents each independently selected from the group consisting of halo, —OH and —O—$C_{1-4}$alkyl; or $C_{1-4}$alkyl substituted with one substituent selected from the group consisting of $C_{3-6}$cycloalkyl, and $R^{14}$;
$R^{14}$ represents phenyl optionally substituted with one, two or three substituents each independently selected from the group consisting of halo;
Het represents a bicyclic aromatic heterocyclic ring system selected from the group consisting of (a-1), (a-2) and (a-3):

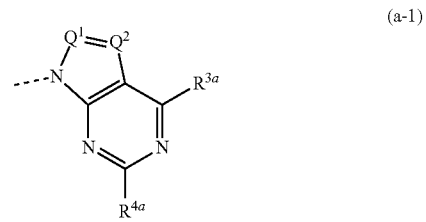

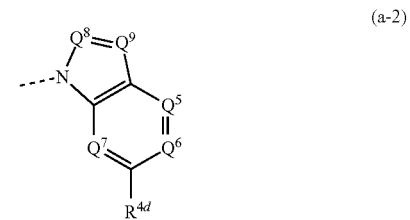

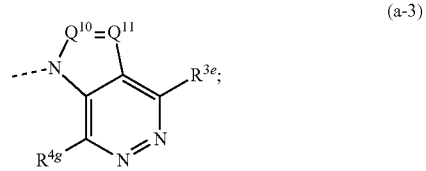

$R^{3a}$, $R^{3d}$ and $R^{3e}$ each independently represent hydrogen, halo, —$NR^{7a}R^{7b}$, $C_{1-4}$alkyl, $C_{2-4}$alkenyl, $C_{3-6}$cycloalkyl, —OH, or —O—$C_{1-4}$alkyl;
$R^{7a}$ represents hydrogen;
$R^{7b}$ represents hydrogen, $C_{3-6}$cycloalkyl, or $C_{1-4}$alkyl;
$R^{4a}$, $R^{4d}$, $R^{4e}$, $R^{4f}$ and $R^{4g}$ each independently represent hydrogen, halo, —$NR^{8a}R^{8b}$, or $C_{1-4}$alkyl;
$R^{8a}$ and $R^{8b}$ each independently represent hydrogen or $C_{1-4}$alkyl;
$Q^1$ represents N or $CR^{6a}$;
$Q^2$ represents N or $CR^{6b}$;
$Q^8$ represents N or $CR^{6g}$;
$Q^9$ represents N or $CR^{6h}$;
$Q^{10}$ represents N or $CR^{6i}$;
$Q^{11}$ represents N or $CR^{6j}$;
$Q^5$ represents $CR^{3d}$; $Q^6$ represents N; and $Q^7$ represents $CR^{4f}$; or
$Q^5$ represents $CR^{3d}$; $Q^6$ represents $CR^{4e}$; and $Q^7$ represents N; or
$Q^5$ represents N; $Q^6$ represents $CR^{4e}$; and $Q^7$ represents $CR^{4f}$; or
$Q^5$ represents N; $Q^6$ represents $CR^{4e}$; and $Q^7$ represents N; or
$Q^5$ represents N; $Q^6$ represents N; and $Q^7$ represents $CR^{4f}$; or
$Q^5$ represents N; $Q^6$ represents N; and $Q^7$ represents N;
$R^{6a}$, $R^{6b}$, $R^{6g}$, $R^{6h}$, $R^{6i}$ and $R^{6j}$ each independently represent hydrogen, halogen, $C_{1-4}$alkyl, —$NR^{9a}R^{9b}$, or $C_{1-4}$alkyl substituted with one, two or three halo atoms;
$R^{9a}$ and $R^{9b}$ each independently represent hydrogen or $C_{1-4}$alkyl;

In an embodiment, the present invention concerns novel compounds of Formula (I), wherein
$R^1$ represents hydrogen; $R^2$ represents hydrogen;
Y represents —$CH_2$—;
Z represents —$CH_2$—, —$CHR^{5i}$—, —X—$CR^{5a}R^{5b}$—, —$CR^{5c}$=$CR^{5d}$—, —$CR^{5e}R^{5g}$—$CR^{5f}R^{5h}$—, —$CR^{5c}R^{5d}$—$CR^{5e}R^{5g}$—$CR^{5f}R^{5h}$—, or —$CR^{5a}R^{5b}$—$CR^{5c}R^{5d}$—$CR^{5e}R^{5g}$—$CR^{5f}R^{5h}$—;
$R^{5a}$, $R^{5b}$, $R^{5c}$, $R^{5d}$, $R^{5e}$, $R^{5f}$, $R^{5g}$, $R^{5h}$, and $R^{5i}$ each independently represent hydrogen or $C_{1-4}$alkyl;
X represents —O—;
Ar represents a monocyclic aromatic ring or a bicyclic ring system;
wherein the monocyclic aromatic ring is selected from the group consisting of pyridinyl, pyrimidinyl, pyrazolyl, and imidazolyl;
wherein the bicyclic ring system is
(i) a 9-membered bicyclic aromatic ring system consisting of a 6-membered ring fused with a 5-membered ring, containing one, two or three heteroatoms each independently selected from O, S, and N, said 9-membered bicyclic aromatic ring being attached to the remainder of the molecule via a ring carbon atom of the 5- or 6-membered ring, or a ring nitrogen atom of the 5-membered ring; or
(ii) a 10-membered bicyclic aromatic ring system consisting of two fused 6-membered rings, wherein 1 or 2 ring carbon atoms are replaced by a nitrogen atom; provided that when the nitrogen atom replaces one of the two fused carbon atoms, a carbonyl group is present in said bicyclic aromatic ring system;
provided that in case Ar represents a 10-membered bicyclic aromatic ring system, Z can only represent —$CR^{5c}R^{5d}$—$CR^{5e}R^{5g}$—$CR^{5f}R^{5h}$— or —$CR^{5a}R^{5b}$—$CR^{5c}R^{5d}$—$CR^{5e}R^{5g}$—$CR^{5f}R^{5h}$—; or
(iii) a fused bicyclic partially aromatic ring system which is attached with the aromatic ring to linker Z, wherein the fused bicyclic partially aromatic ring system is selected from (b-1) and (b-3), wherein ring A is pyridinyl;
wherein ring B is a 5- to 6-membered saturated heterocyclyl containing one or two heteroatoms each independently selected from O and N;
Ar is optionally substituted on the carbon atoms with in total one, two, three or four substituents each independently selected from the group consisting of halo, oxo, —$NH_2$, —NH—$C_{1-4}$alkyl, —$CF_3$, $C_{3-6}$cycloalkyl, and $C_{1-4}$alkyl; and
where possible Ar is optionally substituted on one N-atom with one $C_{1-4}$alkyl;
Het represents a bicyclic aromatic heterocyclic ring system (a-1);
$R^{3a}$ represents halo, —$NR^{7a}R^{7b}$, or —O—$C_{1-4}$alkyl;
$R^{7a}$ represents hydrogen;
$R^{7b}$ represents hydrogen or $C_{1-4}$alkyl;
$R^{4a}$ represents hydrogen;
$Q^1$ represents $CR^{6a}$;
$Q^2$ represents N or $CR^{6b}$;
$R^{6a}$ and $R^{6b}$ each independently represent hydrogen or halogen;
and pharmaceutically acceptable addition salts, and solvates thereof.

In an embodiment, the present invention concerns novel compounds of Formula (I), wherein
$R^1$ represents hydrogen; $R^2$ represents hydrogen;
Y represents —$CH_2$—;
Z represents —$CH_2$—, —$CHR^{5i}$—, —X—$CR^{5a}R^{5b}$—, —$CR^{5c}$=$CR^{5d}$—, —$CR^{5e}R^{5g}$—$CR^{5f}R^{5h}$—, —$CR^{5c}R^{5d}$—$CR^{5e}R^{5g}$—$CR^{5f}R^{5h}$—, or —$CR^{5a}R^{5b}$—$CR^{5c}R^{5d}$—$CR^{5e}R^{5g}$—$CR^{5f}R^{5h}$—;
$R^{5a}$, $R^{5b}$, $R^{5c}$, $R^{5d}$, $R^{5e}$, $R^{5f}$, $R^{5g}$, $R^{5h}$, and $R^{5i}$ each independently represent hydrogen or $C_{1-4}$alkyl;
X represents —O—;
Ar represents a monocyclic aromatic ring or a bicyclic ring system;
wherein the monocyclic aromatic ring is selected from the group consisting of pyridinyl, pyrimidinyl, pyrazolyl, and imidazolyl;
wherein the bicyclic ring system is
(i) a 9-membered bicyclic aromatic ring system consisting of a 6-membered ring fused with a 5-membered ring, containing one, two or three heteroatoms each independently selected from O, S, and N, said 9-membered bicyclic aromatic ring being attached to the remainder of the molecule via a ring carbon atom of the 5- or 6-membered ring, or a ring nitrogen atom of the 5-membered ring; or
(ii) a 10-membered bicyclic aromatic ring system consisting of two fused 6-membered rings, wherein 1 or 2 ring carbon atoms are replaced by a nitrogen atom; provided that when the nitrogen atom replaces one of the two fused carbon atoms, a carbonyl group is present in said bicyclic aromatic ring system;
provided that in case Ar represents a 10-membered bicyclic aromatic ring system, Z can only represent —$CR^{5c}R^{5d}$—$CR^{5e}R^{5g}$—$CR^{5f}R^{5h}$— or —$CR^{5a}R^{5b}$—$CR^{5c}R^{5d}$—$CR^{5e}R^{5g}$—$CR^{5f}R^{5h}$—; or
(iii) a fused bicyclic partially aromatic ring system which is attached with the aromatic ring to linker Z, wherein the fused bicyclic partially aromatic ring system is selected from (b-1) and (b-3),
wherein ring A is pyridinyl;
wherein ring B is a 5- to 6-membered saturated heterocyclyl containing one or two heteroatoms each independently selected from O and N;
Ar is optionally substituted on the carbon atoms with in total one, two, three or four substituents each independently selected from the group consisting of halo, oxo, —$NH_2$, —NH—$C_{1-4}$alkyl, —$CF_3$, $C_{3-6}$cycloalkyl, and $C_{1-4}$alkyl; and
where possible Ar is optionally substituted on one N-atom with one $C_{1-4}$alkyl;
Het represents a bicyclic aromatic heterocyclic ring system (a-1);
$R^{3a}$ represents halo, —$NR^{7a}R^{7b}$, or —O—$C_{1-4}$alkyl;
$R^{7a}$ represents hydrogen;
$R^{7b}$ represents hydrogen or $C_{1-4}$alkyl;
$R^{4a}$ represents hydrogen;
$Q^1$ represents $CR^{6a}$;
$Q^2$ represents $CR^{6b}$;
$R^{6a}$ and $R^{6b}$ each independently represent hydrogen or halogen;
and pharmaceutically acceptable addition salts, and solvates thereof.

In an embodiment, the present invention concerns novel compounds of Formula (I), wherein
$R^1$ represents hydrogen; $R^2$ represents hydrogen;
Y represents —$CH_2$—;
Z represents —$CH_2$—, —$CHR^{5i}$—, —X—$CR^{5a}R^{5b}$—, —$CR^{5c}$=$CR^{5d}$—, —$CR^{5e}R^{5g}$—$CR^{5f}R^{5h}$—, —$CR^{5c}R^{5d}$—$CR^{5e}R^{5g}$—$CR^{5f}R^{5h}$—, or —$CR^{5a}R^{5b}$—$CR^{5c}R^{5d}$—$CR^{5e}R^{5g}$—$CR^{5f}R^{5h}$—;

$R^{5a}$, $R^{5b}$, $R^{5c}$, $R^{5d}$, $R^{5e}$, $R^{5f}$, $R^{5g}$, $R^{5h}$, and $R^{5i}$ each independently represent hydrogen or $C_{1-4}$alkyl;

X represents —O—;

Ar represents a monocyclic aromatic ring or a bicyclic ring system; wherein the monocyclic aromatic ring is selected from the group consisting of pyridinyl, pyrimidinyl, pyrazolyl, and imidazolyl;

wherein the bicyclic ring system is
  (i) a 9-membered bicyclic aromatic ring system consisting of a 6-membered ring fused with a 5-membered ring, containing one, two or three heteroatoms each independently selected from O, S, and N, said 9-membered bicyclic aromatic ring being attached to the remainder of the molecule via a ring carbon atom of the 5- or 6-membered ring, or a ring nitrogen atom of the 5-membered ring; or
  (ii) a 10-membered bicyclic aromatic ring system consisting of two fused 6-membered rings, wherein 1 or 2 ring carbon atoms are replaced by a nitrogen atom; provided that when the nitrogen atom replaces one of the two fused carbon atoms, a carbonyl group is present in said bicyclic aromatic ring system;
    provided that in case Ar represents a 10-membered bicyclic aromatic ring system, Z can only represent —$CR^{5c}R^{5d}$—$CR^{5e}R^{5g}$—$CR^{5f}R^{5h}$— or —$CR^{5a}R^{5b}$—$CR^{5c}R^{5d}$—$CR^{5e}R^{5g}$—$CR^{5f}R^{5h}$—; or
  (iii) a fused bicyclic partially aromatic ring system which is attached with the aromatic ring to linker Z, wherein the fused bicyclic partially aromatic ring system is selected from (b-1) and (b-3),
    wherein ring A is pyridinyl;
    wherein ring B is a 5- to 6-membered saturated heterocyclyl containing one or two heteroatoms each independently selected from O and N;

Ar is optionally substituted on the carbon atoms with in total one, two, three or four substituents each independently selected from the group consisting of halo, oxo, —$NH_2$, —NH—$C_{1-4}$alkyl, —$NHR^{10}$, —$CF_3$, $C_{3-6}$cycloalkyl, and $C_{1-4}$alkyl; and where possible Ar is optionally substituted on one N-atom with one $C_{1-4}$alkyl;

$R^{10}$ represents —(C=O)—$C_{1-4}$alkyl;

Het represents a bicyclic aromatic heterocyclic ring system (a-1);

$R^{3a}$ represents halo, —$NR^{7a}R^{7b}$, or —O—$C_{1-4}$alkyl;

$R^{7a}$ represents hydrogen;

$R^{7b}$ represents hydrogen or $C_{1-4}$alkyl;

$R^{4a}$ represents hydrogen;

$Q^1$ represents $CR^{6a}$;

$Q^2$ represents $CR^{6b}$;

$R^{6a}$ and $R^{6b}$ each independently represent hydrogen or halogen;

and pharmaceutically acceptable addition salts, and solvates thereof.

In an embodiment, the present invention concerns novel compounds of Formula (I), wherein $R^1$ represents hydrogen or —C(=O)—$C_{1-4}$alkyl;

$R^2$ represents hydrogen or —C(=O)—$C_{1-4}$alkyl;

Y represents —$CH_2$— or —$CF_2$—;

Z represents —$CH_2$—, —$CHR^{5i}$—, —X—$CR^{5a}R^{5b}$—, —$CR^{5c}$=$CR^{5d}$—, —$CR^{5e}R^{5g}$—$CR^{5f}R^{5h}$—, —$CR^{5a}R^{5b}$—X—, —C≡C—, —$CR^{5c}R^{5d}$—$CR^{5e}R^{5g}$—$CR^{5f}R^{5h}$—, or —$CR^{5a}R^{5b}$—$CR^{5c}R^{5d}$—$CR^{5e}R^{5g}$—$CR^{5f}R^{5h}$—;

$R^{5a}$, $R^{5b}$, $R^{5c}$, $R^{5d}$, $R^{5e}$, $R^{5f}$, $R^{5g}$, $R^{5h}$, and $R^{5i}$ each independently represent hydrogen or $C_{1-4}$alkyl;

X represents —O—, —S—, or —$NR^{11}$—;

$R^{11}$ represents hydrogen, $C_{1-4}$alkyl, or $C_{1-4}$alkyl substituted with one substituent selected from the group consisting of —OH, —O—$C_{1-4}$alkyl, —$NH_2$, —NH—$C_{1-4}$alkyl, and —N($C_{1-4}$alkyl)$_2$;

Ar represents a monocyclic aromatic ring selected from the group consisting of pyridinyl, pyrimidinyl, pyrazolyl, and imidazolyl;

Ar is optionally substituted on the carbon atoms with in total one, two, three or four substituents each independently selected from the group consisting of halo, oxo, —OH, —$NH_2$, —NH—$C_{1-4}$alkyl, —$NHR^{10}$, cyano, —$CF_3$, $C_{1-4}$alkyloxy, $C_{3-6}$cycloalkyl, —O—$C_{3-6}$cycloalkyl, $C_{2-6}$alkenyl, $C_{1-4}$alkyl, and
  $C_{1-4}$alkyl substituted with one $C_{1-4}$alkyloxy; and where possible Ar is optionally substituted on one N-atom with one substituent selected from the group consisting of $C_{1-4}$alkyl; $C_{3-6}$cycloalkyl; $C_{1-4}$alkyl substituted with one, two or three halo atoms; and $C_{3-6}$cycloalkyl substituted with one, two or three halo atoms;

$R^{10}$ represents —(C=O)—$C_{1-4}$alkyl; $C_{3-6}$cycloalkyl; $R^{14}$; $C_{3-6}$cycloalkyl substituted with one, two or three substituents each independently selected from the group consisting of halo, —OH and —O—$C_{1-4}$alkyl; $C_{1-4}$alkyl substituted with one, two or three substituents each independently selected from the group consisting of halo, —OH and —O—$C_{1-4}$alkyl; or $C_{1-4}$alkyl substituted with one substituent selected from the group consisting of $C_{3-6}$cycloalkyl, and $R^{14}$;

$R^{14}$ represents phenyl optionally substituted with one, two or three substituents each independently selected from the group consisting of halo;

Het represents a bicyclic aromatic heterocyclic ring system selected from the group consisting of (a-1), (a-2) and (a-3);

$R^{3a}$, $R^{3d}$ and $R^{3e}$ each independently represent hydrogen, halo, —$NR^{7a}R^{7b}$, $C_{1-4}$alkyl, $C_{2-4}$alkenyl, $C_{3-6}$cycloalkyl, —OH, or —O—$C_{1-4}$alkyl;

$R^{7a}$ represents hydrogen;

$R^{7b}$ represents hydrogen, $C_{3-6}$cycloalkyl, or $C_{1-4}$alkyl;

$R^{4a}$, $R^{4d}$, $R^{4e}$, $R^{4f}$ and $R^{4g}$ each independently represent hydrogen, halo, —$NR^{8a}R^{8b}$, or $C_{1-4}$alkyl;

$R^{8a}$ and $R^{8b}$ each independently represent hydrogen or $C_{1-4}$alkyl;

$Q^1$ represents N or $CR^{6a}$;

$Q^2$ represents N or $CR^{6b}$;

$Q^8$ represents N or $CR^{6g}$;

$Q^9$ represents N or $CR^{6h}$;

$Q^{10}$ represents N or $CR^{6i}$;

$Q^{11}$ represents N or $CR^{6j}$;

$Q^5$ represents $CR^{3d}$; $Q^6$ represents N; and $Q^7$ represents $CR^{4f}$; or $Q^5$ represents $CR^{3d}$; $Q^6$ represents $CR^{4e}$; and $Q^7$ represents N; or $Q^5$ represents N; $Q^6$ represents $CR^{4e}$; and $Q^7$ represents $CR^{4f}$; or $Q^5$ represents N; $Q^6$ represents $CR^{4e}$; and $Q^7$ represents N; or $Q^5$ represents N; $Q^6$ represents N; and $Q^7$ represents $CR^{4f}$; or $Q^5$ represents N; $Q^6$ represents N; and $Q^7$ represents N;

$R^{6a}$, $R^{6b}$, $R^{6g}$, $R^{6h}$, $R^{6i}$ and $R^{6j}$ each independently represent hydrogen, halogen, $C_{1-4}$alkyl, —$NR^{9a}R^{9b}$, or $C_{1-4}$alkyl substituted with one, two or three halo atoms;

$R^{9a}$ and $R^{9b}$ each independently represent hydrogen or $C_{1-4}$alkyl;

and pharmaceutically acceptable addition salts, and solvates thereof.

In an embodiment, the present invention concerns novel compounds of Formula (I), wherein
$R^1$ represents hydrogen or —C(=O)—$C_{1-4}$alkyl;
$R^2$ represents hydrogen or —C(=O)—$C_{1-4}$alkyl;
Y represents —$CH_2$— or —$CF_2$—;
Z represents —$CH_2$—, —$CHR^{5i}$—, —X—$CR^{5a}R^{5b}$—, —$CR^{5c}$=$CR^{5d}$—, —$CR^{5e}R^{5g}$—$CR^{5f}R^{5h}$—, —$CR^{5a}R^{5b}$—X—, —C≡C—, —$CR^{5c}R^{5d}$—$CR^{5e}R^{5g}$—$CR^{5f}R^{5h}$—, or —$CR^{5a}R^{5b}$—$CR^{5c}R^{5d}$—$CR^{5e}R^{5g}$—$CR^{5f}R^{5h}$—;
$R^{5a}$, $R^{5b}$, $R^{5c}$, $R^{5d}$, $R^{5e}$, $R^{5f}$, $R^{5g}$, $R^{5h}$, and $R^{5i}$ each independently represent hydrogen or $C_{1-4}$alkyl;
X represents —O—, —S—, or —$NR^{11}$—;
$R^{11}$ represents hydrogen, $C_{1-4}$alkyl, or $C_{1-4}$alkyl substituted with one substituent selected from the group consisting of —OH, —O—$C_{1-4}$alkyl, —$NH_2$, —NH—$C_{1-4}$alkyl, and —N($C_{1-4}$alkyl)$_2$;
Ar represents a bicyclic ring system; wherein the bicyclic ring system is
  (i) a 9-membered bicyclic aromatic ring system consisting of a 6-membered ring fused with a 5-membered ring, containing one, two or three heteroatoms each independently selected from O, S, and N, said 9-membered bicyclic aromatic ring being attached to the remainder of the molecule via a ring carbon atom of the 5- or 6-membered ring, or a ring nitrogen atom of the 5-membered ring; or
  (ii) a 10-membered bicyclic aromatic ring system consisting of two fused 6-membered rings, wherein optionally 1 or 2 ring carbon atoms are replaced by a nitrogen atom; provided that when the nitrogen atom replaces one of the two fused carbon atoms, a carbonyl group is present in said bicyclic aromatic ring system;
   provided that in case Ar represents a 10-membered bicyclic aromatic ring system, Z can only represent —$CR^{5c}R^{5d}$—$CR^{5e}R^{5g}$—$CR^{5f}R^{5h}$— or —$CR^{5a}R^{5b}$—$CR^{5c}R^{5d}$—$CR^{5e}R^{5g}$—$CR^{5f}R^{5h}$—; or
  (iii) a fused bicyclic partially aromatic ring system which is attached with the aromatic ring to linker Z, wherein the fused bicyclic partially aromatic ring system is selected from (b-1), (b-2) and (b-3)

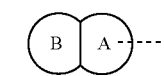

(b-1)

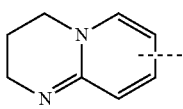

(b-2)

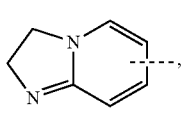

(b-3)

wherein ring A is a monocyclic aromatic ring is selected from the group consisting of pyridinyl, pyrimidinyl, pyrazolyl and imidazolyl;
   wherein ring B is a $C_{5-6}$cycloalkyl or a 5- to 6-membered saturated heterocyclyl containing one or two heteroatoms each independently selected from O, S and N;
Ar is optionally substituted on the carbon atoms with in total one, two, three or four substituents each independently selected from the group consisting of halo, oxo, —OH, —$NH_2$, —NH—$C_{1-4}$alkyl, —$NHR^{10}$, cyano, —$CF_3$, $C_{1-4}$alkyloxy, $C_{3-6}$cycloalkyl, —O—$C_{3-6}$cycloalkyl, $C_{2-6}$alkenyl, $C_{1-4}$alkyl, and
$C_{1-4}$alkyl substituted with one $C_{1-4}$alkyloxy; and
where possible Ar is optionally substituted on one N-atom with one substituent selected from the group consisting of $C_{1-4}$alkyl; $C_{3-6}$cycloalkyl; $C_{1-4}$alkyl substituted with one, two or three halo atoms; and $C_{3-6}$cycloalkyl substituted with one, two or three halo atoms;
$R^{10}$ represents —(C=O)—$C_{1-4}$alkyl; $C_{3-6}$cycloalkyl; $R^{14}$; $C_{3-6}$cycloalkyl substituted with one, two or three substituents each independently selected from the group consisting of halo, —OH and —O—$C_{1-4}$alkyl; $C_{1-4}$alkyl substituted with one, two or three substituents each independently selected from the group consisting of halo, —OH and —O—$C_{1-4}$alkyl; or $C_{1-4}$alkyl substituted with one substituent selected from the group consisting of $C_{3-6}$cycloalkyl, and $R^{14}$;
$R^{14}$ represents phenyl optionally substituted with one, two or three substituents each independently selected from the group consisting of halo;
Het represents a bicyclic aromatic heterocyclic ring system selected from the group consisting of (a-1), (a-2) and (a-3);
$R^{3a}$, $R^{3d}$ and $R^{3e}$ each independently represent hydrogen, halo, —$NR^{7a}R^{7b}$, $C_{1-4}$alkyl, $C_{2-4}$alkenyl, $C_{3-6}$cycloalkyl, —OH, or —O—$C_{1-4}$alkyl;
$R^{7a}$ represents hydrogen;
$R^{7b}$ represents hydrogen, $C_{3-6}$cycloalkyl, or $C_{1-4}$alkyl;
$R^{4a}$, $R^{4d}$, $R^{4e}$, $R^{4f}$ and $R^{4g}$ each independently represent hydrogen, halo, —$NR^{8a}R^{8b}$, or $C_{1-4}$alkyl;
$R^{8a}$ and $R^{8b}$ each independently represent hydrogen or $C_{1-4}$alkyl;
$Q^1$ represents N or $CR^{6a}$;
$Q^2$ represents N or $CR^{6b}$;
$Q^8$ represents N or $CR^{6g}$;
$Q^9$ represents N or $CR^{6h}$;
$Q^{10}$ represents N or $CR^{6i}$;
$Q^{11}$ represents N or $CR^{6j}$;
$Q^5$ represents $CR^{3d}$; $Q^6$ represents N; and $Q^7$ represents $CR^{4f}$; or
$Q^5$ represents $CR^{3d}$; $Q^6$ represents $CR^{4e}$; and $Q^7$ represents N; or
$Q^5$ represents N; $Q^6$ represents $CR^{4e}$; and $Q^7$ represents $CR^{4f}$; or
$Q^5$ represents N; $Q^6$ represents $CR^{4e}$; and $Q^7$ represents N; or
$Q^5$ represents N; $Q^6$ represents N; and $Q^7$ represents $CR^{4f}$; or
$Q^5$ represents N; $Q^6$ represents N; and $Q^7$ represents N;
$R^{6a}$, $R^{6b}$, $R^{6g}$, $R^{6h}$, $R^{6i}$ and $R^{6j}$ each independently represent hydrogen, halogen, $C_{1-4}$alkyl, —$NR^{9a}R^{9b}$, or $C_{1-4}$alkyl substituted with one, two or three halo atoms;
$R^{9a}$ and $R^{9b}$ each independently represent hydrogen or $C_{1-4}$alkyl;
and pharmaceutically acceptable addition salts, and solvates thereof.
In an embodiment, the present invention concerns novel compounds of Formula (I), wherein
$R^1$ represents hydrogen or —C(=O)—$C_{1-4}$alkyl;
$R^2$ represents hydrogen or —C(=O)—$C_{1-4}$alkyl;
Y represents —$CH_2$— or —$CF_2$—;
Z represents —$CH_2$—, —$CHR^{5i}$—, —X—$CR^{5a}R^{5b}$—, —$CR^{5c}$=$CR^{5d}$—, —$CR^{5e}R^{5g}$—$CR^{5f}R^{5h}$—, —$CR^{5a}R^{5b}$—X—, —C≡C—, —$CR^{5c}R^{5d}$—$CR^{5e}R^{5g}$—$CR^{5f}R^{5h}$—, or —$CR^{5a}R^{5b}$—$CR^{5c}R^{5d}$—$CR^{5e}R^{5g}$—$CR^{5f}R^{5h}$—;

$R^{5a}$, $R^{5b}$, $R^{5c}$, $R^{5d}$, $R^{5e}$, $R^{5f}$, $R^{5g}$, $R^{5h}$, and $R^{5i}$ each independently represent hydrogen or $C_{1-4}$alkyl;

X represents —O—, —S—, or —$NR^{11}$—;

$R^{11}$ represents hydrogen, $C_{1-4}$alkyl, or $C_{1-4}$alkyl substituted with one substituent selected from the group consisting of —OH, —O—$C_{1-4}$alkyl, —$NH_2$, —NH—$C_{1-4}$alkyl, and —N($C_{1-4}$alkyl)$_2$;

Ar represents a fused bicyclic partially aromatic ring system which is attached with the aromatic ring to linker Z, wherein the fused bicyclic partially aromatic ring system is selected from (b-1), (b-2) and (b-3)

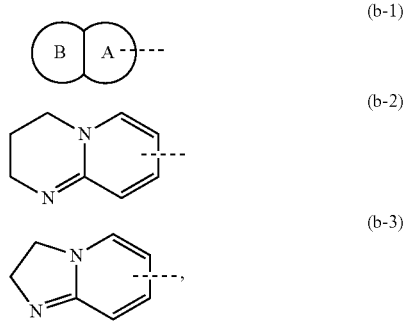

wherein ring A is a monocyclic aromatic ring is selected from the group consisting of pyridinyl, pyrimidinyl, pyrazolyl and imidazolyl;

wherein ring B is a $C_{5-6}$cycloalkyl or a 5- to 6-membered saturated heterocyclyl containing one or two heteroatoms each independently selected from O, S and N;

Ar is optionally substituted on the carbon atoms with in total one, two, three or four substituents each independently selected from the group consisting of halo, oxo, —OH, —$NH_2$, —NH—$C_{1-4}$alkyl, —$NHR^{10}$, cyano, —$CF_3$, $C_{1-4}$alkyloxy, $C_{3-6}$cycloalkyl, —O—$C_{3-6}$cycloalkyl, $C_{2-6}$alkenyl, $C_{1-4}$alkyl, and $C_{1-4}$alkyl substituted with one $C_{1-4}$alkyloxy; and where possible Ar is optionally substituted on one N-atom with one substituent selected from the group consisting of $C_{1-4}$alkyl; $C_{3-6}$cycloalkyl; $C_{1-4}$alkyl substituted with one, two or three halo atoms; and $C_{3-6}$cycloalkyl substituted with one, two or three halo atoms;

$R^{10}$ represents —(C=O)—$C_{1-4}$alkyl; $C_{3-6}$cycloalkyl; $R^{14}$; $C_{3-6}$cycloalkyl substituted with one, two or three substituents each independently selected from the group consisting of halo, —OH and —O—$C_{1-4}$alkyl; $C_{1-4}$alkyl substituted with one, two or three substituents each independently selected from the group consisting of halo, —OH and —O—$C_{1-4}$alkyl; or $C_{1-4}$alkyl substituted with one substituent selected from the group consisting of $C_{3-6}$cycloalkyl, and $R^{14}$;

$R^{14}$ represents phenyl optionally substituted with one, two or three substituents each independently selected from the group consisting of halo;

Het represents a bicyclic aromatic heterocyclic ring system selected from the group consisting of (a-1), (a-2) and (a-3);

$R^{3a}$, $R^{3d}$ and $R^{3e}$ each independently represent hydrogen, halo, —$NR^{7a}R^{7b}$, $C_{1-4}$alkyl, $C_{2-4}$alkenyl, $C_{3-6}$cycloalkyl, —OH, or —O—$C_{1-4}$alkyl;

$R^{7a}$ represents hydrogen;

$R^{7b}$ represents hydrogen, $C_{3-6}$cycloalkyl, or $C_{1-4}$alkyl;

$R^{4a}$, $R^{4d}$, $R^{4e}$, $R^{4f}$ and $R^{4g}$ each independently represent hydrogen, halo, —$NR^{8a}R^{8b}$, or $C_{1-4}$alkyl;

$R^{8a}$ and $R^{8b}$ each independently represent hydrogen or $C_{1-4}$alkyl;

$Q^1$ represents N or $CR^{6a}$;
$Q^2$ represents N or $CR^{6b}$;
$Q^8$ represents N or $CR^{6g}$;
$Q^9$ represents N or $CR^{6h}$;
$Q^{10}$ represents N or $CR^{6i}$;
$Q^{11}$ represents N or $CR^{6j}$;
$Q^5$ represents $CR^{3d}$; $Q^6$ represents N; and $Q^7$ represents $CR^{4f}$; or $Q^5$ represents $CR^{3d}$; $Q^6$ represents $CR^{4e}$; and $Q^7$ represents N; or $Q^5$ represents N; $Q^6$ represents $CR^{4e}$; and $Q^7$ represents $CR^{4f}$; or $Q^5$ represents N; $Q^6$ represents $CR^{4e}$; and $Q^7$ represents N; or $Q^5$ represents N; $Q^6$ represents N; and $Q^7$ represents $CR^{4f}$; or $Q^5$ represents N; $Q^6$ represents N; and $Q^7$ represents N;

$R^{6a}$, $R^{6b}$, $R^{6g}$, $R^{6h}$, $R^{6i}$ and $R^{6j}$ each independently represent hydrogen, halogen, $C_{1-4}$alkyl, —$NR^{9a}R^{9b}$, or $C_{1-4}$alkyl substituted with one, two or three halo atoms;

$R^{9a}$ and $R^{9b}$ each independently represent hydrogen or $C_{1-4}$alkyl;

and pharmaceutically acceptable addition salts, and solvates thereof.

In an embodiment, the present invention concerns novel compounds of Formula (I), wherein $R^1$ represents hydrogen or —C(=O)—$C_{1-4}$alkyl;
$R^2$ represents hydrogen or —C(=O)—$C_{1-4}$alkyl;
Y represents —$CH_2$— or —$CF_2$—;
Z represents —$CH_2$—, —$CHR^{5i}$—, —X—$CR^{5a}R^{5b}$—, —$CR^{5c}$=$CR^{5d}$—, —$CR^{5e}R^{5g}$—$CR^{5f}R^{5h}$—, —$CR^{5a}R^{5b}$—X—, —C≡C—, —$CR^{5c}R^{5d}$—$CR^{5e}R^{5g}$—$CR^{5f}R^{5h}$—, or —$CR^{5a}R^{5b}$—$CR^{5c}R^{5d}$—$CR^{5e}R^{5g}$—$CR^{5f}R^{5h}$—.

$R^{5a}$, $R^{5b}$, $R^{5c}$, $R^{5d}$, $R^{5e}$, $R^{5f}$, $R^{5g}$, $R^{5h}$, and $R^{5i}$ each independently represent hydrogen or $C_{1-4}$alkyl;

X represents —O—, —S—, or —$NR^{11}$—;

$R^{11}$ represents hydrogen, $C_{1-4}$alkyl, or $C_{1-4}$alkyl substituted with one substituent selected from the group consisting of —OH, —O—$C_{1-4}$alkyl, —$NH_2$, —NH—$C_{1-4}$alkyl, and —N($C_{1-4}$alkyl)$_2$;

Ar represents a 9-membered bicyclic aromatic ring system consisting of a 6-membered ring fused with a 5-membered ring, containing one, two or three heteroatoms each independently selected from O, S, and N, said 9-membered bicyclic aromatic ring being attached to the remainder of the molecule via a ring carbon atom of the 5- or 6-membered ring, or a ring nitrogen atom of the 5-membered ring;

Ar is optionally substituted on the carbon atoms with in total one, two, three or four substituents each independently selected from the group consisting of halo, oxo, —OH, —$NH_2$, —NH—$C_{1-4}$alkyl, —$NHR^{10}$, cyano, —$CF_3$, $C_{1-4}$alkyloxy, $C_{3-6}$cycloalkyl, —O—$C_{3-6}$cycloalkyl, $C_{2-6}$alkenyl, $C_{1-4}$alkyl, and $C_{1-4}$alkyl substituted with one $C_{1-4}$alkyloxy; and where possible Ar is optionally substituted on one N-atom with one substituent selected from the group consisting of $C_{1-4}$alkyl; $C_{3-6}$cycloalkyl; $C_{1-4}$alkyl substituted with one, two or three halo atoms; and $C_{3-6}$cycloalkyl substituted with one, two or three halo atoms;

$R^{10}$ represents —(C=O)—$C_{1-4}$alkyl; $C_{3-6}$cycloalkyl; $R^{14}$; $C_{3-6}$cycloalkyl substituted with one, two or three substituents each independently selected from the group consisting of halo, —OH and —O—$C_{1-4}$alkyl; $C_{1-4}$alkyl substituted with one, two or three substituents each independently selected from the group consisting of halo, —OH and —O—$C_{1-4}$alkyl; or $C_{1-4}$alkyl substituted with one substituent selected from the group consisting of $C_{3-6}$cycloalkyl, and $R^{14}$;

$R^{14}$ represents phenyl optionally substituted with one, two or three substituents each independently selected from the group consisting of halo;

Het represents a bicyclic aromatic heterocyclic ring system selected from the group consisting of (a-1), (a-2) and (a-3);

$R^{3a}$, $R^{3d}$ and $R^{3e}$ each independently represent hydrogen, halo, —$NR^{7a}R^{7b}$, $C_{1-4}$alkyl, $C_{2-4}$alkenyl, $C_{3-6}$cycloalkyl, —OH, or —O—$C_{1-4}$alkyl;

$R^{7a}$ represents hydrogen;

$R^{7b}$ represents hydrogen, $C_{3-6}$cycloalkyl, or $C_{1-4}$alkyl;

$R^{4a}$, $R^{4d}$, $R^{4e}$, $R^{4f}$ and $R^{4g}$ each independently represent hydrogen, halo, —$NR^{8a}R^{8b}$, or $C_{1-4}$alkyl;

$R^{8a}$ and $R^{8b}$ each independently represent hydrogen or $C_{1-4}$alkyl;

$Q^1$ represents N or $CR^{6a}$;
$Q^2$ represents N or $CR^{6b}$;
$Q^8$ represents N or $CR^{6g}$;
$Q^9$ represents N or $CR^{6h}$;
$Q^{10}$ represents N or $CR^{6i}$;
$Q^{11}$ represents N or $CR^{6j}$;

$Q^5$ represents $CR^{3d}$; $Q^6$ represents N; and $Q^7$ represents $CR^{4f}$; or $Q^5$ represents $CR^{3d}$; $Q^6$ represents $CR^{4e}$; and $Q^7$ represents N; or $Q^5$ represents N; $Q^6$ represents $CR^{4e}$; and $Q^7$ represents $CR^{4f}$; or $Q^5$ represents N; $Q^6$ represents $CR^{4e}$; and $Q^7$ represents N; or $Q^5$ represents N; $Q^6$ represents N; and $Q^7$ represents $CR^{4f}$; or $Q^5$ represents N; $Q^6$ represents N; and $Q^7$ represents N;

$R^{6a}$, $R^{6b}$, $R^{6g}$, $R^{6h}$, $R^{6i}$ and $R^{6j}$ each independently represent hydrogen, halogen, $C_{1-4}$alkyl, —$NR^{9a}R^{9b}$, or $C_{1-4}$alkyl substituted with one, two or three halo atoms;

$R^{9a}$ and $R^{9b}$ each independently represent hydrogen or $C_{1-4}$alkyl;

and pharmaceutically acceptable addition salts, and solvates thereof.

In an embodiment, the present invention concerns novel compounds of Formula (I), wherein $R^1$ represents hydrogen or —C(=O)—$C_{1-4}$alkyl;
$R^2$ represents hydrogen or —C(=O)—$C_{1-4}$alkyl;
Y represents —$CH_2$— or —$CF_2$—;
Z represents —$CR^{5c}R^{5d}$—$CR^{5e}R^{5g}$—$CR^{5f}R^{5h}$—, or —$CR^{5a}R^{5b}$—$CR^{5c}R^{5d}$—$CR^{5e}R^{5g}$—$CR^{5f}R^{5h}$—; $R^{5a}$, $R^{5b}$, $R^{5c}$, $R^{5d}$, $R^{5e}$, $R^{5f}$, $R^{5g}$, and $R^{5h}$ each independently represent hydrogen or $C_{1-4}$alkyl;

X represents —O—, —S—, or —$NR^{11}$—;

$R^{11}$ represents hydrogen, $C_{1-4}$alkyl, or $C_{1-4}$alkyl substituted with one substituent selected from the group consisting of —OH, —O—$C_{1-4}$alkyl, —$NH_2$, —NH—$C_{1-4}$alkyl, and —$N(C_{1-4}alkyl)_2$;

Ar represents a 10-membered bicyclic aromatic ring system consisting of two fused 6-membered rings, wherein optionally 1 or 2 ring carbon atoms are replaced by a nitrogen atom; provided that when the nitrogen atom replaces one of the two fused carbon atoms, a carbonyl group is present in said bicyclic aromatic ring system;

Ar is optionally substituted on the carbon atoms with in total one, two, three or four substituents each independently selected from the group consisting of halo, oxo, —OH, —$NH_2$, —NH—$C_{1-4}$alkyl, —$NHR^{10}$, cyano, —$CF_3$, $C_{1-4}$alkyloxy, $C_{3-6}$cycloalkyl, —O—$C_{3-6}$cycloalkyl, $C_{2-6}$alkenyl, $C_{1-4}$alkyl, and $C_{1-4}$alkyl substituted with one $C_{1-4}$alkyloxy; and where possible Ar is optionally substituted on one N-atom with one substituent selected from the group consisting of $C_{1-4}$alkyl; $C_{3-6}$cycloalkyl; $C_{1-4}$alkyl substituted with one, two or three halo atoms; and $C_{3-6}$cycloalkyl substituted with one, two or three halo atoms;

$R^{10}$ represents —(C=O)—$C_{1-4}$alkyl; $C_{3-6}$cycloalkyl; $R^{14}$; $C_{3-6}$cycloalkyl substituted with one, two or three substituents each independently selected from the group consisting of halo, —OH and —O—$C_{1-4}$alkyl; $C_{1-4}$alkyl substituted with one, two or three substituents each independently selected from the group consisting of halo, —OH and —O—$C_{1-4}$alkyl; or $C_{1-4}$alkyl substituted with one substituent selected from the group consisting of $C_{3-6}$cycloalkyl, and $R^{14}$;

$R^{14}$ represents phenyl optionally substituted with one, two or three substituents each independently selected from the group consisting of halo;

Het represents a bicyclic aromatic heterocyclic ring system selected from the group consisting of (a-1), (a-2) and (a-3);

$R^{3a}$, $R^{3d}$ and $R^{3e}$ each independently represent hydrogen, halo, —$NR^{7a}R^{7b}$, $C_{1-4}$alkyl, $C_{2-4}$alkenyl, $C_{3-6}$cycloalkyl, —OH, or —O—$C_{1-4}$alkyl;

$R^{7a}$ represents hydrogen;

$R^{7b}$ represents hydrogen, $C_{3-6}$cycloalkyl, or $C_{1-4}$alkyl;

$R^{4a}$, $R^{4d}$, $R^{4e}$, $R^{4f}$ and $R^{4g}$ each independently represent hydrogen, halo, —$NR^{8a}R^{8b}$, or $C_{1-4}$alkyl;

$R^{8a}$ and $R^{8b}$ each independently represent hydrogen or $C_{1-4}$alkyl;

$Q^1$ represents N or $CR^{6a}$;
$Q^2$ represents N or $CR^{6b}$;
$Q^8$ represents N or $CR^{6g}$;
$Q^9$ represents N or $CR^{6h}$;
$Q^{10}$ represents N or $CR^{6i}$;
$Q^{11}$ represents N or $CR^{6j}$;

$Q^5$ represents $CR^{3d}$; $Q^6$ represents N; and $Q^7$ represents $CR^{4f}$; or $Q^5$ represents $CR^{3d}$; $Q^6$ represents $CR^{4e}$; and $Q^7$ represents N; or $Q^5$ represents N; $Q^6$ represents $CR^{4e}$; and $Q^7$ represents $CR^{4f}$; or $Q^5$ represents N; $Q^6$ represents $CR^{4e}$; and $Q^7$ represents N; or $Q^5$ represents N; $Q^6$ represents N; and $Q^7$ represents $CR^{4f}$; or $Q^5$ represents N; $Q^6$ represents N; and $Q^7$ represents N;

$R^{6a}$, $R^{6b}$, $R^{6g}$, $R^{6h}$, $R^{6i}$ and $R^{6j}$ each independently represent hydrogen, halogen, $C_{1-4}$alkyl, —$NR^{9a}R^{9b}$, or $C_{1-4}$alkyl substituted with one, two or three halo atoms;

$R^{9a}$ and $R^{9b}$ each independently represent hydrogen or $C_{1-4}$alkyl;

and pharmaceutically acceptable addition salts, and solvates thereof.

In an embodiment, the present invention concerns novel compounds of Formula (I), wherein $R^1$ represents hydrogen;
$R^2$ represents hydrogen;
Y represents —$CH_2$—;
Z represents —$CH_2$—, —$CHR^{5i}$—, —X—$CR^{5a}R^{5b}$—, —$CR^{5c}$=$CR^{5d}$—, —$CR^{5e}R^{5g}$—$CR^{5f}R^{5h}$—, —$CR^{5a}R^{5b}$—X—, —C≡C—, —$CR^{5c}R^{5d}$—$CR^{5e}R^{5g}$—$CR^{5f}R^{5h}$—, or —$CR^{5a}R^{5b}$—$CR^{5c}R^{5d}$—$CR^{5e}R^{5g}$—$CR^{5f}R^{5h}$—.

$R^{5a}$, $R^{5b}$, $R^{5c}$, $R^{5d}$, $R^{5e}$, $R^{5f}$, $R^{5g}$, $R^{5h}$, and $R^{5i}$ each independently represent hydrogen or $C_{1-4}$alkyl;

X represents —O—, —S—, or —NR$^1$—;

$R^{11}$ represents hydrogen, $C_{1-4}$alkyl, or $C_{1-4}$alkyl substituted with one substituent selected from the group consisting of —OH, —O—$C_{1-4}$alkyl, —NH$_2$, —NH—$C_{1-4}$alkyl, and —N($C_{1-4}$alkyl)$_2$;

Ar represents a monocyclic aromatic ring or a bicyclic ring system;

wherein the monocyclic aromatic ring is selected from the group consisting of pyridinyl, pyrimidinyl, pyrazolyl, and imidazolyl;

wherein the bicyclic ring system is
(i) a 9-membered bicyclic aromatic ring system consisting of a 6-membered ring fused with a 5-membered ring, containing one, two or three heteroatoms each independently selected from O, S, and N,
said 9-membered bicyclic aromatic ring being attached to the remainder of the molecule via a ring carbon atom of the 5- or 6-membered ring, or a ring nitrogen atom of the 5-membered ring; or
(ii) a 10-membered bicyclic aromatic ring system consisting of two fused 6-membered rings, wherein optionally 1 or 2 ring carbon atoms are replaced by a nitrogen atom; provided that when the nitrogen atom replaces one of the two fused carbon atoms, a carbonyl group is present in said bicyclic aromatic ring system;
provided that in case Ar represents a 10-membered bicyclic aromatic ring system, Z can only represent —CR$^{5c}$R$^{5d}$—CR$^{5e}$R$^{5g}$—CR$^{5f}$R$^{5h}$— or —CR$^{5a}$R$^{5b}$—CR$^{5c}$R$^{5d}$—CR$^{5e}$R$^{5g}$—CR$^{5f}$R$^{5h}$—; or
(iii) a fused bicyclic partially aromatic ring system which is attached with the aromatic ring to linker Z, wherein the fused bicyclic partially aromatic ring system is selected from (b-1), (b-2) and (b-3)

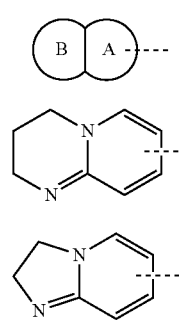

(b-1)

(b-2)

(b-3)

wherein ring A is a monocyclic aromatic ring is selected from the group consisting of pyridinyl, pyrimidinyl, pyrazolyl and imidazolyl;
wherein ring B is a $C_{5-6}$cycloalkyl or a 5- to 6-membered saturated heterocyclyl containing one or two heteroatoms each independently selected from O, S and N;

Ar is optionally substituted on the carbon atoms with in total one, two, three or four substituents each independently selected from the group consisting of halo, oxo, —OH, —NH$_2$, —NH—$C_{1-4}$alkyl, —NHR$^{10}$, cyano, —CF$_3$, $C_{1-4}$alkyloxy, $C_{3-6}$cycloalkyl, —O—$C_{3-6}$cycloalkyl, $C_{2-6}$alkenyl, $C_{1-4}$alkyl, and $C_{1-4}$alkyl substituted with one $C_{1-4}$alkyloxy; and
where possible Ar is optionally substituted on one N-atom with one substituent selected from the group consisting of $C_{1-4}$alkyl; $C_{3-6}$cycloalkyl; $C_{1-4}$alkyl substituted with one, two or three halo atoms; and $C_{3-6}$cycloalkyl substituted with one, two or three halo atoms;

$R^{10}$ represents —(C=O)—$C_{1-4}$alkyl; $C_{3-6}$cycloalkyl; $R^{13}$; $R^{14}$; $C_{3-6}$cycloalkyl substituted with one, two or three substituents each independently selected from the group consisting of halo, —OH and —O—$C_{1-4}$alkyl; $C_{1-4}$alkyl substituted with one, two or three substituents each independently selected from the group consisting of halo, —OH and —O—$C_{1-4}$alkyl; or $C_{1-4}$alkyl substituted with one substituent selected from the group consisting of $C_{3-6}$cycloalkyl, $R^{13}$ and $R^{14}$;

$R^{13}$ represents a 4- to 7-membered monocyclic aromatic ring containing one, two or three heteroatoms each independently selected from O, S, S(=O)$_p$ and N; said 4- to 7-membered monocyclic aromatic ring is optionally substituted with one or two substituents selected from the group consisting of $C_{1-4}$alkyl;

p represents 1 or 2;

$R^{14}$ represents phenyl optionally substituted with one, two or three substituents each independently selected from the group consisting of halo;

Het represents a bicyclic aromatic heterocyclic ring system (a-1);

$R^{3a}$ represents —NR$^{7a}$R$^{7b}$;

$R^{7a}$ represents hydrogen; $R^{7b}$ represents hydrogen;

$R^{4a}$ represents hydrogen;

$Q^1$ represents $CR^{6a}$; $Q^2$ represents $CR^{6b}$;

$R^{6a}$ and $R^{6b}$ represent hydrogen;

and pharmaceutically acceptable addition salts, and solvates thereof.

In an embodiment, the present invention concerns novel compounds of Formula (I), wherein $R^1$ represents hydrogen or —C(=O)—$C_{1-4}$alkyl;
$R^2$ represents hydrogen or —C(=O)—$C_{1-4}$alkyl;
Y represents —CH$_2$— or —CF$_2$—;
Z represents —CH$_2$—, —X—CR$^{5a}$R$^{5b}$—, —CR$^{5c}$=CR$^{5d}$—, —CR$^{5e}$R$^{5g}$—CR$^{5f}$R$^{5h}$—, —CR$^{5a}$R$^{5b}$—X—, or —C≡C—;

$R^{5a}$, $R^{5b}$, $R^{5c}$, $R^{5d}$, $R^{5e}$, $R^{5f}$, $R^{5g}$, and $R^{5h}$ each independently represent hydrogen or $C_{1-4}$alkyl;

X represents —O—, —S—, or —NR$^{11}$—;

$R^{11}$ represents hydrogen, $C_{1-4}$alkyl, or $C_{1-4}$alkyl substituted with one substituent selected from the group consisting of —OH, —O—$C_{1-4}$alkyl, —NH$_2$, —NH—$C_{1-4}$alkyl, and —N($C_{1-4}$alkyl)$_2$;

Ar represents a monocyclic aromatic ring selected from pyridinyl and imidazolyl;

Ar is optionally substituted on the carbon atoms with in total one, two, three or four substituents each independently selected from the group consisting of halo, —OH, —NH$_2$, —NH—$C_{1-4}$alkyl, —NHR$^{10}$, cyano, —CF$_3$, $C_{1-4}$alkyloxy, $C_{3-6}$cycloalkyl, —O—$C_{3-6}$cycloalkyl, $C_{2-6}$alkenyl, $C_{1-4}$alkyl, and $C_{1-4}$alkyl substituted with one $C_{1-4}$alkyloxy;

$R^{10}$ represents —(C=O)—$C_{1-4}$alkyl; $C_{3-6}$cycloalkyl; $R^{13}$; $R^{14}$; $C_{3-6}$cycloalkyl substituted with one, two or three substituents each independently selected from the group consisting of halo, —OH and —O—$C_{1-4}$alkyl; $C_{1-4}$alkyl substituted with one, two or three substituents each independently selected from the group consisting of halo, —OH and —O—$C_{1-4}$alkyl; or $C_{1-4}$alkyl substituted with one substituent selected from the group consisting of $C_{3-6}$cycloalkyl, $R^{13}$ and $R^{14}$;

$R^{13}$ represents a 4- to 7-membered monocyclic aromatic ring containing one, two or three heteroatoms each independently selected from O, S, S(=O)$_p$ and N; said 4- to 7-membered monocyclic aromatic ring is optionally substituted with one or two substituents selected from the group consisting of $C_{1-4}$alkyl;

p represents 1 or 2;

$R^{14}$ represents phenyl optionally substituted with one, two or three substituents each independently selected from the group consisting of halo;

Het represents a bicyclic aromatic heterocyclic ring system selected from the group consisting of (a-1), (a-2) and (a-3);

$R^{3a}$, $R^{3d}$ and $R^{3e}$ each independently represent hydrogen, halo, —$NR^{7a}R^{7b}$, $C_{1-4}$alkyl, $C_{2-4}$alkenyl, $C_{3-6}$cycloalkyl, —OH, or —O—$C_{1-4}$alkyl;

$R^{7a}$ represents hydrogen;

$R^{7b}$ represents hydrogen, $C_{3-6}$cycloalkyl, or $C_{1-4}$alkyl;

$R^{4a}$, $R^{4d}$, $R^{4e}$, $R^{4f}$ and $R^{4g}$ each independently represent hydrogen, halo, —$NR^{8a}R^{8b}$, or $C_{1-4}$alkyl;

$R^{8a}$ and $R^{8b}$ each independently represent hydrogen or $C_{1-4}$alkyl;

$Q^1$ represents N or $CR^{6a}$;
$Q^2$ represents N or $CR^{6b}$;
$Q^8$ represents N or $CR^{6g}$;
$Q^9$ represents N or $CR^{6h}$;
$Q^{10}$ represents N or $CR^{6i}$;
$Q^{11}$ represents N or $CR^{6j}$;

$Q^5$ represents $CR^{3d}$; $Q^6$ represents N; and $Q^7$ represents $CR^{4f}$; or $Q^5$ represents $CR^{3d}$; $Q^6$ represents $CR^{4e}$; and $Q^7$ represents N; or $Q^5$ represents N; $Q^6$ represents $CR^{4e}$; and $Q^7$ represents $CR^{4f}$; or $Q^5$ represents N; $Q^6$ represents $CR^{4e}$; and $Q^7$ represents N; or $Q^5$ represents N; $Q^6$ represents N; and $Q^7$ represents $CR^{4f}$; or $Q^5$ represents N; $Q^6$ represents N; and $Q^7$ represents N;

$R^{6a}$, $R^{6b}$, $R^{6g}$, $R^{6h}$, $R^{6i}$ and $R^{6j}$ each independently represent hydrogen, halogen, $C_{1-4}$alkyl, —$NR^{9a}R^{9b}$, or $C_{1-4}$alkyl substituted with one, two or three halo atoms;

$R^{9a}$ and $R^{9b}$ each independently represent hydrogen or $C_{1-4}$alkyl;

and pharmaceutically acceptable addition salts, and solvates thereof.

In an embodiment, the present invention concerns novel compounds of Formula (I), wherein $R^1$ represents hydrogen or —C(=O)—$C_{1-4}$alkyl;
$R^2$ represents hydrogen or —C(=O)—$C_{1-4}$alkyl;
Y represents —$CH_2$— or —$CF_2$—;
Z represents —$CH_2$—, —X—$CR^{5a}R^{5b}$—, —$CR^{5c}$=$CR^{5d}$—, —$CR^{5e}R^{5g}$—$CR^{5f}R^{5h}$—, —$CR^{5a}R^{5b}$—X—, or —C≡C—;

$R^{5a}$, $R^{5b}$, $R^{5c}$, $R^{5d}$, $R^{5e}$, $R^{5f}$, $R^{5g}$, and $R^{5h}$ each independently represent hydrogen or $C_{1-4}$alkyl;

X represents —O—, —S—, or —$NR^{11}$—;

$R^{11}$ represents hydrogen, $C_{1-4}$alkyl, or $C_{1-4}$alkyl substituted with one substituent selected from the group consisting of —OH, —O—$C_{1-4}$alkyl, —$NH_2$, —NH—$C_{1-4}$alkyl, and —N($C_{1-4}$alkyl)$_2$;

Ar represents a 9-membered bicyclic aromatic ring system consisting of a 6-membered ring fused with a 5-membered ring, containing one, two or three heteroatoms each independently selected from O, S, and N, said 9-membered bicyclic aromatic ring being attached to the remainder of the molecule via a ring carbon atom of the 5- or 6-membered ring, or a ring nitrogen atom of the 5-membered ring;

Ar is optionally substituted on the carbon atoms with in total one, two, three or four substituents each independently selected from the group consisting of halo, —OH, —$NH_2$, —NH—$C_{1-4}$alkyl, —$NHR^{10}$, cyano, —$CF_3$, $C_{1-4}$alkyloxy, $C_{3-6}$cycloalkyl, —O—$C_{3-6}$cycloalkyl, $C_{2-6}$alkenyl, $C_{1-4}$alkyl, and $C_{1-4}$alkyl substituted with one $C_{1-4}$alkyloxy; and where possible Ar is optionally substituted on one N-atom with one substituent selected from the group consisting of $C_{1-4}$alkyl; $C_{3-6}$cycloalkyl; $C_{1-4}$alkyl substituted with one, two or three halo atoms; and $C_{3-6}$cycloalkyl substituted with one, two or three halo atoms;

$R^{10}$ represents —(C=O)—$C_{1-4}$alkyl; $C_{3-6}$cycloalkyl; $R^{13}$; $R^{14}$; $C_{3-6}$cycloalkyl substituted with one, two or three substituents each independently selected from the group consisting of halo, —OH and —O—$C_{1-4}$alkyl; $C_{1-4}$alkyl substituted with one, two or three substituents each independently selected from the group consisting of halo, —OH and —O—$C_{1-4}$alkyl; or $C_{1-4}$alkyl substituted with one substituent selected from the group consisting of $C_{3-6}$cycloalkyl, $R^{13}$ and $R^{14}$;

$R^{13}$ represents a 4- to 7-membered monocyclic aromatic ring containing one, two or three heteroatoms each independently selected from O, S, S(=O)$_p$ and N; said 4- to 7-membered monocyclic aromatic ring is optionally substituted with one or two substituents selected from the group consisting of $C_{1-4}$alkyl;

p represents 1 or 2;

$R^{14}$ represents phenyl optionally substituted with one, two or three substituents each independently selected from the group consisting of halo;

Het represents a bicyclic aromatic heterocyclic ring system selected from the group consisting of (a-1), (a-2) and (a-3);

$R^{3a}$, $R^{3d}$ and $R^{3e}$ each independently represent hydrogen, halo, —$NR^{7a}R^{7b}$, $C_{1-4}$alkyl, $C_{2-4}$alkenyl, $C_{3-6}$cycloalkyl, —OH, or —O—$C_{1-4}$alkyl;

$R^{7a}$ represents hydrogen;

$R^{7b}$ represents hydrogen, $C_{3-6}$cycloalkyl, or $C_{1-4}$alkyl;

$R^{4a}$, $R^{4d}$, $R^{4e}$, $R^{4f}$ and $R^{4g}$ each independently represent hydrogen, halo, —$NR^{8a}R^{8b}$, or $C_{1-4}$alkyl;

$R^{8a}$ and $R^{8b}$ each independently represent hydrogen or $C_{1-4}$alkyl;

$Q^1$ represents N or $CR^{6a}$;
$Q^2$ represents N or $CR^{6b}$;
$Q^8$ represents N or $CR^{6g}$;
$Q^9$ represents N or $CR^{6h}$;
$Q^{10}$ represents N or $CR^{6i}$;
$Q^{11}$ represents N or $CR^{6j}$;

$Q^5$ represents $CR^{3d}$; $Q^6$ represents N; and $Q^7$ represents $CR^{4f}$; or $Q^5$ represents $CR^{3d}$; $Q^6$ represents $CR^{4e}$; and $Q^7$ represents N; or $Q^5$ represents N; $Q^6$ represents $CR^{4e}$; and $Q^7$ represents $CR^{4f}$; or $Q^5$ represents N; $Q^6$ represents $CR^{4e}$; and $Q^7$ represents N; or $Q^5$ represents N; $Q^6$ represents N; and $Q^7$ represents $CR^{4f}$; or $Q^5$ represents N; $Q^6$ represents N; and $Q^7$ represents N;

$R^{6a}$, $R^{6b}$, $R^{6g}$, $R^{6h}$, $R^{6i}$ and $R^{6j}$ each independently represent hydrogen, halogen, $C_{1-4}$alkyl, —$NR^{9a}R^{9b}$, or $C_{1-4}$alkyl substituted with one, two or three halo atoms;

$R^{9a}$ and $R^{9b}$ each independently represent hydrogen or $C_{1-4}$alkyl;

and pharmaceutically acceptable addition salts, and solvates thereof.

In an embodiment, the present invention concerns novel compounds of Formula (I), wherein
$R^1$ represents hydrogen or —C(=O)—$C_{1-4}$alkyl;
$R^2$ represents hydrogen or —C(=O)—$C_{1-4}$alkyl;
Y represents —$CH_2$— or —$CF_2$—;
Z represents —$CH_2$—, —X—$CR^{5a}R^{5b}$—, —$CR^{5c}$=$CR^{5d}$—, —$CR^{5e}R^{5g}$—$CR^{5f}R^{5h}$—, —$CR^{5a}R^{5b}$—X—, or —C≡C—;
$R^{5a}$, $R^{5b}$, $R^{5c}$, $R^{5d}$, $R^{5e}$, $R^{5f}$, $R^{5g}$, and $R^{5h}$ each independently represent hydrogen or $C_{1-4}$alkyl;
X represents —O—, —S—, or —$NR^{11}$—;
$R^{11}$ represents hydrogen, $C_{1-4}$alkyl, or $C_{1-4}$alkyl substituted with one substituent selected from the group consisting of —OH, —O—$C_{1-4}$alkyl, —$NH_2$, —NH—$C_{1-4}$alkyl, and —N($C_{1-4}$alkyl)$_2$;
Ar represents a monocyclic aromatic ring selected from pyridinyl and imidazolyl; or a 9-membered bicyclic aromatic ring system consisting of a 6-membered ring fused with a 5-membered ring, containing one, two or three heteroatoms each independently selected from O, S, and N,
said 9-membered bicyclic aromatic ring being attached to the remainder of the molecule via a ring carbon atom of the 5- or 6-membered ring, or a ring nitrogen atom of the 5-membered ring;
Ar is optionally substituted on the carbon atoms with in total one, two, three or four substituents each independently selected from the group consisting of halo, —OH, —$NH_2$, —NH—$C_{1-4}$alkyl,
—$NHR^{10}$, cyano, —$CF_3$, $C_{1-4}$alkyloxy, $C_{3-6}$cycloalkyl, —O—$C_{3-6}$cycloalkyl, $C_{2-6}$alkenyl, $C_{1-4}$alkyl, and $C_{1-4}$alkyl substituted with one $C_{1-4}$alkyloxy; and
where possible Ar is optionally substituted on one N-atom with one substituent selected from the group consisting of $C_{1-4}$alkyl; $C_{3-6}$cycloalkyl; $C_{1-4}$alkyl substituted with one, two or three halo atoms; and $C_{3-6}$cycloalkyl substituted with one, two or three halo atoms;
$R^{10}$ represents —(C=O)—$C_{1-4}$alkyl; $C_{3-6}$cycloalkyl; $C_{3-6}$cycloalkyl substituted with one, two or three substituents each independently selected from the group consisting of halo, —OH and —O—$C_{1-4}$alkyl; $C_{1-4}$alkyl substituted with one, two or three substituents each independently selected from the group consisting of halo, —OH and —O—$C_{1-4}$alkyl; or $C_{1-4}$alkyl substituted with one $C_{3-6}$cycloalkyl;
Het represents a bicyclic aromatic heterocyclic ring system selected from the group consisting of (a-1), (a-2) and (a-3):

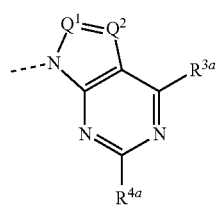
(a-1)

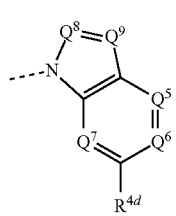
(a-2)

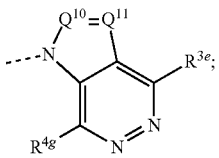
(a-3)

$R^{3a}$, $R^{3d}$ and $R^{3e}$ each independently represent hydrogen, halo, —$NR^{7a}R^{7b}$, $C_{1-4}$alkyl, $C_{2-4}$alkenyl, $C_{3-6}$cycloalkyl, —OH, or —O—$C_{1-4}$alkyl;
$R^{7a}$ represents hydrogen;
$R^{7b}$ represents hydrogen, $C_{3-6}$cycloalkyl, or $C_{1-4}$alkyl;
$R^{4a}$, $R^{4d}$, $R^{4e}$, $R^{4f}$ and $R^{4g}$ each independently represent hydrogen, halo, —$NR^{8a}R^{8b}$, or $C_{1-4}$alkyl;
$R^{8a}$ and $R^{8b}$ each independently represent hydrogen or $C_{1-4}$alkyl;
$Q^1$ represents $CR^{6a}$;
$Q^2$ represents $CR^{6b}$;
$Q^8$ represents $CR^{6g}$;
$Q^9$ represents $CR^{6h}$;
$Q^{10}$ represents $CR^{6i}$;
$Q^{11}$ represents $CR^{6j}$;
$Q^5$ represents $CR^{3d}$; $Q^6$ represents N; and $Q^7$ represents $CR^{4f}$; or
$Q^5$ represents $CR^{3d}$; $Q^6$ represents $CR^{4e}$; and $Q^7$ represents N; or
$Q^5$ represents N; $Q^6$ represents $CR^{4e}$; and $Q^7$ represents $CR^{4f}$; or
$Q^5$ represents N; $Q^6$ represents $CR^{4e}$; and $Q^7$ represents N; or
$Q^5$ represents N; $Q^6$ represents N; and $Q^7$ represents $CR^{4f}$; or
$Q^5$ represents N; $Q^6$ represents N; and $Q^7$ represents N;
$R^{6a}$, $R^{6b}$, $R^{6g}$, $R^{6h}$, $R^{6i}$ and $R^{6j}$ each independently represent hydrogen, halogen, $C_{1-4}$alkyl, —$NR^{9a}R^{9b}$, or $C_{1-4}$alkyl substituted with one, two or three halo atoms;
$R^{9a}$ and $R^{9b}$ each independently represent hydrogen or $C_{1-4}$alkyl;
and pharmaceutically acceptable addition salts, and solvates thereof.
In an embodiment, the present invention concerns novel compounds of Formula (I), wherein
$R^1$ represents hydrogen;
$R^2$ represents hydrogen;
Y represents —$CH_2$—;
Z represents —X—$CR^{5a}R^{5b}$—, —$CR^{5c}$=$CR^{5d}$—, or —$CR^{5e}R^{5g}$—$CR^{5f}R^{5h}$—;
$R^{5a}$, $R^{5b}$, $R^{5c}$, $R^{5d}$, $R^{5e}$, $R^{5f}$, $R^{5g}$, and $R^{5h}$ represent hydrogen;
X represents —O—;
Ar represents a monocyclic aromatic ring selected from pyridinyl and imidazolyl; or
a 9-membered bicyclic aromatic ring system consisting of a 6-membered ring fused with a 5-membered ring, containing one, two or three heteroatoms each independently selected from O, S, and N,
said 9-membered bicyclic aromatic ring being attached to the remainder of the molecule via a ring carbon atom of the 5- or 6-membered ring;
Ar is optionally substituted on the carbon atoms with in total one, two, three or four substituents each independently selected from the group consisting of halo, —$NH_2$, —NH—$C_{1-4}$alkyl, —$CF_3$, $C_{3-6}$cycloalkyl, and $C_{1-4}$alkyl; and where possible Ar is optionally substituted on one N-atom with one substituent selected from the group consisting of $C_{1-4}$alkyl;

Het represents (a-1);
R$^{3a}$ represents halo, —NR$^{7a}$R$^{7b}$, or —O—C$_{1-4}$alkyl;
R$^{7a}$ represents hydrogen;
R$^{7b}$ represents hydrogen, or C$_{1-4}$alkyl;
R$^{4a}$ represents hydrogen;
Q$^1$ represents CR$^{6a}$;
Q$^2$ represents CR$^{6b}$;
R$^{6a}$ and R$^{6b}$ represent hydrogen, or halogen;
and pharmaceutically acceptable addition salts, and solvates thereof.

In an embodiment, the present invention concerns novel compounds of Formula (I). wherein
R$^1$ represents hydrogen;
R$^2$ represents hydrogen;
Y represents —CH$_2$—;
Z represents —X—CR$^{5a}$R$^{5b}$—, —CR$^{5c}$=CR$^{5d}$—, or —CR$^{5e}$R$^{5g}$—CR$^{5f}$R$^{5h}$—;
R$^{5a}$, R$^{5b}$, R$^{5c}$, R$^{5d}$, R$^{5e}$, R$^{5f}$, R$^{5g}$, and R$^{5h}$ represent hydrogen;
X represents —O—;
Ar represents a monocyclic aromatic ring selected from pyridinyl and imidazolyl; or a 9-membered bicyclic aromatic ring system selected from the group consisting of

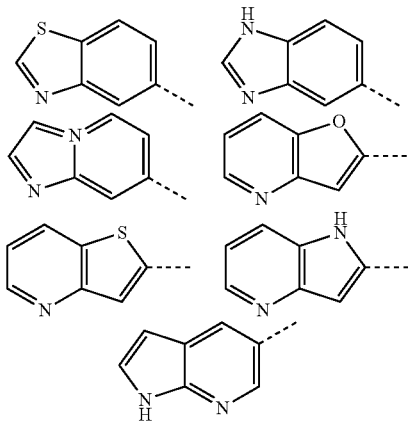

Ar is optionally substituted on the carbon atoms with in total one, two, three or four substituents each independently selected from the group consisting of halo, —NH$_2$, —NH—C$_{1-4}$alkyl, —CF$_3$, C$_{3-6}$cycloalkyl, and C$_{1-4}$alkyl; and
where possible Ar is optionally substituted on one N-atom with one substituent selected from the group consisting of C$_{1-4}$alkyl;
Het represents (a-1);
R$^{3a}$ represents halo, —NR$^{7a}$R$^{7b}$, or —O—C$_{1-4}$alkyl;
R$^{7a}$ represents hydrogen;
R$^{7b}$ represents hydrogen, or C$_{1-4}$alkyl;
R$^{4a}$ represents hydrogen;
Q$^1$ represents CR$^{6a}$;
Q$^2$ represents CR$^{6b}$;
R$^{6a}$ and R$^{6b}$ represent hydrogen, or halogen;
and pharmaceutically acceptable addition salts, and solvates thereof.

In an embodiment, the present invention concerns novel compounds of Formula (I), wherein
R$^1$ represents hydrogen;
R$^2$ represents hydrogen;
Y represents —CH$_2$—;
Z represents —CR$^{5e}$R$^{5g}$—CR$^{5f}$R$^{5h}$—;
R$^{5e}$, R$^{5f}$, R$^{5g}$, and R$^{5h}$ represent hydrogen;

Ar represents

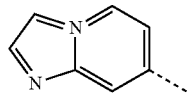

Ar is optionally substituted on the carbon atoms with in total one, two, three or four substituents each independently selected from the group consisting of halo, —NH$_2$, —NH—C$_{1-4}$alkyl, —CF$_3$, C$_{3-6}$cycloalkyl, and C$_{1-4}$alkyl;
Het represents (a-1);
R$^{3a}$ represents —NR$^{7a}$R$^{7b}$;
R$^{7a}$ represents hydrogen;
R$^{7b}$ represents hydrogen;
R$^{4a}$ represents hydrogen;
Q$^1$ represents CR$^{6a}$;
Q$^2$ represents CR$^{6b}$;
R$^{6a}$ and R$^{6b}$ represent hydrogen;
and pharmaceutically acceptable addition salts, and solvates thereof.

In an embodiment, the present invention concerns novel compounds of Formula (I), wherein
R$^1$ represents hydrogen;
R$^2$ represents hydrogen;
Y represents —CH$_2$—;
Z represents —CR$^{5e}$R$^{5g}$—CR$^{5f}$R$^{5h}$—;
R$^{5e}$, R$^{5f}$, R$^{5g}$, and R$^{5h}$ represent hydrogen;
Ar represents

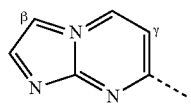

wherein Ar is substituted in the position indicated by β with C$_{1-4}$alkyl;
wherein Ar is optionally substituted in the position indicated by γ with halo;
Het represents (a-1);
R$^{3a}$ represents —NR$^{7a}$R$^{7b}$;
R$^{7a}$ represents hydrogen;
R$^{7b}$ represents hydrogen;
R$^{4a}$ represents hydrogen;
Q$^1$ represents CR$^{6a}$;
Q$^2$ represents CR$^{6b}$;
R$^{6a}$ and R$^{6b}$ represent hydrogen;
and pharmaceutically acceptable addition salts, and solvates thereof.

In an embodiment, the present invention concerns novel compounds of Formula (I), wherein
R$^1$ represents hydrogen; R$^2$ represents hydrogen;
Y represents —CH$_2$— or —CF$_2$—;
Z represents-CH$_2$—, —X—CR$^{5a}$R$^{5b}$—, —CR$^{5c}$=CR$^{5d}$—, —CR$^{5e}$R$^{5g}$—CR$^{5f}$R$^{5h}$—, —CR$^{5a}$R$^{5b}$—X—, or —C≡C—;
R$^{5a}$, R$^{5b}$, R$^{5c}$, R$^{5d}$, R$^{5e}$, R$^{5f}$, R$^{5g}$, and R$^{5h}$ each independently represent hydrogen or C$_{1-4}$alkyl;
X represents —O—, —S—, or —NR$^{11}$—;
R$^{11}$ represents hydrogen, C$_{1-4}$alkyl, or C$_{1-4}$alkyl substituted with one substituent selected from the group consisting of —OH, —O—C$_{1-4}$alkyl, —NH$_2$, —NH—C$_{1-4}$alkyl, and —N(C$_{1-4}$alkyl)$_2$;

Ar represents a monocyclic aromatic ring selected from pyridinyl and imidazolyl; or
a 9-membered bicyclic aromatic ring system consisting of a 6-membered ring fused with a 5-membered ring, containing one, two or three heteroatoms each independently selected from O, S, and N,
said 9-membered bicyclic aromatic ring being attached to the remainder of the molecule via a ring carbon atom of the 5- or 6-membered ring, or a ring nitrogen atom of the 5-membered ring;
Ar is optionally substituted on the carbon atoms with in total one, two, three or four substituents each independently selected from the group consisting of halo, —OH, —NH$_2$, —NH—C$_{1-4}$alkyl,
—NHR$^{10}$, cyano, —CF$_3$, C$_{1-4}$alkyloxy, C$_{3-6}$cycloalkyl, —O—C$_{3-6}$cycloalkyl, C$_{2-6}$alkenyl, C$_{1-4}$alkyl, and C$_{1-4}$alkyl substituted with one C$_{1-4}$alkyloxy; and
where possible Ar is optionally substituted on one N-atom with one substituent selected from the group consisting of C$_{1-4}$alkyl; C$_{3-6}$cycloalkyl; C$_{1-4}$alkyl substituted with one, two or three halo atoms; and C$_{3-6}$cycloalkyl substituted with one, two or three halo atoms;
R$^{10}$ represents —(C=O)—C$_{1-4}$alkyl; C$_{3-6}$cycloalkyl; R$^{13}$; R$^{14}$; C$_{3-6}$cycloalkyl substituted with one, two or three substituents each independently selected from the group consisting of halo, —OH and —O—C$_{1-4}$alkyl; C$_{1-4}$alkyl substituted with one, two or three substituents each independently selected from the group consisting of halo, —OH and —O—C$_{1-4}$alkyl; or C$_{1-4}$alkyl substituted with one substituent selected from the group consisting of C$_{3-6}$cycloalkyl, R$^{13}$ and R$^{14}$;
R$^{13}$ represents a 4- to 7-membered monocyclic aromatic ring containing one, two or three heteroatoms each independently selected from O, S, S(=O)$_p$ and N; said 4- to 7-membered monocyclic aromatic ring is optionally substituted with one or two substituents selected from the group consisting of C$_{1-4}$alkyl;
p represents 1 or 2;
R$^{14}$ represents phenyl optionally substituted with one, two or three substituents each independently selected from the group consisting of halo;
Het represents a bicyclic aromatic heterocyclic ring system selected from the group consisting of (a-1), (a-2) and (a-3);
R$^{3a}$, R$^{3d}$ and R$^{3e}$ each independently represent hydrogen, halo, —NR$^{7a}$R$^{7b}$, C$_{1-4}$alkyl, C$_{2-4}$alkenyl, C$_{3-6}$cycloalkyl, —OH, or —O—C$_{1-4}$alkyl;
R$^{7a}$ represents hydrogen;
R$^{7b}$ represents hydrogen, C$_{3-6}$cycloalkyl, or C$_{1-4}$alkyl;
R$^{4a}$, R$^{4d}$, R$^{4e}$, R$^{4f}$ and R$^{4g}$ each independently represent hydrogen, halo, —NR$^{8a}$R$^{8b}$, or C$_{1-4}$alkyl;
R$^{8a}$ and R$^{8b}$ each independently represent hydrogen or C$_{1-4}$alkyl;
Q$^1$ represents N or CR$^{6a}$;
Q$^2$ represents N or CR$^{6b}$;
Q$^8$ represents N or CR$^{6g}$;
Q$^9$ represents N or CR$^{6h}$;
Q$^{10}$ represents N or CR$^{6i}$;
Q$^{11}$ represents N or CR$^{6j}$;
Q$^5$ represents CR$^{3d}$; Q$^6$ represents N; and Q$^7$ represents CR$^{4f}$; or
Q$^5$ represents CR$^{3d}$; Q$^6$ represents CR$^{4e}$; and Q$^7$ represents N; or
Q$^5$ represents N; Q$^6$ represents CR$^{4e}$; and Q$^7$ represents CR$^{4f}$; or
Q$^5$ represents N; Q$^6$ represents CR$^{4e}$; and Q$^7$ represents N; or
Q$^5$ represents N; Q$^6$ represents N; and Q$^7$ represents CR$^{4f}$; or
Q$^5$ represents N; Q$^6$ represents N; and Q$^7$ represents N;
R$^{6a}$, R$^{6b}$, R$^{6g}$, R$^{6h}$, R$^{6i}$ and R$^{6j}$ each independently represent hydrogen, halogen, C$_{1-4}$alkyl, —NR$^{9a}$R$^{9b}$, or C$_{1-4}$alkyl substituted with one, two or three halo atoms;
R$^{9a}$ and R$^{9b}$ each independently represent hydrogen or C$_{1-4}$alkyl;
and pharmaceutically acceptable addition salts, and solvates thereof.

In an embodiment, the present invention concerns novel compounds of Formula (I), wherein
R$^1$ represents hydrogen or —C(=O)—C$_{1-4}$alkyl;
R$^2$ represents hydrogen or —C(=O)—C$_{1-4}$alkyl;
Y represents —CH$_2$— or —CF$_2$—;
Z represents —CH$_2$—, —X—CR$^{5a}$R$^{5b}$—, —CR$^{5c}$=CR$^{5d}$—, —CR$^{5e}$R$^{5g}$—CR$^{5f}$R$^{5h}$—, —CR$^{5a}$R$^{5b}$—X—, or —C≡C—;
R$^{5a}$, R$^{5b}$, R$^{5c}$, R$^{5d}$, R$^{5e}$, R$^{5f}$, R$^{5g}$, and R$^{5h}$ each independently represent hydrogen or C$_{1-4}$alkyl;
X represents —O—, —S—, or —NR$^{11}$—;
R$^{11}$ represents hydrogen, C$_{1-4}$alkyl, or C$_{1-4}$alkyl substituted with one substituent selected from the group consisting of —OH, —O—C$_{1-4}$alkyl, —NH$_2$, —NH—C$_{1-4}$alkyl, and —N(C$_{1-4}$alkyl)$_2$;
Ar represents a monocyclic aromatic ring selected from pyridinyl and imidazolyl; or a 9-membered bicyclic aromatic ring system consisting of a 6-membered ring fused with a 5-membered ring, containing one, two or three heteroatoms each independently selected from O, S, and N,
said 9-membered bicyclic aromatic ring being attached to the remainder of the molecule via a ring carbon atom of the 5- or 6-membered ring, or a ring nitrogen atom of the 5-membered ring;
Ar is optionally substituted on the carbon atoms with in total one, two, three or four substituents each independently selected from the group consisting of halo, —OH, —NH$_2$, —NH—C$_{1-4}$alkyl,
—NHR$^{10}$, cyano, —CF$_3$, C$_{1-4}$alkyloxy, C$_{3-6}$cycloalkyl, —O—C$_{3-6}$cycloalkyl, C$_{2-6}$alkenyl, C$_{1-4}$alkyl, and C$_{1-4}$alkyl substituted with one C$_{1-4}$alkyloxy; and
where possible Ar is optionally substituted on one N-atom with one substituent selected from the group consisting of C$_{1-4}$alkyl; C$_{3-6}$cycloalkyl; C$_{1-4}$alkyl substituted with one, two or three halo atoms; and C$_{3-6}$cycloalkyl substituted with one, two or three halo atoms;
R$^{10}$ represents —(C=O)—C$_{1-4}$alkyl; C$_{3-6}$cycloalkyl; R$^{13}$; R$^{14}$; C$_{3-6}$cycloalkyl substituted with one, two or three substituents each independently selected from the group consisting of halo, —OH and —O—C$_{1-4}$alkyl; C$_{1-4}$alkyl substituted with one, two or three substituents each independently selected from the group consisting of halo, —OH and —O—C$_{1-4}$alkyl; or C$_{1-4}$alkyl substituted with one substituent selected from the group consisting of C$_{3-6}$cycloalkyl, R$^{13}$ and R$^{14}$;
R$^{13}$ represents a 4- to 7-membered monocyclic aromatic ring containing one, two or three heteroatoms each independently selected from O, S, S(=O)$_p$ and N; said 4- to 7-membered monocyclic aromatic ring is optionally substituted with one or two substituents selected from the group consisting of C$_{1-4}$alkyl;
p represents 1 or 2;
R$^{14}$ represents phenyl optionally substituted with one, two or three substituents each independently selected from the group consisting of halo;
Het represents (a-1);

$R^{3a}$ represents hydrogen, halo, —$NR^{7a}R^{7b}$, $C_{1-4}$alkyl, $C_{2-4}$alkenyl, $C_{3-6}$cycloalkyl, —OH, or —O—$C_{1-4}$alkyl;

$R^{7a}$ represents hydrogen;

$R^{7b}$ represents hydrogen, $C_{3-6}$cycloalkyl, or $C_{1-4}$alkyl;

$R^{4a}$ represents hydrogen, halo, —$NR^{8a}R^{8b}$, or $C_{1-4}$alkyl;

$R^{8a}$ and $R^{8b}$ each independently represent hydrogen or $C_{1-4}$alkyl;

$Q^1$ represents N or $CR^{6a}$;

$Q^2$ represents N or $CR^{6b}$;

$R^{6a}$ and $R^{6b}$ each independently represent hydrogen, halogen, $C_{1-4}$alkyl, —$NR^{9a}R^{9b}$, or $C_{1-4}$alkyl substituted with one, two or three halo atoms;

$R^{9a}$ and $R^{9b}$ each independently represent hydrogen or $C_{1-4}$alkyl;

and pharmaceutically acceptable addition salts, and solvates thereof.

Another embodiment of the present invention relates to those compounds of Formula (I), and pharmaceutically acceptable addition salts, and solvates thereof, or any subgroup thereof as mentioned in any of the other embodiments, wherein one or more of the following restrictions apply:

(i) $R^1$ and $R^2$ represent hydrogen;

(ii) Y represents —$CH_2$—;

(iii) Z represents —X—$CR^{5a}R^{5b}$—, —$CR^{5c}$=$CR^{5d}$—, or —$CR^{5e}R^{5g}$—$CR^{5f}R^{5h}$—;

(iv) $R^{5a}$, $R^{5b}$, $R^{5c}$, $R^{5d}$, $R^{5e}$, $R^{5f}$, $R^{5g}$, and $R^{5h}$ represent hydrogen;

(v) X represents —O—;

(vi) Ar represents a monocyclic aromatic ring selected from pyridinyl and imidazolyl; or a 9-membered bicyclic aromatic ring system consisting of a 6-membered ring fused with a 5-membered ring, containing one, two or three heteroatoms each independently selected from O, S, and N, said 9-membered bicyclic aromatic ring being attached to the remainder of the molecule via a ring carbon atom of the 5- or 6-membered ring;

Ar is optionally substituted on the carbon atoms with in total one, two, three or four substituents each independently selected from the group consisting of halo, —$NH_2$, —NH—$C_{1-4}$alkyl, —$CF_3$, $C_{3-6}$cycloalkyl, and $C_{1-4}$alkyl; and where possible Ar is optionally substituted on one N-atom with one substituent selected from the group consisting of $C_{1-4}$alkyl;

(vii) Het represents (a-1);

(viii) $R^{3a}$ represents halo, —$NR^{7a}R^{7b}$, or —O—$C_{1-4}$alkyl;

(ix) $R^{7a}$ represents hydrogen; $R^{7b}$ represents hydrogen, or $C_{1-4}$alkyl;

(x) $R^{4a}$ represents hydrogen;

(xi) $Q^1$ represents $CR^{6a}$; $Q^2$ represents $CR^{6b}$;

(xii) $R^{6a}$ and $R^{6b}$ represent hydrogen, or halogen.

In an embodiment, the present invention relates to those compounds of Formula (I) and pharmaceutically acceptable addition salts, and solvates thereof, or any subgroup thereof as mentioned in any of the other embodiments, wherein $R^1$ and $R^2$ represent hydrogen.

In an embodiment, the present invention relates to those compounds of Formula (I) and pharmaceutically acceptable addition salts, and solvates thereof, or any subgroup thereof as mentioned in any of the other embodiments, wherein $R^1$ represents -C(=O)—$C_{1-4}$alkyl; $R^2$ represents —C(=O)—$C_{1-4}$alkyl.

In an embodiment, the present invention relates to those compounds of Formula (I) and pharmaceutically acceptable addition salts, and solvates thereof, or any subgroup thereof as mentioned in any of the other embodiments, wherein Y represents —$CH_2$—.

In an embodiment, the present invention relates to those compounds of Formula (I) and pharmaceutically acceptable addition salts, and solvates thereof, or any subgroup thereof as mentioned in any of the other embodiments, wherein maximum one of $Q^1$ and $Q^2$ represents N.

In an embodiment, the present invention relates to those compounds of Formula (I) and pharmaceutically acceptable addition salts, and solvates thereof, or any subgroup thereof as mentioned in any of the other embodiments, wherein $Q^1$ represents $CR^{6a}$; and $Q^2$ represents $CR^{6b}$; in particular wherein $Q^1$ represents CH; and $Q^2$ represents CH.

In an embodiment, the present invention relates to those compounds of Formula (I) and pharmaceutically acceptable addition salts, and solvates thereof, or any subgroup thereof as mentioned in any of the other embodiments, wherein Het represents (a-1).

In an embodiment, the present invention relates to those compounds of Formula (I) and pharmaceutically acceptable addition salts, and solvates thereof, or any subgroup thereof as mentioned in any of the other embodiments, wherein Het represents (a-1); $Q^1$ represents $CR^{6a}$; and $Q^2$ represents $CR^{6b}$; in particular wherein $Q^1$ represents CH; and $Q^2$ represents CH.

In an embodiment, the present invention relates to those compounds of Formula (I) and pharmaceutically acceptable addition salts, and solvates thereof, or any subgroup thereof as mentioned in any of the other embodiments, wherein $Q^5$ represents $CR^{3d}$; $Q^6$ represents N; and $Q^7$ represents $CR^1$; or $Q^5$ represents $CR^{3d}$; $Q^6$ represents $CR^{4e}$; and $Q^7$ represents N; or $Q^5$ represents N; $Q^6$ represents $CR^{4e}$; and $Q^7$ represents $CR^{4f}$; or $Q^5$ represents N; $Q^6$ represents $CR^{4e}$; and $Q^7$ represents N.

In an embodiment, the present invention relates to those compounds of Formula (I) and pharmaceutically acceptable addition salts, and solvates thereof, or any subgroup thereof as mentioned in any of the other embodiments, wherein Het represents a bicyclic aromatic heterocyclic ring system selected from the group consisting of (a-1) and (a-2).

In an embodiment, the present invention relates to those compounds of Formula (I) and pharmaceutically acceptable addition salts, and solvates thereof, or any subgroup thereof as mentioned in any of the other embodiments, wherein Het represents a bicyclic aromatic heterocyclic ring system of Formula (a-1).

In an embodiment, the present invention relates to those compounds of Formula (I) and pharmaceutically acceptable addition salts, and solvates thereof, or any subgroup thereof as mentioned in any of the other embodiments, wherein Het represents a bicyclic aromatic heterocyclic ring system of Formula (a-1);

$R^1$ and $R^2$ represent hydrogen; and $R^{10}$ represents —(C=O)—$C_{1-4}$alkyl; $C_{3-6}$cycloalkyl; $C_{3-6}$cycloalkyl substituted with one, two or three substituents each independently selected from the group consisting of halo, —OH and —O—$C_{1-4}$alkyl; $C_{1-4}$alkyl substituted with one, two or three substituents each independently selected from the group consisting of halo, —OH and —O—$C_{1-4}$alkyl; or $C_{1-4}$alkyl substituted with one $C_{3-6}$cycloalkyl.

In an embodiment, the present invention relates to those compounds of Formula (I) and pharmaceutically acceptable addition salts, and solvates thereof, or any subgroup thereof as mentioned in any of the other embodiments, wherein $R^{10}$ represents —(C=O)—$C_{1-4}$alkyl; $C_{3-6}$cycloalkyl; $C_{3-6}$cycloalkyl substituted with one, two or three substituents each independently selected from the group consisting of halo, —OH and —O—C$_{1-4}$alkyl; C$_{1-4}$alkyl substituted with one, two or three substituents each independently selected from the group consisting of halo, —OH and —O—C$_{1-4}$alkyl; or C$_{1-4}$alkyl substituted with one C$_{3-6}$cycloalkyl.

In an embodiment, the present invention relates to those compounds of Formula (I) and pharmaceutically acceptable addition salts, and solvates thereof, or any subgroup thereof as mentioned in any of the other embodiments, wherein R$^{3a}$, R$^{3d}$, R$^{3e}$ represent hydrogen, halo, —NR$^{7a}$R$^{7b}$, or —O—C$_{1-4}$alkyl; in particular R$^{3a}$, R$^{3d}$, R$^{3e}$ represent halo, —NR$^{7a}$R$^{7b}$, or —O—C$_{1-4}$alkyl;

R$^{4a}$, R$^{4d}$, R$^{4e}$, R$^{4f}$ and R$^{4g}$ represent hydrogen.

In an embodiment, the present invention relates to those compounds of Formula (I) and pharmaceutically acceptable addition salts, and solvates thereof, or any subgroup thereof as mentioned in any of the other embodiments, wherein Ar represents a monocyclic aromatic ring as defined in any other embodiments, or Ar represents a bicyclic ring system according to definition (i) or (ii).

In an embodiment, the present invention relates to those compounds of Formula (I) and pharmaceutically acceptable addition salts, and solvates thereof, or any subgroup thereof as mentioned in any of the other embodiments, wherein Ar represents a monocyclic aromatic ring selected from pyridinyl and imidazolyl; or a 9-membered bicyclic aromatic ring system selected from the group consisting of

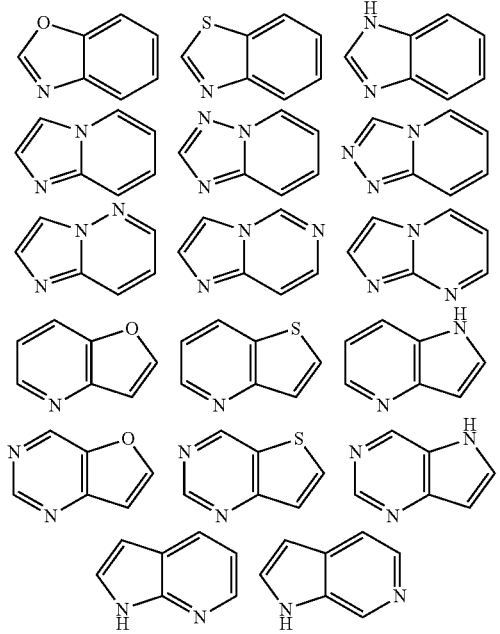

said 9-membered bicyclic aromatic ring being attached to the remainder of the molecule via a ring carbon atom of the 5- or 6-membered ring, or a ring nitrogen atom of the 5-membered ring;

wherein Ar is optionally substituted according to any of the embodiments.

In an embodiment, the present invention relates to those compounds of Formula (I) and pharmaceutically acceptable addition salts, and solvates thereof, or any subgroup thereof as mentioned in any of the other embodiments, wherein Ar represents a monocyclic aromatic ring selected from 2-pyridinyl, 3-pyridinyl, 4-pyridinyl, 1H-imidazol-4-yl and 1H-imidazol-5-yl; or a 9-membered bicyclic aromatic ring system selected from the group consisting of

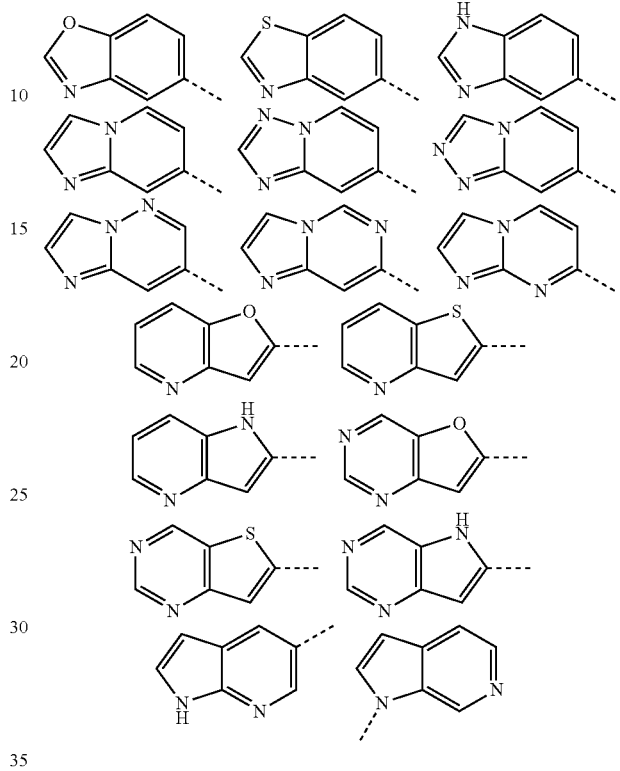

wherein Ar is optionally substituted according to any of the embodiments.

In an embodiment, the present invention relates to those compounds of Formula (I) and pharmaceutically acceptable addition salts, and solvates thereof or any subgroup thereof as mentioned in any of the other embodiments, wherein Ar represents a monocyclic aromatic ring selected from 2-pyridinyl, 3-pyridinyl, 4-pyridinyl, 1H-imidazol-4-yl and 1H-imidazol-5-yl; or a 9-membered bicyclic aromatic ring system selected from the group consisting of

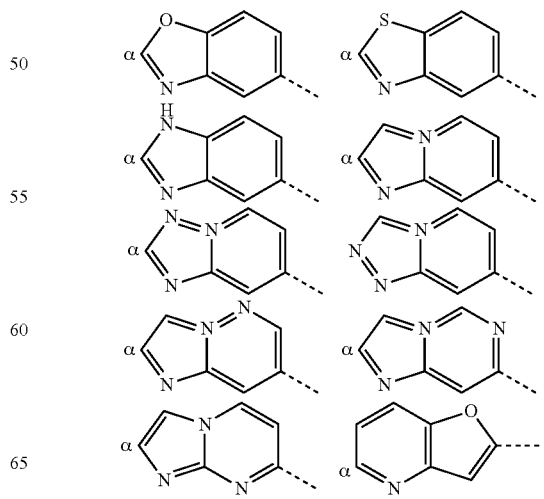

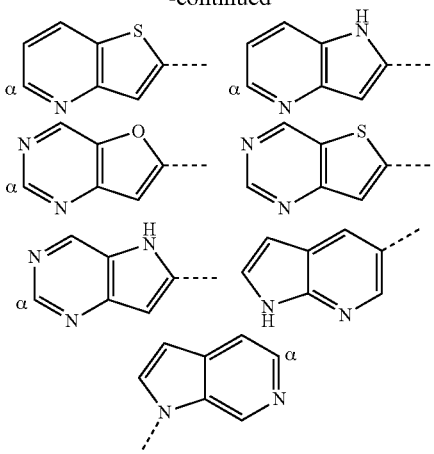

wherein Ar is substituted in the position indicated by α (if any) with —NH$_2$, —NH—C$_{1-4}$alkyl, or —NHR$^{10}$; and wherein Ar is optionally substituted with substituents selected from the list of substituents on Ar in any of the other embodiments.

In an embodiment, the present invention relates to those compounds of Formula (I) and pharmaceutically acceptable addition salts, and solvates thereof or any subgroup thereof as mentioned in any of the other embodiments, wherein Ar represents a monocyclic aromatic ring selected from pyridinyl and imidazolyl; in particular 2-pyridinyl, 3-pyridinyl, 4-pyridinyl, 1H-imidazol-4-yl or 1H-imidazol-5-yl; wherein Ar is optionally substituted according to any of the embodiments.

In an embodiment, the present invention relates to those compounds of Formula (I) and pharmaceutically acceptable addition salts, and solvates thereof, or any subgroup thereof as mentioned in any of the other embodiments, wherein Ar represents a monocyclic aromatic ring selected from the group consisting of pyridinyl, pyrimidinyl, pyrazolyl, and imidazolyl;

wherein Ar is optionally substituted according to any of the embodiments.

In an embodiment, the present invention relates to those compounds of Formula (I) and pharmaceutically acceptable addition salts, and solvates thereof, or any subgroup thereof as mentioned in any of the other embodiments, wherein
Ar represents a bicyclic ring system;
wherein Ar is optionally substituted according to any of the embodiments.

In an embodiment, the present invention relates to those compounds of Formula (I) and pharmaceutically acceptable addition salts, and solvates thereof, or any subgroup thereof as mentioned in any of the other embodiments, wherein Ar represents
a 9-membered bicyclic aromatic ring system consisting of a 6-membered ring fused with a 5-membered ring, containing one, two or three heteroatoms each independently selected from O, S, and N,
said 9-membered bicyclic aromatic ring being attached to the remainder of the molecule via a ring carbon atom of the 5- or 6-membered ring, or a ring nitrogen atom of the 5-membered ring;
wherein Ar is optionally substituted according to any of the embodiments.

In an embodiment, the present invention relates to those compounds of Formula (I) and pharmaceutically acceptable addition salts, and solvates thereof, or any subgroup thereof as mentioned in any of the other embodiments, wherein Ar represents a 10-membered bicyclic aromatic ring system consisting of two fused 6-membered rings, wherein optionally 1 or 2 ring carbon atoms are replaced by a nitrogen atom; provided that when the nitrogen atom replaces one of the two fused carbon atoms, a carbonyl group is present in said bicyclic aromatic ring system; provided that in case Ar represents a 10-membered bicyclic aromatic ring system, Z can only represent —CR$^{5c}$R$^{5d}$—CR$^{5e}$R$^{5g}$—CR$^{5f}$R$^{5h}$— or —CR$^{5a}$R$^{5b}$—CR$^{5c}$R$^{5d}$—CR$^{5e}$R$^{5g}$—CR$^{5f}$R$^{5h}$—;
wherein Ar is optionally substituted according to any of the embodiments.

In an embodiment, the present invention relates to those compounds of Formula (I) and pharmaceutically acceptable addition salts, and solvates thereof, or any subgroup thereof as mentioned in any of the other embodiments, wherein Ar represents a 9-membered bicyclic aromatic ring system consisting of a 6-membered ring fused with a 5-membered ring, containing one, two or three heteroatoms each independently selected from O, S, and N,
said 9-membered bicyclic aromatic ring being attached to the remainder of the molecule via a ring carbon atom of the 5- or 6-membered ring, or a ring nitrogen atom of the 5-membered ring; or
wherein Ar represents a 10-membered bicyclic aromatic ring system consisting of two fused 6-membered rings, wherein optionally 1 or 2 ring carbon atoms are replaced by a nitrogen atom; provided that when the nitrogen atom replaces one of the two fused carbon atoms, a carbonyl group is present in said bicyclic aromatic ring system;
provided that in case Ar represents a 10-membered bicyclic aromatic ring system, Z can only represent —CR$^{5c}$R$^{5d}$—CR$^{5e}$R$^{5g}$—CR$^{5f}$R$^{5h}$— or —CR$^{5a}$R$^{5b}$—CR$^{5c}$R$^{5d}$—CR$^{5e}$R$^{5g}$—CR$^{5f}$R$^{5h}$—;
wherein Ar is optionally substituted according to any of the embodiments.

In an embodiment, the present invention relates to those compounds of Formula (I) and pharmaceutically acceptable addition salts, and solvates thereof, or any subgroup thereof as mentioned in any of the other embodiments, wherein Ar represents a fused bicyclic partially aromatic ring system which is attached with the aromatic ring to linker Z, wherein the fused bicyclic partially aromatic ring system is selected from (b-1), (b-2) and (b-3),
wherein ring A is a monocyclic aromatic ring is selected from the group consisting of pyridinyl, pyrimidinyl, pyrazolyl and imidazolyl;
wherein ring B is a C$_{5-6}$cycloalkyl or a 5- to 6-membered saturated heterocyclyl containing one or two heteroatoms each independently selected from O, S and N;
wherein Ar is optionally substituted according to any of the embodiments.

In an embodiment, the present invention relates to those compounds of Formula (I) and pharmaceutically acceptable addition salts, and solvates thereof, or any subgroup thereof as mentioned in any of the other embodiments, wherein Ar represents a 9-membered bicyclic aromatic ring system selected from

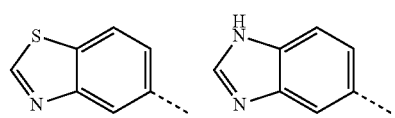

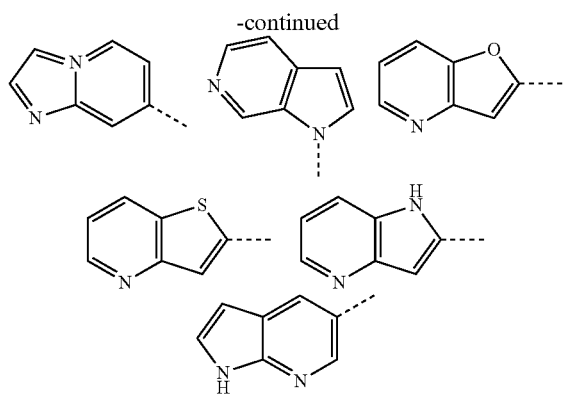

wherein Ar is optionally substituted according to any of the embodiments.

In an embodiment, the present invention relates to those compounds of Formula (I) and pharmaceutically acceptable addition salts, and solvates thereof, or any subgroup thereof as mentioned in any of the other embodiments, wherein Ar represents a 10-membered bicyclic aromatic ring system selected from

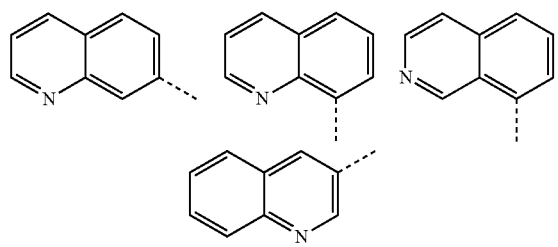

wherein Ar is optionally substituted according to any of the embodiments.

In an embodiment, the present invention relates to those compounds of Formula (I) and pharmaceutically acceptable addition salts, and solvates thereof, or any subgroup thereof as mentioned in any of the other embodiments, wherein Ar represents a fused bicyclic partially aromatic ring system selected from

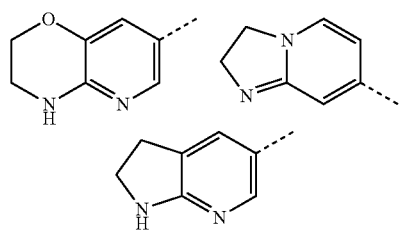

wherein Ar is optionally substituted according to any of the embodiments.

In an embodiment, the present invention relates to those compounds of Formula (I) and pharmaceutically acceptable addition salts, and solvates thereof, or any subgroup thereof as mentioned in any of the other embodiments, wherein Ar represents a monocyclic aromatic ring selected from pyridinyl, pyrimidinyl, pyrazolyl, and imidazolyl; or a bicyclic ring system selected from

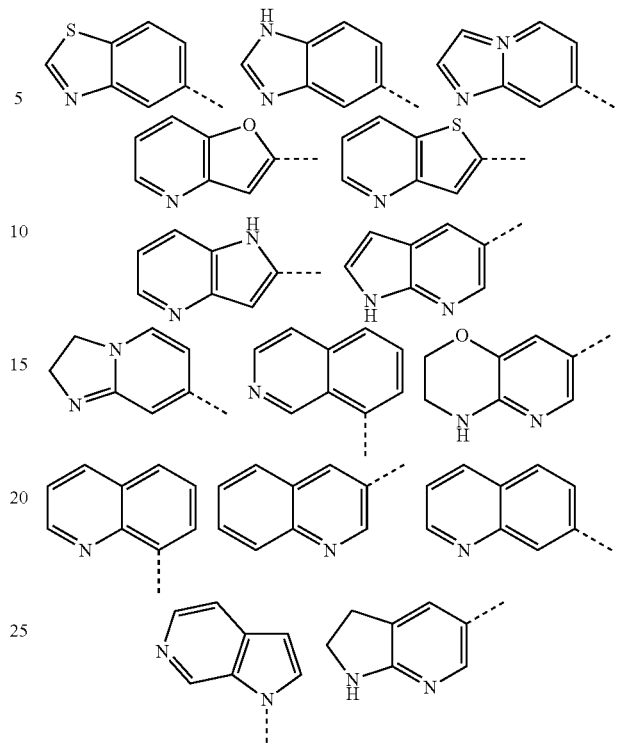

wherein Ar is optionally substituted according to any of the embodiments.

In an embodiment, the present invention relates to those compounds of Formula (I) and pharmaceutically acceptable addition salts, and solvates thereof, or any subgroup thereof as mentioned in any of the other embodiments, wherein Ar represents a 9-membered bicyclic aromatic ring system selected from the group consisting of

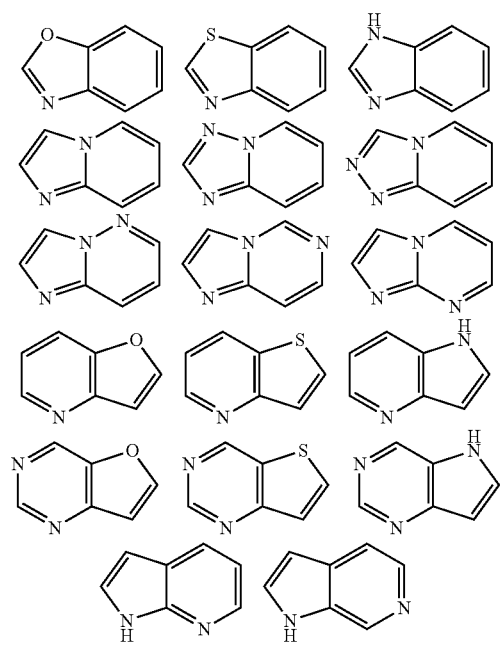

said 9-membered bicyclic aromatic ring being attached to the remainder of the molecule via a ring carbon atom of the 5- or 6-membered ring, or a ring nitrogen atom of the 5-membered ring;

wherein Ar is optionally substituted according to any of the embodiments.

In an embodiment, the present invention relates to those compounds of Formula (I) and pharmaceutically acceptable addition salts, and solvates thereof, or any subgroup thereof as mentioned in any of the other embodiments, wherein Ar represents a 9-membered bicyclic aromatic ring system selected from the group consisting of

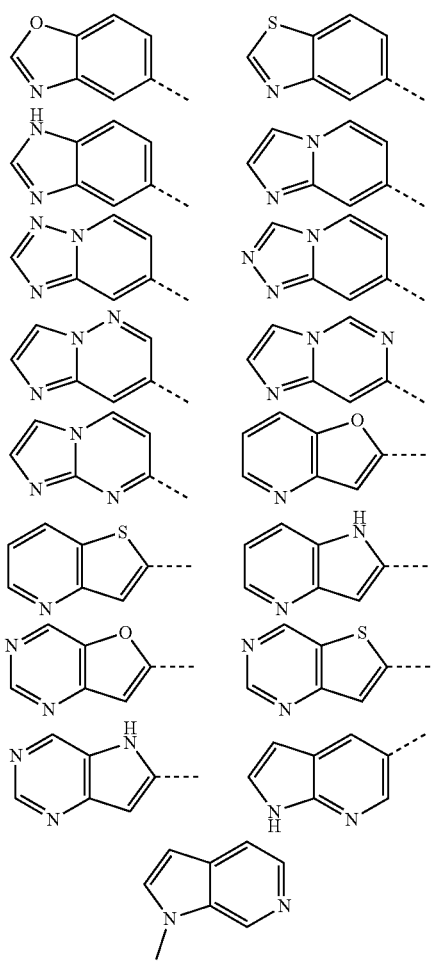

wherein Ar is optionally substituted according to any of the embodiments.

In an embodiment, the present invention relates to those compounds of Formula (I) and pharmaceutically acceptable addition salts, and solvates thereof, or any subgroup thereof as mentioned in any of the other embodiments, wherein Ar represents a 9-membered bicyclic aromatic ring system selected from the group consisting of

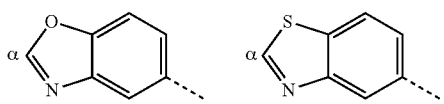

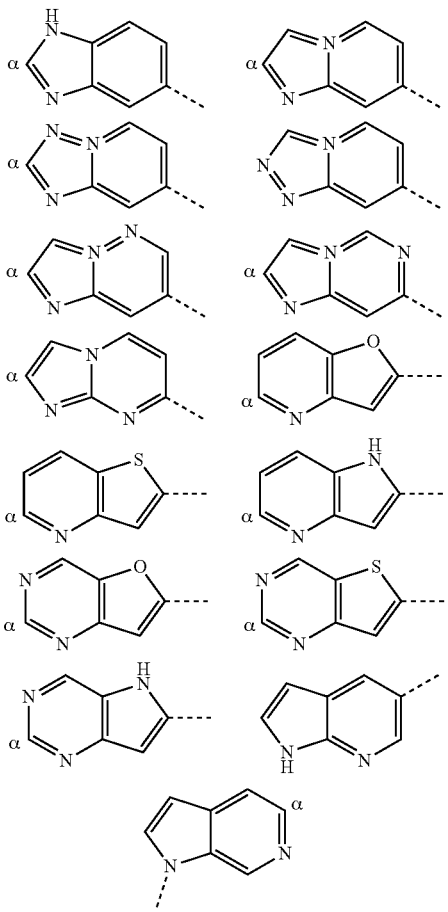

wherein Ar is substituted in the position indicated by α (if any) with —NH$_2$, —NH—C$_{1-4}$alkyl, or —NHR$^{10}$; and wherein Ar is optionally substituted with substituents selected from the list of substituents on Ar in any of the other embodiments.

In an embodiment, the present invention relates to those compounds of Formula (I) and pharmaceutically acceptable addition salts, and solvates thereof, or any subgroup thereof as mentioned in any of the other embodiments, wherein Ar represents a bicyclic ring system selected from the group consisting of

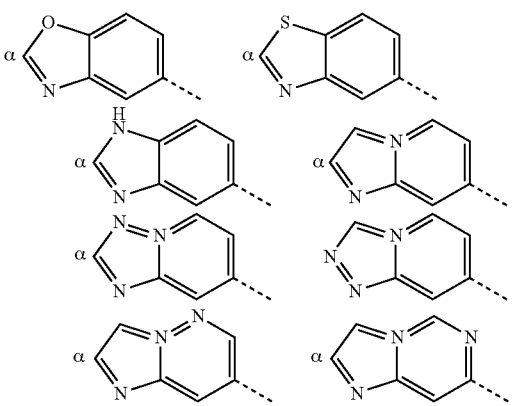

-continued

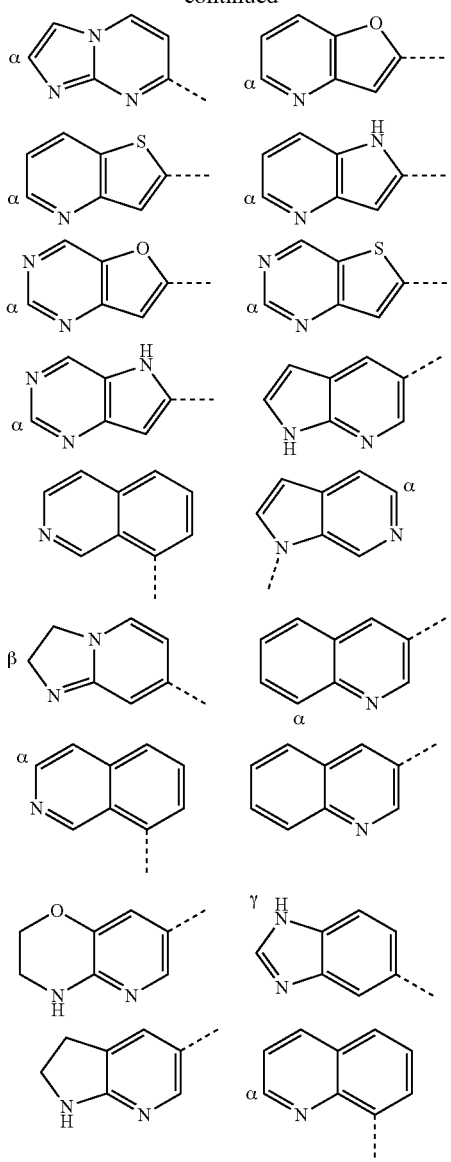

wherein Ar is substituted in the position indicated by α (if any) with —NH$_2$, —NH—C$_{1-4}$alkyl, or —NHR$^{10}$;

wherein Ar is substituted in the position indicated by β (if any) with oxo;

wherein Ar is substituted in the position indicated by γ (if any) with C$_{1-4}$alkyl;

and wherein Ar is optionally substituted with substituents selected from the list of substituents on Ar in any of the other embodiments.

In an embodiment, the present invention relates to those compounds of Formula (I) and pharmaceutically acceptable addition salts, and solvates thereof, or any subgroup thereof as mentioned in any of the other embodiments, wherein Z represents —CR$^{5c}$R$^{5d}$—CR$^{5e}$R$^{5g}$—CR$^{5f}$R$^{5h}$—, or —CR$^{5a}$R$^{5b}$—CR$^{5c}$R$^{5d}$CR$^{5e}$R$^{5g}$—CR$^{5f}$R$^{5h}$—; R$^{5a}$, R$^{5b}$, R$^{5c}$, R$^{5d}$, R$^{5e}$, R$^{5f}$, R$^{5g}$, R$^{5h}$, and R$^{5i}$ represent hydrogen;

Ar represents a bicyclic ring system selected from the group consisting of

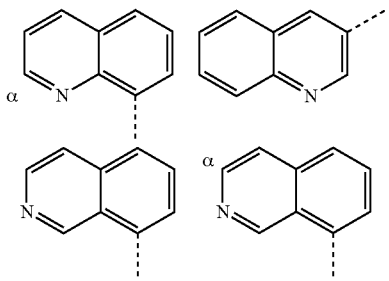

wherein Ar is substituted in the position indicated by α (if any) with —NH$_2$.

In an embodiment, the present invention relates to those compounds of Formula (I) and pharmaceutically acceptable addition salts, and solvates thereof, or any subgroup thereof as mentioned in any of the other embodiments, wherein Z represents —CR$^{5c}$R$^{5d}$—CR$^{5e}$R$^{5g}$—CR$^{5f}$R$^{5h}$—, or —CR$^{5a}$R$^{5b}$—CR$^{5c}$R$^{5d}$CR$^{5e}$R$^{5g}$—CR$^{5f}$R$^{5h}$—; R$^{5a}$, R$^{5b}$, R$^{5c}$, R$^{5d}$, R$^{5e}$, R$^{5f}$, R$^{5g}$, R$^{5h}$, and R$^{5i}$ represent hydrogen;

Ar represents a bicyclic ring system selected from the group consisting of

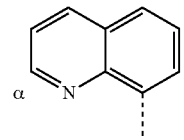

wherein Ar is substituted in the position indicated by α with —NH$_2$.

In an embodiment, the present invention relates to those compounds of Formula (I) and pharmaceutically acceptable addition salts, and solvates thereof, or any subgroup thereof as mentioned in any of the other embodiments, wherein Ar is substituted with one substituent selected from the group consisting of —NH$_2$, —NH—C$_{1-4}$alkyl, —NHR$^{10}$; and wherein Ar is optionally substituted with another substituent selected from the list of substituents on Ar in any of the other embodiments.

In an embodiment, the present invention relates to those compounds of Formula (I) and pharmaceutically acceptable addition salts, and solvates thereof, or any subgroup thereof as mentioned in any of the other embodiments, wherein Ar represents a monocyclic aromatic ring selected from pyridinyl and imidazolyl;

Ar is optionally substituted on the carbon atoms with in total one, two, three or four substituents each independently selected from the group consisting of halo, —OH, —NH$_2$, —NH—C$_{1-4}$alkyl, —NHR$^{10}$, cyano, —CF$_3$, C$_{1-4}$alkyloxy, C$_{3-6}$cycloalkyl, —O—C$_{3-6}$cycloalkyl, C$_{2-6}$alkenyl, C$_{1-4}$alkyl, and C$_{1-4}$alkyl substituted with one C$_{1-4}$alkyloxy.

In an embodiment, the present invention relates to those compounds of Formula (I) and pharmaceutically acceptable addition salts, and solvates thereof, or any subgroup thereof as mentioned in any of the other embodiments, wherein Ar represents a monocyclic aromatic ring selected from pyridinyl and imidazolyl; wherein Ar is optionally substituted according to any of the embodiments.

In an embodiment, the present invention relates to those compounds of Formula (I) and pharmaceutically acceptable addition salts, and solvates thereof, or any subgroup thereof as mentioned in any of the other embodiments, wherein Ar represents a 9-membered bicyclic aromatic ring system consisting of a 6-membered ring fused with a 5-membered ring, containing one, two or three heteroatoms each independently selected from O, S, and N, said 9-membered bicyclic aromatic ring being attached to the remainder of the molecule via a ring carbon atom of the 5- or 6-membered ring, or a ring nitrogen atom of the 5-membered ring;

Ar is optionally substituted on the carbon atoms with in total one, two, three or four substituents each independently selected from the group consisting of halo, —OH, —NH$_2$, —NH—C$_{1-4}$alkyl, —NHR$^{10}$, cyano, —CF$_3$, C$_{1-4}$alkyloxy, C$_{3-6}$cycloalkyl, —O—C$_{3-6}$cycloalkyl, C$_{2-6}$alkenyl, C$_{1-4}$alkyl, and C$_{1-4}$alkyl substituted with one C$_{1-4}$alkyloxy; and where possible Ar is optionally substituted on one N-atom with one substituent selected from the group consisting of C$_{1-4}$alkyl; C$_{3-6}$cycloalkyl; C$_{1-4}$alkyl substituted with one, two or three halo atoms; and C$_{3-6}$cycloalkyl substituted with one, two or three halo atoms.

In an embodiment, the present invention relates to those compounds of Formula (I) and pharmaceutically acceptable addition salts, and solvates thereof, or any subgroup thereof as mentioned in any of the other embodiments, wherein Ar represents a 9-membered bicyclic aromatic ring system consisting of a 6-membered ring fused with a 5-membered ring, containing one, two or three heteroatoms each independently selected from O, S, and N, said 9-membered bicyclic aromatic ring being attached to the remainder of the molecule via a ring carbon atom of the 5- or 6-membered ring, or a ring nitrogen atom of the 5-membered ring;

wherein Ar is optionally substituted according to any of the embodiments.

In an embodiment, the present invention relates to those compounds of Formula (I) and pharmaceutically acceptable addition salts, and solvates thereof, or any subgroup thereof as mentioned in any of the other embodiments, wherein R$^{5b}$, R$^{5g}$ and R$^{5h}$ represent hydrogen.

In an embodiment, the present invention relates to those compounds of Formula (I) and pharmaceutically acceptable addition salts, and solvates thereof, or any subgroup thereof as mentioned in any of the other embodiments, wherein Q$^1$ represents CR$^{6a}$; and Q$^2$ represents CR$^{6b}$.

In an embodiment, the present invention relates to those compounds of Formula (I) and pharmaceutically acceptable addition salts, and solvates thereof, or any subgroup thereof as mentioned in any of the other embodiments, wherein R$^{5b}$, R$^{5g}$ and R$^{5h}$ represent hydrogen;

Y represents —CH$_2$—;

Het represents (a-1);

Q$^1$ represents CR$^{6a}$; and Q$^2$ represents CR$^{6b}$; in particular wherein Q$^1$ represents CH; and Q$^2$ represents CH.

In an embodiment, the present invention relates to those compounds of Formula (I) and pharmaceutically acceptable addition salts, and solvates thereof, or any subgroup thereof as mentioned in any of the other embodiments, wherein Q$^2$ represents CR$^{6b}$.

In an embodiment, the present invention relates to those compounds of Formula (I) and pharmaceutically acceptable addition salts, and solvates thereof, or any subgroup thereof as mentioned in any of the other embodiments, wherein Y represents —CH$_2$—.

In an embodiment, the present invention relates to those compounds of Formula (I) and pharmaceutically acceptable addition salts, and solvates thereof, or any subgroup thereof as mentioned in any of the other embodiments, wherein Z represents —X—CR$^{5a}$R$^{5b}$—, —CR$^{5c}$=CR$^{5d}$—, or —CR$^{5e}$R$^{5g}$—CR$^{5f}$R$^{5h}$—;

R$^{5a}$, R$^{5b}$, R$^{5c}$, R$^{5d}$, R$^{5e}$, R$^{5f}$, R$^{5g}$, and R$^{5h}$ represent hydrogen;

X represents —O—.

In an embodiment, the present invention relates to those compounds of Formula (I) and pharmaceutically acceptable addition salts, and solvates thereof, or any subgroup thereof as mentioned in any of the other embodiments, wherein Z represents —X—CR$^{5a}$R$^{5b}$—, —CR$^{5c}$=CR$^{5d}$—, or —CR$^{5e}$R$^{5g}$—CR$^{5f}$R$^{5h}$—.

In an embodiment, the present invention relates to those compounds of Formula (I) and pharmaceutically acceptable addition salts, and solvates thereof, or any subgroup thereof as mentioned in any of the other embodiments, wherein Z represents —CH$_2$—, —X—CR$^{5a}$R$^{5b}$—, —CR$^{5c}$=CR$^{5d}$—, —CR$^{5e}$R$^{5g}$—CR$^{5f}$R$^{5h}$—, or —C≡C—.

In an embodiment, the present invention relates to those compounds of Formula (I) and pharmaceutically acceptable addition salts, and solvates thereof, or any subgroup thereof as mentioned in any of the other embodiments, wherein Z represents —X—CR$^{5a}$R$^{5b}$—, —CR$^{5c}$=CR$^{5d}$—, —CR$^{5e}$R$^{5g}$—CR$^{5f}$R$^{5h}$—, —CR$^{5a}$R$^{5b}$—X—, or —C≡C—.

In an embodiment, the present invention relates to those compounds of Formula (I) and pharmaceutically acceptable addition salts, and solvates thereof, or any subgroup thereof as mentioned in any of the other embodiments, wherein Z represents —X—CR$^{5a}$R$^{5b}$—.

In an embodiment, the present invention relates to those compounds of Formula (I) and pharmaceutically acceptable addition salts, and solvates thereof, or any subgroup thereof as mentioned in any of the other embodiments, wherein Z represents —O—CH$_2$—.

In an embodiment, the present invention relates to those compounds of Formula (I) and pharmaceutically acceptable addition salts, and solvates thereof, or any subgroup thereof as mentioned in any of the other embodiments, wherein Z represents —X—CR$^{5a}$R$^{5b}$—; X represents —O—; and R$^{5a}$ and R$^{5b}$ represent hydrogen.

In an embodiment, the present invention relates to those compounds of Formula (I) and pharmaceutically acceptable addition salts, and solvates thereof, or any subgroup thereof as mentioned in any of the other embodiments, wherein X represents —O— or —NR$^{11}$—; in particular X represents —O—.

In an embodiment, the present invention relates to those compounds of Formula (I) and pharmaceutically acceptable addition salts, and solvates thereof, or any subgroup thereof as mentioned in any of the other embodiments, wherein R$^{7a}$ and R$^{7b}$ represent hydrogen.

In an embodiment, the present invention relates to those compounds of Formula (I) and pharmaceutically acceptable addition salts, and solvates thereof, or any subgroup thereof as mentioned in any of the other embodiments, wherein Het represents (a-1);

R$^{3a}$ represents —NR$^{7a}$R$^{7b}$; and R$^{7a}$ and R$^{7b}$ represent hydrogen.

In an embodiment, the present invention relates to those compounds of Formula (I) and pharmaceutically acceptable addition salts, and solvates thereof, or any subgroup thereof as mentioned in any of the other embodiments, wherein R$^{3a}$, R$^{3d}$ and R$^{3e}$ represent other than halo.

In an embodiment, the present invention relates to those compounds of Formula (I) and pharmaceutically acceptable addition salts, and solvates thereof, or any subgroup thereof as mentioned in any of the other embodiments, wherein $R^{3a}$, $R^{3d}$ and $R^{3e}$ represent —$NR^{7a}R^{7b}$;
$R^{7a}$ represents hydrogen;
$R^{7b}$ represents hydrogen.

In an embodiment, the present invention relates to those compounds of Formula (I) and pharmaceutically acceptable addition salts, and solvates thereof, or any subgroup thereof as mentioned in any of the other embodiments, wherein $R^{3a}$, $R^{3d}$ and $R^{3e}$ represent —$NH_2$.

In an embodiment, the present invention relates to those compounds of Formula (I) and pharmaceutically acceptable addition salts, and solvates thereof, or any subgroup thereof as mentioned in any of the other embodiments, wherein Z represents —$CH_2$—, —$CHR^{5i}$—, —X—$CR^{5a}R^{5b}$—, —$CR^{5c}$=$CR^{5d}$—, —$CR^{5e}R^{5g}$—$CR^{5f}R^{5h}$—, —$CR^{5c}R^{5d}$—$CR^{5e}R^{5g}$—$CR^{5f}R^{5h}$—, or —$CR^{5a}R^{5b}$—$CR^{5c}R^{5d}$—$CR^{5e}R^{5g}$—$CR^{5f}R^{5h}$—;

$R^{5a}$, $R^{5b}$, $R^{5c}$, $R^{5d}$, $R^{5e}$, $R^{5f}$, $R^{5g}$, $R^{5h}$, and $R^{5i}$ each independently represent hydrogen or $C_{1-4}$alkyl;

X represents —O—;

Het represents a bicyclic aromatic heterocyclic system (a-1);

$R^{3a}$ represents halo, —$NR^{7a}R^{7b}$, or —O—$C_{1-4}$alkyl;
$Q^1$ represents $CR^{6a}$;
$Q^2$ represents $CR^{6b}$.

In an embodiment, the present invention relates to those compounds of Formula (I) and pharmaceutically acceptable addition salts, and solvates thereof, or any subgroup thereof as mentioned in any of the other embodiments, wherein Z represents —X—$CR^{5a}R^{5b}$—, —$CR^{5c}$=$CR^{5d}$—, —$CR^{5e}R^{5g}$—$CR^{5f}R^{5h}$—, —$CR^{5c}R^{5d}$—$CR^{5e}R^{5g}$—$CR^{5f}R^{5h}$—, or —$CR^{5a}R^{5b}$—$CR^{5c}R^{5d}$—$CR^{5e}R^{5g}$—$CR^{5f}R^{5h}$—;

$R^{5a}$, $R^{5b}$, $R^{5c}$, $R^{5d}$, $R^{5e}$, $R^{5f}$, $R^{5g}$, and $R^{5h}$ each independently represent hydrogen or $C_{1-4}$alkyl;

X represents —O—;

Het represents a bicyclic aromatic heterocyclic system (a-1);

$R^{3a}$ represents —$NR^{7a}R^{7b}$;
$R^{7a}$ and $R^{7b}$ represent hydrogen;
$Q^1$ represents $CR^{6a}$;
$Q^2$ represents $CR^{6b}$.

In an embodiment, the present invention relates to those compounds of Formula (I) and pharmaceutically acceptable addition salts, and solvates thereof, or any subgroup thereof as mentioned in any of the other embodiments, wherein Z represents —$CH_2$—, —$CHR^{5i}$—, —$CR^{5c}$=$CR^{5d}$—, —$CR^{5e}R^{5g}$—$CR^{5f}R^{5h}$—, —$CR^{5c}R^{5d}$—$CR^{5e}R^{5g}$—$CR^{5f}R^{5h}$—, or —$CR^{5a}R^{5b}$—$CR^{5c}R^{5d}$—$CR^{5e}R^{5g}$—$CR^{5f}R^{5h}$—;

$R^{5a}$, $R^{5b}$, $R^{5c}$, $R^{5d}$, $R^{5e}$, $R^{5f}$, $R^{5g}$, $R^{5h}$, and $R^{5i}$ each independently represent hydrogen or $C_{1-4}$alkyl;

Het represents a bicyclic aromatic heterocyclic system (a-1);

$R^{3a}$ represents halo, —$NR^{7a}R^{7b}$, or —O—$C_{1-4}$alkyl;
$Q^1$ represents $CR^{6a}$;
$Q^2$ represents $CR^{6b}$.

In an embodiment, the present invention relates to those compounds of Formula (I) and pharmaceutically acceptable addition salts, and solvates thereof, or any subgroup thereof as mentioned in any of the other embodiments, wherein Z represents —$CR^{5c}$=$CR^{5d}$—, —$CR^{5e}R^{5g}$—$CR^{5f}R^{5h}$—, —$CR^{5c}R^{5d}$—$CR^{5e}R^{5g}$—$CR^{5f}R^{5h}$—, or —$CR^{5a}R^{5b}$—$CR^{5c}R^{5d}$—$CR^{5e}R^{5g}$—$CR^{5f}R^{5h}$—;

$R^{5a}$, $R^{5b}$, $R^{5c}$, $R^{5d}$, $R^{5e}$, $R^{5f}$, $R^{5g}$, and $R^{5h}$ each independently represent hydrogen or $C_{1-4}$alkyl;

Het represents a bicyclic aromatic heterocyclic ring system (a-1);

$R^{3a}$ represents —$NR^{7a}R^{7b}$;
$R^{7a}$ and $R^{7b}$ represent hydrogen;
$Q^1$ represents $CR^{6a}$;
$Q^2$ represents $CR^{6b}$.

In an embodiment, the present invention relates to those compounds of Formula (I) and pharmaceutically acceptable addition salts, and solvates thereof, or any subgroup thereof as mentioned in any of the other embodiments, wherein the compounds of Formula (I) are restricted to compounds of Formula (I-a1):

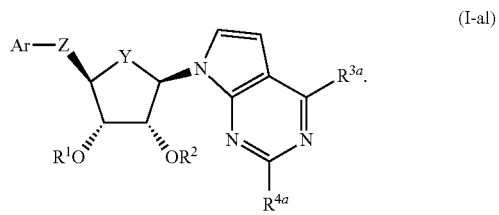

(I-a1)

It will be clear that all variables in the structure of Formula (I-a1), may be defined as defined for the compounds of Formula (I) or any subgroup thereof as mentioned in any of the other embodiments.

In an embodiment, the present invention relates to those compounds of Formula (I) and pharmaceutically acceptable addition salts, and solvates thereof, or any subgroup thereof as mentioned in any of the other embodiments, wherein the compounds of Formula (I) are restricted to compounds of Formula (I-a1):

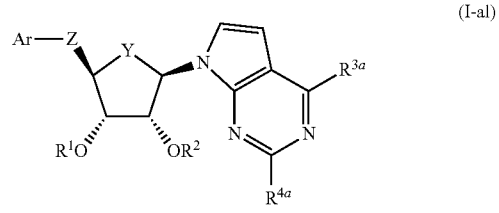

(I-a1)

wherein $R^{3a}$ represents —$NH_2$; and $R^{4a}$ represents hydrogen.

In an embodiment, the present invention relates to those compounds of Formula (I) and pharmaceutically acceptable addition salts, and solvates thereof or any subgroup thereof as mentioned in any of the other embodiments, wherein Z represents —X—$CR^{5a}R^{5b}$— or —$CH_2CH_2$-.

In an embodiment, the present invention relates to those compounds of Formula (I) and pharmaceutically acceptable addition salts, and solvates thereof, or any subgroup thereof as mentioned in any of the other embodiments, wherein Z represents —X—$CR^{5a}R^{5b}$— or —$CH_2CH_2$—;
$R^{5b}$ represents hydrogen.

In an embodiment, the present invention relates to those compounds of Formula (I) and pharmaceutically acceptable addition salts, and solvates thereof, or any subgroup thereof as mentioned in any of the other embodiments, wherein $R^{5b}$ represents hydrogen.

In an embodiment, the present invention relates to those compounds of Formula (I) and pharmaceutically acceptable addition salts, and solvates thereof, or any subgroup thereof as mentioned in any of the other embodiments, wherein Z represents —X—CR$^{5a}$R$^{5b}$— or —CH$_2$CH$_2$—;
R$^{5a}$ and R$^{5b}$ represent hydrogen;
X represents —O—.

In an embodiment, the present invention relates to those compounds of Formula (I) and pharmaceutically acceptable addition salts, and solvates thereof, or any subgroup thereof as mentioned in any of the other embodiments, wherein
Z represents —X—CR$^{5a}$R$^{5b}$— or —CH$_2$CH$_2$—;
R$^{5a}$ and R$^{5b}$ represent hydrogen;
X represents —O—;
Het represents (a-1).

In an embodiment, the present invention relates to those compounds of Formula (I) and pharmaceutically acceptable addition salts, and solvates thereof, or any subgroup thereof as mentioned in any of the other embodiments, wherein
Z represents —X—CR$^{5a}$R$^{5b}$— or —CH$_2$CH$_2$—;
R$^{5a}$ and R$^{5b}$ represent hydrogen;
X represents —O—;
Het represents (a-1);
R$^{3a}$ represents-NR$^{5a}$R$^{7b}$;
R$^{7a}$ represents hydrogen;
R$^{7b}$ represents hydrogen.

In an embodiment, the present invention relates to those compounds of Formula (I) and pharmaceutically acceptable addition salts, and solvates thereof, or any subgroup thereof as mentioned in any of the other embodiments, wherein X represents —O—.

In an embodiment, the present invention relates to those compounds of Formula (I) and pharmaceutically acceptable addition salts, and solvates thereof, or any subgroup thereof as mentioned in any of the other embodiments, wherein
Het represents (a-1);
R$^{3a}$ represents —NR$^{7a}$R$^{7b}$;
R$^{7a}$ represents hydrogen;
R$^{7b}$ represents hydrogen.

In an embodiment, the present invention relates to those compounds of Formula (I) and pharmaceutically acceptable addition salts, and solvates thereof, or any subgroup thereof as mentioned in any of the other embodiments, wherein
R$^{3a}$, R$^{3d}$ and R$^{3e}$ represent —NR$^{7a}$R$^{7b}$;
R$^{7a}$ represents hydrogen;
R$^{7b}$ represents hydrogen, C$_{3-6}$cycloalkyl, or C$_{1-4}$alkyl.

In an embodiment, the present invention relates to those compounds of Formula (I) and pharmaceutically acceptable addition salts, and solvates thereof, or any subgroup thereof as mentioned in any of the other embodiments, wherein
R$^{3a}$, R$^{3d}$ and R$^{3e}$ represent —NR$^{7a}$R$^{7b}$;
R$^{7a}$ represents hydrogen;
R$^{7b}$ represents hydrogen.

In an embodiment, the present invention relates to those compounds of Formula (I) and pharmaceutically acceptable addition salts, and solvates thereof, or any subgroup thereof as mentioned in any of the other embodiments, wherein Y represents —CH$_2$—; and Z represents —CH$_2$CH$_2$—.

In an embodiment, the present invention relates to those compounds of Formula (I) and pharmaceutically acceptable addition salts, and solvates thereof, or any subgroup thereof as mentioned in any of the other embodiments, wherein
R$^1$ represents hydrogen; R$^2$ represents hydrogen;
Y represents —CH$_2$—;
Z represents —CH$_2$—, —CHR$^{5i}$—, —X—CR$^{5a}$R$^{5b}$—, —CR$^{5c}$=CR$^{5d}$—, —CR$^{5e}$R$^{5g}$—CR$^{5f}$R$^{5h}$—, —CR$^{5c}$R$^{5d}$—CR$^{5e}$R$^{5g}$—CR$^{5f}$R$^{5h}$—, or —CR$^{5a}$R$^{5b}$—CR$^{5c}$R$^{5d}$—CR$^{5e}$R$^{5g}$—CR$^{5f}$R$^{5h}$—;
R$^{5a}$, R$^{5b}$, R$^{5c}$, R$^{5d}$, R$^{5e}$, R$^{5f}$, R$^{5g}$, R$^{5h}$, and R$^{5i}$ each independently represent hydrogen or C$_{1-4}$alkyl;
X represents —O—;

Het represents a bicyclic aromatic heterocyclic ring system (a-1);
R$^{3a}$ represents halo, —NR$^{7a}$R$^{7b}$, or —O—C$_{1-4}$alkyl;
R$^{7a}$ represents hydrogen;
R$^{7b}$ represents hydrogen or C$_{1-4}$alkyl;
R$^{4a}$ represents hydrogen;
Q$^1$ represents CR$^{6a}$;
Q$^2$ represents N or CR$^{6b}$;
R$^{6a}$ and R$^{6b}$ each independently represent hydrogen or halogen.

In an embodiment, the present invention relates to a subgroup of Formula (I) as defined in the general reaction schemes.

In an embodiment the compound of Formula (I) is selected from the group consisting of any of the exemplified compounds,
and the free bases, the pharmaceutically acceptable addition salts, and the solvates thereof.

All possible combinations of the above-indicated embodiments are considered to be embraced within the scope of this invention.

Methods for the Preparation

In this section, as in all other sections unless the context indicates otherwise, references to Formula (I) also include all other sub-groups and examples thereof as defined herein.

The general preparation of some typical examples of the compounds of Formula (I) is described hereunder and in the specific examples, and are generally prepared from starting materials which are either commercially available or prepared by standard synthetic processes commonly used by those skilled in the art. The following schemes are only meant to represent examples of the invention and are in no way meant to be a limit of the invention.

Alternatively, compounds of the present invention may also be prepared by analogous reaction protocols as described in the general schemes below, combined with standard synthetic processes commonly used by those skilled in the art of organic chemistry.

The skilled person will realize that in the reactions described in the Schemes, it may be necessary to protect reactive functional groups, for example hydroxy, amino, or carboxy groups, where these are desired in the final product, to avoid their unwanted participation in the reactions. Conventional protecting groups can be used in accordance with standard practice. This is illustrated in the specific examples.

The skilled person will realize that in the reactions described in the Schemes, it may be advisable or necessary to perform the reaction under an inert atmosphere, such as for example under N$_2$-gas atmosphere, for example when NaH is used in the reaction.

It will be apparent for the skilled person that it may be necessary to cool the reaction mixture before reaction work-up (refers to the series of manipulations required to isolate and purify the product(s) of a chemical reaction such as for example quenching, column chromatography, extraction).

The skilled person will realize that heating the reaction mixture under stirring may enhance the reaction outcome. In some reactions microwave heating may be used instead of conventional heating to shorten the overall reaction time.

The skilled person will realize that another sequence of the chemical reactions shown in the Schemes below, may also result in the desired compound of Formula (I).

The skilled person will realize that intermediates and compounds shown in the schemes below may be further functionalized according to methods well-known by the person skilled in the art.

The skilled person will realize that more Compounds of Formula (I) can be prepared by using similar synthetic protocols as described in the Schemes below.

In case one of the starting materials is available as a salt form, the skilled person will realize that it may be necessary to first treat the salt with a base, such as for example N,N-diisopropylethylamine (DIPEA).

All variables are defined as mentioned hereabove unless otherwise is indicated or is clear from the context.

The skilled person will understand that analogous chemistry as described in Schemes 1 to 9 (wherein Het is showns as (a-1)), may also be applied to make compounds of Formula (I) wherein Het represents a bicyclic aromatic heterocyclic rings system (a-2) or (a-3). In addition, this information may be combined with standard synthetic processes commonly used by those skilled in the art of organic chemistry to obtain more compounds of Formula (I) wherein Het represents (a-2) or (a-3).

In general, compounds of Formula (I) can be prepared according to Scheme 1:

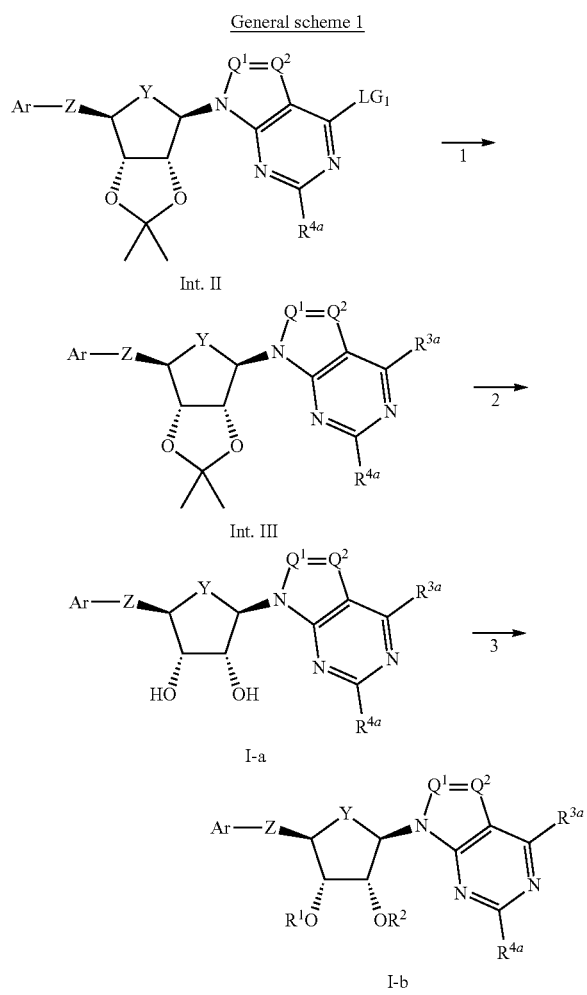

In scheme 1, 'LG$_1$' is defined as a suitable leaving group such as for example halogen.

All other variables in Scheme 1 are defined according to the scope of the present invention.

In scheme 1, the following reaction conditions typically apply:

1: Different sets of reaction conditions dependent on the definition of R$^{3a}$;

1a: When R$^{3a}$ is halogen, step 1 can be skipped.

1b: When R$^{3a}$ is NR$^{7a}$R$^{7b}$, in the presence of a suitable amine of formula HNR$^{7a}$R$^{7b}$, with a suitable solvent such as for example, H$_2$O, MeOH, or EtOH, at a suitable temperature such as for example between 100-130° C. typicall under microwave conditions or using an autoclave vessel for heating.

1c: When R$^{3a}$ is —O—C$_{1-4}$alkyl, in the presence of a suitable HO—C$_{1-4}$alkyl, with a suitable base such as for example NaH, potassium tert-butoxide (tBuOK) in a suitable solvent such as for example tetrahydrofuran (THF) at a suitable temperature. Alternatively in the presence of the suitable HO—C$_{1-4}$alkyl as solvent with a suitable acid such as for example HCl.

1d: When R$^{3a}$ is hydrogen, under hydrogenation conditions: H$_2$-gas atmosphere in the presence of a catalyst such as for example Raney Ni, Pd/C (for example 5 wt % or 10 wt %) or Pt/C (for example 5 wt %) in a suitable solvent such as for example methanol (MeOH), ethanol (EtOH) or THF.

1e: When R$^{3a}$ is C$_{1-4}$alkyl, in the presence of a suitable boronic acid or ester such as for example methylboronic acid with a suitable catalyst such as for example 1,1'-bis(diphenylphosphino)ferrocene and with with a suitable base such as for example K$_3$PO$_4$ in a in a suitable solvent mixture such as for example dioxane/H$_2$O ratio 5 to 1 at a suitable temperature such as for example 100° C.

2: in the presence of a suitable acid, such as for example 4M HCl in dioxane or 4M HCl in MeOH, with a suitable solvent such as for example MeOH at a suitable temperature such as for example room temperature; or alternatively in the presence of a suitable acid such as for example trifluoroacetic acid (TFA) in dichloromethane (DCM) at a suitable temperature, or acetic acid in THF and water at a suitable temperature such as for example room temperature.

3: in the presence of suitable acid anhydride of formula (C$_{1-4}$alkylC=O)$_2$O with a suitable solvent such as pyridine at a suitable temperature. When R$^{3a}$ is NH$_2$, (C$_{1-4}$alkylC=O)$_2$O can react with the NH$_2$ to obtain the N(C$_{1-4}$alkylC=O)$_2$ intermediate. Such an intermediate can be converted to the targeted product in a suitable solvent such as for example MeOH at a suitable temperature such as for example 100-130° C. under microwave conditions or using an autoclave vessel for heating. The reaction may benefit from the presence of an acid, such as HCl or C$_{1-4}$alkylCO$_2$H.

The starting materials in scheme 1 are commercially available or can be prepared by standard means obvious to those skilled in the art or as described in following general schemes.

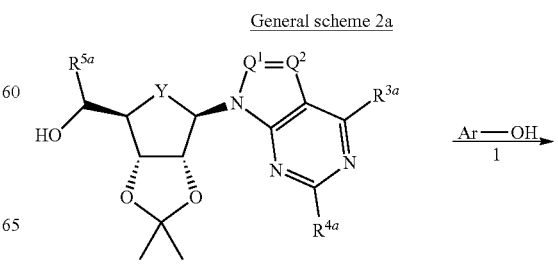

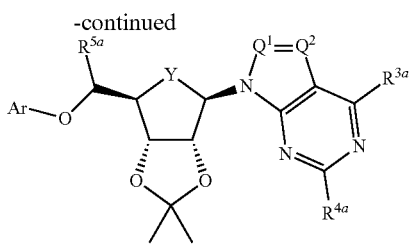

In general, intermediates of Formula III wherein Z represents —O—CHR$^{5a}$— can be prepared according to Scheme 2a. All other variables in Scheme 2a are defined according to the scope of the present invention. The skilled person will realize a suitable protection group is needed when R$^{3a}$ is —NH$_2$ or —NHR$^{7b}$;

In scheme 2a, the following reaction conditions apply:
1: The Mitsunobu reaction:
1a: In the presence of PPh$_3$-Polymer supported, diisopropyl azodicarboxylate (DIAD) or diethyl azodicarboxylate (DEAD) or Bis(1,1-dimethylethyl)-azodicarboxylate (DBAD) in a suitable solvent such as for example anhydrous THF at a suitable temperature such as for example room temperature.
1b: In the presence of triphenylphosphine (PPh$_3$), DIAD or DEAD in a suitable solvent such as for example anhydrous THF at a suitable temperature such as for example room temperature.
1c: In the presence of cyanomethylenetributylphosphorane (CMBP) or cyanomethlenethylenetrimethylphosphorane (CMMP), in a suitable solvent such as for example anhydrous toluene at a suitable temperature such as for example 80° C.

The starting materials in scheme 2a are commercially available or can be prepared by standard means obvious to those skilled in the art or as described in following general schemes. The skilled person will realize that when R$^{5a}$ is C$_{1-4}$alkyl, the different isomers can be separated from each other by using Reversed-Phase High-Performance Liquid Chromatography (RP-HPLC) or Supercritical Fluid Chromatography (SFC).

General scheme 2b

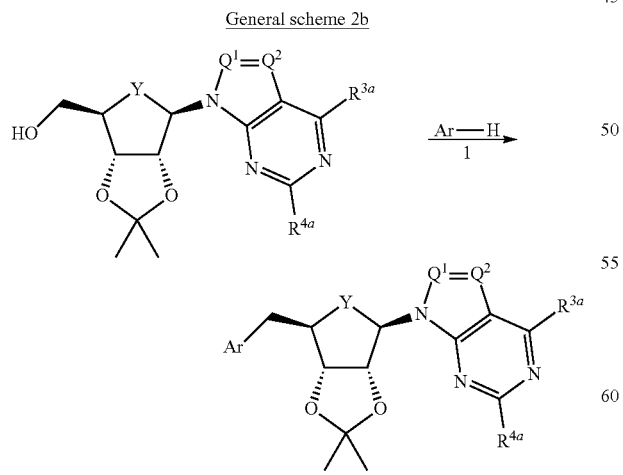

In general, intermediates of Formula III wherein Z represents —CHR$^{5a}$— can be prepared according to Scheme 2b. All other variables in Scheme 2b are defined according to the scope of the present invention. The skilled person will realize a suitable protection group is needed when R$^{3a}$ is —NH$_2$ or —NHR$^{7b}$;

In scheme 2b, the following reaction conditions apply:
1: The Mitsunobu reaction:
1a: In the presence of PPh$_3$-Polymer supported diisopropyl azodicarboxylate (DIAD) or diethyl azodicarboxylate (DEAD) or Bis(1,1-dimethylethyl)-azodicarboxylate (DBAD) in a suitable solvent such as for example anhydrous THF at a suitable temperature such as for example room temperature.
1b: In the presence of triphenylphosphine (PPh$_3$), DIAD or DEAD in a suitable solvent such as for example anhydrous THF at a suitable temperature such as for example room temperature.
1c: In the presence of cyanomethylenetributylphosphorane (CMBP) or cyanomethylenetrimethylphosphorane (CMMP), in a suitable solvent such as for example anhydrous toluene at a suitable temperature such as for example 80° C.

The starting materials in scheme 2b are commercially available or can be prepared by standard means obvious to those skilled in the art or as described in following general schemes. The skilled person will realize that when R$^{5a}$ is C$_{1-4}$alkyl, the different isomers can be separated from each other by using Reversed-Phase High-Performance Liquid Chromatography (RP-HPLC) or Supercritical Fluid Chromatography (SFC).

A skilled person will realize that scheme 2b can also be used to prepared analogous intermediates wherein Z represents —CR$^{5e}$R$^{5g}$—CR$^{5f}$R$^{5h}$—.

General scheme 2c

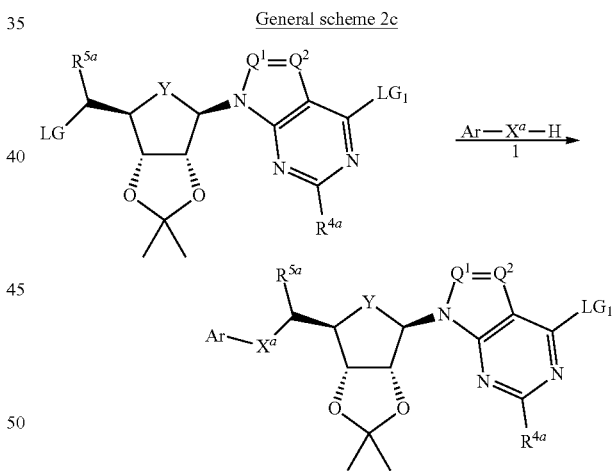

Intermediates of Formula II wherein Z represents —X$^{a}$—CHR$^{5a}$— can be prepared according to Scheme 2c. In scheme 2c, 'X$^{a}$' is defined as O or S; 'LG' is defined as a leaving group such as for example halogen, mesylate (MsO) and tosylate (TosO), preferably TosO. 'LG$_1$' is defined as leaving group such as for example halogen. All other variables in Scheme 2c are defined according to the scope of the present invention.

In scheme 2c, the following reaction conditions apply:
1: in the presence of a base such as for example K$_2$CO$_3$, triethylamine (Et$_3$N) or DIPEA, in a suitable solvent such as CH$_3$CN, DCM or N,N-dimethylacetamide (DMA).

The starting materials in scheme 2c are commercially available or can be prepared by standard means obvious to those skilled in the art or as described in following general schemes. The skilled person will realize that when $R^{5a}$ is $C_{1-4}$alkyl, the different isomers can be separated from each other by using Reversed-Phase High-Performance Liquid Chromatography (RP-HPLC) or Supercritical Fluid Chromatography (SFC).

General scheme 2d

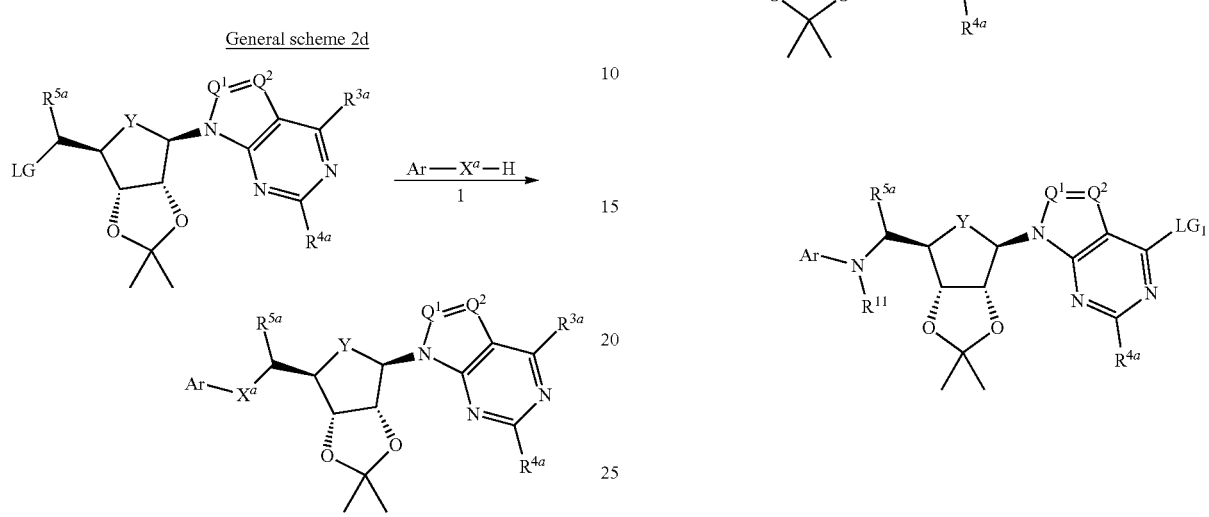

Intermediates of Formula III wherein Z represents —$X^a$—$CHR^{5a}$— can be prepared according to Scheme 2d. In scheme 2d '$X^a$' is defined as O or S. 'LG' is defined as a leaving group such as for example halogen, MsO or TosO, preferably TosO. All other variables in Scheme 2d are defined according to the scope of the present invention. The skilled person will realize that a suitable protection group is needed when $R^{3a}$ is —$NH_2$ or —$NHR^{7b}$.

In scheme 2d, the following reaction conditions apply:

1: in the presence of a base such as for example $K_2CO_3$, $Et_3N$ or DIPEA, in a suitable solvent such as $CH_3CN$, DCM or N,N-dimethylacetamide (DMA).

The starting materials in scheme 2d are commercially available or can be prepared by standard means obvious to those skilled in the art or as described in following general schemes. The skilled person will realize that when $R^{5a}$ is $C_{1-4}$alkyl, the different isomers can be separated from each other by using Reversed-Phase High-Performance Liquid Chromatography (RP-HPLC) or Supercritical Fluid Chromatography (SFC).

General scheme 3

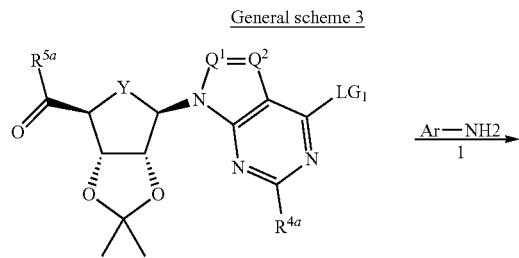

In general, intermediates wherein Z represents —X—$CHR^{5a}$—; and wherein X represents —NH— or —$NR^{11}$ can be prepared according to Scheme 3. In scheme 3, '$LG_1$' is defined as a leaving group such as for example halogen. All other variables in Scheme 3 are defined according to the scope of the present invention.

In scheme 3, the following reaction conditions apply:

1: in the presence of a suitable reduction reagent such as for example sodium triacetoxyborohydride ($NaBH(AcO)_3$) together with a suitable solvent such as for example DCM at a suitable temperature such as for example room temperature; or alternatively $NaBH_3CN$ together with a suitable solvent such as for example MeOH at a suitable temperature such as for example between room temperature and 50° C.

2: in the presence of a suitable base such as for example NaH together with a suitable solvent such as for example anhydrous THF, N,N-dimethylformamide (DMF), DMA at a suitable temperature such as for example between room temperature and 50° C. The starting materials in scheme 3 are commercially available or can be prepared by standard means obvious to those skilled in the art or as described in the specific experimental part. The skilled person will realize that when $R^{5a}$ is $C_{1-4}$alkyl, the different isomers can be separated from each other by using Reversed-Phase High-Performance Liquid Chromatography (RP-HPLC) or Supercritical Fluid Chromatography (SFC).

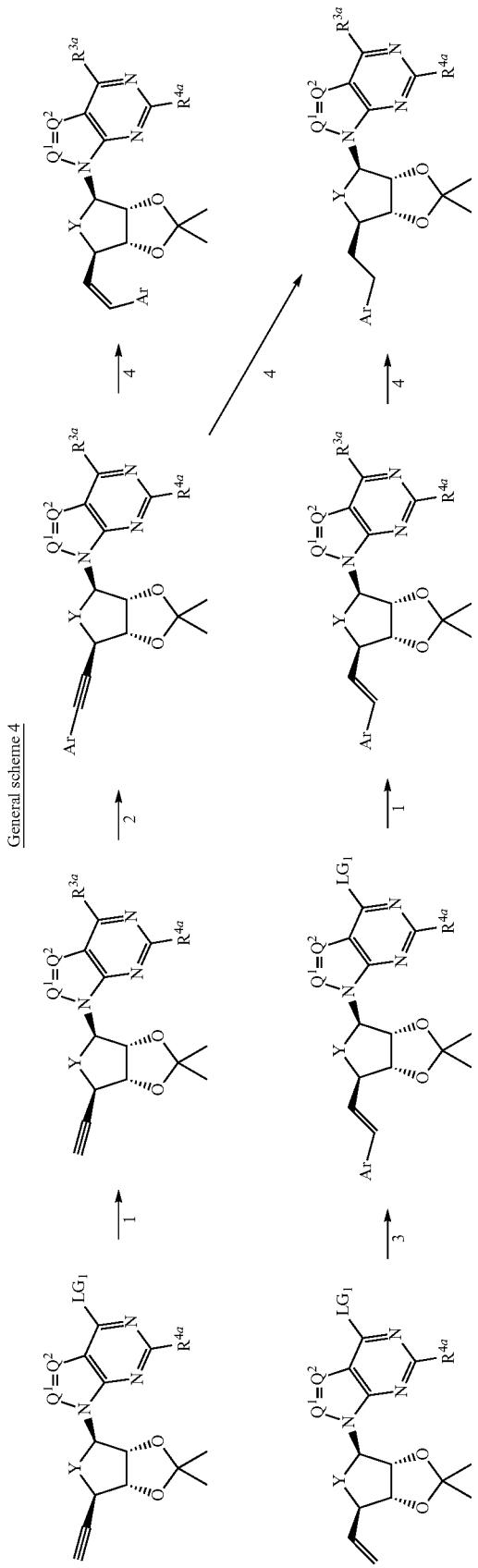

In general, intermediates wherein Z represents —C≡C—, —CH=CH—, or —CH₂—CH₂— can be prepared according to Scheme 4. In scheme 4, 'LG₁' is defined as a leaving group such as for example halogen. All other variables in Scheme 4 are defined according to the scope of the present invention.

In scheme 4, the following reaction conditions apply:

1: In the presence of suitable amine, such as HNR'R" or NaOR', with a suitable solvent such as for example H₂O, MeOH, or EtOH at a suitable temperature such as for example between 100-130° C. under microwave condition or using an autoclave vessel for heating.

2: In the presence of a suitable Ar-bromide or Ar-iodide, a suitable catalyst, such as bis(triphenylphosphine)palladium(II) dichloride and copper(I) iodide in a suitable solvent, such as 2-methyltetrahydrofuran with a suitable base, such as for example triethylamine at a suitable temperature, such as for example 80° C.

3: in the presence of a suitable Ar-bromide or Ar-iodide, a suitable salt, such as for example tetraethylammonium chloride (Et₄NCl), in a suitable solvent, such as for example DMF, with a suitable base such as for example DIPEA and a palladium catalyst, such as for example Pd(OAc)₂ (palladium(II) acetate) at suitable temperature such as for example 100° C.

4: in the presence of a H2-gas atmosphere and a catalyst such as for example Pd/C (for example 5 wt % or 10 wt %) in a suitable solvent such as for example MeOH.

The starting materials in scheme 4 are commercially available or can be prepared by standard means obvious to those skilled in the art or as described in the specific experimental part.

General scheme 5

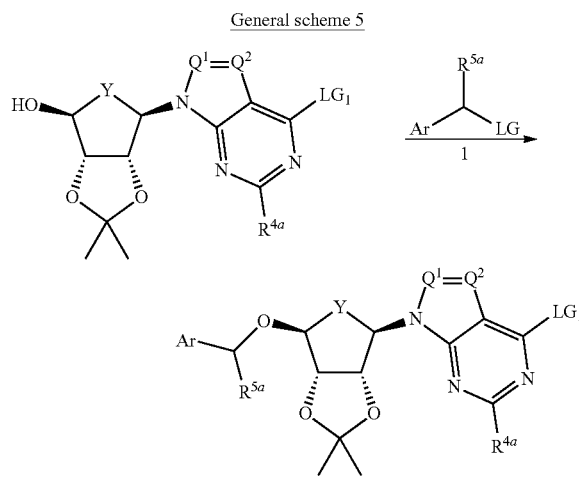

In general, intermediates wherein Z represents —CH₂O— can be prepared according to Scheme 5. In scheme 5, 'LG₁' is defined as a leaving group such as for example halogen. All other variables in Scheme 5 are defined according to the scope of the present invention.

In scheme 5, the following reaction conditions apply:

1: in the presence of a base such as for example K₂CO₃, Et₃N or DIPEA, in a suitable solvent such as CH₃CN, DCM or N,N-dimethylacetamide (DMA).

General scheme 6

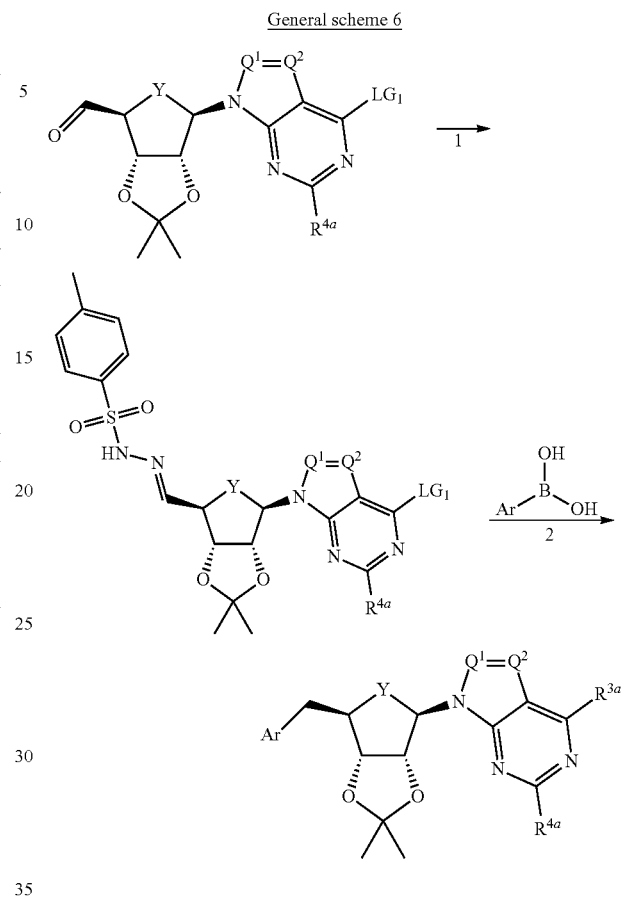

In general, intermediates wherein Z represents —CH₂— can be prepared according to Scheme 6. In scheme 6, 'LG₁' is defined as a leaving group such as for example halogen. All other variables in Scheme 6 are defined according to the scope of the present invention.

In scheme 6, the following reaction conditions apply:

1: In the presence of tosylhydrazide, with a suitable solvent such as for example, MeOH, EtOH, or DCM at a suitable temperature such as room temperature.

2: In the presence of Boronic acids, with a suitable base such as K₂CO₃, Na₂CO₃, Cs₂CO₃, with a suitable solvent such as for example, 1,4-dioxane at a suitable temperature such 90° C.

The starting materials in scheme 6 are commercially available or can be prepared by standard means obvious to those skilled in the art or as described in the specific experimental part.

General scheme 7

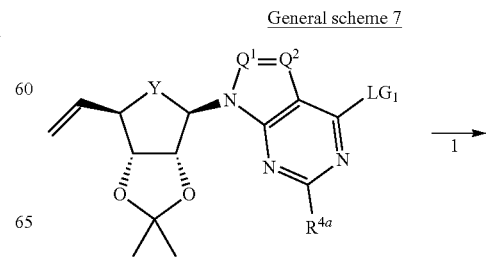

-continued

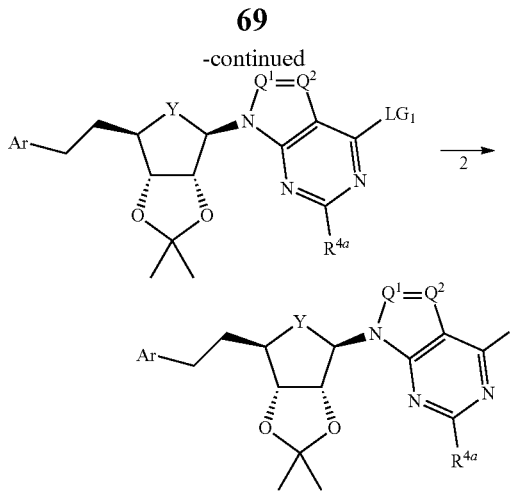

In general, intermediates wherein Z represents —CH$_2$—CH$_2$— can be prepared according to Scheme 7. In scheme 7, 'LG$_1$' is defined as a leaving group such as for example halogen. All other variables in Scheme 7 are defined according to the scope of the present invention.

In scheme 7, the following reaction conditions typically apply:

1: In a first step in the presence of an alkene precursor and a 9-Borabicyclo(3.3.1)nonane (9-BBN) solution 0.5 M in THF under nitrogen atmosphere at a temperature between room temperature and reflux and a reaction time between 1 to 3 hours. In a second step in the presence of, for example, a suitable Ar-bromide or Ar-iodide and a suitable catalyst as for example 1,1'-bis(diphenylphosphino)ferrocene]dichloropalladium(II) and in the presence of a suitable base as for example potassium phosphate tribasic in a suitable solvent mixture as for example THF and water at a suitble temperature between 50° C. and reflux and a suitable reaction time between 1 and 3 hours.

2: Different sets of reaction conditions dependent on the definition of R$^{3a}$:

2a: When R$^{3a}$ is halogen, step 1 can be skipped;

2b: When R$^{3a}$ is NR$^{7a}$R$^{7b}$, in the presence of a suitable amine of formula HNR$^{7a}$R$^{7b}$, with a suitable solvent such as for example, H$_2$O, MeOH, or EtOH, at a suitable temperature such as for example between 100-130° C. typicall under microwave conditions or using an autoclave vessel for heating.

2c: When R$^{3a}$ is —O—C$_{1-4}$alkyl, in the presence of a suitable HO—C$_{1-4}$alkyl, with a suitable base such as for example NaH, potassium tert-butoxide (tBuOK) in a suitable solvent such as for example tetrahydrofuran (THF) at a suitable temperature. Alternatively in the presence of the suitable HO—C$_{1-4}$alkyl as solvent with a suitable acid such as for example HCl.

2d: When R$^{3a}$ is hydrogen, under hydrogenation conditions: H$_2$-gas atmosphere in the presence of a catalyst such as for example Raney Ni, Pd/C (for example 5 wt % or 10 wt %) or Pt/C (for example 5 wt %) in a suitable solvent such as for example methanol (MeOH), ethanol (EtOH) or THF;

2e: When R$^{3a}$ is C$_{1-4}$alkyl, in the presence of a suitable boronic acid or ester such as for example methylboronic acid with a suitable catalyst such as for example 1,1'-bis(diphenylphosphino)ferrocene and with with a suitable base such as for example K$_3$PO$_4$ in a in a suitable solvent mixture such as for example dioxane/H$_2$O ratio 5 to 1 at a suitable temperature such as for example 100° C.

The starting materials in scheme 7 are commercially available or can be prepared by standard means obvious to those skilled in the art or as described in the specific experimental part.

General scheme 8

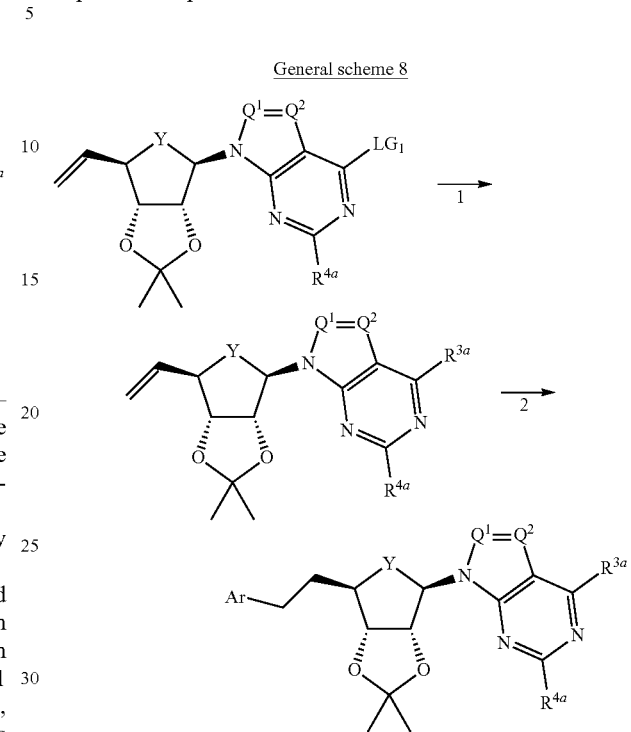

In general, intermediates wherein Z represents —CH$_2$—CH$_2$— can be prepared according to Scheme 8. In scheme 8, 'LG$_1$' is defined as a leaving group such as for example halogen. All other variables in Scheme 8 are defined according to the scope of the present invention.

In scheme 8, the following reaction conditions typically apply:

1: Different sets of reaction conditions dependent on the definition of R$^{3a}$:

1a: When R$^{3a}$ is halogen, step 1 can be skipped.

1b: When R$^{3a}$ is NR$^{7a}$R$^{7b}$, in the presence of a suitable amine of formula HNR$^{7a}$R$^{7b}$, with a suitable solvent such as for example, H$_2$O, MeOH, or EtOH, at a suitable temperature such as for example between 100-130° C. typicall under microwave conditions or using an autoclave vessel for heating.

1c: When R$^{3a}$ is —O—C$_{1-4}$alkyl, in the presence of a suitable HO—C$_{1-4}$alkyl, with a suitable base such as for example NaH, potassium tert-butoxide (tBuOK) in a suitable solvent such as for example tetrahydrofuran (THF) at a suitable temperature. Alternatively in the presence of the suitable HO—C$_{1-4}$alkyl as solvent with a suitable acid such as for example HCl.

1d: When R$^{3a}$ is hydrogen, under hydrogenation conditions: H$_2$-gas atmosphere in the presence of a catalyst such as for example Raney Ni, Pd/C (for example 5 wt % or 10 wt %) or Pt/C (for example 5 wt %) in a suitable solvent such as for example methanol (MeOH), ethanol (EtOH) or THE.

1e: When R$^{3a}$ is C$_{1-4}$alkyl, in the presence of a suitable boronic acid or ester such as for example methylboronic acid with a suitable catalyst such as for example 1,1'-bis(diphenylphosphino)ferrocene and with with a suitable base such as for example K$_3$PO$_4$ in a in a suitable solvent mixture such as for example dioxane/H$_2$O ratio 5 to 1 at a suitable temperature such as for example 100° C.

2: In a first step in the presence of an alkene precursor and a 9-BBN solution 0.5 M in THF under nitrogen atmosphere at a temperature between room temperature and reflux and a reaction time between 1 to 3 hours. In a second step in the presence of suitable Ar-bromide or Ar-iodide and a suitable catalyst as for example 1,1'-bis(diphenylphosphino)ferrocene]dichloropalladium(II) and in the presence of a suitable base as for example potassium phosphate tribasic in a suitable solvent mixture as for example THF and water at a suitable temperature between 50° C. and reflux and a suitable reaction time between 1 and 3 hours.

The starting materials in scheme 8 are commercially available or can be prepared by standard means obvious to those skilled in the art or as described in the specific experimental part.

General scheme 9

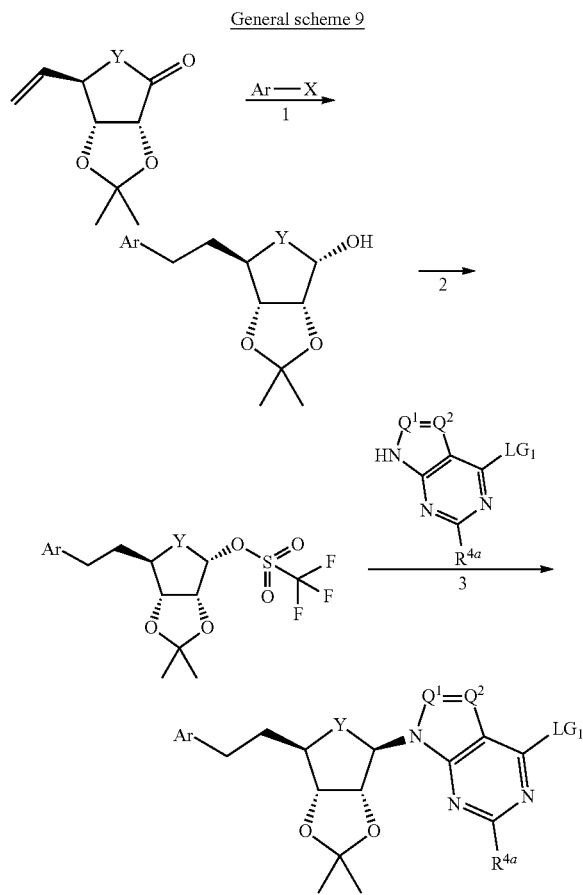

In general, intermediates as shown in Scheme 9 wherein Z represents —CH$_2$—CH$_2$— can be prepared according to Scheme 9. In scheme 9, 'LG$_1$' is defined as a leaving group such as for example halogen. All other variables in Scheme 9 are defined according to the scope of the present invention 1: In a first step in the presence of an alkene precursor and a 9-BBN solution 0.5 M in THF under nitrogen atmosphere at a temperature between room temperature and reflux and a reaction time between 1 to 3 hours. In a second step in the presence of, for example, a suitable Ar-bromide or Ar-iodide (X being Br or I respectively) and a suitable catalyst as for example 1,1'-bis(diphenylphosphino)ferrocenedichloropalladium(II) and in the presence of a suitable base as for example potassium phosphate tribasic in a suitable solvent mixture as for example THF and water at a suitable temperature between 50° C. and reflux and a suitable reaction time between 1 and 3 hours.

2: In the presence of triflic anhydride and a suitable base as for example pyridine in a suitable solvent as for example DCM at a suitable temperature as for example 0° C. under an inert atmosphere of N$_2$ gas.

3: In the presence of a suitable base as for example Cs$_2$CO$_3$ in a suitable solvent as for example DMF at a suitable temperature as for example room temperature under an inert atmosphere of N$_2$ gas.

The starting materials in scheme 9 are commercially available or can be prepared by standard means obvious to those skilled in the art or as described in the specific experimental part.

In all these preparations, the reaction products may be isolated from the reaction medium and, if necessary, further purified according to methodologies generally known in the art such as, for example, extraction, crystallization, trituration and chromatography.

The chirally pure forms of the compounds of Formula (I) form a preferred group of compounds. It is therefore that the chirally pure forms of the intermediates and their salt forms are particularly useful in the preparation of chirally pure compounds of Formula (I). Also enantiomeric mixtures of the intermediates are useful in the preparation of compounds of Formula (I) with the corresponding configuration.

Pharmacology

It has been found that the compounds of the present invention inhibit PRMT5 activity.

In particular compounds of the present invention bind to the PRMT5 enzyme, and competitively with natural substrate SAM (S-adenosyl-L-methionine), to inhibit such enzyme.

It is therefore anticipated that the compounds according to the present invention or pharmaceutical compositions thereof may be useful for treating or preventing, in particular treating, of diseases such as a blood disorder, metabolic disorders, autoimmune disorders, cancer, inflammatory diseases, cardiovascular diseases, neurodegenerative diseases, pancreatitis, multiorgan failure, kidney diseases, platelet aggregation, sperm motility, transplantation rejection, graft rejection, lung injuries and the like.

In particular the compounds according to the present invention or pharmaceutical compositions thereof may be useful for treating or preventing, in particular treating, of diseases such as allergy, asthma, hematopoietic cancer, lung cancer, prostate cancer, melanoma, metabolic disorder, diabetes, obesity, blood disorder, sickle cell anemia, and the like.

The compounds according to the present invention or pharmaceutical compositions thereof may be useful for treating or preventing, in particular treating, of diseases such as a proliferative disorder, such as an autoimmune disease, cancer, a benign neoplasm, or an inflammatory disease.

The compounds according to the present invention or pharmaceutical compositions thereof may be useful for treating or preventing, in particular treating, of diseases such as a metabolic disorder comprising diabetes, obesity; a proliferative disorder comprising cancer, hematopoietic cancer, lung cancer, prostate cancer, melanoma, or pancreatic cancer; blood disorder; hemoglobinopathy; sickle cell anemia; β-thalessenmia, an inflammatory disease, and autoimmune disease e.g. rheumatoid arthritis, systemic lupus erythematosus, Sjogren's syndrome, diarrhea, gastroesophageal reflux disease, and the like.

In some embodiments, the inhibition of PRMT5 by a provided compound may be useful in treating or preventing, in particular treating, the following non-limiting list of cancers: breast cancer, lung cancer, esophageal cancer, bladder cancer, hematopoietic cancer, lymphoma, medulloblastoma, rectum adenocarcinoma, colon adenocarcinoma, gastric cancer, pancreatic cancer, liver cancer, adenoid cystic carcinoma, lung adenocarcinoma, head and neck squamous cell carcinoma, brain tumors, hepatocellular carcinoma, renal cell carcinoma, melanoma, oligodendroglioma, ovarian clear cell carcinoma, and ovarian serous cystadenoma.

Examples of metabolic disorders which may be treated or prevented, in particular treated, include, but are not limited to, diabetes or obesity.

Examples of blood disorders which may be treated or prevented, in particular treated, include, but are not limited to, hemoglobinopathy, such as sickle cell disease or β-thalassemia.

Examples of cancers which may be treated or prevented, in particular treated, include, but are not limited to, acoustic neuroma, adenocarcinoma, adrenal gland cancer, anal cancer, angiosarcoma (e.g., lymphangio sarcoma, lymphangioendothelio sarcoma, hemangio sarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), chordoma, choriocarcinoma, craniopharyngioma, colorectal cancer (e.g., colon cancer, rectal cancer, colorectal adenocarcinoma), epithelial carcinoma, ependymoma, endothelio sarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarinoma), Ewing sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., pharyngeal cancer, laryngeal cancer, nasopharyngeal cancer, oropharyngeal cancer)), hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HIL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenstrom's macro globulinemia"), immunoblastic large cell lymphoma, hairy cell leukemia (HCL), precursor B-lymphoblastic lymphoma and primary central nervous system (CNS) lymphoma; and T-cell NHL such as precursor T-lymphoblastic lymphomaleukemia, peripheral T-cell lymphoma (PTCL) (e.g., cutaneous T-cell lymphoma (CTCL) (e.g., micosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma (MM)), heavy chain disease (e.g., alpha chain disease, gamma chain disease, mu chain disease), hemangioblastoma, inflammatory myofibroblastic tumors, immunocytic anmyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, non-small cell lung cancer (NSCLC), squamous lung cancer (SLC), adenocarcinoma of the lung, Lewis lung carcinoma, lung neuroendocrine tumors: typical carcinoid, atypical carcinoid, small cell lung cancer (SCLC), and large cell neuroendocrine carcinoma), leiomyosarcoma (LMS), mastocytosis (e.g., systemic mastocytosis), myelodysplastic syndromes (MDS), mesothelioma, myeloproliferative disorder (MPD) (e.g., polycythemia Vera (PV), essential thrombocytosis (ET), agnogenic myeloid metaplasia (AMM) a.k.a. mielofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofrofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMNN), Islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer, and vulvar cancer (e.g., Paget's disease of the vulva).

Examples of neurodegenerative diseases which may be treated or prevented, in particular treated, include, but are not limited to, motor neurone disease, progressive supranuclear palsy, corticobasal degeneration, Pick's disease, Alzheimer's disease, AIDS-related dementia, Parkinson's disease, amyotropic lateral sclerosis, retinitis pigmentosa, spinal muscular atropy, and cerebellar degeneration.

Examples of cardiovascular diseases which may be treated or prevented, in particular treated, include, but are not limited to, cardiac hypertrophy, restenosis, atherosclerosis, and glomerulonephritis.

Examples of inflammatory diseases which may be treated or prevented, in particular treated, include, but are not limited to, inflammation associated with acne, anemia (e.g., aplastic anemia, haemolytic autoimmune anaemia), rhinitis, asthma, arteritis (e.g., polyarteritis, temporal arteritis, periarteritis nodosa, Takayasu's arteritis), arthritis (e.g., crystalline arthritis, osteoarthritis, psoriatic arthritis, gouty arthritis, reactive arthritis, rheumatoid arthritis and Reiter's arthritis), upper respiratory tract disease, ankylosing spondylitis, amylosis, amyotrophic lateral sclerosis, autoimmune diseases, allergies or allergic reactions, atherosclerosis, bronchitis, bursitis, chronic prostatitis, conjunctivitis, Chagas disease, chronic obstructive pulmonary disease, diverticulitis, cermatomyositis, diabetes (e.g., type I diabetes mellitus, type 2 diabetes mellitus), a skin condition (e.g., psoriasis, eczema, eczema hypersensitivity reactions, burns, dermatitis, pruritus (itch)), endometriosis, Guillain-Barre syndrome, infection, ischaemic heart disease, Kawasaki disease, glomerulonephritis, gingivitis, hypersensitivity, headaches (e.g., migraine headaches, tension headaches), ileus (e.g., postoperative ileus and ileus during sepsis), idiopathic thrombocytopenic purpura, interstitial cystitis (painful bladder syndrome), gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), lupus, morphea, myeasthenia gravis, myocardial ischemia, multiple sclerosis, nephrotic syndrome, pemphigus vulgaris, pernicious aneaemia, peptic ulcers, polymyositis, primary biliary cirrhosis, neuroinflammation associated with brain disorders (e.g., Parkinson's disease, Huntington's disease, and Alzheimer's disease), prostatitis, chronic inflammation associated with cranial radiation injury, pelvic inflammatory disease, reperfusion injury, regional enteritis, rheumatic fever, systemic lupus erythematosus, schleroderma, scierodoma, sarcoidosis, spondyloarthopathies, Sjogren's syndrome, thyroiditis, transplantation rejection, tendonitis, trauma or injury (e.g., frostbite, chemical irritants, toxins, scarring, burns, physical injury), vasculitis, vitiligo and Wegener's granulomatosis.

In particular the inflammatory disease is an acute inflammatory disease (e.g., for example, inflammation resulting from infection). In particular the inflammatory disease is a chronic inflammatory disease (e.g., conditions resulting from asthma, arthritis and inflammatory bowel disease). The compounds may also be useful in treating inflammation associated with trauma and non-inflammatory myalgia. The compounds may also be useful in treating inflammation associated with cancer.

Examples of autoimmune diseases which may be treated or prevented, in particular treated, include, but are not limited to, arthritis (including rheumatoid arthritis, spondyloarthopathies, gouty arthritis, degenerative joint diseases such as osteoarthritis, systemic lupus erythematosus, Sjogren's syndrome, ankylosing spondylitis, undifferentiated spondvlitis, Behcet's disease, haemolytic autoimmune anaemias, amyotrophic lateral sclerosis, amylosis, multiple sclerosis, acute painful shoulder, psoriatic, and juvenile arthritis), asthma, atherosclerosis, osteoporosis, bronchitis, tendonitis, bursitis, skin condition (e.g., psoriasis, eczema, eczema, hypersensitiviy reactions, burns, dermatitis, pruritus (itch)), enuresis, eosinophilic disease, gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymnphocytic colitis, ischaenmic colitis, diversion colitis, Behcet's syndrome, indeterminate colitis) and inflammatory bowel syndrome (IBS)), and disorders ameliorated by a gastroprokinetic agent (e.g., ileus, postoperative ileus and ileus during sepsis; gastroesophageal reflux disease (GORD, or its synonym GERD); eosinophilic esophagitis, gastroparesis such as diabetic gastroparesis; food intolerances and food allergies and other functional bowel disorders, such as non-ulcerative dyspepsia (NUD) and non-cardiac chest pain (NCCP, including costo-chondritis)).

In a particular embodiment, a provided compound may be useful in somatic cell reprogramming, such as reprogramming somatic cells into stem cells. In a particular embodiment, a provided compound may be useful in germ cell development, and are thus envisioned useful in the areas of reproductive technology and regenerative medicine.

Other diseases which may be treated or prevented, in particular treated, include, but are not limited to, ischemic injury associated myocardial infarctions, immunological diseases, stroke, arrhythmia, toxin-induced or alcohol related liver diseases, aspirin-sensitive rhinosinusitis, cystic fibrosis, cancer pain, and haemnatological diseases, for example chronic anemia and aplastic anemia.

The compounds of the present invention may also have therapeutic applications in sensitising tumour cells for radiotherapy and chemotherapy.

Hence the compounds of the present invention may be used as "radiosensitizer" and/or "chemosensitizer" or can be given in combination with another "radiosensitizer" and/or "chemosensitizer".

The term "radiosensitizer", as used herein, is defined as a molecule, preferably a low molecular weight molecule, administered to animals in therapeutically effective amounts to increase the sensitivity of the cells to ionizing radiation and/or to promote the treatment of diseases which are treatable with ionizing radiation.

The term "chemosensitizer", as used herein, is defined as a molecule, preferably a low molecular weight molecule, administered to animals in therapeutically effective amounts to increase the sensitivity of cells to chemotherapy and/or promote the treatment of diseases which are treatable with chemotherapeutics.

Several mechanisms for the mode of action of radiosensitizers have been suggested in the literature including: hypoxic cell radiosensitizers (e.g., 2-nitroimidazole compounds, and benzotriazine dioxide compounds) mimicking oxygen or alternatively behave like bioreductive agents under hypoxia; non-hypoxic cell radiosensitizers (e.g., halogenated pyrimidines) can be analogoues of DNA bases and preferentially incorporate into the DNA of cancer cells and thereby promote the radiation-induced breaking of DNA molecules and/or prevent the normal DNA repair mechanisms; and various other potential mechanisms of action have been hypothesized for radiosensitizers in the treatment of disease.

Many cancer treatment protocols currently employ radiosensitizers in conjunction with radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumour with or without additional radiation; or other therapeutically effective compounds for treating cancer or other diseases.

Chemosensitizers may be administered in conjunction with a therapeutically effective amount of one or more other compounds, including but not limited to: compounds which promote the incorporation of chemosensitizers to the target cells; compounds which control the flow of therapeutics, nutrients, and/or oxygen to the target cells; chemotherapeutic agents which act on the tumour or other therapeutically effective compounds for treating cancer or other disease. Calcium antagonists, for example verapamil, are found useful in combination with antineoplastic agents to establish chemosensitivity in tumor cells resistant to accepted chemotherapeutic agents and to potentiate the efficacy of such compounds in drug-sensitive malignancies.

The compounds of the present invention might also reduce the risk of cancer recurrence.

The invention relates to compounds of Formula (I) and pharmaceutically acceptable addition salts, and solvates thereof, for use as a medicament.

The invention relates to compounds of Formula (I) and pharmaceutically acceptable addition salts, and solvates thereof, for use in the inhibition of PRMT5 activity.

The compounds of the present invention can be "anticancer agents", which term also encompasses "anti-tumor cell growth agents" and "anti-neoplastic agents".

The invention relates to compounds of Formula (I) and pharmaceutically acceptable addition salts, and solvates thereof, for use in the treatment of diseases mentioned above.

The invention relates to compounds of Formula (I) and pharmaceutically acceptable addition salts, and solvates thereof, for the treatment or prevention, in particular for the treatment, of said diseases.

The invention relates to compounds of Formula (I) and pharmaceutically acceptable addition salts, and solvates thereof, for the treatment or prevention, in particular in the treatment, of PRMT5 mediated diseases or conditions.

The invention relates to compounds of Formula (I) and pharmaceutically acceptable addition salts, and solvates thereof, for the manufacture of a medicament.

The invention relates to compounds of Formula (I) and pharmaceutically acceptable addition salts, and solvates thereof, for the manufacture of a medicament for the inhibition of PRMT5.

The invention relates to compounds of Formula (I) and pharmaceutically acceptable addition salts, and solvates thereof, for the manufacture of a medicament for the treatment or prevention, in particular for the treatment, of any one of the disease conditions mentioned hereinbefore.

The invention relates to compounds of Formula (I) and pharmaceutically acceptable addition salts, and solvates thereof, for the manufacture of a medicament for the treatment of any one of the disease conditions mentioned hereinbefore.

The invention relates to compounds of Formula (I) and pharmaceutically acceptable addition salts, and solvates thereof, can be administered to mammals, preferably humans, for the treatment or prevention of any one of the diseases mentioned hereinbefore.

In view of the utility of the compounds of Formula (I) and pharmaceutically acceptable addition salts, and solvates thereof, there is provided a method of treating warm-blooded animals, including humans, suffering from or a method of preventing warm-blooded animals, including humans, to suffer from any one of the diseases mentioned hereinbefore.

Said methods comprise the administration, i.e. the systemic or topical administration, preferably oral administration, of an effective amount of a compound of Formula (I) or a pharmaceutically acceptable addition salt, or a solvate thereof, to warm-blooded animals, including humans.

Those of skill in the treatment of such diseases could determine the effective therapeutic daily amount from the test results presented hereinafter. An effective therapeutic daily amount would be from about 0.005 mg/kg to 50 mg/kg, in particular 0.01 mg/kg to 50 mg/kg body weight, more in particular from 0.01 mg/kg to 25 mg/kg body weight, preferably from about 0.01 mg/kg to about 15 mg/kg, more preferably from about 0.01 mg/kg to about 10 mg/kg, even more preferably from about 0.01 mg/kg to about 1 mg/kg, most preferably from about 0.05 mg/kg to about 1 mg/kg body weight. A particular effective therapeutic daily amount might be from about 0.01 to 1.00 g twice a day (BID), more in particular 0.30 to 0.85 g BID; even more in particular 0.40 g BID. The amount of a compound according to the present invention, also referred to here as the active ingredient, which is required to achieve a therapeutically effect will of course, vary on case-by-case basis, for example with the particular compound, the route of administration, the age and condition of the recipient, and the particular disorder or disease being treated.

A method of treatment may also include administering the active ingredient on a regimen of between one and four intakes per day. In these methods of treatment the compounds according to the invention are preferably formulated prior to administration. As described herein below, suitable pharmaceutical formulations are prepared by known procedures using well known and readily available ingredients.

The compounds of the present invention, that can be suitable to treat or prevent cancer or cancer-related conditions, may be administered alone or in combination with one or more additional therapeutic agents. Combination therapy includes administration of a single pharmaceutical dosage formulation which contains a compound of Formula (I), a pharmaceutically acceptable addition salt, or a solvate thereof, and one or more additional therapeutic agents, as well as administration of the compound of Formula (I), a pharmaceutically acceptable addition salt, or a solvate thereof, and each additional therapeutic agents in its own separate pharmaceutical dosage formulation. For example, a compound of Formula (I), a pharmaceutically acceptable addition salt, or a solvate thereof, and a therapeutic agent may be administered to the patient together in a single oral dosage composition such as a tablet or capsule, or each agent may be administered in separate oral dosage formulations.

While it is possible for the active ingredient to be administered alone, it is preferable to present it as a pharmaceutical composition.

Accordingly, the present invention further provides a pharmaceutical composition and, as active ingredient, a therapeutically effective amount of a compound of Formula (I), a pharmaceutically acceptable addition salt, or a solvate thereof.

Accordingly, the present invention further provides a pharmaceutical composition comprising a pharmaceutically acceptable carrier and, as active ingredient, a therapeutically effective amount of a compound of Formula (I), a pharmaceutically acceptable addition salt, or a solvate thereof.

The carrier or diluent must be "acceptable" in the sense of being compatible with the other ingredients of the composition and not deleterious to the recipients thereof.

For ease of administration, the subject compounds may be formulated into various pharmaceutical forms for administration purposes. The compounds according to the invention, in particular the compounds of Formula (I) and pharmaceutically acceptable addition salts, and solvates thereof, or any subgroup or combination thereof may be formulated into various pharmaceutical forms for administration purposes. As appropriate compositions there may be cited all compositions usually employed for systemically administering drugs.

To prepare the pharmaceutical compositions of this invention, an effective amount of the particular compound as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions containing a compound of Formula (I), a pharmaceutically acceptable addition salt, or a solvate thereof, may be formulated in an oil for prolonged action. Appropriate oils for this purpose are, for example, peanut oil, sesame oil, cottonseed oil, corn oil, soybean oil, synthetic glycerol esters of long chain fatty acids and mixtures of these and other oils. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. Acid or base addition salts of compounds of Formula (I) due to their increased water solubility over the corresponding base or acid form, are more suitable in the preparation of aqueous compositions.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

In order to enhance the solubility and/or the stability of the compounds of Formula (I) and pharmaceutically acceptable addition salts, and solvates thereof in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the invention in pharmaceutical compositions.

Depending on the mode of administration, the pharmaceutical composition will preferably comprise from 0.05 to 99% by weight, more preferably from 0.1 to 70% by weight, even more preferably from 0.1 to 50% by weight of the compound of Formula (I), a pharmaceutically acceptable addition salt, or a solvate thereof, and from 1 to 99.95% by weight, more preferably from 30 to 99.9% by weight, even more preferably from 50 to 99.9% by weight of a pharmaceutically acceptable carrier, all percentages being based on the total weight of the composition.

As another aspect of the present invention, a combination of a compound of the present invention with another anti-cancer agent is envisaged, especially for use as a medicine, more specifically for use in the treatment of cancer or related diseases.

For the treatment of the above conditions, the compounds of the invention may be advantageously employed in combination with antibody based immune cell redirection, for example T-cell/neutrophil redirection. This can be achieved for example by the use of bispecific monoclonal antibodies or artificial T-cell receptors.

For the treatment of the above conditions, the compounds of the invention may be advantageously employed in combination with one or more other medicinal agents, more particularly, with other anti-cancer agents or adjuvants in cancer therapy.

Examples of anti-cancer agents or adjuvants (supporting agents in the therapy) include but are not limited to:
  platinum coordination compounds for example cisplatin optionally combined with amifostine, carboplatin or oxaliplatin;
  taxane compounds for example paclitaxel, paclitaxel protein bound particles (Abraxane™) or docetaxel;
  topoisomerase I inhibitors such as camptothecin compounds for example irinotecan, SN-38, topotecan, topotecan hcl;
  topoisomerase II inhibitors such as anti-tumour epipodophyllotoxins or podophyllotoxin derivatives for example etoposide, etoposide phosphate or teniposide;

anti-tumour *vinca* alkaloids for example vinblastine, vincristine or vinorelbine;

anti-tumour nucleoside derivatives for example 5-fluorouracil, leucovorin, gemcitabine, gemcitabine hcl, capecitabine, cladribine, fludarabine, nelarabine;

alkylating agents such as nitrogen mustard or nitrosourea for example cyclophosphamide, chlorambucil, carmustine, thiotepa, mephalan (melphalan), lomustine, altretamine, busulfan, dacarbazine, estramustine, ifosfamide optionally in combination with mesna, pipobroman, procarbazine, streptozocin, temozolomide, uracil;

anti-tumour anthracycline derivatives for example daunorubicin, doxorubicin optionally in combination with dexrazoxane, doxil, idarubicin, mitoxantrone, epirubicin, epirubicin hcl, valrubicin;

molecules that target the IGF-1 receptor for example picropodophilin;

tetracarcin derivatives for example tetrocarcin A;

glucocoorticoids for example prednisone;

antibodies for example trastuzumab (HER2 antibody), rituximab (CD20 antibody), gemtuzumab, gemtuzumab ozogamicin, cetuximab, pertuzumab, bevacizumab, alemtuzumab, eculizumab, ibritumomab tiuxetan, nofetumomab, panitumumab, tositumomab, CNTO 328;

estrogen receptor antagonists or selective estrogen receptor modulators or inhibitors of estrogen synthesis for example tamoxifen, fulvestrant, toremifene, droloxifene, faslodex, raloxifene or letrozole;

aromatase inhibitors such as exemestane, anastrozole, letrazole, testolactone and vorozole;

differentiating agents such as retinoids, vitamin D or retinoic acid and retinoic acid metabolism blocking agents (RAMBA) for example accutane;

DNA methyl transferase inhibitors for example azacytidine or decitabine;

antifolates for example premetrexed disodium;

antibiotics for example antinomycin D, bleomycin, mitomycin C, dactinomycin, carminomycin, daunonmycin, levamisole, plicamycin, mithramycin;

antimetabolites for example clofarabine, aminopterin, cytosine arabinoside or methotrexate, azacitidine, cytarabine, floxuridine, pentostatin, thioguanine;

apoptosis inducing agents and antiangiogenic agents such as Bcl-2 inhibitors for example YC 137, BH 312, ABT 737, gossypol, HA 14-1, TW 37 or decanoic acid;

tubuline-binding agents for example combrestatin, colchicines or nocodazole;

kinase inhibitors (e.g. EGFR (epithelial growth factor receptor) inhibitors, MTKI (multi target kinase inhibitors), mTOR inhibitors) for example flavoperidol, imatinib mesylate, erlotinib, gefitinib, dasatinib, lapatinib, lapatinib ditosylate, sorafenib, sunitinib, sunitinib maleate, temsirolimus;

famesyltransferase inhibitors for example tipifarnib;

histone deacetylase (HDAC) inhibitors for example sodium butyrate, suberoylanilide hydroxamic acid (SAHA), depsipeptide (FR 901228), NVP-LAQ824, R306465, JNJ-26481585, trichostatin A, vorinostat;

Inhibitors of the ubiquitin-proteasome pathway for example PS-341, MLN 0.41 or bortezomib;

Yondelis;

Telomerase inhibitors for example telomestatin;

Matrix metalloproteinase inhibitors for example batimastat, marimastat, prinostat or metastat.

Recombinant interleukins for example aldesleukin, denileukin diftitox, interferon alfa 2a, interferon alfa 2b, peginterferon alfa 2b MAPK inhibitors Retinoids for example alitretinoin, bexarotene, tretinoin Arsenic trioxide Asparaginase Steroids for example dromostanolone propionate, megestrol acetate, nandrolone (decanoate, phenpropionate), dexamethasone Gonadotropin releasing hormone agonists or antagonists for example abarelix, goserelin acetate, histrelin acetate, leuprolide acetate Thalidomide, lenalidomide Mercaptopurine, mitotane, pamidronate, pegademase, pegaspargase, rasburicase BH3 mimetics for example ABT-737

MEK inhibitors for example PD98059, AZD6244, CI-1040 colony-stimulating factor analogs for example filgrastim, pegfilgrastim, sargramostim; erythropoietin or analogues thereof (e.g. darbepoetin alfa); interleukin 11; oprelvekin; zoledronate, zoledronic acid; fentanyl; bisphosphonate; palifermin a steroidal cytochrome P450 17alpha-hydroxylase-17,20-lyase inhibitor (CYP17), e.g. abiraterone, abiraterone acetate Glycolysis inhibitors, such as 2-deoxyglucose mTOR inhibitors such as rapamycins and rapalogs, and mTOR kinase inhibitors PI3K inhibitors and dual mTOR/PI3K inhibitors autophagy inhibitors, such as chloroquine and hydroxychloroquine antibodies that re-activate the immune response to tumors, for example nivolumab (anti-PD-1), lambrolizumab (anti-PD-1), ipilimumab (anti-CTLA4), and MPDL3280A (anti-PD-L1).

The present invention further relates to a product containing as first active ingredient a compound according to the invention and as further active ingredient one or more anticancer agents, as a combined preparation for simultaneous, separate or sequential use in the treatment of patients suffering from cancer.

The one or more other medicinal agents and the compound according to the present invention may be administered simultaneously (e.g. in separate or unitary compositions) or sequentially in either order. In the latter case, the two or more compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and compound of the present invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of Formula (I) and another anticancer agent may range from 1/10 to 10/1, more in particular from 1/5 to 5/1, even more in particular from 1/3 to 3/1.

The platinum coordination compound is advantageously administered in a dosage of 1 to 500 mg per square meter (mg/m$^2$) of body surface area, for example 50 to 400 mg/m$^2$, particularly for cisplatin in a dosage of about 75 mg/m$^2$ and for carboplatin in about 300 mg/m$^2$ per course of treatment.

The taxane compound is advantageously administered in a dosage of 50 to 400 mg per square meter (mg/m$^2$) of body surface area, for example 75 to 250 mg/m$^2$, particularly for paclitaxel in a dosage of about 175 to 250 mg/m$^2$ and for docetaxel in about 75 to 150 mg/m$^2$ per course of treatment.

The camptothecin compound is advantageously administered in a dosage of 0.1 to 400 mg per square meter (mg/m$^2$) of body surface area, for example 1 to 300 mg/m$^2$, particularly for irinotecan in a dosage of about 100 to 350 mg/m$^2$ and for topotecan in about 1 to 2 mg/m$^2$ per course of treatment.

The anti-tumour podophyllotoxin derivative is advantageously administered in a dosage of 30 to 300 mg per square meter (mg/m$^2$) of body surface area, for example 50 to 250 mg/m$^2$, particularly for etoposide in a dosage of about 35 to 100 mg/m$^2$ and for teniposide in about 50 to 250 mg/m$^2$ per course of treatment.

The anti-tumour *vinca* alkaloid is advantageously administered in a dosage of 2 to 30 mg per square meter (mg/m$^2$) of body surface area, particularly for vinblastine in a dosage of about 3 to 12 mg/m$^2$, for vincristine in a dosage of about 1 to 2 mg/m$^2$, and for vinorelbine in dosage of about 10 to 30 mg/m$^2$ per course of treatment.

The anti-tumour nucleoside derivative is advantageously administered in a dosage of 200 to 2500 mg per square meter (mg/m$^2$) of body surface area, for example 700 to 1500 mg/m$^2$, particularly for 5-FU in a dosage of 200 to 500 mg/m$^2$, for gemcitabine in a dosage of about 800 to 1200 mg/m$^2$ and for capecitabine in about 1000 to 2500 ng/m$^2$ per course of treatment.

The alkylating agents such as nitrogen mustard or nitrosourea is advantageously administered in a dosage of 100 to 500 mg per square meter (mg/m$^2$) of body surface area, for example 120 to 200 mg/m$^2$, particularly for cyclophosphamide in a dosage of about 100 to 500 mg/nm, for chlorambucil in a dosage of about 0.1 to 0.2 mg/kg, for carmustine in a dosage of about 150 to 200 mg/m$^2$, and for lomustine in a dosage of about 100 to 150 mg/m$^2$ per course of treatment.

The anti-tumour anthracycline derivative is advantageously administered in a dosage of 10 to 75 mg per square meter (mg/m$^2$) of body surface area, for example 15 to 60 mg/m$^2$, particularly for doxorubicin in a dosage of about 40 to 75 mg/m$^2$, for daunorubicin in a dosage of about 25 to 45 mg/m$^2$, and for idarubicin in a dosage of about 10 to 15 mg/m$^2$ per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter (mg/m$^2$) of body surface area, or as known in the art, if different. Trastuzumab is advantageously administered in a dosage of 1 to 5 mg per square meter (mg/m$^2$) of body surface area, particularly 2 to 4 mg/m$^2$ per course of treatment.

These dosages may be administered for example once, twice or more per course of treatment, which may be repeated for example every 7, 14, 21 or 28 days.

The following examples illustrate the present invention. In case no specific stereochemistry is indicated for a stereocenter of a compound, this means that a mixture of the R and the S enantiomers was obtained. In case more than 1 stereocenter is present in a structure, each stereocenter for which no specific stereochemistry is indicated was obtained as a mixture of R and S.

The skilled person will realize that typically after a column purification, the desired fractions were collected and the solvent was evaporated to obtain the desired compound or intermediate.

EXAMPLES

Hereinafter, the term "rt", "r.t." or "RT" means room temperature; "Me" means methyl; "MeOH" means methanol; "Et" means ethyl; "EtOH" means ethanol; "NaH" means sodium hydride; "Boc" means tert-butoxycarbonyl; "(Boc)$_2$O" means tert-butoxycarbonyl anhydride; "EtOAc" means ethyl acetate; "Et$_2$O" means di-ethylether; "Et$_3$N" means triethylanine; "DCM" means dichloromethane; "q.s." means quantum sufficit; "Int." means intermediate; "MeCN" or "ACN" means acetonitrile; "DMF" means N,N-dimethyl formamide; "PdCl$_2$(dppf)" means [1,1'-Bis(diphenylphosphino)ferrocene]dichloropalladium(II); "THF" means tetrahydrofuran; "IPA" or "iPrOH" means 2-propanol; "LC" means liquid chromatography; "LCMS" means Liquid Chromatography/Mass spectrometry; "HPLC" means high-performance liquid chromatography; "TFA" means trifluoroacetic acid; "RP" means reversed phase; "min" means minute(s); "h" means hour(s); "v/v" means volume per volume; "Celite®" means diatomaceous earth; "DMSO" means dimethyl sulfoxide; "SFC" means Supercritical Fluid Chromatography; "DIPE" means diisopropyl ether; "DIPEA" means N,N-diisopropylethylamine; "PPh$_3$" means triphenylphosphine; "Pd$_2$(dba)$_3$" means Tris(dibenzylideneacetone)dipalladium; "DIAD" means diisopropyl azodicarboxylate; "TBAF" means tetrabutylammonium fluoride; "psi" means pound-force per square inch; "eq." means equivalent(s); "Pd(OAc)$_2$" means palladium(II) acetate; "DMAP" means 4-(dimethylamino)pyridine; "t-BuOK" or "KOtBu" means potassium tert-butoxide; "Dess-Martin periodinane" means 1,1,1-Triacetoxy-1,1-dihydro-1,2-benziodoxol-3(1H)-one; "TBDMSCl" means tert-Butyldimethylsilyl chloride; "Bn" means benzyl; "9-BBN" means 9-Borabicyclo[3.3.1]nonane; "Pd-118" means Dichloro[1,1'-bis(di-tert-butylphosphino)ferrocene]palladium(II); "Tf₂O" means triflic anhydride; "TBDMS" means tertButyl dimethylsilyl; "TMSCl" trimethylsilyl chloride; "BuLi" means n-butyllithium; "aq." means aqueous; "NaOMe" means sodium methoxide; "tBuOH" means tert-butyl alcohol; "n-BuOH" means n-butanol; "NaHMDS" means sodium bis(trimethylsilyl)amide; "Diazald®" means N-Methyl-N-(p-tolylsulfonyl)nitrosamide; "Ts" or "Tos" means tosyl (p-toluenesulfonyl).

Intermediates and compounds containing a double bond with substituents which may be in the E or the Z configuration are show in one particular configuration in the experimental part below. However, unless explicitly indicated by E or Z, it was not determined if these intermediates and compounds were obtained in the E or Z configuration or as a mixture of both configurations. For example intermediates 86, 90, 91, and 139 might be in the E or Z configuration or might be mixtures thereof.

For example compounds 30, 34, 35, 36, and 37, were obtained in the E configuration and are explicitly indicated as such E in the experimental part below.

A. Preparation of Intermediates

Example A1

Preparation of Intermediate 1

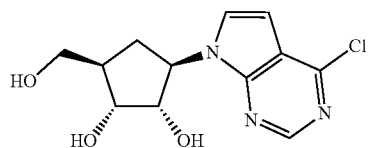

intermediate 1

To a mixture of 4,6-dichloro-5-(2,2-diethoxyethyl)pyrimidine (14.0 g, 52.8 mmol) and (1R,2S,3R,5R)-3-amino-5-(hydroxymethyl)cyclopentane-1,2-diol hydrochloride (10.7 g, 58.1 mmol) in propan-2-ol/H₂O (208 mL, 7:1), was added Et₃N (13.4 g, 132 mmol) in one portion at 25° C. under N₂. The mixture was stirred at 90° C. for 23 hours. The mixture was cooled to 50° C. and 4M HCl (24 mL, 106 mmol) was added slowly. The residue was then stirred at 50° C. for 2 hours. The reaction mixture was cooled to 25° C. and NaHCO₃ (14 g, 100 mmol) was added slowly. Ethyl acetate (230 mL) was added, followed by the addition of a half-saturated NaHCO₃ solution (q.s.). The organic phase was isolated and the aqueous phase was extracted with ethyl acetate (230 mL×2). The combined organic phases were dried with anhydrous MgSO₄, filtered and concentrated in vacuum to afford intermediate 1 as yellow solid (17.4 g, quantitative yield in 2 steps). The crude product was directly used as such in the next reaction step without further purification.

Example A2

Preparation of Intermediate 2

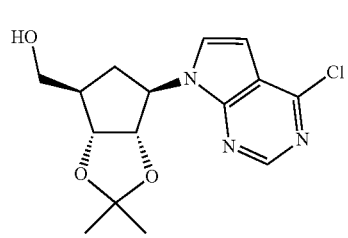

intermediate 2

To a mixture of intermediate 1 (17.4 g, 52.7 mmol) in acetone (250 mL) was added 2,2-dimethoxypropane (11.0 g, 105 mmol) and TsOH.H₂O (908 mg, 5.27 mmol) in one portion at 25° C. under N₂. The mixture was stirred at 60° C. for 2 hours. The mixture was cooled to 25° C. and the solution was partially concentrated in vacuum, quenched by slow addition of saturated NaHCO₃ (100 mL) and then extracted with ethyl acetate (100 mL×3). The combined organic phases were washed with saturated brine (100 mL), dried with anhydrous MgSO₄, filtered and concentrated in vacuum. The residue was purified by flash chromatography on silica gel (gradient elution: DCM/Ethyl acetate from 1/0 to 2/1) to afford intermediate 2 as light yellow gum (15.5 g, 89% yield).

Example A3

Preparation of Intermediate 3

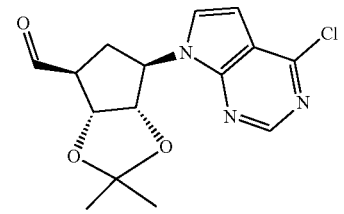

intermediate 3

To a mixture of intermediate 2 (2.85 g, 8.8 mmol) in DCM (130 mL) was added Dess-Martin periodinane (4.85 g, 11.4 mmol) at 0° C. under N₂. The mixture was stirred at room temperature for 2 hours. The mixture was treated with Na₂S₂O₃ (15 g) dissolved in a saturated NaHCO₃ solution (65 mL) and stirred for another 30 min. The layers were separated and the aqueous phase was extracted with DCM (50 mL×3). The combined organic phases were washed with a saturated NaHCO₃ solution (65 mL) dried with anhydrous MgSO₄, filtered and concentrated in vacuum to afford crude intermediate 3 (2.9 g) which was directly used in the next reaction step without further purification.

Example A4

Preparation of Intermediate 4

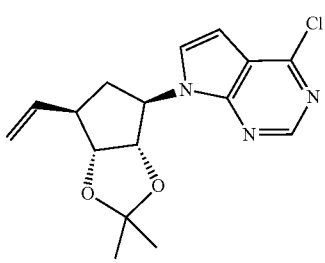

Intermediate 4

Method 1

To a mixture of methyltriphenylphosphonium bromide (4.87 g, 13.62 mmol) in THF (500 mL) was added t-BuOK (11.4 mL, 1 M in THF, 1.27 g, 11.35 mmol,) dropwise at 0° C. under $N_2$. The suspension was turned to bright yellow and stirred at 0° C. for 0.5 h and then warmed to 25° C. for 0.5 h. The mixture was cooled to −40° C. A solution of intermediate 3 (1.46 g, theoretically 4.54 mmol) in THF (130 mL) was added drop-wise and then stirred at −20° C. for 1 h, after this, the mixture was warmed to 25° C. for 2 h. To the mixture was added saturated $NH_4Cl$ (300 ml) and the mixture was stirred for 10 min. The layers were separated and the aqueous phase was extracted with DCM (300 mL×2). The combined organic phases were washed with saturated brine (500 mL), dried with anhydrous $MgSO_4$, filtered and concentrated in vacuum. The residue was purified by silica gel chromatography (ISCO®; 80 g SepaFlash® Silica Flash Column, Gradient eluention: From 0% to 15% of Ethyl acetate/Petroleum ether). The desired fractions were collected and the solvent was evaporated. Intermediate 4 was obtained as an off-white solid (530 mg, 36% yield).

Method 2

A solution of intermediate 3 (10.0 g, theoretically 31.1 mmol) in THF (100 mL) was added dropwise under $N_2$ over a period of 30 minutes to a bis(iodozincio)methane solution in THF (180 mL, 0.31 M, 55.9 mmol, prepared according to the procedure described in Tetrahedron 2002, 58, 8255-8262), stirring was continued until complete conversion (approximately 2 hours). The reaction mixture was quenched by the slow addition of a saturated aqueous $NH_4Cl$ solution, during which salt formation was observed. Prior to extraction (EtOAc, 2×200 mL), the salts were dissolved again by the addition of an aqueous ammonia solution (25%). The combined organic phases were washed with an aqueous sodium bisulfite solution and brine, dried with anhydrous $MgSO_4$, filtered and concentrated in vacuum. The residue was purified by silica gel chromatography (eluent: dichloromethane/EtOAc 95/5) to provide intermediate 4 as an off-white solid (6.9 g, 66%).

Method 3

Step 1

Preparation of Intermediate 5

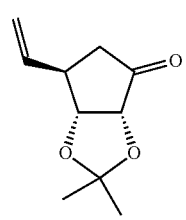

intermediate 5

Acetylacetonatobis(ethylene)rhodium(I) (0.837 g, 3.24 mmol) and (R)—N,N-dimethyldinaphtho[2,1-D:1',2'-F][1,3,2]dioxaphosphepin-4-amine (2.91 g, 8.11 mmol) were dissolved in EtOH (625 mL) under nitrogen atmosphere. The mixture was stirred at room temperature and flushed through with nitrogen gas for 15 minutes. Then (−)-(3AR,6AR)-3A,6A-dihydro-2,2-dimethyl-4H-cyclopenta-1,3-dioxol-4-one (25 g, 162.16 mmol) and potassium vinyltrifluoroborate (45.73 g, 324.33 mmol) were added and then the reaction mixture was stirred and refluxed for 4 hours. The reaction mixture (suspension) was cooled down to room temperature. The precipitate was filtered off over a pad of Celite® and washed with ethanol. The solvents of the filtrate were evaporated. 1 L heptane was added to the residue. The resulting suspension was filtered off over a pad of Celite® and washed with heptanes resulting in a dark brown solid residue. The filtrate was washed three times with 300 mL $NH_4OH$, washed with brine, dried with $MgSO_4$, filtered and the solvents of the filtrate evaporated yielding intermediate 5 (16.18 g, 51% yield).

Step 2

Preparation of Intermediate 6

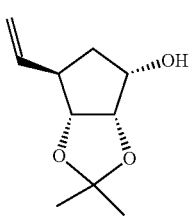

intermediate 6

A solution of intermediate 5 (16.18 g, 82.58 mmol) in THF (200 mL) was added dropwise to a stirred solution of lithium aluminum hydride in THF (24.78 mL, 1 M, 24.78 mmol) in THF (400 mL) at −78° C. under nitrogen atmosphere. The reaction mixture was stirred at −78° C. under nitrogen atmosphere for 30 minutes. The reaction was quenched by the dropwise addition of acetone (6.1 mL) followed by 50 mL water at −78° C. After addition the reaction mixture was allowed to warm up to room temperature and then 400 mL EtOAc was added. The mixture was shaken vigorously. The organic layer was separated, washed three times with water, washed with brine, dried with MgSO$_4$, filtered and the solvents of the filtrate evaporated. The residue was dissolved in ethyl acetate and purified over a SiO$_2$ column, type Grace Reveleris SRC, 80 g, Si 40, on an Armen Spot II Ultimate purification system using ethyl acetate and heptane as eluent in a gradient starting from 100% heptane and ending with 50% heptane and 50% ethyl acetate. The fractions containing product were combined and the solvents were evaporated yielding intermediate 6 (10.77 g, 71% yield).

Step 3

Preparation of Intermediate 7

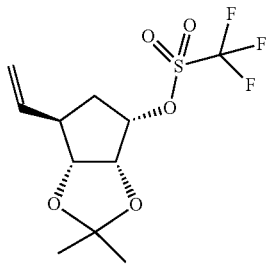

intermediate 7

A solution of Tf$_2$O (13.3 mL, 80.9 mmol) in DCM, anhydrous (60 ml) was added dropwise to a mixture of intermediate 6 (9.94 g, 53.95 mmol) and pyridine, anhydrous (85 mL) in DCM, anhydrous (140 mL) at 0° C. The reaction mixture was stirred for 30 minutes and then 75 mL cold water was added. The layers were separated and the organic layer was washed three times with 75 mL water, dried with MgSO$_4$, filtered and the solvents evaporated and co-evaporated with 200 mL toluene. The residue was dissolved in heptane and ethyl acetate and purified over a SiO$_2$ column, type Grace Reveleris SRC, 40 g, Si 40, on an Armen Spot II Ultimate purification system using ethyl acetate and heptane as eluent in a gradient starting from 100% heptane and ending with 50% heptane and 50% ethyl acetate. The fractions containing product were combined and the solvents were evaporated yielding intermediate 7 (13.0 g, 67% yield).

Below intermediates were prepared by an analogous reaction protocol as was used for the preparation of intermediate 7 using the appropriate starting materials (Table 22)

TABLE 22

| Int. | structure | Starting materials |
|---|---|---|
| 97 | 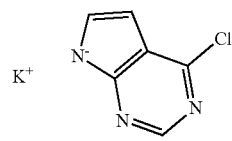 | intermediate 96 |
| 116 | 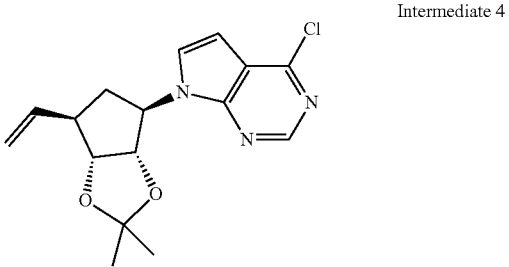 [SMILES: C=C[C@H]1C[C@@H](n2ccc3c(Cl)ncnc32)[C@@H]2OC(C)(C)O[C@@H]21] | intermediate 115 |

Step 4

Preparation of Intermediate 8

Intermediate 8

A mixture of 4-chloro-7H-pyrrolo [2,3-D]pyrimidine (100 g, 651 mmol) and KOtBu (73.07 g, 651 mmol) in THF (1 L) was stirred at room temperature for 45 minutes until a clear solution was obtained. The solvents were evaporated. The residue was triturated in DIPE. The white solids were filtered off and dried in vacuo at 30° C. yielding intermediate 8 (112.6 g, 90% yield).

Step 5

Preparation of Intermediate 4

Intermediate 4

A solution of intermediate 7 (13 g, 41.1 mmol) in DMF (50 mL) was added dropwise to a stirred solution of intermediate 8 (7.88 g, 41.1 mmol) in DMF (150 mL) at 0° C. After addition the reaction mixture was allowed to warm to room temperature and was then stirred for 18 hours. An additional amount of intermediate 8 (1.57 g, 8.22 mmol) was added. The reaction mixture was stirred at room temperature for 2 hours. The reaction mixture was poured out into a beaker with ice and water (~0.5 L). The resulting suspension was stirred for 2 hours and then filtered off. The filter cake was washed three times with water and then dried in vacuo at 50° C. yielding intermediate 4 as a white solid (8.75 g, 65% yield).

Below intermediates were prepared by an analogous reaction protocol as was used for the preparation of intermediate 4 using the appropriate starting materials (Table 23)

TABLE 23

| Int. | structure | Starting materials |
|---|---|---|
| 98 | 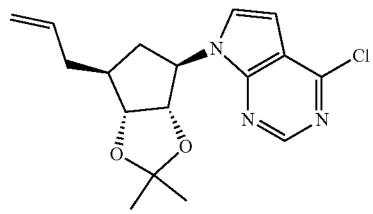 [SMILES: C=CC[C@H]1C[C@@H](n2ccc3c(Cl)ncnc32)[C@@H]2OC(C)(C)O[C@H]12] | intermediate 97 |
| 117 | 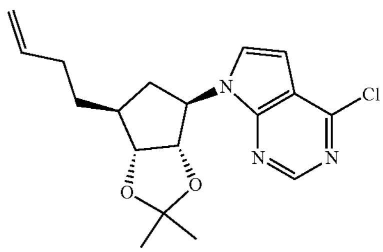 [SMILES: C=CCC[C@H]1C[C@@H](n2ccc3c(Cl)ncnc32)[C@@H]2OC(C)(C)O[C@H]12] | intermediate 116 |

Example A5

Preparation of Intermediate 9

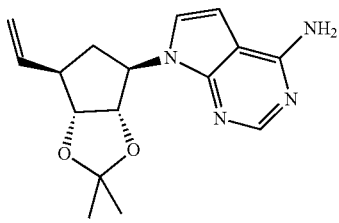

intermediate 9

A solution of intermediate 4 (18.3 g, 57.22 mmol) in a mixture of aqueous ammonia (25%, 100 ml) and THF (100 ml) was heated in a sealed metal pressure vessel at 110° C. until complete conversion (~16 h). The reaction mixture was allowed to cool to room temperature, after which ethyl acetate and brine were added. Both layers were separated, the water layer was extracted once with ethyl acetate. The combined organic phases were washed with brine, dried with anhydrous $MgSO_4$, filtered and concentrated in vacuum to give intermediate 9 as a light yellow solid (17.2 g, 100% yield), which was used in the next reaction step without further purification.

Below intermediates were prepared by an analogous reaction protocol as was used for the preparation of intermediate 9 using the appropriate starting materials (Table 24)

TABLE 24

| Int. | structure | Starting materials |
|---|---|---|
| 99 | 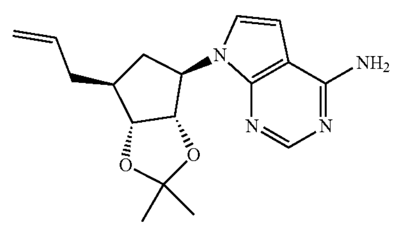 [SMILES: C=CC[C@H]1C[C@@H](n2ccc3c(N)ncnc32)[C@@H]2OC(C)(C)O[C@H]12] | intermediate 98 |
| 118 | 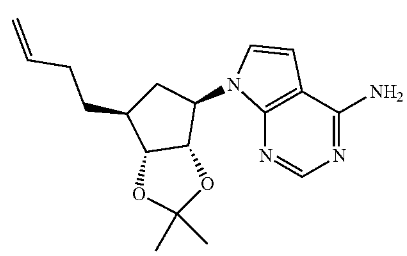 [SMILES: C=CCC[C@H]1C[C@@H](n2ccc3c(N)ncnc32)[C@@H]2OC(C)(C)O[C@H]12] | Intermediate 117 |

Example A 31

Preparation of Intermediate 96

Step 1

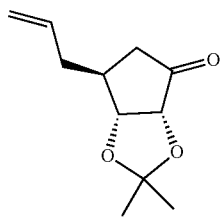

intermediate 95

A solution of cuprous iodide (43.7 g, 228 mmol) and lithium chloride (9.68 g, 228 mmol) in THF (320 mL) was stirred for 5 minutes at room temperature before cooling down to −78° C. under nitrogen atmosphere. Allyl magnesium bromide, 1M in Et$_2$O (220 mL, 1 M, 220 mmol) was added to the solution dropwise over 20 minutes. After the reaction was stirred for 30 minutes, TMSCl (30 mL, 235 mmol) and hexamethylphosphoramide (42 mL, 241 mmol) were added, followed by the dropwise addition of (−)-(3AR, 6AR)-3A,6A-dihydro-2,2-dimethyl-4H-cyclopenta-1,3-dioxol-4-one (12.8 g, 83.0 mmol) in THF (110 mL). After addition the reaction mixture was stirred for 2 hours, warmed to 0° C. and quenched with a saturated aqueous NH$_4$Cl solution (100 mL). After addition of EtOAc (1 L), the organic layer was separated, washed with water (200 mL) and brine (200 mL), then dried over MgSO$_4$. The solvent was evaporated under reduced pressure. The residue was purified over a SiO$_2$ column, type Grace Reveleris SRC, 180 g, Si 40, on a Grace Reveleris X2 purification system using heptane and ethyl acetate as eluens in a gradient starting from 100% heptane to 70% heptane and 30% ethyl acetate. The fractions containing product were combined and the solvents were evaporated yielding intermediate 95 (8.00 g, 47% yield).

Below intermediates were prepared by an analogous reaction protocol as was used for the preparation of intermediate 95 using the appropriate starting materials (Table 25)

TABLE 25

| Int. | structure | Starting materials |
|---|---|---|
| 114 | 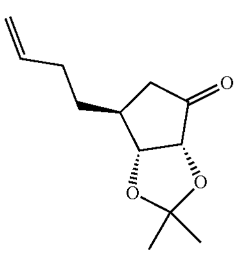 | (−)-(3AR,6AR)-3A, 6A-dihydro-2,2-dimethyl-4H-cyclopenta-1,3-dioxol-4-one and 3-butenylmagnesium bromide |

Step 2

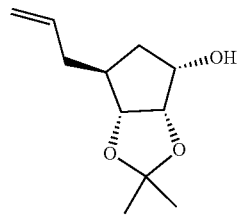

intermediate 96

A solution intermediate 95 (8 g, 39.5 mmol) in THF (40 mL) was added dropwise to a stirred solution of lithium bromide, 2M in THF (5.931 mL, 2 M, 11.86 mmol) in THF (40 mL) at 0° C. under nitrogen atmosphere. After addition the reaction mixture was stirred at room temperature for 2 hours. The reaction was quenched by the addition of 8 mL water followed by 15 mL aqeous NaOH (1N), and again by 8 mL water. The resulting solid was filtered off and the solvents of the filtrate were diluted with ethyl acetate. The organic layer was washed with water, washed with brine, dried with MgSO$_4$, filtered and the solvents of the filtrate evaporated yielding intermediate 96 (7.41 g, 92% yield).

Below intermediates were prepared by an analogous reaction protocol as was used for the preparation of intermediate 96 using the appropriate starting materials (Table 26)

TABLE 26

| Int. | structure | Starting materials |
|---|---|---|
| 115 | 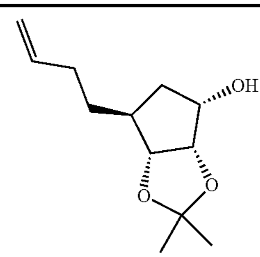 | Intermediate 114 |

Example A 26

Preparation of Intermediate 42

Step 1

Preparation of Intermediate 39

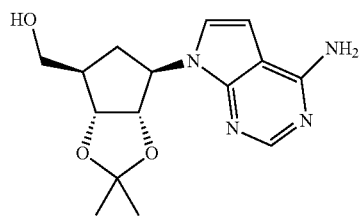

intermediate 39

Intermediate 2 (10 g, 30.5 mmol) was stirred in a mixture of THF (100 ml) and aq. NH$_4$OH 28% (100 ml) at 120° C. for two days in an autoclave. The volatiles were evaporated in vacuo. The aqueous layer was extracted several times with DCM/MeOH 90/10. The combined organic layers were concentrated under reduced pressure. The crude was redissolved in a minimum amount of MeOH, to which toluene was added. The obtained solution was concentrated again, and this process was repeated two times until intermediate 39 (10.2 g, 100% yield) was obtained as a solid product which was used as such in the next step.

Step 2

Preparation of Intermediate 40

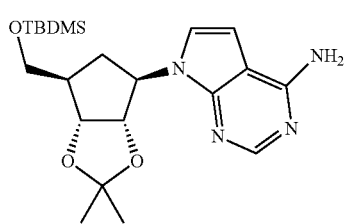

intermediate 40

A solution of TBDMSCl (7.6 g, 50.2 mmol, 1.5 eq.) in DMF (50 mL) was dropwise added into a reaction flask charged with intermediate 39 (10.2 g, 33.5 mmol), imidazole (4.6 g, 67.0 mmol, 2.0 eq.) and DMF (120 mL). The resulting reaction mixture was stirred overnight at room temperature. Water was added and extraction was carried out with diethyl ether. The combined organic layers were washed with water, dried with MgSO₄, and concentrated under reduced pressure to give intermediate 40 (10.4 g, 74% yield).

Step 3

Preparation of Intermediate 41

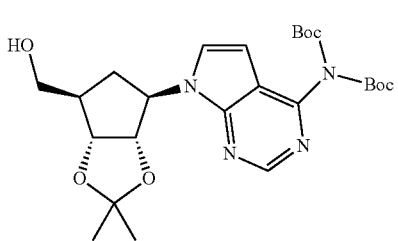

intermediate 41

A solution of (Boc)₂O (20.0 g, 86.9 mmol, 3.5 eq.) in THF (40 mL) was added dropwise into a reaction flask charged with intermediate 40 (10.4 g, 24.8 mmol), DMAP (607 mg, 5.0 mmol, 0.2 eq.) and THF (85 mL). The resulting reaction mixture was stirred at room temperature for 4 h. Next, TBAF in THF (1 M, 42.2 mL, 42.2 mmol, 1.7 eq.) was added dropwise and stirring was continued until complete conversion was observed. The reaction mixture was poured into water and extracted once with diethyl ether. The organice layer was separated, washed with brine, dried with MgSO₄, and concentrated in vacuo. The crude product was purified by silica chromatography (30% to 0% gradient of heptane in ethyl acetate) to give intermediate 41 (12.1 g, 96% yield).

Below intermediates were prepared by an analogous reaction protocol as was used for the preparation of intermediate 41 using the appropriate starting materials (Table 27)

TABLE 27

| Int. | structure | Starting materials |
|---|---|---|
| 143 | 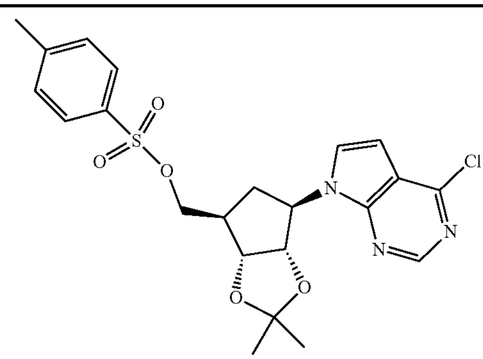 | Intermediate 2 |

Steep 4

Preparation of Intermediate 42

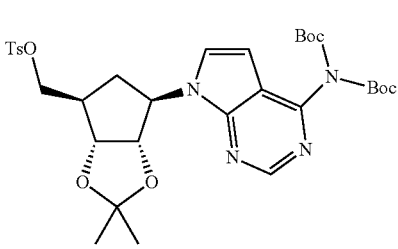

intermediate 42 p-Toluenesulfonyl chloride (5.1 g, 26.7 mmol) was added portion wise to a solution of intermediate 41 (9.0 g, 17.8 mmol), Et₃N (4.5 g, 44.5 mmol, 2.5 eq.) and DMAP (218 mg, 1.8 mmol, 0.1 eq.) in CH₂Cl₂ (50 mL) at 0° C. The reaction mixture was stirred at room temperature overnight.

Water was added, the organic layer was separated, and the aqueous layer was extracted with CH₂Cl₂. The combined organic layers were washed with brine, dried with MgSO₄, and concentrated under reduced pressure. The crude product was purified by silica chromatography (5% EtOH in CH₂Cl₂) to give intermediate 42 (10.6 g, 90% yield).

Example A6

Preparation of Intermediate 13

Step 1

Preparation of Intermediate 10

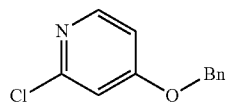

intermediate 10

A solution of benzyl alcohol (18.2 g, 168 mmol, 1.0 eq.) in DMF (100 mL) was added dropwise to suspension of NaH (60% dispersion in mineral oil, 6.5 g, 168 mmol, 1.0 eq.) in DMF (300 mL) under a nitrogen atmosphere. The reaction mixture was stirred at room temperature for an extra 30 minutes. A solution of 2,4-dichloropyridine (24.9 g, 168 mmol, 1.0 eq.) in DMF (100 mL) was added dropwise. The reaction mixture was stirred for 2 h, after which an additional portion of NaH (60% dispersion in mineral oil, 1.3 g, 33.6 mmol, 0.2 eq.) was added. Stirring was continued until complete conversion. Upon completion, the reaction mixture was quenched by the slow addition of water, and extracted with diethyl ether. The combined organic phases were dried with MgSO₄ and concentrated under reduced pressure. The crude product was suspended in heptane, filtered and dried under high vacuum to give intermediate 10 (19.3 g, 52% yield).

Step 2

Preparation of Intermediate 11

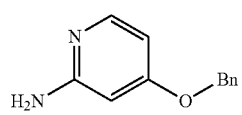

intermediate 11

LiHMDS (105.4 mL, 1 M solution in THF, 105.4 mmol) was added to a solution of intermediate 10 (19.3 g, 87.9 mmol), Pd₂(dba)₃ (2.0 g, 2.2 mmol, 0.025 eq.) and 2-dicyclohexylphosphinobiphenyl (2.5 g, 5.2 mmol, 0.06 eq.) in anhydrous THF (90 mL) under a nitrogen atmosphere, the resulting mixture was stirred at 65° C. for 1 h. The reaction was then allowed to cool to room temperature and 1N aqueous HCl was added. Following 5 min of vigorous stirring, the reaction mixture was neutralized with saturated Na₂CO₃ and extracted with CH₂Cl₂. The combined organic phases were dried over MgSO₄ and concentrated under reduced pressure. The crude product was suspended in isopropyl ether and stirred for 15 min at reflux temperature, after which it was allowed to cool to room temperature overnight. The precipitate was filtered off and dried under high vacuum to give intermediate 11 (14.7 g, 82% yield).

Step 3

Preparation of Intermediate 12

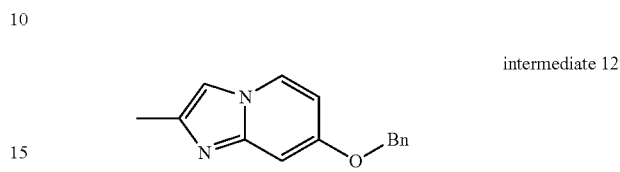

intermediate 12

Chloroacetone (1.75 mL, 22.0 mmol, 1.1 eq.) was added dropwise to a solution of intermediate 11 (4.0 g, 20.0 mmol) in EtOH (20 mL). The reaction mixture was stirred at reflux temperature overnight. The residue obtained after concentration of the reaction mixture under reduced pressure, was taken up in a mixture of ethyl acetate and water. The organic layer was separated and the water layer was further extracted with CH₂Cl₂ (+MeOH), the combined organic phases (ethyl acetate and CH₂Cl₂ (+MeOH)) were concentrated under reduced pressure. The crude product was purified by silica chromatography (1% to 6% gradient of MeOH in CH₂Cl₂) to give intermediate 12 (1.95 g, 42% yield).

Step 4

Preparation of Intermediate 13

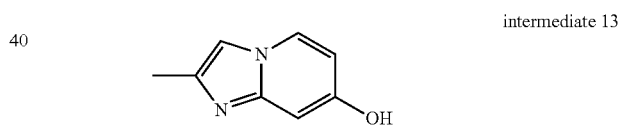

intermediate 13

A solution of intermediate 12 (2.2 g, 9.2 mmol) in methanol was hydrogenated under atmospheric pressure for 2 h with Pd (10% on carbon, 491 mg, 0.46 mmol, 0.05 eq.) as catalyst. The reaction mixture was filtered over Celite® and the filtrate concentrated under reduced pressure to give intermediate 13 (1.4 g, 100% yield) as a brown solid.

Below intermediates were prepared by an analogous reaction protocol as was used for the preparation of intermediate 12 and intermediate 13 using the appropriate starting materials (Table 1)

TABLE 1

| Int. | structure | Starting materials |
|---|---|---|
| 14 | F₃C— (structure) —OH | intermediate 11 and 1-bromo-3,3,3-trifluoroacetone |

Example A7

Preparation of Intermediate 18

Step 1

Preparation of Intermediate 15

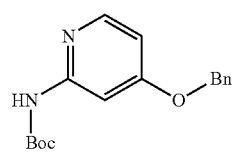

intermediate 15

A mixture intermediate 11 (5.0 g, 25.0 mmol) and (Boc)$_2$O (6.0 g, 27.5 mmol, 1.1 eq.) in tBuOH (55 mL) was stirred at 50° C. for 1 h. The reaction mixture was cooled to room temperature and diluted with ethanol, the precipitate was filtered off and dried under high vacuum to give intermediate 15 (6.0 g, 80% yield).

Below intermediates were prepared by an analogous reaction protocol as was used for the preparation of intermediate 15 and using the appropriate starting materials (Table 2)

TABLE 2

| Int. | structure | Starting materials |
| --- | --- | --- |
| 19 | 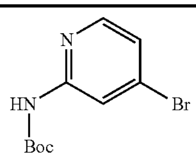 | 2-amino-4-bromopyridine |
| 22 | 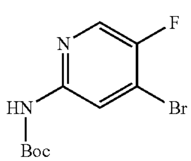 [SMILES: CC(C)(C)OC(=O)Nc1cc(Br)c(F)cn1] | 2-amino-5-fluoro-4-bromopyridine |
| 25 | 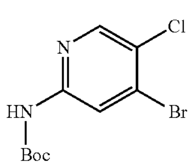 | 2-amino-4-bromo-5-chloropyridine |

Step 2

Preparation of Intermediate 16

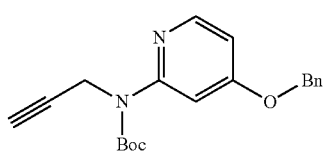

intermediate 16

To a solution of intermediate 15 (6.0 g, 20.0 mmol) in anhydrous DMF (80 mL) was added NaH (1.1 g, 60% dispersion in mineral oil, 30.0 mmol, 1.4 eq.) in portions at room temperature under a nitrogen atmosphere. Upon complete addition, the reaction mixture was stirred for an extra 10 min. Propargyl bromide (3.1 mL, 30.0 mmol, 1.4 eq.) was added and stirring was continued until complete conversion. The reaction was quenched by the addition of water and extracted with diethyl ether. The combined organic phases were washed with water, dried with MgSO$_4$ and concentrated under reduced pressure. The crude product was purified by silica chromatography (0% to 1.5% gradient of MeOH in CH$_2$Cl$_2$) to give intermediate 16 (4.9 g, 72.5% yield).

Below intermediates were prepared by an analogous reaction protocol as was used for the preparation of intermediate 16 and using the appropriate starting materials (Table 3)

TABLE 3

| Int. | structure | Starting materials |
| --- | --- | --- |
| 20 | 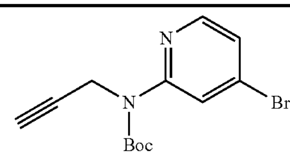 | intermediate 19 |
| 23 | 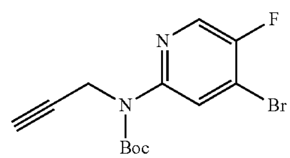 | intermediate 22 |
| 26 | 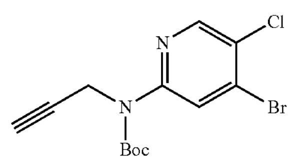 [SMILES: C#CCN(C(=O)OC(C)(C)C)c1cc(Br)c(Cl)cn1] | intermediate 25 |

Step 3

Preparation of Intermediate 17

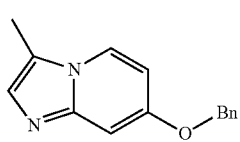

intermediate 17

KOtBu (1.9 g, 17.0 mmol, 1.2 eq.) was added to a solution of intermediate 16 (4.8 g, 14.2 mmol) in THF (145 mL). The reaction mixture was stirred at room temperature until complete conversion (typically ca. 30 min). Water was added and extraction was carried out with ethyl acetate. The combined organic phases were dried with MgSO$_4$ and concentrated under reduced pressure. The product was purified by silica chromatography (1% to 4% gradient of MeOH in CH$_2$Cl$_2$) to give intermediate 17 (2.1 g, 62% yield).

Below intermediates were prepared by an analogous reaction protocol as was used for the preparation of intermediate 17 and using the appropriate starting materials (Table 4)

TABLE 4

| Int. | structure | Starting materials |
|---|---|---|
| 21 | 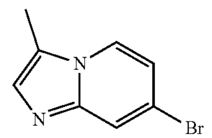 | intermediate 20 |
| 24 | 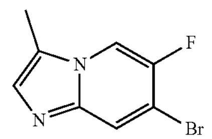 | intermediate 23 |
| 27 | 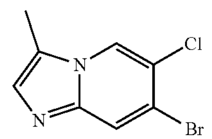 | intermediate 26 |

Step 4

Preparation of Intermediate 18

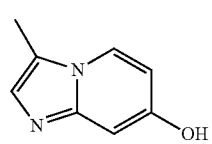

intermediate 18

A solution of 4 intermediate 17 (2.1 g, 8.8 mmol) in methanol was hydrogenated under atmospheric pressure for 2 h with Pd (10% on carbon, 470 mg, 0.44 mmol, 0.05 eq.) as catalyst. The reaction mixture was filtered over Celite® and the filtrate concentrated under reduced pressure to give intermediate 18 (1.27 g, 97% yield).

Example A8

Preparation of Intermediate 29

Step 1

Preparation of Intermediate 28

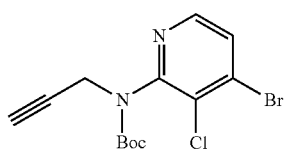

intermediate 28

To an ice-cold mixture of 2-amino-4-bromo-3-chloropyridine (4.5 g, 21.7 mmol) and (Boc)$_2$O (5.9 g, 26.0 mmol, 1.2 eq.) in anhydrous THF (165 mL) under nitrogen, was added dropwise NaHMDS (27.1 mL of a 2 M solution in THF, 54.2 mmol, 2.5 eq.). The resulting suspension was allowed to warm to room temperature and stirred until complete conversion (typically ca. 1 h). Anhydrous DMF (165 mL) was added, followed by the addition of propargyl bromide (3.4 mL, 30.4 mmol, 1.4 eq.). The reaction mixture was stirred overnight, quenched by the addition of water, and extracted with ether. The combined organic phases were washed with water, dried with MgSO$_4$ and concentrated under reduced pressure to give crude product. The product was purified by silica chromatography (10% ethyl acetate in heptane) to give intermediate 28 (6.4 g, 85% yield).

Step 2

Preparation of Intermediate 29

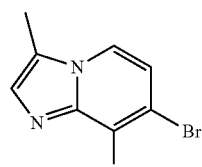

intermediate 29

KOtBu (2.6 g, 23.1 mmol, 1.25 eq.) was added to a solution of intermediate 28 (6.4 g, 18.5 mmol) in THF (90 mL). The reaction mixture was stirred at room temperature until complete conversion (typically ca. 30 min). Water was added and extraction was carried out with ethyl acetate. The combined organic phases were dried with MgSO$_4$ and concentrated under reduced pressure. Intermediate 29 (565 mg, 12.5% yield) was isolated after two successive purifications by silica chromatography (first run: 0% to 1.5% gradient of MeOH in CH$_2$Cl$_2$, second run: 50% ethyl acetate in heptane).

Example A9

Preparation of Intermediate 32

Step 1

Preparation of Intermediate 30

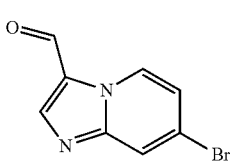

intermediate 30

A solution of 2-amino-4-bromopyridine (10.0 g, 57.8 mmol) and 2-bromomalonaldehyde (10.5 g, 69.4 mmol, 1.2 eq.) in EtOH (200 mL) was stirred at reflux temperature overnight. The reaction mixture was allowed to cool to room temperature and concentrated under reduced pressure. The crude product was suspended in CH$_2$Cl$_2$, the precipitate was filtered off and dried under high vacuum to give intermediate 30 (8.8 g, 67% yield), which was used as such in the next step.

Step 2

Preparation of Intermediate 31

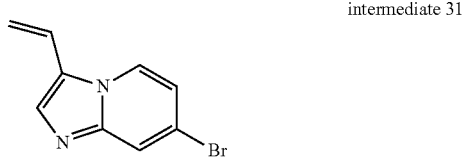

intermediate 31

A reaction flask charged with methyltriphenylphosphonium bromide (30 g, 84.0 mmol, 1.9 eq.) and THF (450 mL), was cooled to −78° C. To this, a solution of KOtBu in THF (1M, 111 mL, 111 mmol, 2.5 eq.) was added and the resulting suspension was stirred at −78° C. for 30 min. A solution of intermediate 30 (10 g, 44.4 mmol) in THF (50 mL) was added dropwise, the reaction mixture was stirred at −78° C. for 2 h, after which it was allowed to warm to room temperature and stirred for an extra 2 h. A saturated $NH_4Cl$ was used for quenching and extraction was carried out with $CH_2Cl_2$, the combined organic phases were washed with brine, dried with $Na_2SO_4$ and concentrated under reduced pressure. The product was purified by silica chromatography (5% to 100% gradient of ethyl acetate in petroleum ether) to give intermediate 31 as a white solid (6.4 g, 85% yield).

Step 3

Preparation of Intermediate 32

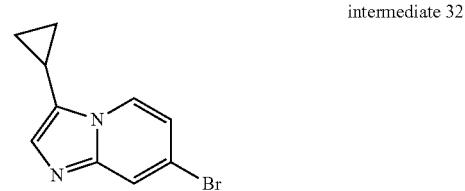 [SMILES: Brc1ccn2c(C3CC3)cnc2c1]

intermediate 32

Intermediate 31 (1.1 g, 4.5 mmol) was dissolved in an ethereal diazomethane solution (400 mL), freshly prepared from Diazald® (20 g, 93 mmol, 20.0 eq.). The reaction mixture was cooled in an ice-bath and $Pd(OAc)_2$ (100 mg, 0.44 mmol, 0.1 eq.) was added. The reaction mixture was stirred at room temperature overnight. The volatiles were removed under reduced pressure, and the desired product was isolated by silica chromatography (5% to 100% gradient of ethyl acetate in petroleum ether). A final purification by preparative reversed phase HPLC Column type: Kromasil 150×25 mm, 10 μm, Condition: A: water (0.05% ammonia hydroxide v/v); B: MeCN at the beginning: A (61%) and B (39%); at the end: A (61%) and B (39%), Gradient Time (min) 8; 100% B Hold Time (min) 2; Flow Rate (ml/min) 30, yielded intermediate 32 as a white solid (160 mg, 15% yield).

Example A10

Preparation of Intermediate 34

Step 1

Preparation of Intermediate 33

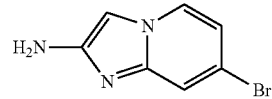

intermediate 33

A solution of Carbamic acid, N-(7-bromoimidazo[1,2-α]pyridin-2-yl)-, 1,1-dimethylethyl ester (740 mg, 2.37 mmol) in methanolic hydrochloric acid (15 mL of a 4 M solution, 60 mmol, 25 eq.) was stirred at room temperature for 2 h. The reaction mixture was concentrated under reduced pressure, the resulting residue was basified with aqueous ammonia and extracted with ethyl acetate, the combined organic phases were dried with $Na_2SO_4$ and concentrated under reduced pressure to give intermediate 33 as a white solid (500 mg, 99% yield).

Step 2

Preparation of Intermediate 34

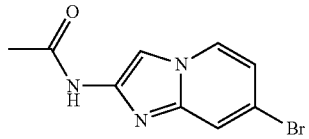

intermediate 34

Acetyl chloride (201 μL, 2.83 mmol, 1.2 eq.) was added to a solution of intermediate 33 (500 mg, 2.36 mmol) and $Et_3N$ (492 μL, 3.54 mmol, 1.5 eq.) in $CH_2Cl_2$ at 0° C., the resulting reaction mixture was stirred for 30 min at 0° C. Water was added, the organic layer was separated and the water layer was extracted with $CH_2Cl_2$. The combined organic phases were washed with brine, dried with $Na_2SO_4$ and concentrated under reduced pressure to give intermediate 34 (700 mg, 97% yield).

Example A11

Preparation of Intermediate 35

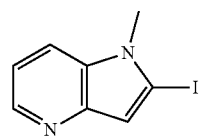

NaH 60% in mineral oil (82 mg, 2 mmol) was added portionwise into the solution of 1H-pyrrolo[3,2-b]pyridine, 2-iodo-(500 mg, 2 mmol) in DMF (20 ml) at 0° C. under $N_2$ atmosphere. The mixture was stirred for 0.5 hours. Then dimethylsulfate (0.32 g, 2.54 mmol) was added drop-wise into the mixture over 30 minutes. Then the mixture was stirred at room temperature for 2 hours. The mixture was treated with water and was extracted by ethyl acetate. The organic layer was filtered, washed with brine and dried over Na$_2$SO$_4$. The organic phase was concentrated to afford intermediate 35 (400 mg, 57% yield) as a yellow solid.

Below intermediates were prepared by an analogous reaction protocol as was used for the preparation of intermediate 35 using the appropriate starting materials (Table 5)

TABLE 5

| Int. | structure | Starting materials |
|---|---|---|
| 36 | 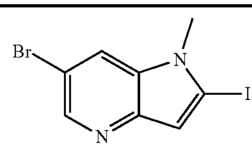 | 1H-pyrrolo[3,2-b]pyridine, 6-bromo-2-iodo- |

Example a 12

Preparation of Intermediate 37

BuLi 2.5 M (22 ml, 55 mmol) was added dropwise to a solution of 1H-pyrrolo[3,2-b]pyridine-1-carboxylic acid, 1,1-dimethylethyl ester (10 g, 45.8 mmol) in dry THF (200 ml) at −78° C. under N$_2$ atmosphere. The mixture was allowed to warm to −60° C. and stirred for two hours. Then a solution of I$_2$ (12.8 g, 50.4 mmol) in THF was slowly added at −72° C. Then the reaction mixture was stirred at room temperature overnight. Then the reaction mixture was quenched with Na$_2$S$_2$O$_3$ and extracted with ethyl acetate (100 mL×3). The organic layer was washed with H$_2$O (50 mL×3), dried over Na$_2$SO$_4$, and concentrated under reduced pressure. The residue was purified by column chromatography (eluent: petroleum ether/ethyl acetate ratio 1/0 to 3/1). The product fractions were collected and the solvent was evaporated to afford intermediate 37 (2 g, 11% yield) as a yellow oil.

Below intermediates were prepared by an analogous reaction protocol as was used for the preparation of intermediate 37 using the appropriate starting materials (Table 6)

TABLE 6

| Int. | structure | Starting materials |
|---|---|---|
| 38 | 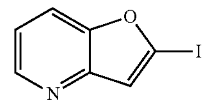 | Furo[3,2-b]pyridine |

Example A 13

Preparation of Intermediate 45

A reaction flask was charged with intermediate 4 (442 mg, 1.39 mmol) followed by the addition of a 9-BBN solution in THF (0.5 M, 5.5 mL, 2.8 mmol, 2.0 eq.), the reaction mixture was stirred under nitrogen at room temperature for 2 h. THF (5 mL), K$_3$PO$_4$ (1.5 g, 6.9 mmol, 5 eq.) and H$_2$O (1.5 mL) were added and stirring was continued for 10 min. After this, intermediate 27 (407 mg, 1.9 mmol, 1.1 eq.) and PdCl$_2$(dppf) (101 mg, 0.14 mmol, 0.1 eq.) were added, the resulting reaction mixture was purged with nitrogen for 10 min and stirred at reflux temperature until complete conversion (typically ca. 2 h). The reaction mixture was allowed to cool to room temperature, diluted with EtOAc, washed with water and brine, dried with MgSO$_4$ and concentrated under reduced pressure. The crude product was purified by silica chromatography (3% methanol in dichloromethane) to give intermediate 45 (110 mg, 16% yield).

Below intermediates were prepared by an analogous reaction protocol as was used for the preparation of intermediate 45 using the appropriate starting materials (Table 7)

TABLE 7

| Int. | structure | Starting materials |
|---|---|---|
| 46 | 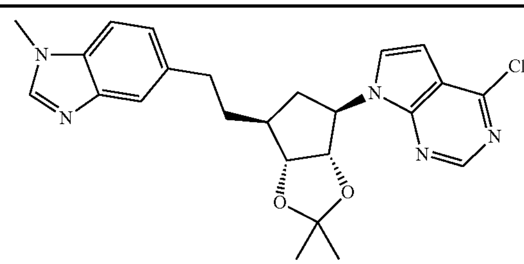 | Intermediate 4 and 5-bromo-1-methyl-1H-Benzimidazole |

TABLE 7-continued

| Int. | structure | Starting materials |
|---|---|---|
| 47 | 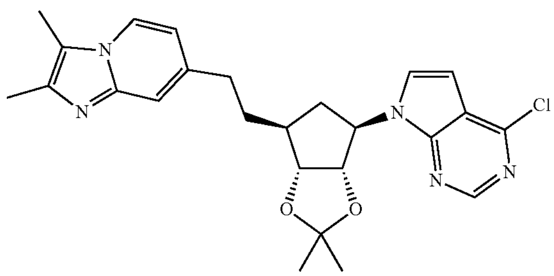 [SMILES: Cc1nc2cc(CC[C@H]3C[C@@H](n4ccc5c(Cl)ncnc54)[C@@H]4OC(C)(C)O[C@H]34)ccn2c1C] | Intermediate 4 and 7-bromo-2,3-dimethyl-imidazo[1,2-a]pyridine |
| 48 | 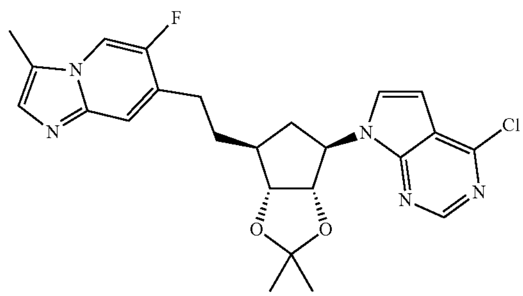 [SMILES: Cc1cnc2cc(CC[C@H]3C[C@@H](n4ccc5c(Cl)ncnc54)[C@@H]4OC(C)(C)O[C@H]34)c(F)cn12] | Intermediate 4 and intermediate 24 |

Example a 14

Preparation of Intermediate 50

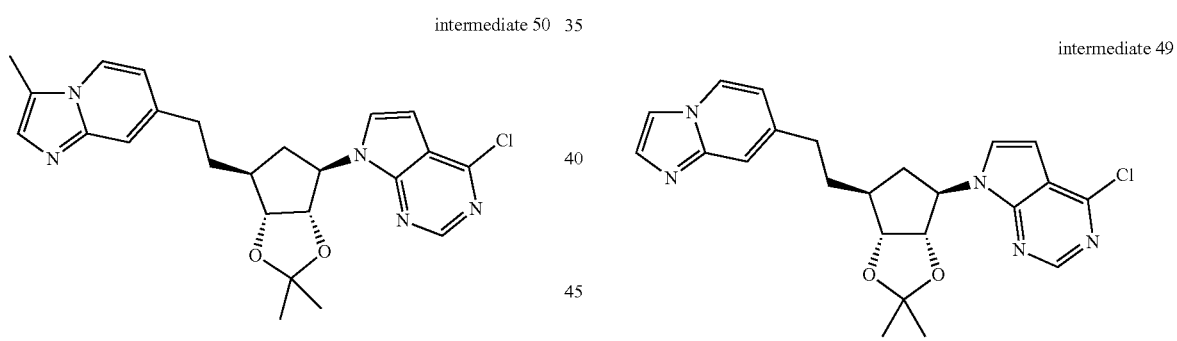

A reaction flask was charged with intermediate 4 (560 mg, 1.75 mmol) followed by the addition of a 9-BBN solution in THF (0.5 M, 7.0 mL, 3.5 mmol, 2.0 eq.), the reaction mixture was stirred under nitrogen at room temperature for 2 h. THF (5 mL), K₃PO₄ (1.9 g, 8.8 mmol, 5 eq.) and H₂O (3 mL) were added and stirring was continued for 10 min. After this, intermediate 21 (407 mg, 1.9 mmol, 1.1 eq.) and PdCl₂(dppf) (256 mg, 0.35 mmol, 0.2 eq.) were added, the resulting reaction mixture was purged with nitrogen for 10 min and stirred at reflux temperature until complete conversion (typically ca. 3 h). The reaction mixture was allowed to cool to room temperature, diluted with EtOAc, washed with water and brine, dried with MgSO₄ and concentrated under reduced pressure. The crude product was purified by silica chromatography (0% to 3.5% gradient of methanol in dichloromethane) to give intermediate 50 (300 mg, 38% yield).

Example a 15

Preparation of Intermediate 49

A mixture of intermediate 4 (1000 mg, 3.12 mmol) in 9-BBN 0.5 M in THF (31.3 mL, 15.6 mmol) was refluxed for 1 h under N₂. The mixture was cooled to room temperature, then K₃PO₄ (1990 mg, 9.4 mmol) in H₂O (10 mL) was added, followed by THF (100 mL), 7-bromo-imidazo[1,2-α]pyridine (924 mg, 4.7 mmol) and Pd-118 (204 mg, 0.31 mmol). The resulting mixture was refluxed for 3 h. The mixture was concentrated. The residue was dissolved in EtOAc (30 mL), washed with water (10 mL) and brine (10 mL). The organic phase was dried over Na₂SO₄, filtered and concentrated. The residue was purified by chromatography column on silica (eluent: EtOAc/MeOH ratio 10/1). The desired fractions were collected and concentrated to give intermediate 49 (486 mg, 35. 5% yield) as a solid.

Below intermediates were prepared by an analogous reaction protocol as was used for the preparation of intermediate 49 using the appropriate starting materials (Table 8)

TABLE 8

| Int. | structure | Starting materials |
|---|---|---|
| 51 | 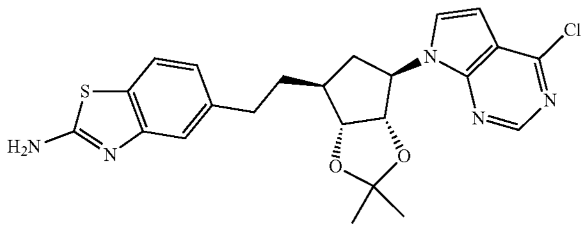 [SMILES: CC1(C)O[C@@H]2[C@@H](CCc3ccc4sc(N)nc4c3)C[C@@H](n3ccc4c(Cl)ncnc43)[C@@H]2O1] | Intermediate 4 and 2-amino-5-bromobenzothiazole |
| 52 | 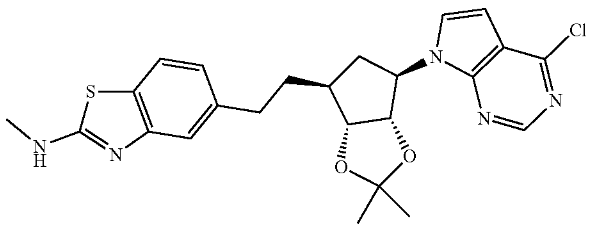 [SMILES: CNc1nc2cc(CC[C@H]3C[C@@H](n4ccc5c(Cl)ncnc54)[C@@H]4OC(C)(C)O[C@H]34)ccc2s1] | Intermediate 4 and 5-bromo-N-methyl-2-Benzothiazolamine |
| 53 | 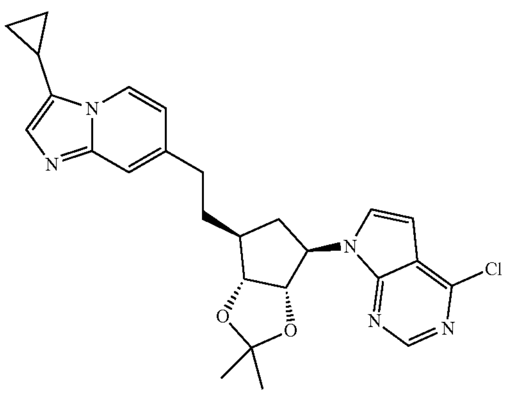 [SMILES: CC1(C)O[C@@H]2[C@@H](CCc3ccn4c(C5CC5)cnc4c3)C[C@@H](n3ccc4c(Cl)ncnc43)[C@@H]2O1] | Intermediate 4 and Intermediate 32 |

Example A16

Preparation of Intermediate 54

Example A17

Preparation of Intermediate 55

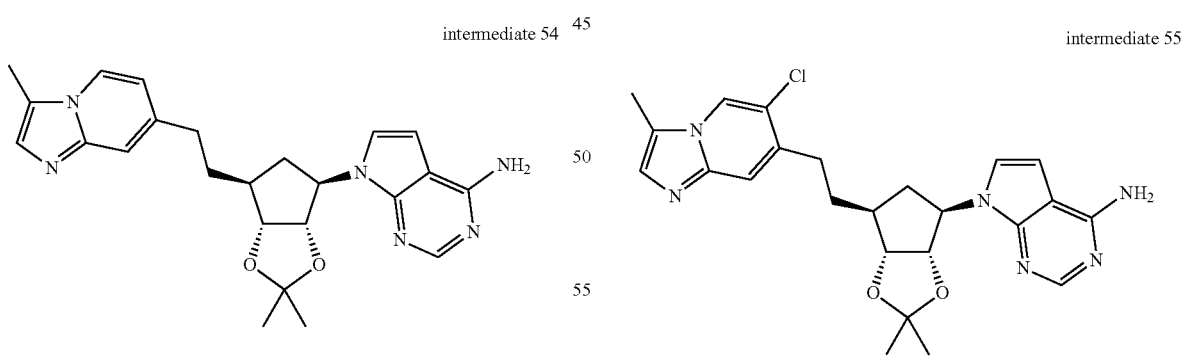

intermediate 54 intermediate 55

A metal pressure vessel (75 mL) charged with intermediate 50 (270 mg, 0.60 mmol), THF (30 mL) and aqueous ammonia 25% (30 ml) was heated at 100° C. for one day. The reaction mixture was concentrated under reduced pressure to give crude intermediate 54 which was used as such in the subsequent step.

A metal pressure vessel (75 mL) charged with intermediate 45 (110 mg, 0.23 mmol), THF (30 mL) and aqueous ammonia 25% (30 ml) was heated at 100° C. for two days. The reaction mixture was concentrated under reduced pressure to give crude intermediate 55 which was used as such in the subsequent step Below intermediates were prepared by an analogous reaction protocol as was used for the preparation of intermediate 54 and intermediate 55 using the appropriate starting materials (Table 9)

TABLE 9

| Int. | structure | Starting materials |
|---|---|---|
| 56 | 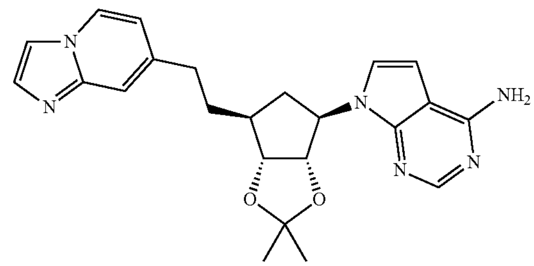 [SMILES: CC1(C)O[C@@H]2[C@@H](CCc3ccn4ccnc4c3)C[C@@H](n3ccc4c(N)ncnc43)[C@@H]2O1] | Intermediate 49<br>NH$_4$OH |
| 57 | 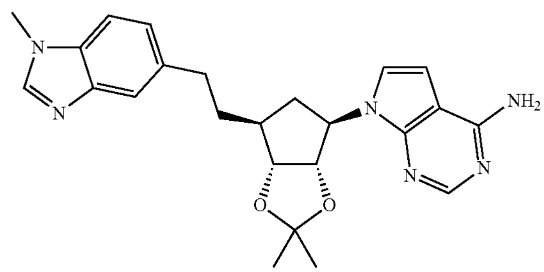 [SMILES: Cn1cnc2cc(CC[C@H]3C[C@@H](n4ccc5c(N)ncnc54)[C@@H]4OC(C)(C)O[C@H]34)ccc21] | Intermediate 46<br>NH$_4$OH |
| 58 | 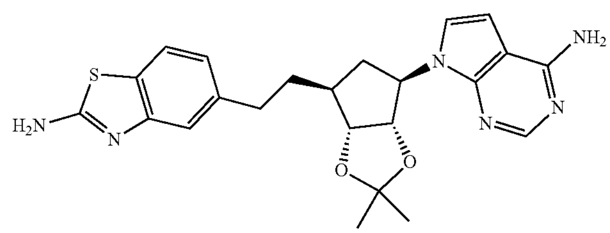 [SMILES: CC1(C)O[C@@H]2[C@@H](CCc3ccc4sc(N)nc4c3)C[C@@H](n3ccc4c(N)ncnc43)[C@@H]2O1] | Intermediate 51<br>NH$_4$OH |
| 60 | 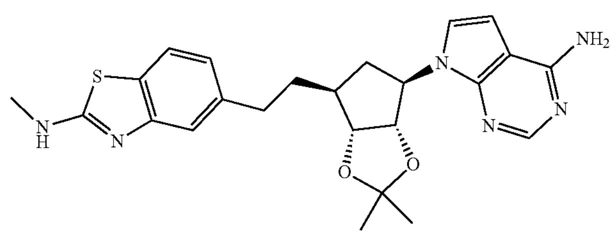 [SMILES: CNc1nc2cc(CC[C@H]3C[C@@H](n4ccc5c(N)ncnc54)[C@@H]4OC(C)(C)O[C@H]34)ccc2s1] | Intermediate 52<br>NH$_4$OH |
| 61 | 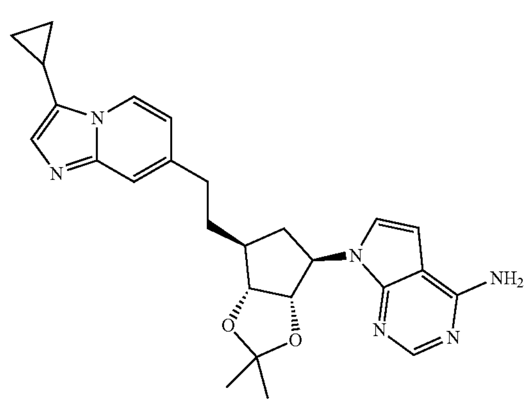 [SMILES: CC1(C)O[C@@H]2[C@@H](CCc3ccn4c(C5CC5)cnc4c3)C[C@@H](n3ccc4c(N)ncnc43)[C@@H]2O1] | Intermediate 53<br>NH$_4$OH |

TABLE 9-continued

| Int. | structure | Starting materials |
|---|---|---|
| 62 | 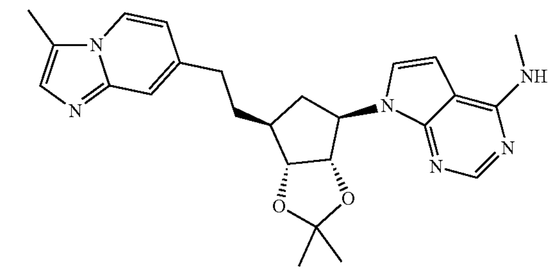 [SMILES: CNc1ncnc2c1ccn2[C@@H]1C[C@H](CCc2ccn3c(C)cnc3c2)[C@H]2OC(C)(C)O[C@H]21] | Intermediate 50<br>Methylamine |
| 63 | 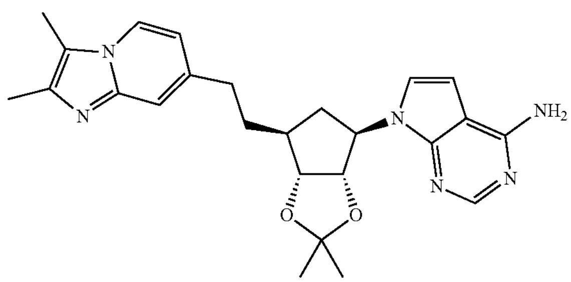 [SMILES: Cc1nc2cc(CC[C@H]3C[C@@H](n4ccc5c(N)ncnc54)[C@@H]4OC(C)(C)O[C@H]34)ccn2c1C] | Intermediate 47<br>NH₄OH |
| 64 | 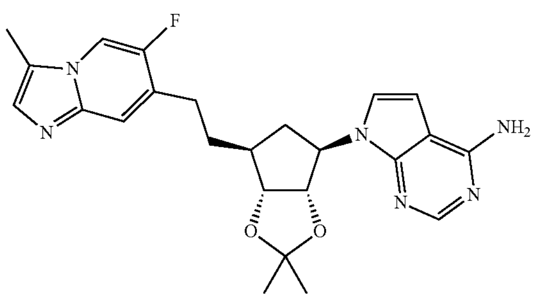 [SMILES: Cc1cnc2cc(CC[C@H]3C[C@@H](n4ccc5c(N)ncnc54)[C@@H]4OC(C)(C)O[C@H]34)c(F)cn12] | Intermediate 48<br>NH₄OH |
| 141 | 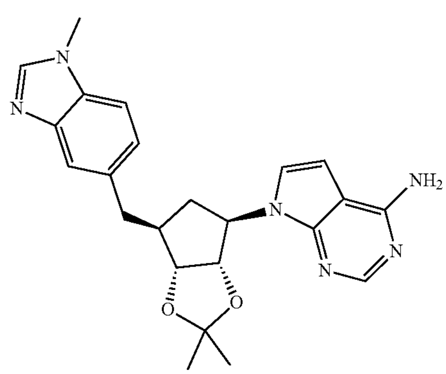 [SMILES: Cn1cnc2cc(C[C@H]3C[C@@H](n4ccc5c(N)ncnc54)[C@@H]4OC(C)(C)O[C@H]34)ccc21] | Intermediate 140<br>NH₄OH |

Example A18

Preparation of Intermediate 65

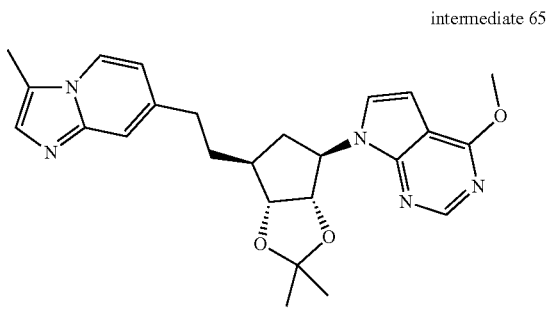 [SMILES: COc1ncnc2c1ccn2[C@@H]1C[C@H](CCc2ccn3c(C)cnc3c2)[C@H]2OC(C)(C)O[C@H]21]

intermediate 65

A mixture of intermediate 50 (500 mg, 1.1 mmol) and NaOMe (478 mg, 8.85 mmol) in MeOH (15 mL) was stirred at 60° C. overnight. The mixture was diluted with water (20 mL) and extracted with $CH_2Cl_2$ (50 mL×3). The organic phase was washed with brine (10 mL), dried over $Na_2SO_4$, filtered and concentrated to give crude intermediate 65 (510 mg, 64% yield) which used for the next step without further purification.

Example A21

Preparation of Intermediate 75

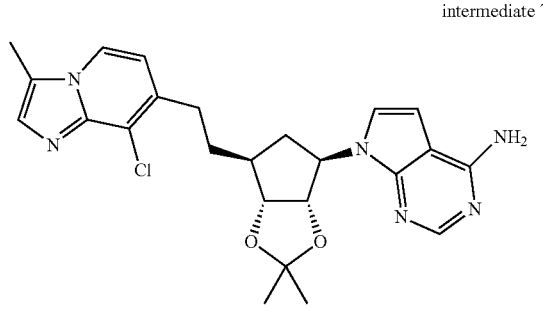

intermediate 75

A reaction flask was charged with intermediate 9 (538 mg, 1.79 mmol) followed by the addition of a 9-BBN solution in THF (0.5 M, 12.5 mL, 6.2 mmol, 3.5 eq.), the reaction mixture was stirred under nitrogen at room temperature for 2 h. $K_3PO_4$ (2.0 g, 8.96 mmol, 5 eq.) and $H_2O$ (2.5 mL) were added and stirring was continued for 10 min. Next intermediate 29 (484 mg, 1.97 mmol, 1.1 eq.) and $PdCl_2(dppf)$ (131 mg, 0.18 mmol, 0.1 eq.) were added, the reaction mixture was purged with nitrogen for 10 min and heated at reflux temperature until complete conversion. The reaction mixture was allowed to cool to room temperature and diluted with EtOAc, the organic phase was washed with water and brine, dried with $MgSO_4$ and concentrated under reduced pressure. The crude product was purified by silica chromatography (4% methanol in dichloromethane) to give intermediate 75 which was used as such in the next step.

Below intermediates were prepared by an analogous reaction protocol as was used for the preparation of intermediate 75 and using the appropriate starting materials (Table 12)

TABLE 12

| Int. | structure | Starting materials |
| --- | --- | --- |
| 76 | 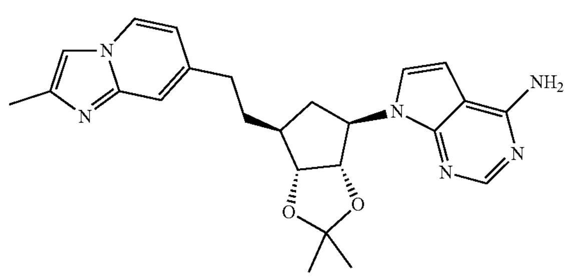 [SMILES: Cc1cn2ccc(CC[C@H]3C[C@@H](n4ccc5c(N)ncnc54)[C@@H]4OC(C)(C)O[C@H]34)cc2n1] | Intermediate 9 and 7-Bromo-2-methylmethyl-imidazo[1,2-a]pyridine |
| 77 | 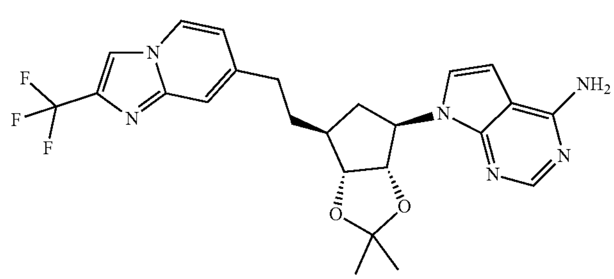 [SMILES: CC1(C)O[C@@H]2[C@@H](CCc3ccn4cc(C(F)(F)F)nc4c3)C[C@@H](n3ccc4c(N)ncnc43)[C@@H]2O1] | Intermediate 9 and 7-Bromo-2-trifluoromethyl-imidazol[1,2-a]pyridine |

TABLE 12-continued

| Int. | structure | Starting materials |
|---|---|---|
| 87 | 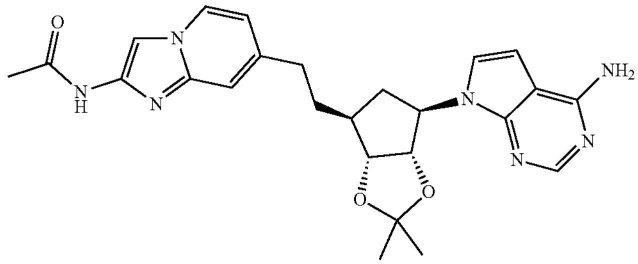 [SMILES: CC(=O)Nc1cn2ccc(CC[C@H]3C[C@@H](n4ccc5c(N)ncnc54)[C@@H]4OC(C)(C)O[C@H]34)cc2n1] | Intermediate 9 and Intermediate 34 |

Example A19

Preparation of Intermediate 66

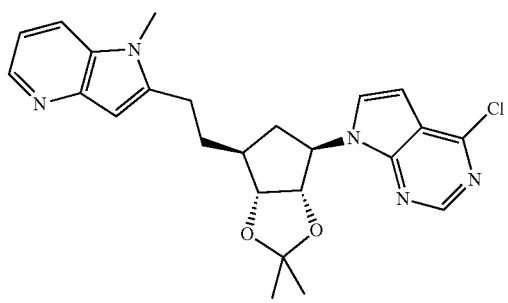 [SMILES: Cn1c(CC[C@H]2C[C@@H](n3ccc4c(Cl)ncnc43)[C@@H]3OC(C)(C)O[C@H]23)cc2ncccc21]

A mixture of intermediate 4 (300 mg, 0.94 mmol) in 9-BBN 0.5 M in THF (5.63 mL, 2.81 mmol) was refluxed for 1.5 h under $N_2$. The mixture was cooled to room temperature, then $K_3PO_4$ (597 mg, 2.81 mmol) in $H_2O$ (2 mL) was added, followed by THF (20 mL), intermediate 35 (290.5 mg, 1.12 mmol) and Pd-118 (79 5 mg, 0.112 mmol). The resulting mixture was refluxed for 3 h. The residue was dissolved in EtOAc (30 mL), washed with (brine (5×50 mL). The organic phase was dried over $Na_2SO_4$, filtered and concentrated. The residue was purified by chromatography column on silica (eluent: EtOAc/petroleum ether ratio 2/1). The desired fractions were collected and concentrated to give intermediate 66 (100 mg, yield 21.2%) as yellow oil.

Below intermediates were prepared by an analogous reaction protocol as was used for the preparation of intermediate 66 using the appropriate starting materials (Table 10)

TABLE 10

| Int. | structure | Starting materials |
|---|---|---|
| 67 | 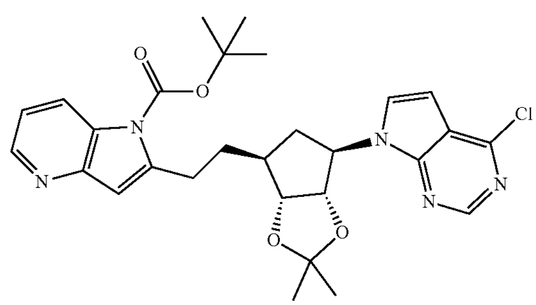 [SMILES: CC(C)(C)OC(=O)n1c(CC[C@H]2C[C@@H](n3ccc4c(Cl)ncnc43)[C@@H]3OC(C)(C)O[C@H]23)cc2ncccc21] | Intermediate 4 Intermediate 37 |
| 68 | 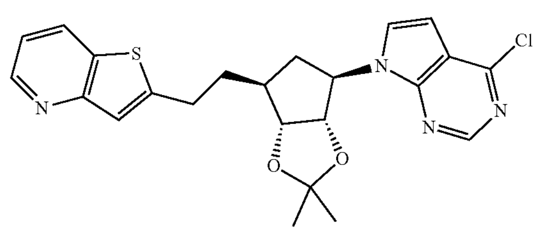 [SMILES: CC1(C)O[C@@H]2[C@@H](CCc3cc4ncccc4s3)C[C@@H](n3ccc4c(Cl)ncnc43)[C@@H]2O1] | Intermediate 4 2-iodo-thieno[3,2-b]pyridine |

TABLE 10-continued

| Int. | structure | Starting materials |
|---|---|---|
| 69 | 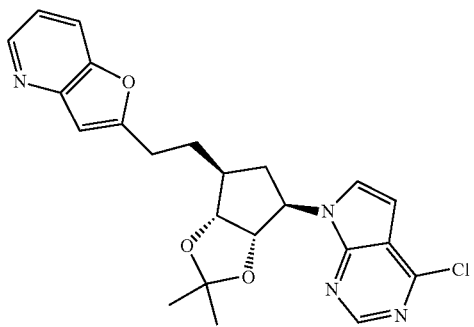 [SMILES: CC1(C)O[C@@H]2[C@@H](CCc3cc4ncccc4o3)C[C@@H](n3ccc4c(Cl)ncnc43)[C@@H]2O1] | Intermediate 4<br>Intermediate 38 |
| 70 | 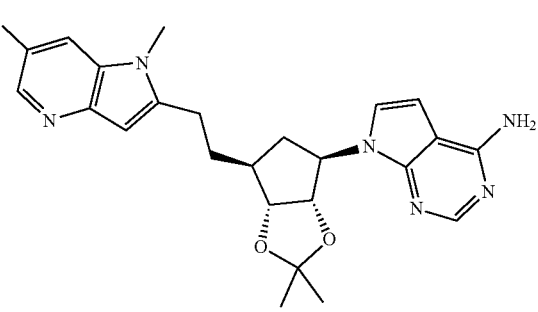 | Intermediate 9<br>Intermediate 36 |

Example A20

Preparation of Intermediate 71 intermediate 71

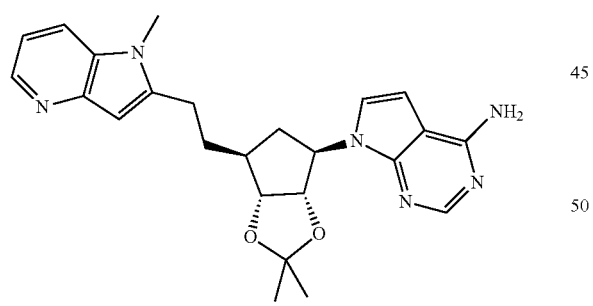

Intermediate 66 (100 mg, 0.22 mmol) was dissolved in NH$_4$OH 28% (20 ml) and dioxane (8 ml). The reaction mixture was stirred at 100° C. for 12 hours in a sealed tube. The mixture was concentrated. The residue was dissolved in ethyl acetate, washed by brine and dried over anhydrous Na$_2$SO$_4$. The organic phase was concentrated to afford intermediate 71 (100 mg, 99% yield) as an oil.

Below intermediates were prepared by an analogous reaction protocol as was used for the preparation of intermediate 71 using the appropriate starting materials (Table 11).

TABLE 11

| Int. | structure | Starting materials |
|---|---|---|
| 72 | 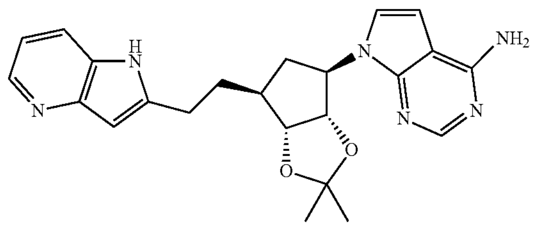 [SMILES: CC1(C)O[C@@H]2[C@@H](CCc3cc4ncccc4[nH]3)C[C@@H](n3ccc4c(N)ncnc43)[C@@H]2O1] | intermediate 67<br>NH₄OH |
| 73 | 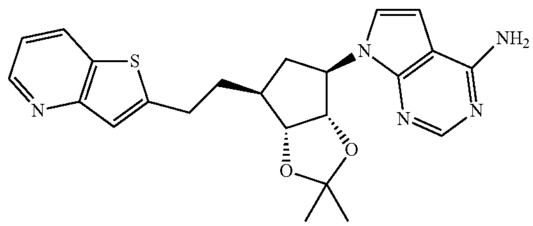 [SMILES: CC1(C)O[C@@H]2[C@@H](CCc3cc4ncccc4s3)C[C@@H](n3ccc4c(N)ncnc43)[C@@H]2O1] | intermediate 68<br>NH₄OH |
| 74 | 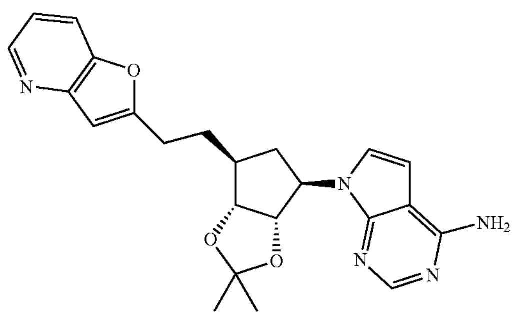 [SMILES: CC1(C)O[C@@H]2[C@@H](CCc3cc4ncccc4o3)C[C@@H](n3ccc4c(N)ncnc43)[C@@H]2O1] | intermediate 69<br>NH₄OH |

Example A22

Preparation of Intermediate 78

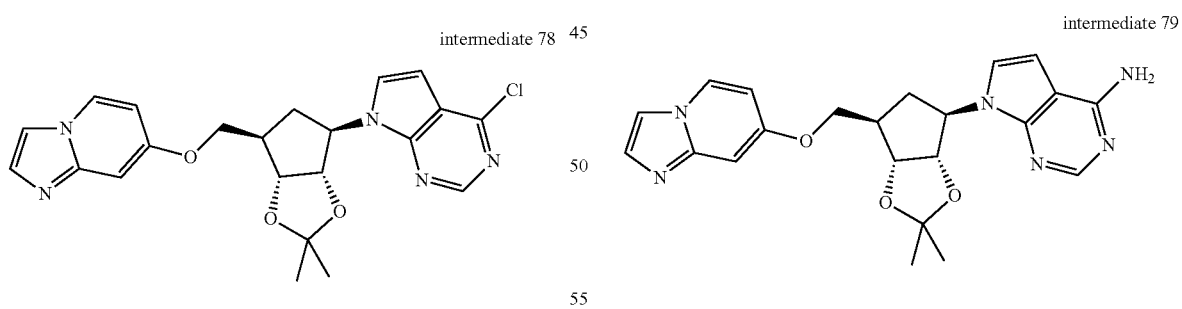

intermediate 78

To a solution of intermediate 1 (500 mg, 1.54 mmol, 1.0 eq) and Imidazo[1,2-a]pyridin-7-ol (248.6 mg, 1.85 mmol, 1.2 eq) in THF (20 mL) was added tributylphosphane (624.9 mg, 3.1 mmol, 2.0 eq) and (NE)-N-(piperidine-1-carbonylimino)piperidine-1-carboxamide (779 mg, 3.1 mmol, 2.0 eq). The mixture was stirred at 15° C. for 15 hrs. The solvent was removed. The residue was purified by flash column on silica gel (ISCO®; 12 g SepaFlash® Silica Flash Column, Eluent from 0% to 3% MeOH/DCM gradient @ 30 mL/min) and intermediate 78 (240 mg, 33.7% yield) was obtained as a light yellow solid.

Example A23

Preparation of Intermediate 79 intermediate 79

A solution of intermediate 78 (600 mg, 1.36 mmol, 1.0 eq) in THF (4 mL), IPA (4 mL) and NH₃H2O (8 mL) was stirred at 85° C. in a sealed tube for 48 hrs. The solvent was removed under reduced pressure. The residue was purified by flash column on silica gel (ISCO®; 40 g SepaFlash® Silica Flash Column, Eluent from 0% to 10% MeOH (NH₃)/DCM gradient @ 40 mL/min) and intermediate 79 (415 mg, 69% yield) was obtained as a light yellow solid.

Example A24

Preparation of Intermediate 80

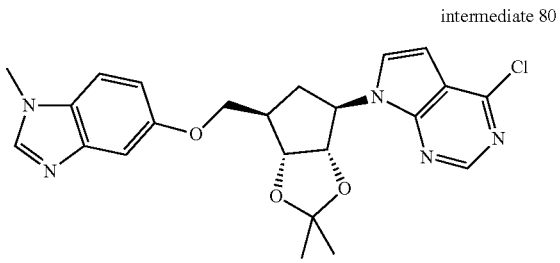 [SMILES: Cn1cnc2cc(OC[C@H]3C[C@@H](n4ccc5c(Cl)ncnc54)[C@@H]4OC(C)(C)O[C@H]34)ccc21]

intermediate 80

To a solution of intermediate 1 (250 mg, 772 umol, 1.0 eq) and 1H-Benzimidazol-5-ol, 1-methyl-(149 mg, 1.0 mmol, 1.3 eq) in THF (10 mL) was added PPh$_3$ (263 mg, 1.0 mmol, 1.30 eq.) and DIAD (203 mg, 1.0 mmol, 1.3 eq). The mixture was stirred at 15° C. for 2 hrs. The solvent was removed. The residue was purified by flash column on silica:eluent:gradient from 0% to 50% ethyl acetate/petroleum ether and second purification eluent: gradient from 0% to 5% MeOH/DCM and intermediate 80 (240 mg, 61.6% yield) was obtained as a colorless solid.

Example A25

Preparation of Intermediate 81

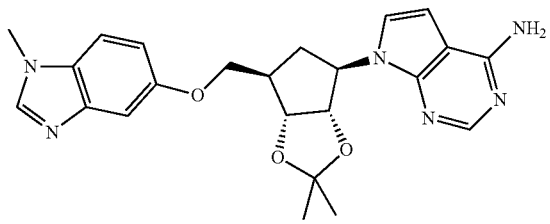 [SMILES: Cn1cnc2cc(OC[C@H]3C[C@@H](n4ccc5c(N)ncnc54)[C@@H]4OC(C)(C)O[C@H]34)ccc21]

To a solution of intermediate 80 (500 mg, 1.1 mmol, 1.0 eq) in THF (3 mL) was added IPA (3 mL) and NH$_3$H2O (6 mL). The mixture was stirred at 85° C. for 72 hrs in a sealed tube. The solvent was removed under reduced pressure. The residue was purified by flash column on silica gel (ISCO®; 12 g SepaFlash® Silica Flash Column, eluent gradient from 0% to 7% MEOH/DCM @ 30 mL/min) and intermediate 81 (370 mg, 73.5% yield) was obtained as a white solid.

Example A27

Preparation of Intermediate 82

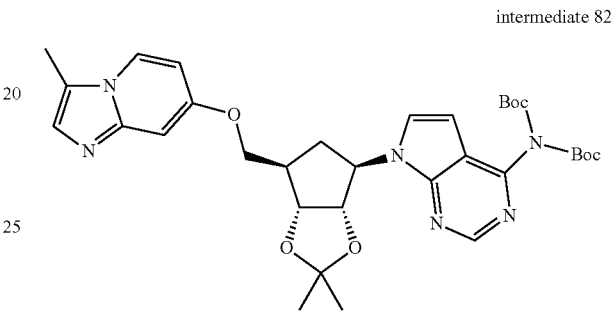

intermediate 82

Cs$_2$CO$_3$ (1.48 g, 4.55 mmol, 3 eq.) was added to a solution of intermediate 42 (1.0 g, 1.52 mmol) and intermediate 18 (292 mg, 1.97 mmol, 1.3 eq.) in DMF (20 mL). The reaction mixture was stirred at room temperature for 3 days after which the intermediate 82 was precipitated by the addition of water. The precipitate was isolated by centrifugation and washed with water (re-suspension in water followed by centrifugation). The wet product was used as such in the next step.

Below intermediates were prepared by an analogous reaction protocol as was used for the preparation of intermediate 82 using the appropriate starting materials (Table 18).

TABLE 18

| Int. | structure | Starting materials |
|---|---|---|
| 89 | 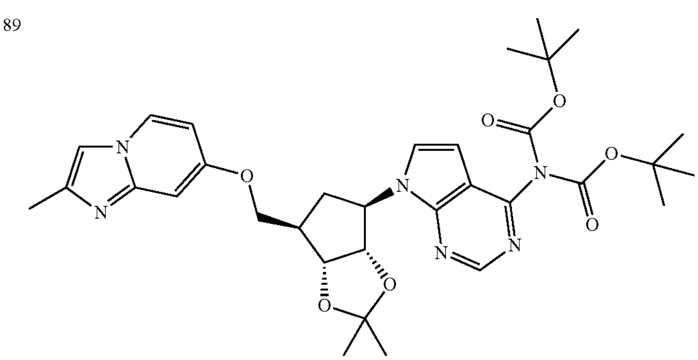 | intermediate 42<br>intermediate 13 |

TABLE 18-continued

| Int. | structure | Starting materials |
|---|---|---|
| 144 | 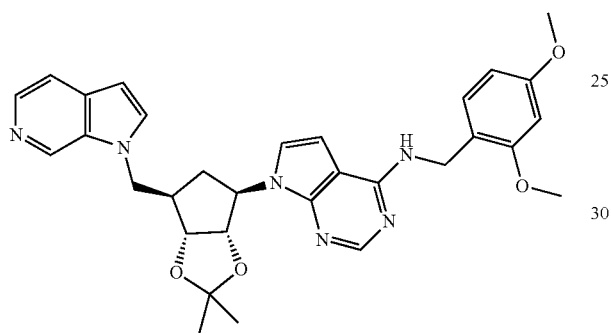 | intermediate 143 and 6-azaindole |

Example A33

Preparation of Intermediate 145

A solution of intermediate 144 (150 mg, 0.29 mmol), 2,4-dimethoxybenzylamine hydrochloride (387 mg, 2.3 mmol) and DIPEA (112 mg, 0.87 mml) in n-BuOH (0.5 ml) was stirred at 140° C. for one day. The mixture was poured into H₂O (5 mL) and extracted with DCM (3 mL×3). The organic layer was washed with brine (3 mL) and dried with anhydrous Na₂SO₄ and evaporated under reduced pressure to give the crude product as brown oil.

The crude product was purified by column chromatography over silica gel (petroleum ether/ethyl acetate ratio 1:0 to petroleum ether/ethyl acetate ratio 1:9). The pure fractions were collected and the solvent was evaporated under vacuum to give intermediate 145 (135 mg, 78% yield) as a brown oil.

Example A34

Preparation of Intermediate 146

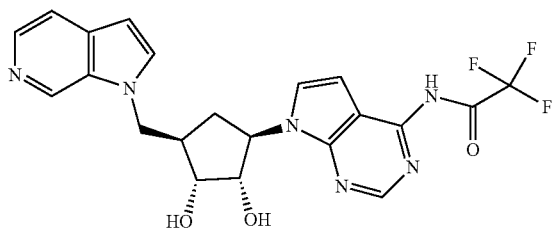 [SMILES: O=C(Nc1ncnc2c1ccn2[C@@H]1C[C@H](Cn2ccc3ccncc32)[C@@H](O)[C@H]1O)C(F)(F)F]

Intermediate 145 (135 mg, 0.23 mmol) and TFA (2 ml) were stirred at 80° C. for 1.5 hours. The mixture was evaporated under vacuum to give the crude intermediate 146 (100 mg) as a brown oil which was used as such in the next step.

Example A28

Preparation of Intermediate 83

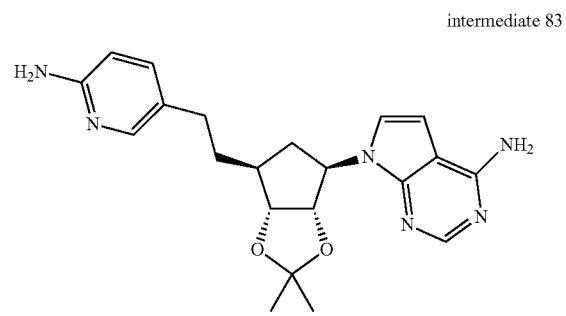 [SMILES: CC1(C)O[C@@H]2[C@@H](CCc3ccc(N)nc3)C[C@@H](n3ccc4c(N)ncnc43)[C@@H]2O1]

intermediate 83

A mixture of intermediate 9 (0.5 g, 1.66 mmol) in a solution of 9-Borabicyclo[3.3.1]nonane (20.0 mL, 0.5 M in THF, 10.0 mmol) was stirred at room temperature under nitrogen atmosphere for 2 hour to have full conversion into the 9-BBN adduct. A with nitrogen gas flushed solution of potassium phosphate tribasic (2.83 g, 13.3 mmol) in water (5 mL) was added. The reaction mixture was stirred at room temperature for 10 minutes and then a with nitrogen gas flushed solution of 1,1'-Bis(di-tert-butylphosphino)ferrocene palladium dichloride (219 mg, 0.33 mmol) and 2-amino-5-bromopyridine (288 mg, 1.66 mmol) in THF (20 mL) was added. The resulting mixture was flushed through with nitrogen gas for 15 minutes. The reaction mixture was stirred at 70° C. under nitrogen atmosphere for 30 minutes. The reaction mixture was diluted with ethyl acetate and washed twice with diluted NH₄OH and one time with water. The organic layer was separated, dried with MgSO₄, filtered and the solvents of the filtrate evaporated. The residue was dissolved in dichloromethane and purified over a SiO₂ column, type Grace Reveleris SRC, 4 g, Si 40, on a Armen Spot II Ultimate purification system using dichloromethane and methanol as eluent in a gradient starting from 100% dichloromethane and ending with 10% methanol and 90% dichloromethane. The fractions containing product were combined and the solvents were evaporated yielding intermediate 83 (0.18 g, 23% yield).

Below intermediates were prepared by an analogous reaction protocol as was used for the preparation of intermediate 83 using the appropriate starting materials (Table 13).

TABLE 13

| Intermediate | Structure | Starting materials |
|---|---|---|
| 84 | 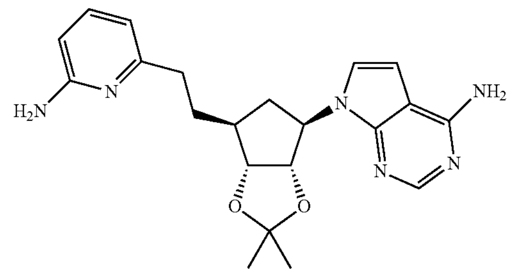 [SMILES: CC1(C)O[C@@H]2[C@@H](CCc3cccc(N)n3)C[C@@H](n3ccc4c(N)ncnc43)[C@@H]2O1] | Intermediate 9 and 2-amino-6-bromopyridine |
| 85 | 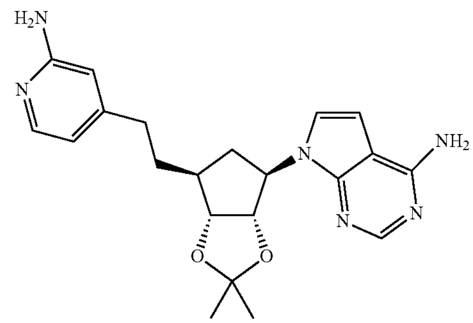 [SMILES: CC1(C)O[C@@H]2[C@@H](CCc3ccnc(N)c3)C[C@@H](n3ccc4c(N)ncnc43)[C@@H]2O1] | Intermediate 9 and 2-amino-4-bromopyridine |
| 88 | 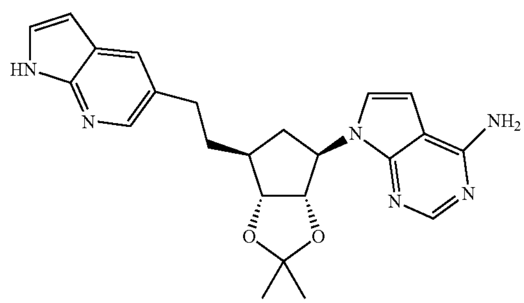 [SMILES: CC1(C)O[C@@H]2[C@@H](CCc3cnc4[nH]ccc4c3)C[C@@H](n3ccc4c(N)ncnc43)[C@@H]2O1] | Intermediate 9 and 5-bromo-1h-pyrrolo[2,3-b]pyridine |
| 100 | 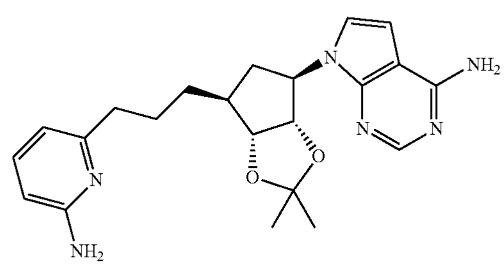 [SMILES: CC1(C)O[C@@H]2[C@@H](CCCc3cccc(N)n3)C[C@@H](n3ccc4c(N)ncnc43)[C@@H]2O1] | Intermediate 99 and 2-amino-6-bromopyridine |
| 101 | 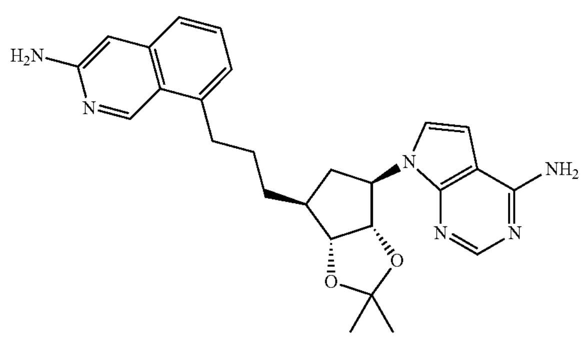 [SMILES: CC1(C)O[C@@H]2[C@@H](CCCc3cccc4cc(N)ncc34)C[C@@H](n3ccc4c(N)ncnc43)[C@@H]2O1] | Intermediate 99 and 8-bromoisoquinolin-3-amine |

TABLE 13-continued

| Intermediate | Structure | Starting materials |
| --- | --- | --- |
| 102 | 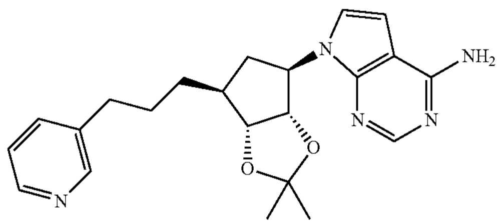 [SMILES: CC1(C)O[C@@H]2[C@@H](CCCc3cccnc3)C[C@@H](n3ccc4c(N)ncnc43)[C@@H]2O1] | Intermediate 99 and 3-bromopyridine |
| 103 | 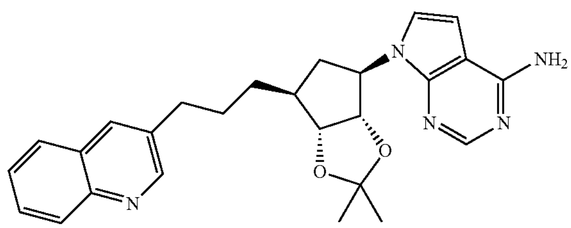 [SMILES: CC1(C)O[C@@H]2[C@@H](CCCc3cnc4ccccc4c3)C[C@@H](n3ccc4c(N)ncnc43)[C@@H]2O1] | Intermediate 99 and 3-bromoquinoline |
| 104 | 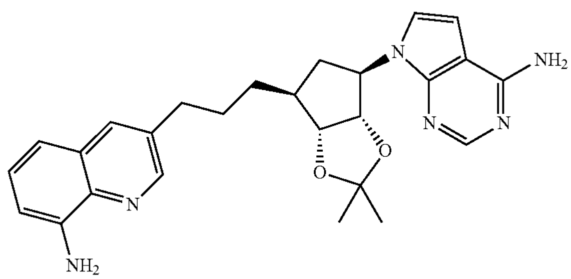 [SMILES: CC1(C)O[C@@H]2[C@@H](CCCc3cnc4c(N)cccc4c3)C[C@@H](n3ccc4c(N)ncnc43)[C@@H]2O1] | intermediate 99 and 3-bromoquinolin-8-amine |
| 105 | 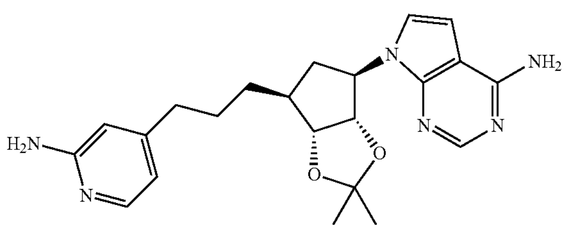 [SMILES: CC1(C)O[C@@H]2[C@@H](CCCc3ccnc(N)c3)C[C@@H](n3ccc4c(N)ncnc43)[C@@H]2O1] | intermediate 99 and 2-amino-4-bromopyridine |
| 106 | 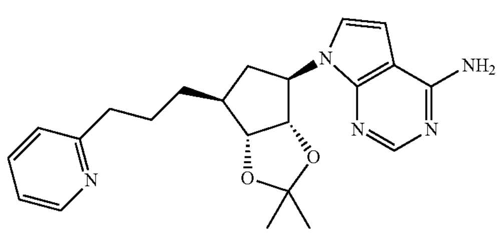 [SMILES: CC1(C)O[C@@H]2[C@@H](CCCc3ccccn3)C[C@@H](n3ccc4c(N)ncnc43)[C@@H]2O1] | intermediate 99 and 2-iodopyridine |
| 107 | 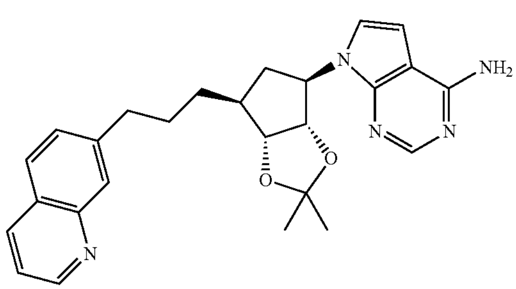 [SMILES: CC1(C)O[C@@H]2[C@@H](CCCc3ccc4cccnc4c3)C[C@@H](n3ccc4c(N)ncnc43)[C@@H]2O1] | intermediate 99 and 7-bromoquinoline |

TABLE 13-continued

| Intermediate | Structure | Starting materials |
| --- | --- | --- |
| 108 | 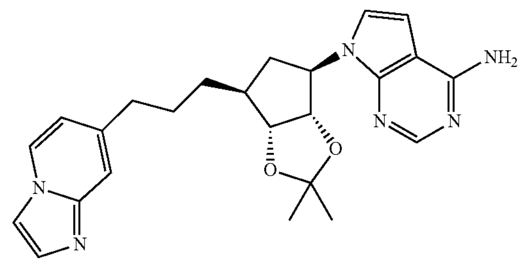 [SMILES: CC1(C)O[C@@H]2[C@@H](CCCc3ccn4ccnc4c3)C[C@@H](n3ccc4c(N)ncnc43)[C@@H]2O1] | intermediate 99 and 7-bromo-imidazo[1,2-a]pyridine |
| 109 | 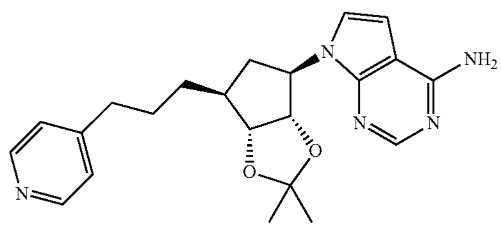 [SMILES: CC1(C)O[C@@H]2[C@@H](CCCc3ccncc3)C[C@@H](n3ccc4c(N)ncnc43)[C@@H]2O1] | intermediate 99 and 4-iodopyridine |
| 110 | 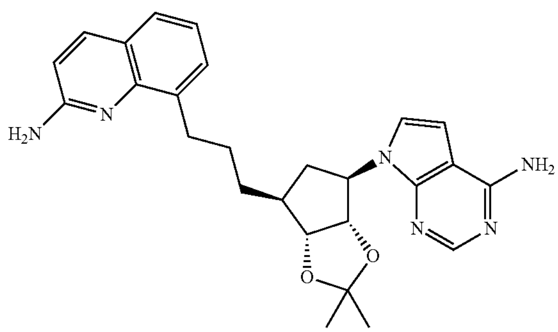 [SMILES: CC1(C)O[C@@H]2[C@@H](CCCc3cccc4ccc(N)nc34)C[C@@H](n3ccc4c(N)ncnc43)[C@@H]2O1] | intermediate 99 and 8-bromoquinolin-2-amine |
| 111 | 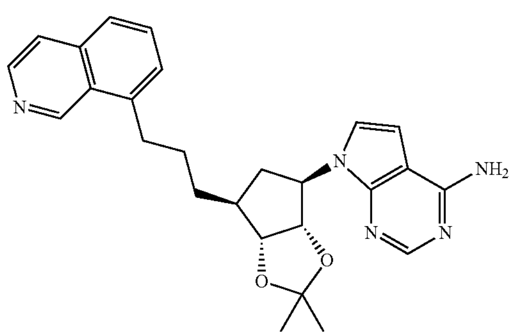 [SMILES: CC1(C)O[C@@H]2[C@@H](CCCc3cccc4ccncc34)C[C@@H](n3ccc4c(N)ncnc43)[C@@H]2O1] | intermediate 99 and 8-bromoisoquinoline |
| 112 | 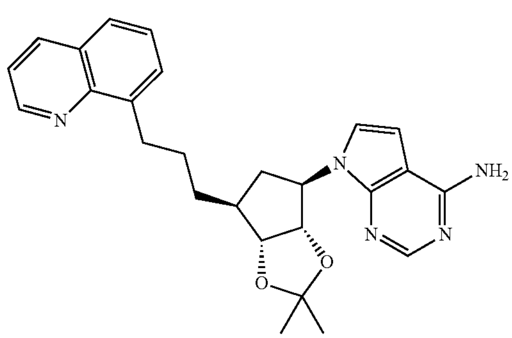 [SMILES: CC1(C)O[C@@H]2[C@@H](CCCc3cccc4cccnc34)C[C@@H](n3ccc4c(N)ncnc43)[C@@H]2O1] | intermediate 99 and 8-bromoquinoline |

TABLE 13-continued

| Intermediate | Structure | Starting materials |
| --- | --- | --- |
| 113 | 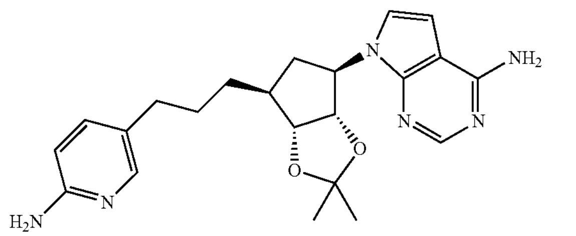 [SMILES: CC1(C)O[C@@H]2[C@@H](CCCc3ccc(N)nc3)C[C@@H](n3ccc4c(N)ncnc43)[C@@H]2O1] | intermediate 99 and 2-amino-5-bromopyridine |
| 119 | 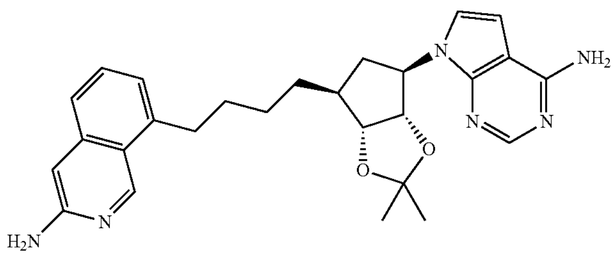 [SMILES: CC1(C)O[C@@H]2[C@@H](CCCCc3cccc4cc(N)ncc34)C[C@@H](n3ccc4c(N)ncnc43)[C@@H]2O1] | intermediate 118 and 8-bromoisoquinolin-3-amine |
| 120 | 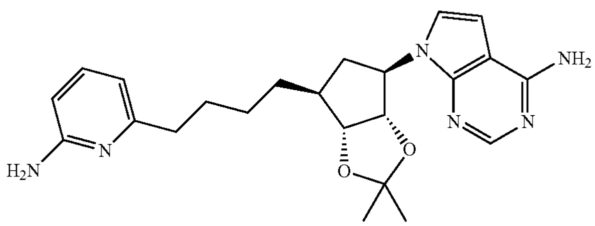 [SMILES: CC1(C)O[C@@H]2[C@@H](CCCCc3cccc(N)n3)C[C@@H](n3ccc4c(N)ncnc43)[C@@H]2O1] | intermediate 118 and 2-amino-6-bromopyridine |
| 121 | 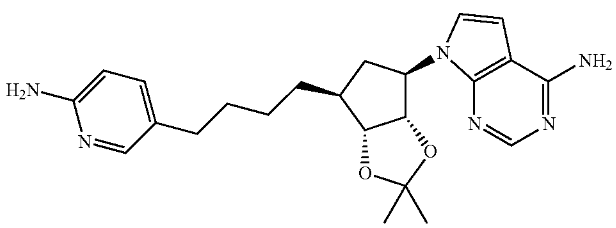 [SMILES: CC1(C)O[C@@H]2[C@@H](CCCCc3ccc(N)nc3)C[C@@H](n3ccc4c(N)ncnc43)[C@@H]2O1] | intermediate 118 and 2-amino-5-bromopyridine |
| 122 | 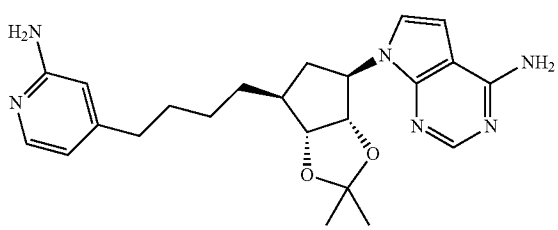 [SMILES: CC1(C)O[C@@H]2[C@@H](CCCCc3ccnc(N)c3)C[C@@H](n3ccc4c(N)ncnc43)[C@@H]2O1] | intermediate 118 and 2-amino-4-bromopyridine |
| 123 | 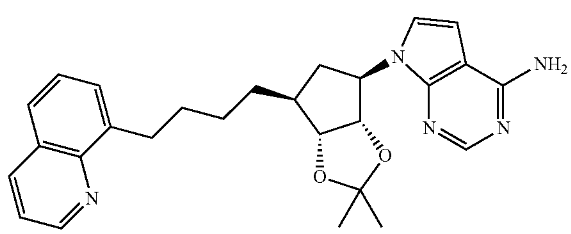 [SMILES: CC1(C)O[C@@H]2[C@@H](CCCCc3cccc4cccnc34)C[C@@H](n3ccc4c(N)ncnc43)[C@@H]2O1] | intermediate 118 and 8-bromoquinoline |

TABLE 13-continued

| Intermediate | Structure | Starting materials |
|---|---|---|
| 124 | 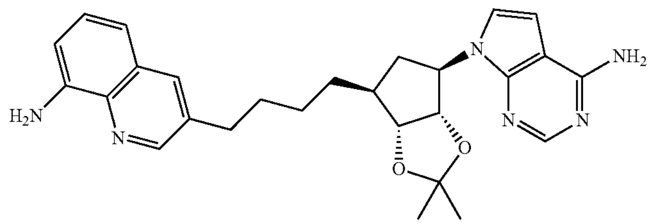 [SMILES: CC1(C)O[C@@H]2[C@@H](CCCCc3cnc4c(N)cccc4c3)C[C@@H](n3ccc4c(N)ncnc43)[C@@H]2O1] | intermediate 118 and 3-bromoquinolin-8-amine |
| 125 | 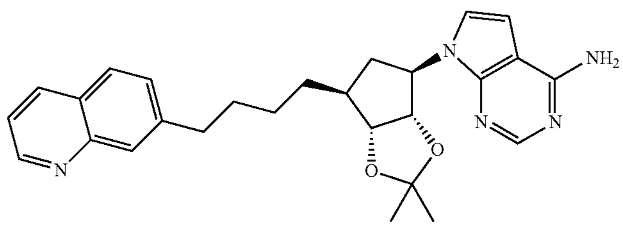 [SMILES: CC1(C)O[C@@H]2[C@@H](CCCCc3ccc4cccnc4c3)C[C@@H](n3ccc4c(N)ncnc43)[C@@H]2O1] | intermediate 118 and 7-bromoquinoline |
| 126 | 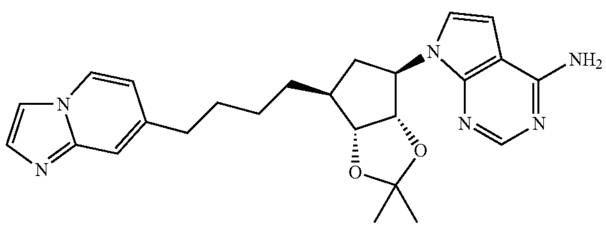 [SMILES: CC1(C)O[C@@H]2[C@@H](CCCCc3ccn4ccnc4c3)C[C@@H](n3ccc4c(N)ncnc43)[C@@H]2O1] | intermediate 118 and 7-bromo-imidazo[1,2-a]pyridine |
| 127 | 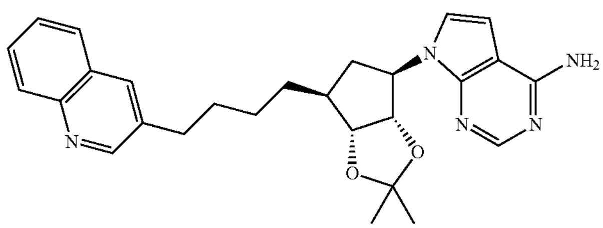 [SMILES: CC1(C)O[C@@H]2[C@@H](CCCCc3cnc4ccccc4c3)C[C@@H](n3ccc4c(N)ncnc43)[C@@H]2O1] | intermediate 118 and 3-bromoquinoline |
| 128 | 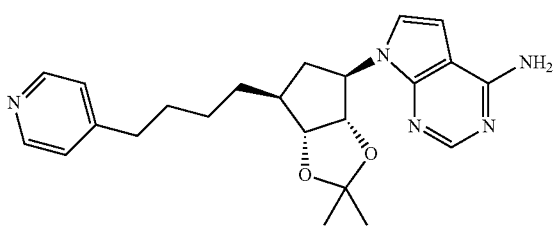 [SMILES: CC1(C)O[C@@H]2[C@@H](CCCCc3ccncc3)C[C@@H](n3ccc4c(N)ncnc43)[C@@H]2O1] | intermediate 118 and 4-iodopyridine |
| 129 | 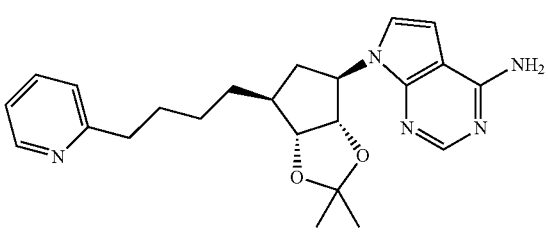 [SMILES: CC1(C)O[C@@H]2[C@@H](CCCCc3ccccn3)C[C@@H](n3ccc4c(N)ncnc43)[C@@H]2O1] | intermediate 118 and 2-iodopyridine |

TABLE 13-continued

| Intermediate | Structure | Starting materials |
|---|---|---|
| 130 | 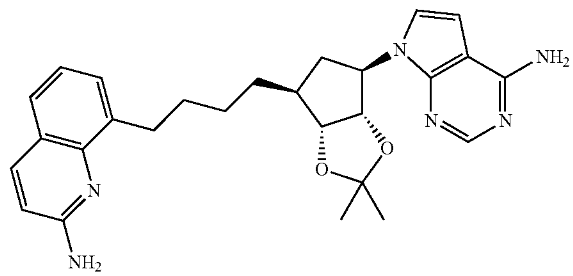 [SMILES: CC1(C)O[C@@H]2[C@@H](CCCCc3cccc4ccc(N)nc34)C[C@@H](n3ccc4c(N)ncnc43)[C@@H]2O1] | intermediate 118 and 8-bromoquinolin-2-amine |
| 131 | 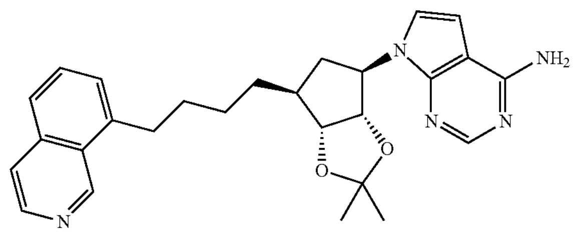 [SMILES: CC1(C)O[C@@H]2[C@@H](CCCCc3cccc4ccncc34)C[C@@H](n3ccc4c(N)ncnc43)[C@@H]2O1] | intermediate 118 and 8-bromoisoquinoline |
| 132 | 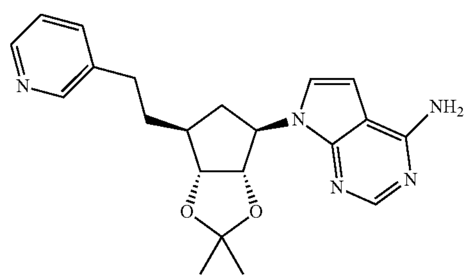 [SMILES: CC1(C)O[C@@H]2[C@@H](CCc3cccnc3)C[C@@H](n3ccc4c(N)ncnc43)[C@@H]2O1] | Intermediate 9 and 3-bromopyridine |
| 133 | 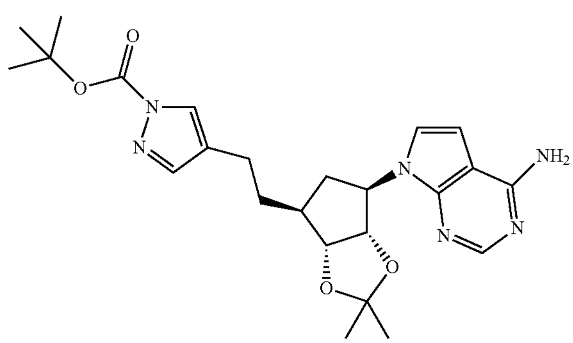 [SMILES: CC(C)(C)OC(=O)n1cc(CC[C@H]2C[C@@H](n3ccc4c(N)ncnc43)[C@@H]3OC(C)(C)O[C@H]23)cn1] | Intermediate 9 and 1H-Pyrazole-1-carboxylic acid, 4-bromo-, 1,1-dimethylethyl ester |
| 134 | 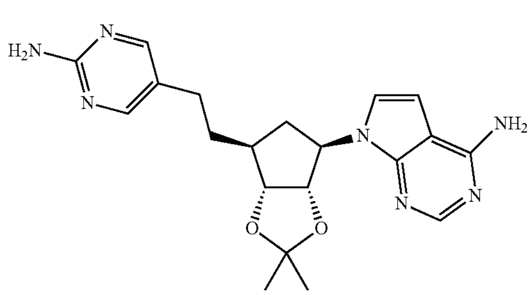 [SMILES: CC1(C)O[C@@H]2[C@@H](CCc3cnc(N)nc3)C[C@@H](n3ccc4c(N)ncnc43)[C@@H]2O1] | Intermediate 9 and 5-iodo-2-amino pyrimidine |

TABLE 13-continued

| Intermediate | Structure | Starting materials |
|---|---|---|
| 135 | 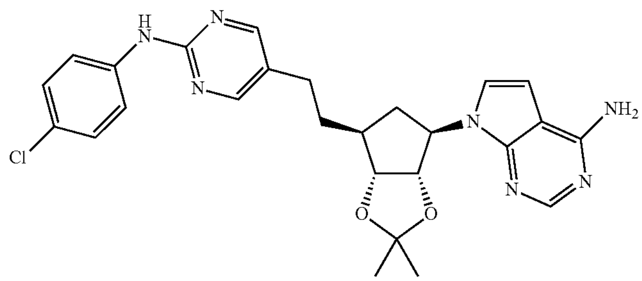 [SMILES: CC1(C)O[C@@H]2[C@@H](CCc3cnc(Nc4ccc(Cl)cc4)nc3)C[C@@H](n3ccc4c(N)ncnc43)[C@@H]2O1] | Intermediate 9 and 2-Pyrimidinamine, N-(4-chlorophenyl)-5-iodo- |
| 136 | 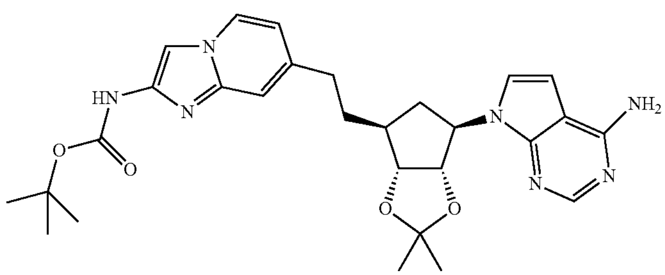 [SMILES: CC(C)(C)OC(=O)Nc1cn2ccc(CC[C@H]3C[C@@H](n4ccc5c(N)ncnc54)[C@@H]4OC(C)(C)O[C@H]34)cc2n1] | Intermediate 9 and 2-Carbamic acid, N-(7-bromoimidazo[1,2-a]pyridin-2-yl)-, 1,1-dimethylethyl ester |
| 137 | 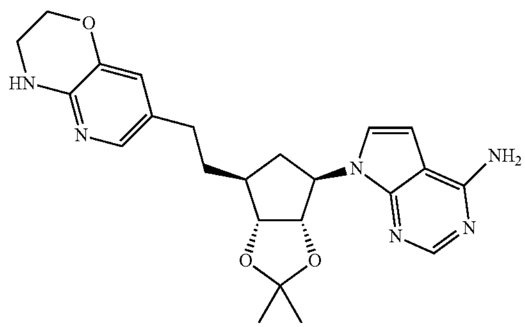 [SMILES: CC1(C)O[C@@H]2[C@@H](CCc3cnc4c(c3)OCCN4)C[C@@H](n3ccc4c(N)ncnc43)[C@@H]2O1] | Intermediate 9 and 7-bromo-3,4-dihydro-2h-pyrido[3,2-b][1,4]oxazine |
| 138 | 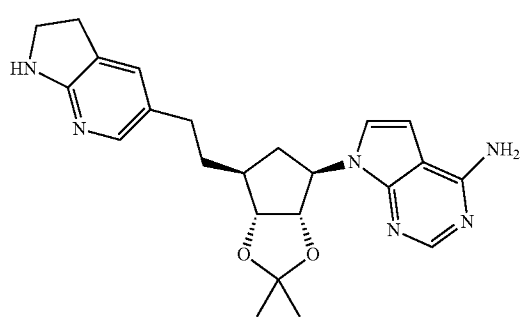 [SMILES: CC1(C)O[C@@H]2[C@@H](CCc3cnc4c(c3)CCN4)C[C@@H](n3ccc4c(N)ncnc43)[C@@H]2O1] | Intermediate 9 and 5-bromo-2,3-dihydro-1h-pyrrolo[2,3-b]pyridine |

Example A29

Preparation of Intermediate 86

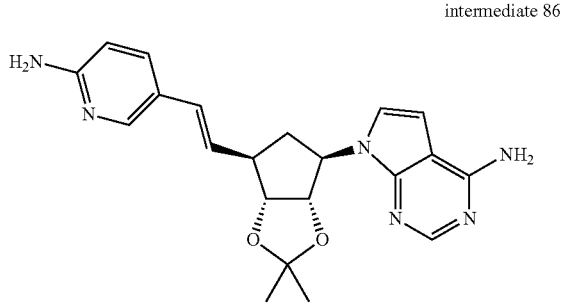 [SMILES: CC1(C)O[C@@H]2[C@H](O1)[C@@H](/C=C/c1ccc(N)nc1)C[C@H]2n1ccc2c(N)ncnc21]

intermediate 86

A mixture of intermediate 9 (500 mg, 1.66 mmol), tetraethylammonium chloride (0.30 g, 1.83 mmol) and 2-amino-5-bromopyridine (0.33 g, 1.91 mmol) in DMF (15 mL) was stirred and flushed through with nitrogen gas for 15 minutes. Then DIPEA (1.43 mL, 8.32 mmol) and Pd(OAc)$_2$ (56.0 mg, 0.25 mmol) were added. The reaction vial was sealed and the reaction mixture was stirred and heated at 100° C. for 3 days. The reaction mixture was poured into water and the product was extracted three times with ethyl acetate. The combined organic layers were dried with MgSO$_4$, filtered and the solvents of the filtrate evaporated. The residue was dissolved in dichloromethane and purified over a SiO$_2$ column, type Grace Reveleris SRC, 4 g, Si 40, on a Armen Spot II Ultimate purification system using dichloromethane and methanol as eluent in a gradient starting from 100% dichloromethane and ending with 10% methanol and 90% dichloromethane. The fractions containing product were combined and the solvents were evaporated yielding 0.26 g intermediate 86 (0.26 g, 39% yield).

Below intermediates were prepared by an analogous reaction protocol as was used for the preparation of intermediate 86 using the appropriate starting materials (Table 20).

TABLE 20

| Intermediate | Structure | Starting materials |
|---|---|---|
| 90 | 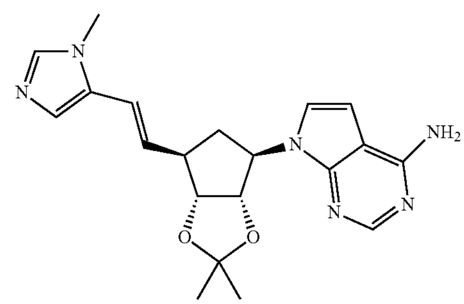 [SMILES: Cn1cncc1/C=C/[C@H]1C[C@@H](n2ccc3c(N)ncnc32)[C@@H]2OC(C)(C)O[C@@H]21] | Intermediate 9 and 5-bromo-1-methyl-1h-imidazole |
| 91 | 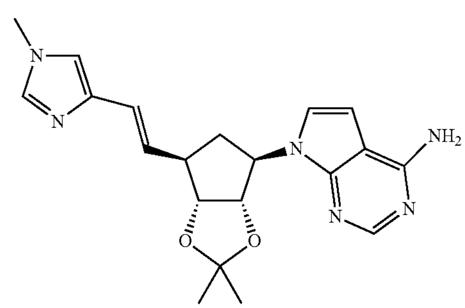 [SMILES: Cn1cnc(/C=C/[C@H]2C[C@@H](n3ccc4c(N)ncnc43)[C@@H]3OC(C)(C)O[C@@H]32)c1] | Intermediate 9 and 4-iodo-1-methyl-1h-imidazole |
| 92 | 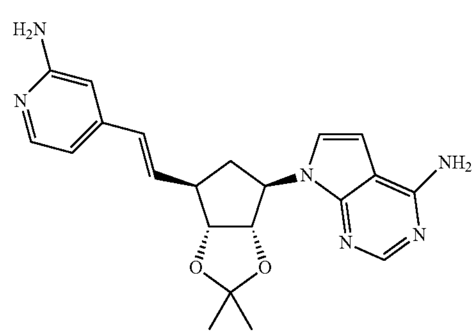 [SMILES: CC1(C)O[C@@H]2[C@H](O1)[C@@H](/C=C/c1ccnc(N)c1)C[C@H]2n1ccc2c(N)ncnc21] | Intermediate 9 and 2-amino-4-bromopyridine |

TABLE 20-continued

| Intermediate | Structure | Starting materials |
|---|---|---|
| 93 | 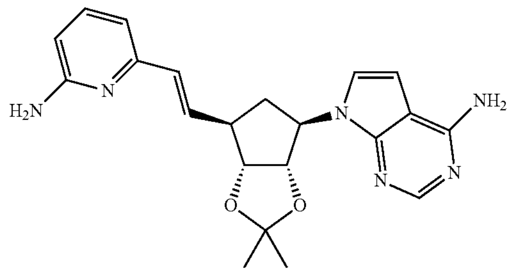 [SMILES: CC1(C)O[C@@H]2[C@H](O1)[C@@H](/C=C/c1cccc(N)n1)C[C@H]2n1ccc2c(N)ncnc21] | Intermediate 9 and 2-amino-6-bromopyridine |

Example A30

Preparation of Intermediate 94 intermediate 94

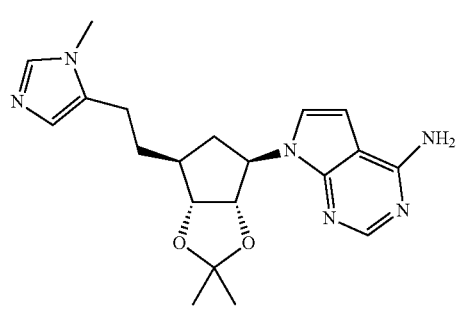

A mixture of intermediate 90 (0.1 g, 0.23 mmol) in THF (30 ml) was hydrogenated with Pd/C 10% (30 mg) and thiophene solution 0.4% in dipe (1 mL) at room temperature under hydrogen atmosphere until 1 eq. hydrogen was absorbed. The catalyst was removed by filtration over dicalite. The combined solvents of the filtrate were evaporated. The residue was dissolved in dichloromethane and purified over a SiO$_2$ column, type Grace Reveleris SRC, 4 g, Si 40, on a Grace Reveleris X$_2$ purification system using dichloromethane and methanol as eluens in a gradient starting from 100% dichloromethane to 80% dichloromethane and 20% methanol. The fractions containing product were combined and the solvents were evaporated yielding intermediate 94 (66.4 mg, 44% yield)

Example A32

Step 1

Preparation of Intermediate 139

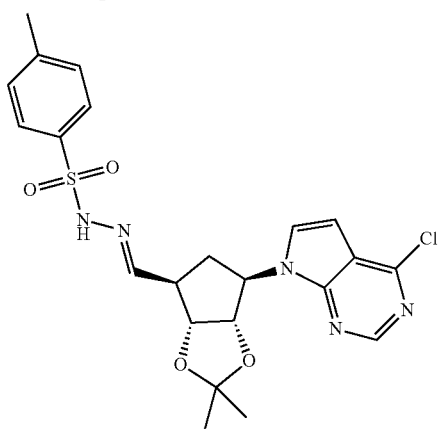 [SMILES: Cc1ccc(S(=O)(=O)N/N=C/[C@H]2C[C@@H](n3ccc4c(Cl)ncnc43)[C@@H]3OC(C)(C)O[C@@H]32)cc1]

Tosylhydrazine (413 mg, 2.2 mmol) was added to a solution of intermediate 3 (1.3 g, 2.2 mmol) in MEOH (50 ml). The reaction mixture was stirred at 60° C. for 1 hour. The reaction mixture was concentrated to dryness. The residue was purified by flash column chromatography over silica gel (eluent: petroleum ether/ethyl acetate from 100/0 to 70/30) to give intermediate 139 as bright yellow oil.

Step 2

Preparation of Intermediate 140

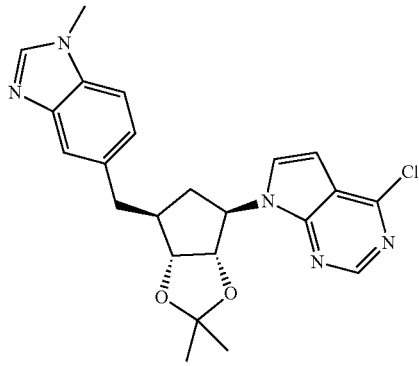 [SMILES: Cn1cnc2cc(C[C@H]3C[C@@H](n4ccc5c(Cl)ncnc54)[C@@H]4OC(C)(C)O[C@H]34)ccc21]

Boronic acid, B-(1-methyl-1H-benzimidazol-5-yl)-(389 mg, 1.77 mmol), intermediate 139 (1.3 g, 2.12 mmol) and cesium carbonate (0.86 g, 2.65 mmol) were stirred in dioxane (30 ml) at 110° C. under N$_2$ for 3 hours. The reaction mixture was filtered and concentrated under vacuum. The residue was purified by flash column chromatography over silica gel (eluent: petroleum ether/ethyl acetate from 100/0 to 0/100). The desired fractions were collected and the solvent was evaporated.

The residue was re-purified by preparative high-performance liquid chromatography. Column type: Gemini 150× 25 mm, 5 µm, Condition: A: water (10 mM NH$_4$HCO$_3$); B: MeCN at the beginning: A (51%) and B (49%); at the end: A: (36%) and B (64%), Gradient Time (min) 9.5; 100% B Hold Time (min) 2.5; Flow Rate (ml/min) 30 The pure fractions were collected and the solvent was evaporated under vacuum to give intermediate 140 (100 mg, 12% yield).

B. Preparation of Final Compounds

Example B1

Preparation of Compound 1

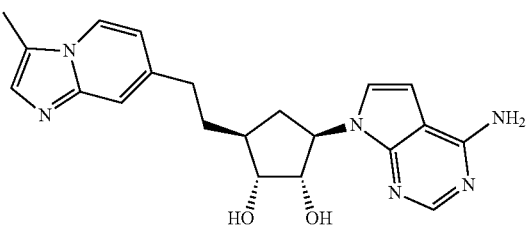
compound 1

Intermediate 54 (0.59 mmol was dissolved in EtOH (5 mL), followed by the addition of 1 M aqueous HCl (3 mL, 3.0 mmol). The resulting reaction mixture was stirred at room temperature until complete deprotection (approximately 3 days), after which it was basified by the addition of $Na_2CO_3$ (253 mg) and concentrated under reduced pressure. The residue was subjected to purification by preparative reversed phase HPLC (Stationary phase: XBridge C18, 3.5 μM, 4.6 mm×100 mm; mobile phase: 0.25% aqueous $NH_4CO_3$, MeOH), to give compound 1 (110 mg, 47% yield).

Example B2

Preparation of Compound 2

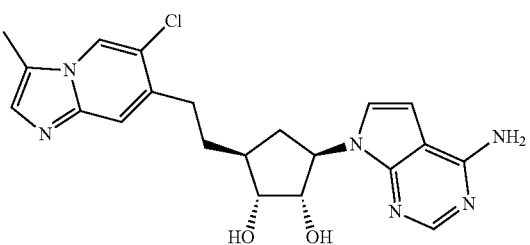
compound 2

Intermediate 55 was dissolved in EtOH (2 mL), followed by the addition of 1 M aqueous HCl (9.86 mL, 9.86 mmol). The resulting reaction mixture was stirred at room temperature until complete deprotection (typically ca. 2 days), after which it was basified by the addition of aqueous ammonia and concentrated under reduced pressure. The residue was directly subjected to purification by preparative reversed phase HPLC (Stationary phase: XBridge C18, 3.5 μM, 4.6 mm×100 mm; mobile phase: 0.25% aqueous $NH_4CO_3$, MeOH), to give compound 2 (82 mg, 52% yield).

Below final compounds were prepared by an analogous reaction protocol as was used for the preparation of compound 1 and compound 2 using the appropriate starting materials (Table 14)

TABLE 14

| compound | structure | Starting materials |
|---|---|---|
| 3 | 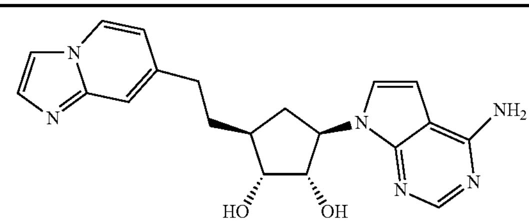 | Intermediate 56 |
| 4 | 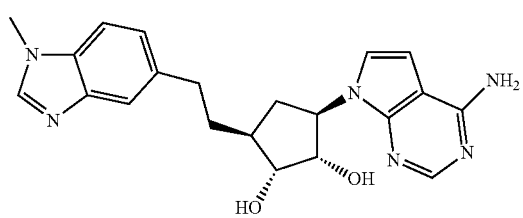 [SMILES: Cn1cnc2cc(CC[C@H]3C[C@@H](n4ccc5c(N)ncnc54)[C@H](O)[C@@H]3O)ccc21] | Intermediate 57 |
| 5 | 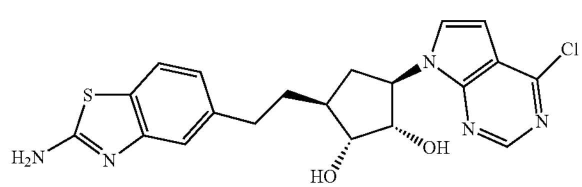 [SMILES: Nc1nc2cc(CC[C@H]3C[C@@H](n4ccc5c(Cl)ncnc54)[C@H](O)[C@@H]3O)ccc2s1] | Intermediate 51 |
| 6 | 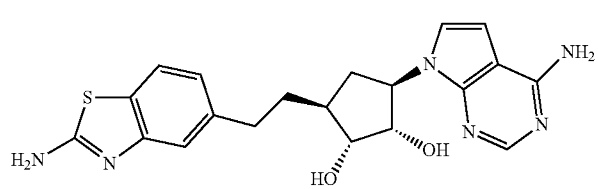 [SMILES: Nc1nc2cc(CC[C@H]3C[C@@H](n4ccc5c(N)ncnc54)[C@H](O)[C@@H]3O)ccc2s1] | Intermediate 58 |

TABLE 14-continued

| compound | structure | Starting materials |
| --- | --- | --- |
| 7 | 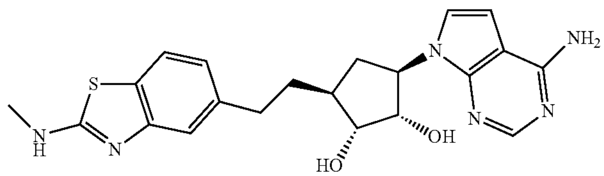 [SMILES: CNc1nc2cc(CC[C@H]3C[C@@H](n4ccc5c(N)ncnc54)[C@H](O)[C@@H]3O)ccc2s1] | Intermediate 60 |
| 8 | 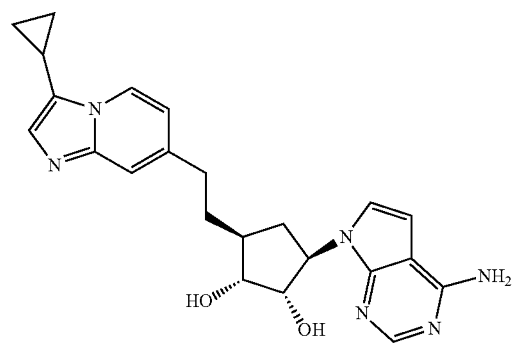 [SMILES: Nc1ncnc2c1ccn2[C@@H]1C[C@H](CCc2ccn3c(C4CC4)cnc3c2)[C@@H](O)[C@H]1O] | Intermediate 61 |
| 9 | 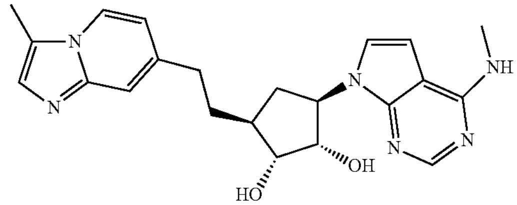 [SMILES: CNc1ncnc2c1ccn2[C@@H]1C[C@H](CCc2ccn3c(C)cnc3c2)[C@@H](O)[C@H]1O] | Intermediate 62 |
| 10 | 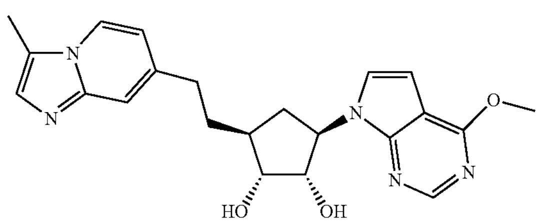 | Intermediate 65 |
| 11 | 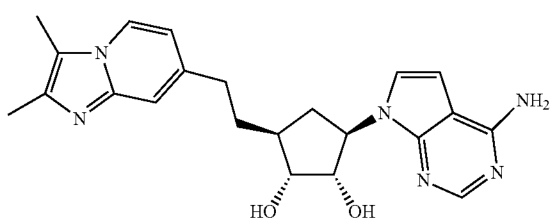 [SMILES: Cc1nc2cc(CC[C@H]3C[C@@H](n4ccc5c(N)ncnc54)[C@H](O)[C@@H]3O)ccn2c1C] | Intermediate 63 |
| 12 | 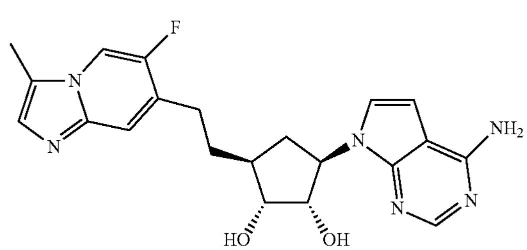 [SMILES: Cc1cnc2cc(CC[C@H]3C[C@@H](n4ccc5c(N)ncnc54)[C@H](O)[C@@H]3O)c(F)cn12] | Intermediate 64 |

TABLE 14-continued

| compound | structure | Starting materials |
|---|---|---|
| 22 | 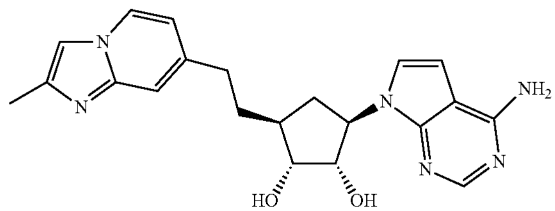 [SMILES: Cc1cn2ccc(CC[C@H]3C[C@@H](n4ccc5c(N)ncnc54)[C@H](O)[C@@H]3O)cc2n1] | Intermediate 76 |
| 23 | 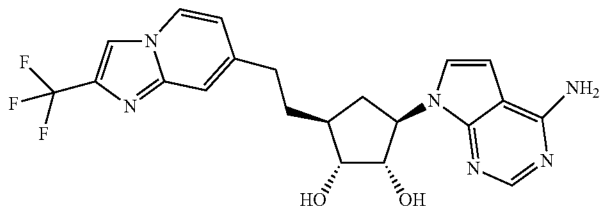 [SMILES: Nc1ncnc2c1ccn2[C@@H]1C[C@H](CCc2ccn3cc(C(F)(F)F)nc3c2)[C@@H](O)[C@H]1O] | Intermediate 77 |
| 74 | 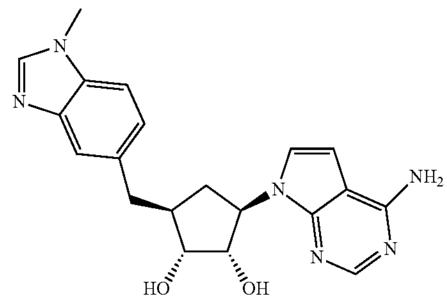 [SMILES: Cn1cnc2cc(C[C@H]3C[C@@H](n4ccc5c(N)ncnc54)[C@H](O)[C@@H]3O)ccc21] | Intermediate 141 |

Example B 3

Preparation of Compound 16

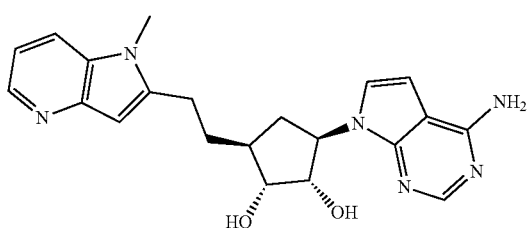

compound 16

A solution of intermediate 71 (100 mg, 0.23 mmol) in HCl 4M in MeOH (10 ml) was stirred at room temperature for 1 hour. Then NH$_4$OH was added into the mixture until the pH>7. The mixture was concentrated. The residue was purified by prep. HPLC: Column type: Waters Xbridge Prep OBD C18: 150×30 mm, 5 μm. Condition: A: water (0.05% ammonia hydroxide v/v); B: MeCN at the beginning: A (87%) and B (13%); at the end: A: (57%) and B (43%). Gradient Time (min) 10; 100% B Hold Time (min) 3; Flow Rate (ml/min) 25 to give the 34 mg compound 16 (34 mg, 37% yield) as a white solid.

Below final compounds were prepared by an analogous reaction protocol as was used for the preparation of compound 16 (using the appropriate starting materials (Table 15)

TABLE 15

| compound | structure | Starting materials |
|---|---|---|
| 17 | 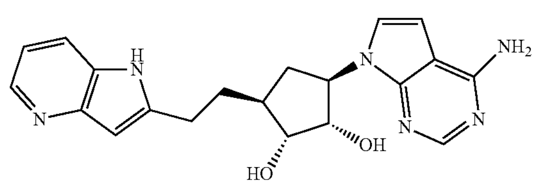 [SMILES: Nc1ncnc2c1ccn2[C@@H]1C[C@H](CCc2cc3ncccc3[nH]2)[C@@H](O)[C@H]1O] | intermediate 72 |

TABLE 15-continued

| compound | structure | Starting materials |
|---|---|---|
| 18 | 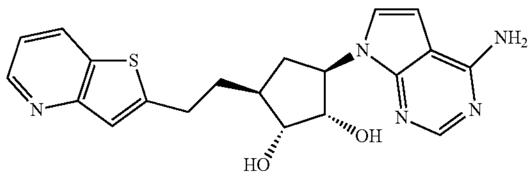 [SMILES: Nc1ncnc2c1ccn2[C@@H]1C[C@H](CCc2cc3ncccc3s2)[C@@H](O)[C@H]1O] | intermediate 73 |
| 19 | 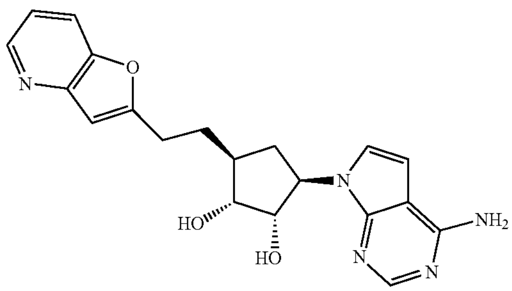 [SMILES: Nc1ncnc2c1ccn2[C@@H]1C[C@H](CCc2cc3ncccc3o2)[C@@H](O)[C@H]1O] | intermediate 74 |
| 20 | 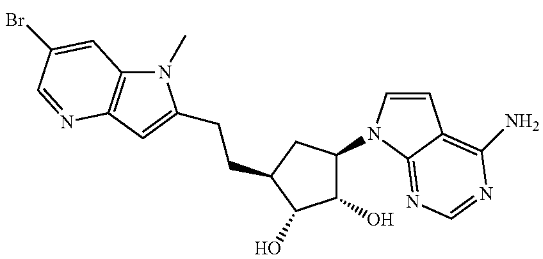 [SMILES: Cn1c(CC[C@H]2C[C@@H](n3ccc4c(N)ncnc43)[C@H](O)[C@@H]2O)cc2ncc(Br)cc21] | intermediate 70 |

Example B4

Preparation of Compound 21 compound 21

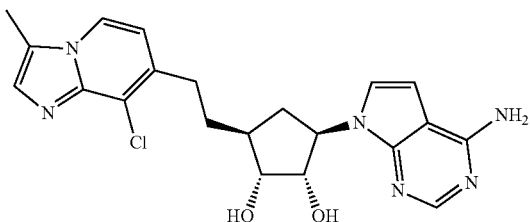

Intermediate 75 (1.79 mmol) was dissolved in EtOH (2 mL), followed by the addition of 1 M aqueous HCl (9.86 mL, 9.86 mmol). The resulting reaction mixture was stirred at room temperature until complete deprotection (typically ca. 2 days), after which it was basified by the addition of aqueous ammonia and concentrated under reduced pressure. The residue was directly subjected to purification by preparative reversed phase HPLC (Stationary phase: XBridge C18, 3.5 µM, 4.6 mm×100 mm; mobile phase: 0.25% aqueous $NH_4CO_3$, MeOH), to give compound 21 (82 mg, 52% yield).

Example B5

Preparation of Compound 24 compound 24

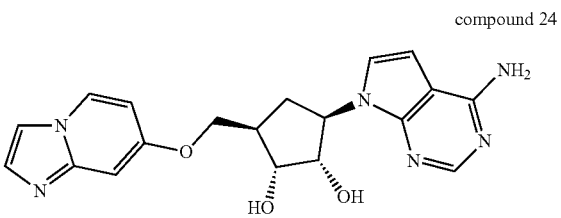 [SMILES: Nc1ncnc2c1ccn2[C@@H]1C[C@H](COc2ccn3ccnc3c2)[C@@H](O)[C@H]1O]

A solution of intermediate 79 (365 mg, 1.0 eq) in MeOH (3 mL) and HCl/dioxane (3 mL) was stirred at 25° C. for 2 hrs. The solvent was removed. The residue was adjusted to pH=7 with $NH_3H2O$, and then was washed with $H_2O$ (10 mL×2) and $CH_3CN$ (10 mL×2) to give compound 24 (235 mg, 67.6% yield).

Example B6

Preparation of Compound 25

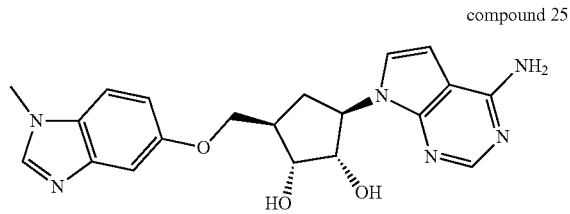 [SMILES: Cn1cnc2cc(OC[C@H]3C[C@@H](n4ccc5c(N)ncnc54)[C@H](O)[C@@H]3O)ccc21]

compound 25

To a solution of intermediate 81 (320 mg, 736.5 umol, 1.0 eq) in MeOH (2.5 mL) was added HCl/dioxane (2.5 mL). The mixture was stirred at 20° C. for 15 hrs. The solvent was removed under reduce pressure. The residue was adjusted to pH>7 with $NH_3H_2O$. The mixture was crystallized from $H_2O$ (10 mL). The precipitate was washed with $CH_3CN$ to give compound 25 (230 mg, 75% yield) as a white solid.

Example B7

Preparation of Compound 26

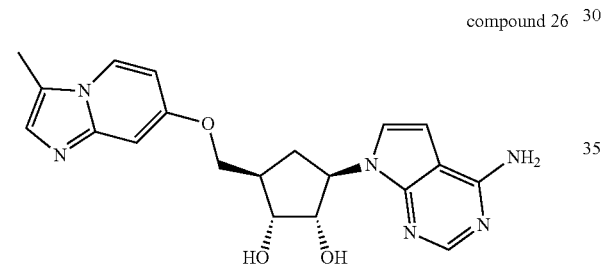

compound 26

Intermediate 82 (1.52 mmol) was dissolved in EtOH (20 mL), followed by the addition of 1 M aqueous HCl (15.2 mL, 15.2 mmol). The reaction mixture was stirred at room temperature until complete deprotection (typical ca. 3 days), after which it was basified by the addition of aqueous ammonia and directly subjected to purification by preparative reversed phase HPLC (Stationary phase: XBridge C18, 3.5 μM, 4.6 mm×100 mm; mobile phase: 0.25% aqueous $NH_4CO_3$, MeOH), to give compound 26 (135 mg, 22.5%).

Below final compounds were prepared by an analogous reaction protocol as was used for the preparation of compound 26 using the appropriate starting materials (Table 19)

Example B8

Preparation of Compound 27 compound 27

HCl (3.92 mL, 1 M in $H_2O$, 3.92 mmol) was added dropwise to a stirred solution of intermediate 83 (0.18 g, 0.392 mmol) in iPrOH (5 mL) at room temperature. After addition the reaction mixture was stirred at room temperature for 3 hours. $NH_3$ (28% in $H_2O$) (0.53 mL, 7.85 mmol) was added. The solvents were evaporated. The residue was dissolved in 30 mL methanol and purified with Prep HPLC (Stationary phase: RP XBridge Prep C18 OBD-10 μm, 30×150 mm, Mobile phase: 0.25% $NH_4HCO_3$ solution in water, MeOH) yielding compound 27 (102 mg, 73% yield).

Below compounds were prepared by an analogous reaction protocol as was used for the preparation of compound 27 using the appropriate starting materials (Table 16).

TABLE 19

| compound | structure | Starting materials |
|---|---|---|
| 33 | 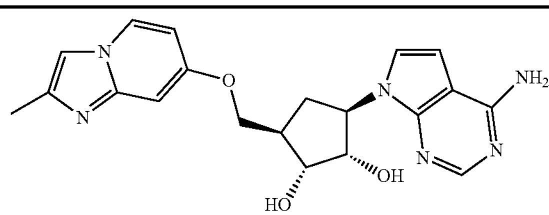 | intermediate 89 |

TABLE 16

| compound | Structure | Starting materials |
|---|---|---|
| 28 | 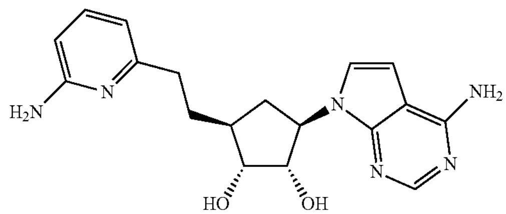 [SMILES: Nc1cccc(CC[C@H]2C[C@@H](n3ccc4c(N)ncnc43)[C@H](O)[C@@H]2O)n1] | Intermediate 84 |
| 29 | 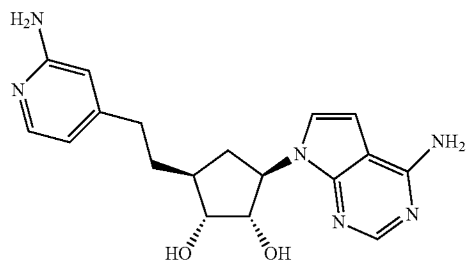 [SMILES: Nc1cc(CC[C@H]2C[C@@H](n3ccc4c(N)ncnc43)[C@H](O)[C@@H]2O)ccn1] | Intermediate 85 |
| 32 | 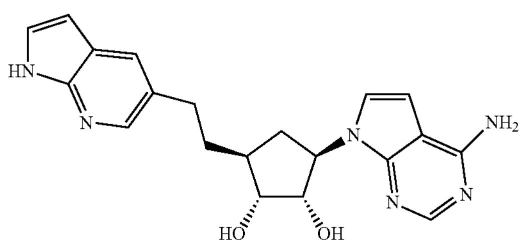 [SMILES: Nc1ncnc2c1ccn2[C@@H]1C[C@H](CCc2cnc3[nH]ccc3c2)[C@@H](O)[C@H]1O] | Intermediate 88 |
| 40 | 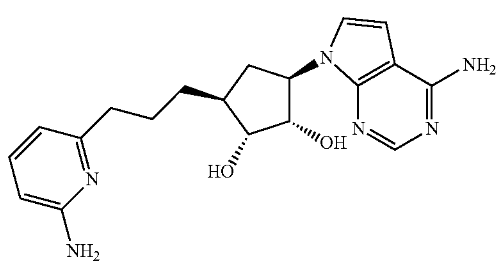 [SMILES: Nc1cccc(CCC[C@H]2C[C@@H](n3ccc4c(N)ncnc43)[C@H](O)[C@@H]2O)n1] | Intermediate 100 |
| 41 | 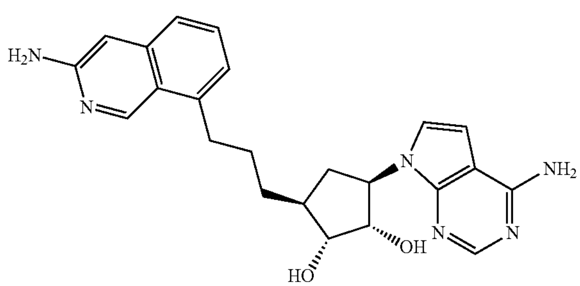 [SMILES: Nc1cc2cccc(CCC[C@H]3C[C@@H](n4ccc5c(N)ncnc54)[C@H](O)[C@@H]3O)c2cn1] | Intermediate 101 |
| 42 | 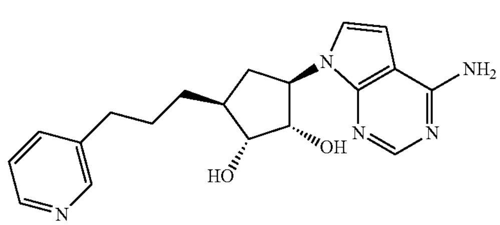 [SMILES: Nc1ncnc2c1ccn2[C@@H]1C[C@H](CCCc2cccnc2)[C@@H](O)[C@H]1O] | Intermediate 102 |

TABLE 16-continued

| compound | Structure | Starting materials |
|---|---|---|
| 43 | 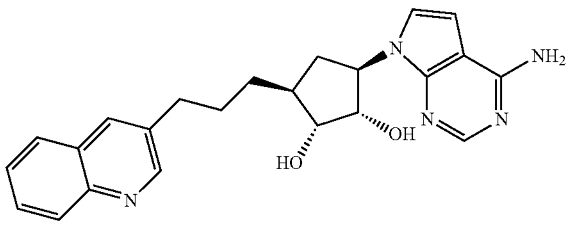 [SMILES: Nc1ncnc2c1ccn2[C@@H]1C[C@H](CCCc2cnc3ccccc3c2)[C@@H](O)[C@H]1O] | Intermediate 103 |
| 44 | 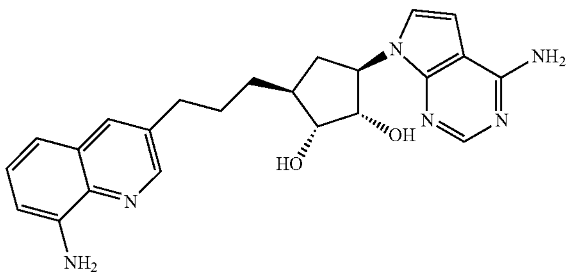 [SMILES: Nc1ncnc2c1ccn2[C@@H]1C[C@H](CCCc2cnc3c(N)cccc3c2)[C@@H](O)[C@H]1O] | Intermediate 104 |
| 45 | 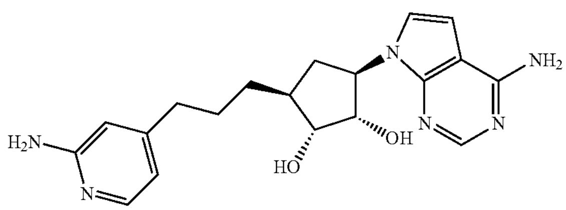 [SMILES: Nc1cc(CCC[C@H]2C[C@@H](n3ccc4c(N)ncnc43)[C@H](O)[C@@H]2O)ccn1] | Intermediate 105 |
| 46 | 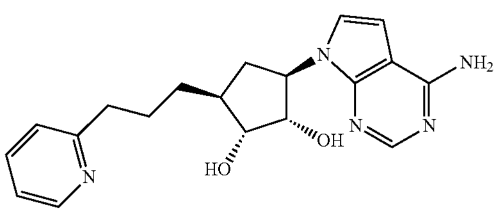 [SMILES: Nc1ncnc2c1ccn2[C@@H]1C[C@H](CCCc2ccccn2)[C@@H](O)[C@H]1O] | Intermediate 106 |
| 47 | 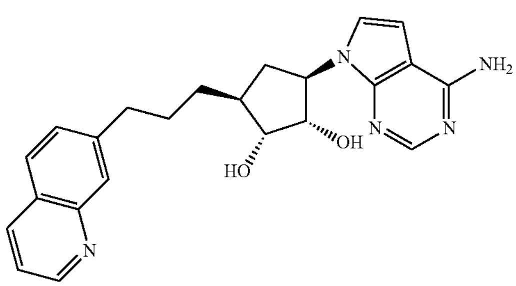 [SMILES: Nc1ncnc2c1ccn2[C@@H]1C[C@H](CCCc2ccc3cccnc3c2)[C@@H](O)[C@H]1O] | Intermediate 107 |
| 48 | 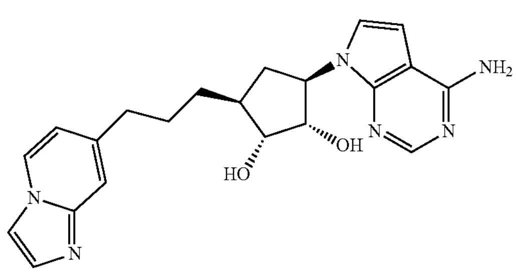 [SMILES: Nc1ncnc2c1ccn2[C@@H]1C[C@H](CCCc2ccn3ccnc3c2)[C@@H](O)[C@H]1O] | Intermediate 108 |

TABLE 16-continued

| compound | Structure | Starting materials |
|---|---|---|
| 49 | 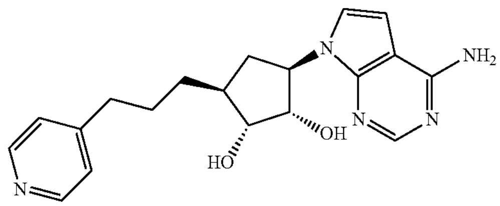 | Intermediate 109 |
| 50 | 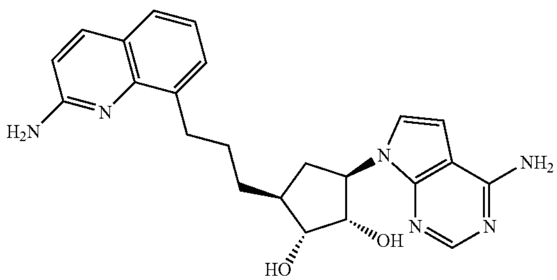 [SMILES: Nc1ccc2cccc(CCC[C@H]3C[C@@H](n4ccc5c(N)ncnc54)[C@H](O)[C@@H]3O)c2n1] | Intermediate 110 |
| 51 | 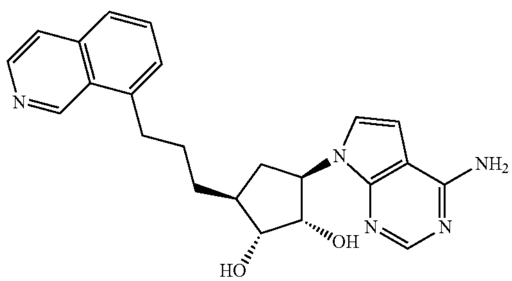 [SMILES: Nc1ncnc2c1ccn2[C@@H]1C[C@H](CCCc2cccc3ccncc23)[C@@H](O)[C@H]1O] | Intermediate 111 |
| 52 | 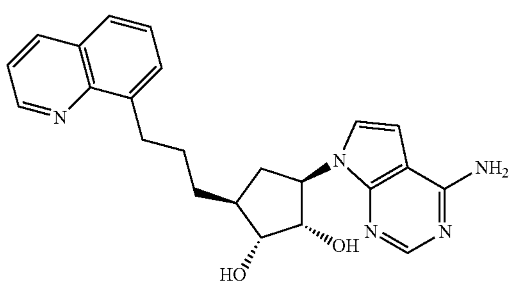 [SMILES: Nc1ncnc2c1ccn2[C@@H]1C[C@H](CCCc2cccc3cccnc23)[C@@H](O)[C@H]1O] | Intermediate 112 |
| 53 | 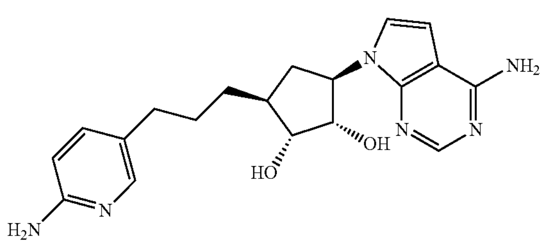 [SMILES: Nc1ccc(CCC[C@H]2C[C@@H](n3ccc4c(N)ncnc43)[C@H](O)[C@@H]2O)cn1] | Intermediate 113 |
| 54 | 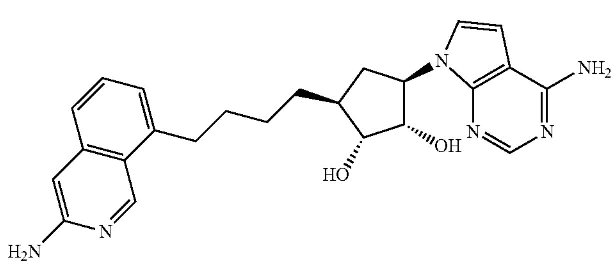 [SMILES: Nc1cc2cccc(CCCC[C@H]3C[C@@H](n4ccc5c(N)ncnc54)[C@H](O)[C@@H]3O)c2cn1] | Intermediate 119 |

TABLE 16-continued
| compound | Structure | Starting materials |
|---|---|---|
| 55 | 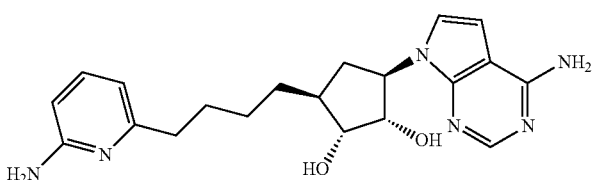 | Intermediate 120 |
| 56 | 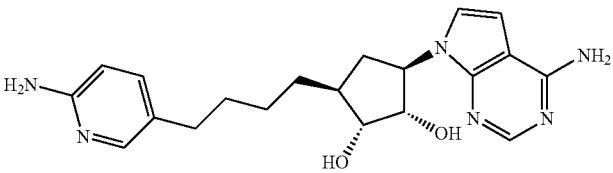 [SMILES: Nc1ccc(CCCC[C@H]2C[C@@H](n3ccc4c(N)ncnc43)[C@H](O)[C@@H]2O)cn1] | Intermediate 121 |
| 57 | 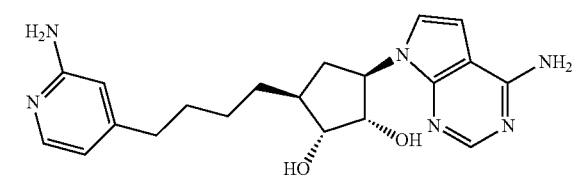 [SMILES: Nc1cc(CCCC[C@H]2C[C@@H](n3ccc4c(N)ncnc43)[C@H](O)[C@@H]2O)ccn1] | Intermediate 122 |
| 58 | 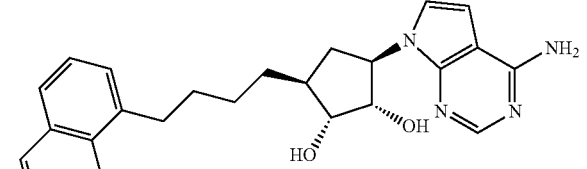 | Intermediate 123 |
| 59 | 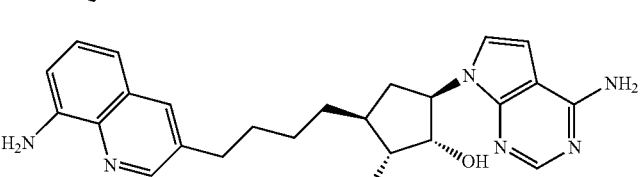 | Intermediate 124 |
| 60 | 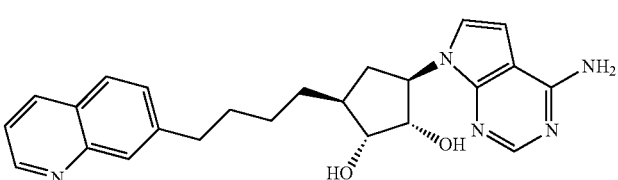 | Intermeidate 125 |
| 61 | 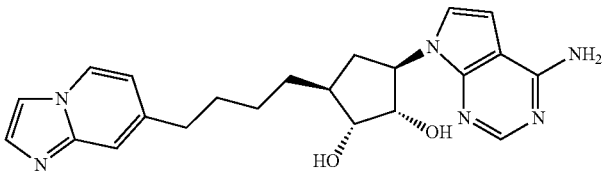 [SMILES: Nc1ncnc2c1ccn2[C@@H]1C[C@H](CCCCc2ccn3ccnc3c2)[C@@H](O)[C@H]1O] | Intermediate 126 |
| 62 | 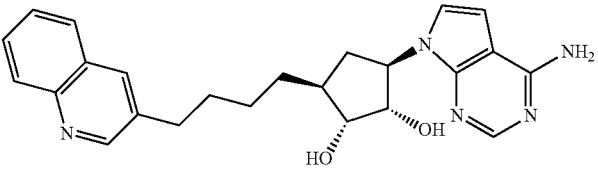 [SMILES: Nc1ncnc2c1ccn2[C@@H]1C[C@H](CCCCc2cnc3ccccc3c2)[C@@H](O)[C@H]1O] | Intermediate 127 |

TABLE 16-continued

| compound | Structure | Starting materials |
|---|---|---|
| 63 | 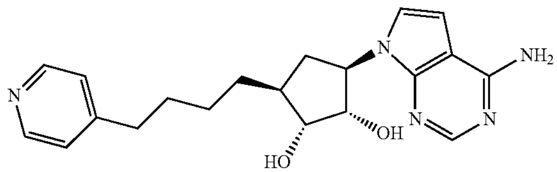 [SMILES: Nc1ncnc2c1ccn2[C@@H]1C[C@H](CCCCc2ccncc2)[C@@H](O)[C@H]1O] | Intermediate 128 |
| 64 | 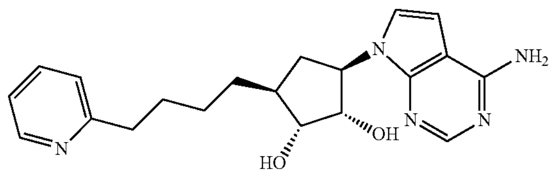 [SMILES: Nc1ncnc2c1ccn2[C@@H]1C[C@H](CCCCc2ccccn2)[C@@H](O)[C@H]1O] | Intermediate 129 |
| 65 | 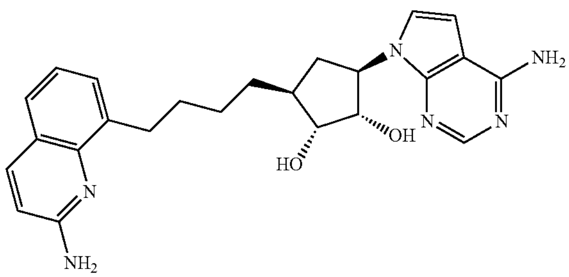 [SMILES: Nc1ccc2cccc(CCCC[C@H]3C[C@@H](n4ccc5c(N)ncnc54)[C@H](O)[C@@H]3O)c2n1] | Intermediate 130 |
| 66 | 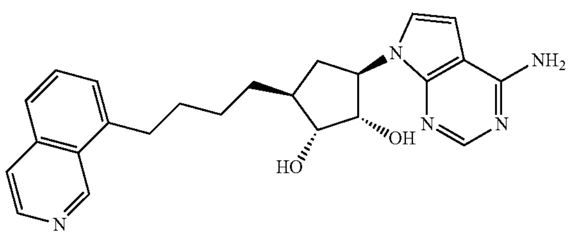 [SMILES: Nc1ncnc2c1ccn2[C@@H]1C[C@H](CCCCc2cccc3ccncc23)[C@@H](O)[C@H]1O] | Intermediate 131 |
| 67 | 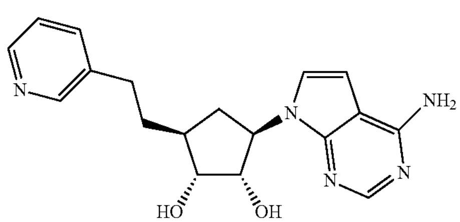 [SMILES: Nc1ncnc2c1ccn2[C@@H]1C[C@H](CCc2cccnc2)[C@@H](O)[C@H]1O] | Intermediate 132 |
| 68 | 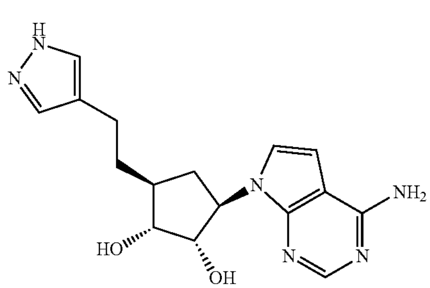 [SMILES: Nc1ncnc2c1ccn2[C@@H]1C[C@H](CCc2cn[nH]c2)[C@@H](O)[C@H]1O] | Intermediate 133 |

TABLE 16-continued

| compound | Structure | Starting materials |
|---|---|---|
| 69 | 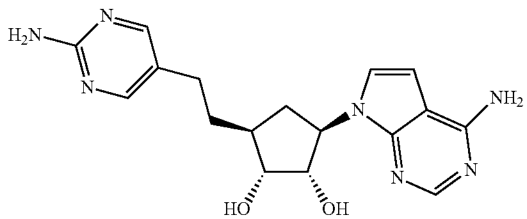 [SMILES: Nc1ncc(CC[C@H]2C[C@@H](n3ccc4c(N)ncnc43)[C@H](O)[C@@H]2O)cn1] | Intermediate 134 |
| 70 | 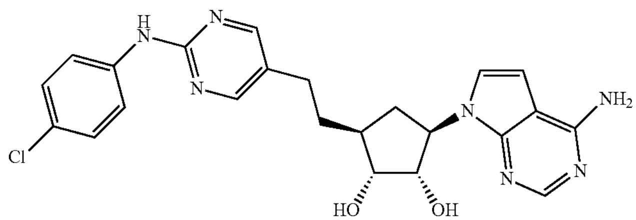 [SMILES: Nc1ncnc2c1ccn2[C@@H]1C[C@H](CCc2cnc(Nc3ccc(Cl)cc3)nc2)[C@@H](O)[C@H]1O] | Intermediate 135 |
| 71 | 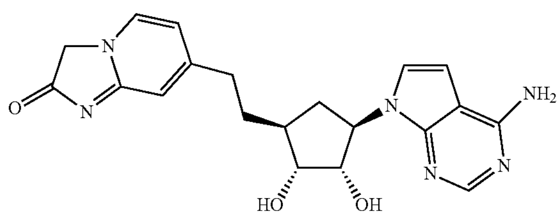 [SMILES: Nc1ncnc2c1ccn2[C@@H]1C[C@H](CCC2=CC3=NC(=O)CN3C=C2)[C@@H](O)[C@H]1O] | Intermediate 136 |
| 72 | 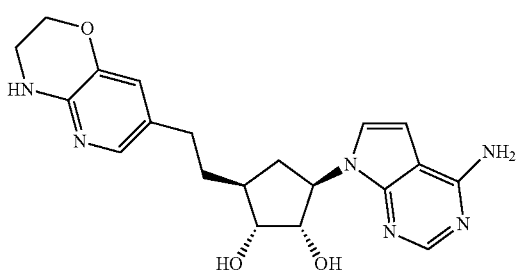 [SMILES: Nc1ncnc2c1ccn2[C@@H]1C[C@H](CCc2cnc3c(c2)OCCN3)[C@@H](O)[C@H]1O] | Intermediate 137 |
| 73 | 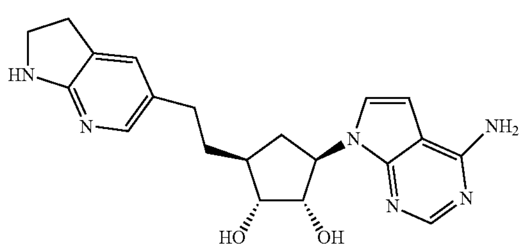 [SMILES: Nc1ncnc2c1ccn2[C@@H]1C[C@H](CCc2cnc3c(c2)CCN3)[C@@H](O)[C@H]1O] | Intermediate 138 |

Example B9

Preparation of Compound 30

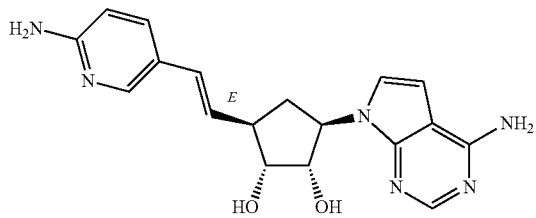

compound 30

HCl (6.62 mL, 1 M in H$_2$O, 6.6 mmol) was added dropwise to a stirred solution of intermediate 86 (0.26 g, 0.66 mmol) in MeOH (8 mL) at room temperature. After addition the reaction mixture was stirred at room temperature for 3 hours. NH$_3$ (28% in H$_2$O) (0.90 mL, 13.2 mmol) was added. The solvents were evaporated. The residue was dissolved in 30 mL methanol and purified with Prep HPLC (Stationary phase: RP XBridge Prep C18 OBD-10 μm, 30×150 mm, Mobile phase: 0.25% NH$_4$HCO$_3$ solution in water, MeOH) yielding compound 30 (143 mg, 57% yield).

Below compounds were prepared by an analogous reaction protocol as was used for the preparation of compound 30 using the appropriate starting materials (Table 21).

TABLE 21

| compound | Structure | Starting materials |
|---|---|---|
| 34 | 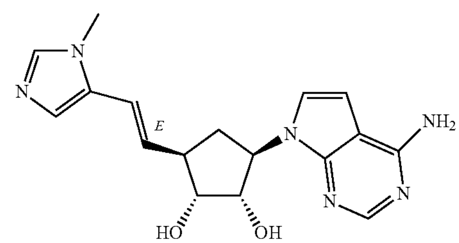 | Intermediate 90 |
| 35 | 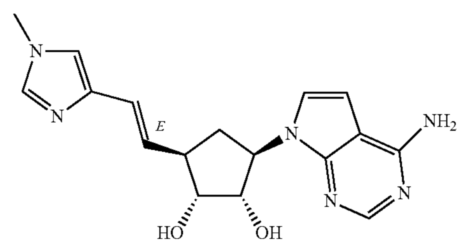 | Intermediate 91 |
| 36 | 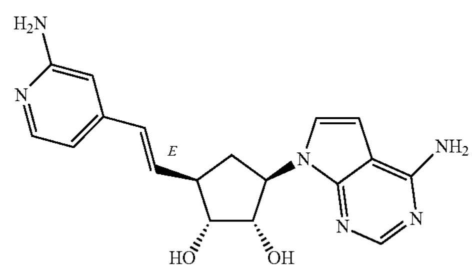 | Intermediate 92 |
| 37 | 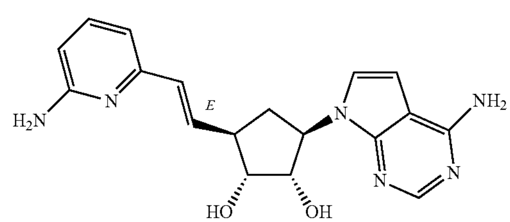 | Intermediate 93 |

TABLE 21-continued

| compound | Structure | Starting materials |
|---|---|---|
| 38 | 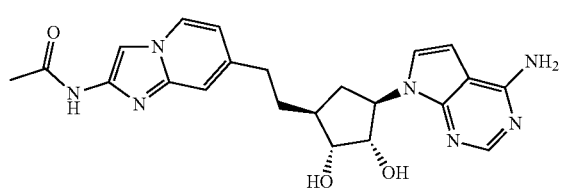 | Intermediate 94 |
| 39 | 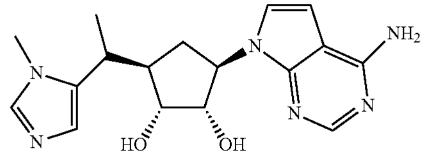 [SMILES: CC(c1cncn1C)[C@H]1C[C@@H](n2ccc3c(N)ncnc32)[C@H](O)[C@@H]1O] | Intermediate 94 |

Example B10

Preparation of Compound 31 compound 31

To a solution of intermediate 87 (400 mg, 0.69 mmol) in MeOH (10 ml) was added TFA (5 ml). The mixture was stirred at room temperature for 5 hours. The solvent was concentrated under vacuum. The residue was taken up into water, basified with $NH_3.H_2O$ to pH>7 and extracted with ethyl acetate (100 mL×2). The combined organic layers were washed with brine, dried ($Na_2SO_4$), filtered and concentrated by vacuum to give the crude product as a brown oil. The crude product was purified by preparative high-performance liquid chromatography:

Column: Xtimate C18 150×25 mm, 5 μm

Condition: A: water (10 mM $NH_4HCO_3$) B: ACN at the beginning: A (92%) and B (8%) at the end: A (62%) and B (38%)

Gradient Time (min) 14; 100% B Hold Time (min) 2.5; Flow Rate (ml/min) 25. The pure fractions were collected and the organic solvent was evaporated under vacuum. The aqueous layer was lyophilized to dryness to give compound 31 (83 mg, 27% yield) as a white solid.

Example B11

Preparation of Compound 75

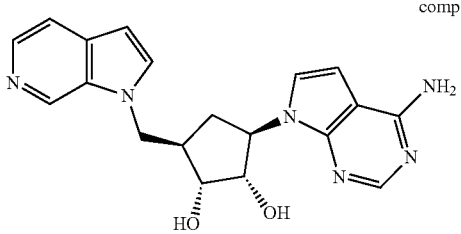

compound 75

Intermediate 146 (100 mg, 0.22 mmol) and $K_2CO_3$ (270 mg) were added to MeOH (4 ml) and refluxed for 2 hours. The mixture was evaporated under vacuum. The crude product was purified by preparative HPLC. Column: Xtimate C18 150×25 mm×5 μm Condition: A: water (0.05% ammonia hydroxide v/v) B: MeCN, at the beginning: A (90%) and B (10%), at the end: A (60%) and B (40%). Gradient Time (min) 10; 100% B Hold Time (min) 2.5; Flow Rate (ml/min) 25.

The pure fractions were collected and the solvent was evaporated under vacuum.

The aqueous layer was lyophilized to dryness to give compound 75 (22.8 mg, 28.6% yield) as a white solid.

C. Conversions of Final Compounds

Example C1

Preparation of Compound 13

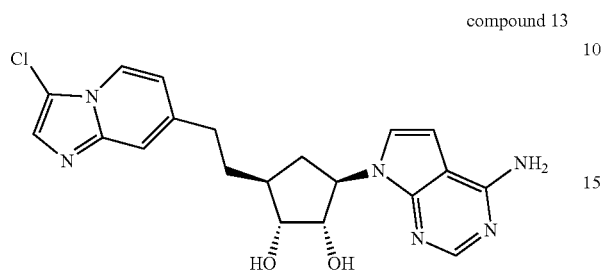

compound 13

Compound 3 (50 mg, 0.13 mmol) was stirred in DMF (2 mL). N-Chlorosuccinimide (17.6 mg, 0.13 mmol) was added. The reaction mixture was stirred overnight. The reaction mixture was diluted to 10 mL with DMF and used as such for RP purification (XBRidge C18_3.5 μM (100×4.6 mm), aq. $NH_4CO_3$ and MeOH) yielding compound 13 (27 rag, 49.5% yield).

Below final compounds were prepared by an analogous reaction protocol as was used for the preparation of compound 13 using the appropriate starting materials (Table 17).

TABLE 17

| compound | structure | Starting materials |
|---|---|---|
| 14 | ![structure 14] | Compound 3 and N-Bromosuccinimide |
| 15 | ![structure 15] | Compound 1 and N-Bromosuccinimide |

Analytical Part

NMR

For a number of compounds, $^1$H NMR spectra were recorded on a Bruker Avance 400 operating at 400 MHz, or on a Varian 400MR spectrometer operating at 400 MHz. As solvents Methanol-$d_4$ or DMSO-$d_6$ (deuterated DMSO, dimethyl-d6 sulfoxide) were used. Chemical shifts (δ) are reported in parts per million (ppm) relative to tetramethylsilane (TMS), which was used as internal standard.

|  | ¹H NMR (δ ppm) |
|---|---|
| Compound 24 | ¹H NMR (400 MHz, DMSO-d₆) δ ppm 1.62-1.77 (m, 1 H), 2.34 (s, 1 H), 2.43 (s, 1 H), 3.95 (br s, 1 H), 4.14-4.36 (m, 3 H), 4.77-5.01 (m, 3 H), 6.61 (d, J = 3.5 Hz, 1 H), 6.92 (dd, J = 7.5, 2.2 Hz, 1 H), 7.13 (br s, 3 H), 7.33 (d, J = 3.5 Hz, 1 H), 7.67 (s, 1 H), 7.93 (s, 1 H), 8.08 (s, 1 H), 8.56 (d, J = 7.5 Hz, 1 H) |
| Compound 3 | ¹H NMR (400 MHz, DMSO-d₆) δ ppm 1.39-1.56 (m, 1 H), 1.67 (m, J = 13.2 Hz, 1 H), 1.78-2.00 (m, 2 H), 2.14-2.28 (m, 1 H), 2.58-2.74 (m, 2 H), 3.66-3.78 (m, 1 H), 4.12-4.24 (m, 1 H), 4.62 (d, J = 4.9 Hz, 1 H), 4.70-4.83 (m, 2 H), 6.52 (d, J = 3.5 Hz, 1 H), 6.78 (dd, J = 7.1, 1.8 Hz, 1 H), 6.88 (br s, 2 H), 7.23 (d, J = 3.5 Hz, 1 H), 7.34 (s, 1 H), 7.46 (s, 1 H), 7.82 (s, 1 H), 8.00 (s, 1 H), 8.43 (d, J = 7.1 Hz, 1 H) |
| Compound 33 | ¹H NMR (400 MHz, DMSO-d₆) δ ppm 1.59-1.75 (m, 1 H), 2.26 (s, 3 H), 2.28-2.45 (m, 2 H), 3.94 (br q, J = 4.0 Hz, 1 H), 4.08 (dd, J = 9.2, 6.2 Hz, 1 H), 4.15 (dd, J = 9.5, 6.2 Hz, 1 H), 4.23-4.35 (m, 1 H), 4.82 (br d, J = 4.2 Hz, 1 H), 4.86-4.98 (m, 2 H), 6.55 (s, 2 H), 6.84 (br d, J = 1.8 Hz, 1 H), 6.90 (br s, 2 H), 7.29 (d, J = 3.5 Hz, 1 H), 7.45 (s, 1 H), 8.04 (s, 1 H), 8.28 (d, J = 7.5 Hz, 1 H) |
| Compound 23 | ¹H NMR (400 MHz, DMSO-d₆) δ ppm 1.42-1.58 (m, 1 H), 1.71 (br s, 1 H), 1.78-2.01 (m, 2 H), 2.24 (m, J = 12.3, 7.9, 7.9 Hz, 1 H), 2.68-2.80 (m, 2 H), 3.67-3.83 (m, 1 H), 4.15-4.26 (m, 1 H), 4.66 (d, J = 4.9 Hz, 1 H), 4.72-4.89 (m, 2 H), 6.54 (d, J = 3.5 Hz, 1 H), 6.92 (br s, 2 H), 7.00 (br dd, J = 7.1, 1.3 Hz, 1 H), 7.25 (d, J = 3.5 Hz, 1 H), 7.49 (s, 1 H), 8.02 (s, 1 H), 8.44 (s, 1 H), 8.51 (d, J = 7.1 Hz, 1 H) |
| Compound 26 | ¹H NMR (400 MHz, DMSO-d₆) δ ppm 1.68 (ddd, J = 12.5, 10.2, 8.1 Hz, 1 H), 2.28-2.46 (m, 2 H), 2.42 (d, J = 0.7 Hz, 3 H), 3.95 (br s, 1 H), 4.14 (dd, J = 9.7, 6.2 Hz, 1 H), 4.21 (dd, J = 9.7, 6.2 Hz, 1 H), 4.26-4.35 (m, 1 H), 4.82 (br s, 1 H), 4.85-4.99 (m, 2 H), 6.57 (d, J = 3.5 Hz, 1 H), 6.78 (dd, J = 7.5, 2.4 Hz, 1 H), 6.92 (br s, 2 H), 7.01 (d, J = 2.2 Hz, 1 H), 7.28 (s, 1 H), 7.30 (d, J = 3.5 Hz, 1 H), 8.04 (s, 1 H), 8.21 (d, J = 7.5 Hz, 1 H) |
| Compound 1 | ¹H NMR (400 MHz, DMSO-d₆) δ ppm 1.43-1.58 (m, 1 H), 1.62-1.76 (m, 1 H), 1.79-1.91 (m, 1 H), 1.91-2.01 (m, 1 H), 2.24 (dt, J = 12.6, 7.9 Hz, 1 H), 2.43 (d, J = 0.7 Hz, 3 H), 2.57-2.79 (m, 2 H), 3.75 (q, J = 5.1 Hz, 1 H), 4.13-4.25 (m, 1 H), 4.62 (d, J = 5.1 Hz, 1 H), 4.71-4.90 (m, 2 H), 6.54 (d, J = 3.5 Hz, 1 H), 6.84 (dd, J = 6.9, 1.7 Hz, 1 H), 6.89 (s, 2 H), 7.25 (d, J = 3.5 Hz, 1 H), 7.27 (d, J = 0.7 Hz, 1 H), 7.33 (s, 1 H), 8.03 (s, 1 H), 8.16 (d, J = 7.0 Hz, 1 H) |
| Compound 11 | ¹H NMR (400 MHz, DMSO-d₆) δ ppm 1.43-1.56 (m, 1 H), 1.61-1.74 (m, 1 H), 1.78-1.99 (m, 2 H), 2.16-2.24 (m, 1 H), 2.27 (s, 3 H), 2.35 (s, 3 H), 2.59-2.77 (m, 2 H), 3.75 (br t, J = 5.1 Hz, 1 H), 4.20 (br t, J = 6.7 Hz, 1 H), 4.61 (br s, 1 H), 4.69-4.85 (m, 2 H), 6.54 (d, J = 3.5 Hz, 1 H), 6.77 (dd, J = 7.0, 1.5 Hz, 1 H), 6.89 (br s, 2 H), 7.21 (br s, 1 H), 7.24 (d, J = 3.5 Hz, 1 H), 8.03 (s, 1 H), 8.06 (d, J = 7.0 Hz, 1 H) |
| Compound 8 | ¹H NMR (400 MHz, METHANOL-d₄) δ ppm 0.64-0.74 (m, 2 H), 1.03-1.12 (m, 2 H), 1.60-1.74 (m, 1 H), 1.77-1.89 (m, 1 H), 1.89-2.00 (m, 1 H), 2.01-2.13 (m, 2 H), 2.37-2.49 (m, 1 H), 2.76-2.91 (m, 2 H), 3.92 (dd, J = 6.2, 4.9 Hz, 1 H), 4.34 (dd, J = 7.5, 6.2 Hz, 1 H), 6.61 (d, J = 3.5 Hz, 1 H), 6.96 (dd, J = 7.1, 1.8 Hz, 1 H), 7.23 (s, 1 H), 7.24 (d, J = 3.5 Hz, 1 H), 7.35 (s, 1 H), 8.06 (s, 1 H), 8.37 (d, J = 7.1 Hz, 1 H) |
| Compound 2 | ¹H NMR (400 MHz, DMSO-d₆) δ ppm 1.45-1.60 (m, 1 H), 1.68 (br d, J = 4.8 Hz, 1 H), 1.85-2.00 (m, 2 H), 2.23-2.35 (m, 1 H), 2.45 (s, 3 H), 2.79 (m, J = 7.4, 7.4 Hz, 2 H), 3.77 (m, J = 5.3 Hz, 1 H), 4.16-4.26 (m, 1 H), 4.66 (d, J = 4.8 Hz, 1 H), 4.75-4.87 (m, 2 H), 6.54 (d, J = 3.5 Hz, 1 H), 6.89 (br s, 2 H), 7.25 (d, J = 3.5 Hz, 1 H), 7.35 (s, 1 H), 7.53 (s, 1 H), 8.03 (s, 1 H), 8.50 (s, 1 H) |
| Compound 21 | ¹H NMR (400 MHz, DMSO-d₆) δ ppm 1.45-1.60 (m, 1 H), 1.62-1.76 (m, 1 H), 1.85-1.98 (m, 1 H), 2.26-2.36 (m, 1 H), 2.45 (d, J = 0.7 Hz, 1 H), 2.84 (m, J = 6.5, 6.5 Hz, 2 H), 3.77 (br s, 1 H), 4.21 (br s, 1 H), 4.66 (br s, 1 H), 4.73-4.85 (m, 2 H), 6.54 (d, J = 3.5 Hz, 1 H), 6.88 (br s, 2 H), 6.96 (d, J = 7.0 Hz, 1 H), 7.25 (d, J = 3.5 Hz, 1 H), 7.35 (s, 1 H), 8.03 (s, 1 H), 8.21 (d, J = 7.0 Hz, 1 H) |
| Compound 12 | ¹H NMR (400 MHz, DMSO-d₆) δ ppm 1.45-1.58 (m, 1 H), 1.71 (m, J = 8.1 Hz, 1 H), 1.82-2.01 (m, 2 H), 2.22-2.32 (m, 1 H), 2.42 (s, 3 H), 2.69-2.81 (m, 2 H), 3.71-3.82 (m, 1 H), 4.15-4.24 (m, 1 H), 4.65 (br s, 1 H), 4.71-4.86 (m, 2 H), 6.54 (d, J = 3.5 Hz, 1 H), 6.89 (br s, 2 H), 7.25 (d, J = 3.7 Hz, 1 H), 7.34 (s, 1 H), 7.48 (d, J = 7.3 Hz, 1 H), 8.03 (s, 1 H), 8.45 (d, J = 5.7 Hz, 1 H) |
| Compound 14 | ¹H NMR (400 MHz, DMSO-d₆) δ ppm 1.44-1.60 (m, 1 H), 1.63-1.79 (m, 1 H), 1.80-2.03 (m, 2 H), 2.25 (dt, J = 12.6, 7.9 Hz, 1 H), 2.60-2.83 (m, 2 H), 3.76 (q, J = 5.1 Hz, 1 H), 4.14-4.28 (m, 1 H), 4.62 (d, J = 5.1 Hz, 1 H), 4.72-4.87 (m, 2 H), 6.54 (d, J = 3.5 Hz, 1 H), 6.89 (s, 2 H), 7.02 (dd, J = 7.0, 1.5 Hz, 1 H), 7.25 (d, J = 3.5 Hz, 1 H), 7.47 (s, 1 H), 7.64 (s, 1 H), 8.03 (s, 1 H), 8.26 (d, J = 7.0 Hz, 1 H) |
| Compound 13 | ¹H NMR (400 MHz, DMSO-d₆) δ ppm 1.43-1.60 (m, 1 H), 1.63-1.80 (m, 1 H), 1.85 (br s, 1 H), 1.93 (br dd, J = 14.5, 6.4 Hz, 1 H), 2.25 (dt, J = 12.6, 7.9 Hz, 1 H), 2.62-2.85 (m, 2 H), 3.76 (q, J = 5.1 Hz, 1 H), 4.13-4.29 (m, 1 H), 4.62 (d, J = 5.1 Hz, 1 H), 4.70-4.90 (m, 2 H), 6.54 (d, J = 3.5 Hz, 1 H), 6.89 (br s, 2 H), 7.03 (dd, J = 7.0, 1.3 Hz, 1 H), |

| | ¹H NMR (δ ppm) |
|---|---|
| | 7.25 (d, J = 3.5 Hz, 1 H), 7.47 (s, 1 H), 7.62 (s, 1 H), 8.03 (s, 1 H), 8.27 (d, J = 7.0 Hz, 1 H), 8.27 (s, 1 H) |
| Compound 15 | ¹H NMR (400 MHz, DMSO-d₆) δ ppm 1.45-1.57 (m, 1 H), 1.60-1.78 (m, 1 H), 1.78-2.02 (m, 2 H), 2.17-2.28 (m, 1 H), 2.43 (s, 3 H), 2.58-2.77 (m, 2 H), 3.73 (m, J = 5.1 Hz, 1 H), 4.16-4.27 (m, 1 H), 4.63 (d, J = 4.8 Hz, 1 H), 4.79 (d, J = 6.3 Hz, 1 H), 4.81-4.92 (m, 1 H), 6.68 (br s, 2 H), 6.85 (d, J = 7.0 Hz, 1 H), 7.28 (s, 1 H), 7.33 (s, 1 H), 7.59 (s, 1 H), 8.08 (s, 1 H), 8.17 (d, J = 7.0 Hz, 1 H) |
| Compound 22 | ¹H NMR (400 MHz, DMSO-d₆) δ ppm 1.43-1.58 (m, 1 H), 1.61-1.76 (m, 1 H), 1.80-2.01 (m, 2 H), 2.23 (dt, J = 12.6, 7.9 Hz, 1 H), 2.29 (s, 3 H), 2.56-2.75 (m, 2 H), 3.75 (q, J = 5.1 Hz, 1 H), 4.14-4.26 (m, 1 H), 4.61 (d, J = 5.1 Hz, 1 H), 4.71-4.86 (m, 2 H), 6.54 (d, J = 3.5 Hz, 1 H), 6.72 (dd, J = 7.0, 1.5 Hz, 1 H), 6.88 (s, 2 H), 7.22 (s, 1 H), 7.24 (d, J = 3.5 Hz, 1 H), 7.56 (s, 1 H), 8.03 (s, 1 H), 8.33 (d, J = 6.8 Hz, 1 H) |
| Compound 31 | ¹H NMR (400 MHz, DMSO-d₆) δ ppm 1.42-1.58 (m, 1 H), 1.62-1.76 (m, 1 H), 1.79-1.99 (m, 2 H), 2.05 (s, 3 H), 2.25 (dt, J = 12.4, 7.6 Hz, 1 H), 2.57-2.79 (m, 2 H), 3.75 (q, J = 5.0 Hz, 1 H), 4.11-4.28 (m, 1 H), 4.61 (d, J = 5.1 Hz, 1 H), 4.71-4.87 (m, 2 H), 6.54 (d, J = 3.5 Hz, 1 H), 6.76 (dd, J = 6.9, 1.7 Hz, 1 H), 6.89 (br s, 2 H), 7.21 (s, 1 H), 7.25 (d, J = 3.5 Hz, 1 H), 7.97 (s, 1 H), 8.03 (s, 1 H), 8.41 (d, J = 6.8 Hz, 1 H), 10.58 (s, 1 H) |
| Compound 61 | ¹H NMR (400 MHz, DMSO-d₆) δ ppm 1.30-1.46 (m, 4 H) 1.56-1.70 (m, 3 H) 1.78-1.90 (m, 1 H) 2.17 (dt, J = 12.5, 7.9 Hz, 1 H) 2.63 (t, J = 7.6 Hz, 2 H) 3.60-3.70 (m, 1 H) 4.13-4.21 (m, 1 H) 4.57 (br d, J = 4.2 Hz, 1 H) 4.71-4.82 (m, 2 H) 6.53 (d, J = 3.5 Hz, 1 H) 6.77 (dd, J = 6.9, 1.7 Hz, 1 H) 6.88 (br s, 2 H) 7.22 (d, J = 4.0 Hz, 1 H) 7.31 (br s, 1 H) 7.47 (d, J = 1.1 Hz, 1 H) 7.83 (s, 1 H) 8.02 (s, 1 H) 8.42 (d, J = 6.8 Hz, 1 H) |
| Compound 72 | ¹H NMR (400 MHz, DMSO-d₆) δ ppm 1.41-1.51 (m, 1 H) 1.52-1.62 (m, 1 H) 1.68-1.90 (m, 2 H) 2.20 (dt, J = 12.7, 7.7 Hz, 1 H) 2.33-2.48 (m, 2 H) 3.34-3.39 (m, 2 H) 3.71 (t, J = 5.0 Hz, 1 H) 4.04-4.13 (m, 2 H) 4.19 (br t, J = 6.8 Hz, 1 H) 4.51-4.67 (m, 1 H) 4.78 (m, J = 8.0, 8.0 Hz, 2 H) 6.39 (br s, 1 H) 6.54 (d, J = 3.5 Hz, 1 H) 6.83 (d, J = 1.8 Hz, 1 H) 6.88 (br s, 2 H) 7.24 (d, J = 3.5 Hz, 1 H) 7.42 (d, J = 2.0 Hz, 1 H) 8.03 (s, 1 H) |
| Compound 56 | ¹H NMR (400 MHz, DMSO-d₆) δ ppm 1.23-1.65 (m, 7 H) 1.75-1.87 (m, 1 H) 2.16 (dt, J = 12.5, 7.9 Hz, 1 H) 2.38 (t, J = 7.6 Hz, 2 H) 3.65 (br t, J = 5.4 Hz, 1 H) 4.12-4.22 (m, 1 H) 4.57 (br s, 1 H) 4.70-4.83 (m, 2 H) 5.59 (br s, 2 H) 6.38 (d, J = 8.5 Hz, 1 H) 6.54 (d, J = 4.0 Hz, 1 H) 6.88 (br s, 2 H) 7.16-7.27 (m, 2 H) 7.72 (d, J = 2.0 Hz, 1 H) 8.02 (s, 1 H) |
| Compound 65 | ¹H NMR (400 MHz, DMSO-d₆) δ ppm 1.33-1.47 (m, 4 H) 1.57-1.76 (m, 3 H) 1.82-1.97 (m, 1 H) 2.17 (dt, J = 12.6, 7.9 Hz, 1 H) 2.93-3.06 (m, 2 H) 3.68 (t, J = 5.3 Hz, 1 H) 4.17 (dd, J = 7.7, 5.9 Hz, 1 H) 4.55-4.83 (m, 3 H) 6.29 (br s, 2 H) 6.53 (d, J = 3.5 Hz, 1 H) 6.73 (d, J = 8.8 Hz, 1 H) 6.88 (br s, 2 H) 7.01-7.08 (m, 1 H) 7.22 (d, J = 3.5 Hz, 1 H) 7.32 (dd, J = 6.9, 1.2 Hz, 1 H) 7.43 (dd, J = 7.9, 1.3 Hz, 1 H) 7.83 (d, J = 8.8 Hz, 1 H) 8.03 (s, 1 H) |
| Compound 53 | ¹H NMR (400 MHz, DMSO-d₆) δ ppm 1.28-1.46 (m, 2 H) 1.49-1.61 (m, 3 H) 1.79-1.90 (m, 1 H) 2.17 (dt, J = 12.5, 7.8 Hz, 1 H) 2.40 (br t, J = 6.9 Hz, 2 H) 3.65 (br t, J = 5.1 Hz, 1 H) 4.14 (br t, J = 6.8 Hz, 1 H) 4.57 (br s, 1 H) 4.68-4.85 (m, 2 H) 5.60 (br s, 2 H) 6.38 (d, J = 8.4 Hz, 1 H) 6.52 (d, J = 3.5 Hz, 1 H) 6.87 (br s, 2 H) 7.18-7.25 (m, 2 H) 7.73 (d, J = 2.0 Hz, 1 H) 8.02 (s, 1 H) |

LCMS (Liquid Chromatography/Mass Spectrometry)

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software. Compounds are described by their experimental retention times ($R_t$) and ions. If not specified differently in the table of data, the reported molecular ion corresponds to the [M+H]⁺ (protonated molecule) and/or [M−H]⁻ (deprotonated molecule). In case the compound was not directly ionizable the type of adduct is specified (i.e. [M+NH₄]⁺, [M+HCOO]⁻, etc. . . . ). For molecules with multiple isotopic patterns (Br, Cl), the reported value is the one obtained for the lowest isotope mass. All results were obtained with experimental uncertainties that are commonly associated with the method used.

Hereinafter, "SQD" means Single Quadrupole Detector, "MSD" Mass Selective Detector, "RT" room temperature, "BEH" bridged ethylsiloxane/silica hybrid, "DAD" Diode Array Detector, "HSS" High Strength silica., "Q-Tof" Quadrupole Time-of-flight mass spectrometers, "CLND", ChemiLuminescent Nitrogen Detector, "ELSD" Evaporative Light Scanning Detector,

TABLE

LCMS Method codes (Flow expressed in mL/min; column temperature (T) in °C.; Run time in minutes).

| Method code | Instrument | Column | Mobile phase | Gradient | Flow Col T | Run time |
|---|---|---|---|---|---|---|
| 1 | Waters: Acquity® UPLC®-DAD and SQD | Waters: HSS T3 (1.8 μm, 2.1 * 100 mm) | A: 10 mM $CH_3COONH_4$ in 95% $H_2O$ + 5% $CH_3CN$ B: $CH_3CN$ | From 100% A to 5% A in 2.10 min, to 0% A in 0.90 min, to 5% A in 0.5 min | 0.7 55 | 3.5 |
| 2 | Waters: Acquity® UPLC®-DAD and SQD | Waters: BEH C18 (1.7 μm, 2.1 * 50 mm) | A: 10 mM $CH_3COONH_4$ in 95% $H_2O$ + 5% $CH_3CN$ B: $CH_3CN$ | From 95% A to 5% A in 1.3 min, held for 0.7 min. | 0.8 55 | 2 |
| 3 | Waters: Acquity® UPLC®-DAD and SQD | Waters: HSS T3 (1.8 μm, 2.1 * 100 mm) | A: 10 mM $CH_3COONH_4$ in 95% $H_2O$ + 5% $CH_3CN$ B: $CH_3CN$ | From 100% A to 5% A in 2.10 min, to 0% A in 0.90 min, to 5% A in 0.5 min | 0.7 55 | 3.5 |
| 4 | Waters: Acquity® UPLC®-DAD and SQD | Waters: HSS T3 (1.8 μm, 2.1 * 100 mm) | A: 10 mM $CH_3COONH_4$ in 95% $H_2O$ + 5% $CH_3CN$ B: $CH_3CN$ | From 100% A to 5% A in 2.10 min, to 0% A in 0.90 min, to 5% A in 0.5 min | 0.7 55 | 3.5 |
| 5 | Agilent: 1200-DAD and MSD6110 | Phenomenex: Luna-C18 (5 μm, 2 × 50 mm) | A: $CF_3COOH$ 0.1% in water, B: $CF_3COOH$ 0.05% in $CH_3CN$ | 100% A for 1 min, to 40% A in 4 min, to 15% A in 2.5 min, back to 100% A in 2 min. | 0.8 50 | 10 |
| 6 | Agilent: 1100/1200-DAD and MSD | Waters: XBridge™ Shield RP18 (5 μm, 2.1 × 50 mm) | A: $NH_4OH$ 0.05% in water, B: $CH_3CN$ | 100% A for 1 min, to 40% A in 4 min, held for 2.5 min, back to 100% A in 2 min. | 0.8 40 | 10.5 |

TABLE

Co. No. means compound number; Retention time ($R_t$) in min; n.d. means not determined.

| Co. No. | $R_t$ | $[M + H]^+$ | LCMS Method |
|---|---|---|---|
| 25 | 3.33 | 395 | 6 |
| 24 | 3.19 | 381 | 6 |
| 3 | 3.365 | 379 | 6 |
| 4 | 3.558 | 393 | 6 |
| 5 | 3.732 | 430 | 5 |
| 18 | 2.886 | 396 | 5 |
| 19 | 3.603 | 380 | 6 |
| 17 | 3.373 | 379 | 6 |
| 2 | 1.36 | 427 | 3 |
| 11 | 1.19 | 407 | 4 |
| 9 | 2.777 | 407 | 5 |
| 10 | 4.057 | 408 | 6 |
| 12 | 1.24 | 411 | 3 |
| 21 | 1.22 | 427 | 4 |
| 27 | 0.99 | 355 | 4 |
| 28 | 1.04 | 355 | 1 |
| 29 | 0.45 | 355 | 2 |
| 30 | 0.98 | 353 | 4 |
| 20 | 1.43 | 471 | 4 |
| 22 | 3.623 | 393 | 6 |
| 26 | 0.49 | 395 | 2 |
| 23 | 1.38 | 447 | 4 |
| 31 | 1.09 | 436 | 4 |
| 32 | 1.20 | 379 | 4 |
| 33 | 1.05 | 395 | 4 |
| 34 | 0.93 | 341 | 4 |
| 35 | 0.97 | 341 | 4 |
| 36 | 0.96 | 353 | 4 |
| 37 | 1.07 | 353 | 4 |
| 71 | 0.86 | 395 | 3 |
| 39 | 0.90 | 343 | 4 |
| 38 | 0.90 | 343 | 4 |
| 6 | 2.947 | 411 | 5 |
| 1 | 3.535 | 393 | 6 |
| 7 | 1.35 | 425 | 4 |
| 16 | 2.68 | 393 | 5 |
| 13 | 1.30 | 413 | 4 |
| 14 | 1.33 | 457 | 4 |
| 15 | 1.32 | 471 | 3 |
| 8 | 1.31 | 419 | 4 |
| 61 | 1.24 | 407 | 4 |
| 72 | 1.13 | 397 | 4 |
| 58 | 1.62 | 418 | 4 |
| 62 | 1.51 | 418 | 4 |
| 57 | 1.15 | 383 | 4 |
| 47 | 1.41 | 404 | 4 |
| 55 | 1.21 | 383 | 4 |
| 63 | 1.26 | 368 | 4 |
| 67 | 1.10 | 340 | 4 |
| 56 | 1.18 | 383 | 4 |
| 54 | 1.42 | 433 | 4 |
| 49 | 1.17 | 354 | 4 |
| 64 | 1.29 | 368 | 4 |
| 46 | 1.20 | 354 | 4 |
| 48 | 1.16 | 393 | 4 |
| 59 | 1.51 | 433 | 4 |
| 50 | 1.42 | 419 | 4 |
| 65 | 1.48 | 433 | 4 |
| 53 | 1.07 | 369 | 4 |
| 60 | 1.49 | 418 | 4 |
| 52 | 1.50 | 404 | 4 |
| 51 | 1.40 | 404 | 4 |
| 69 | 1.00 | 356 | 3 |
| 70 | 1.00 | 466 | 3 |
| 41 | 1.34 | 419 | 4 |
| 43 | 1.42 | 404 | 4 |
| 40 | 1.13 | 369 | 4 |
| 45 | 1.08 | 369 | 4 |
| 42 | 1.18 | 354 | 4 |
| 73 | 1.12 | 381 | 4 |
| 44 | 1.41 | 419 | 4 |
| 68 | 0.98 | 329 | 4 |
| 66 | 1.49 | 418 | 4 |
| 75 | 1.07 | 365 | 4 |
| 74 | 1.11 | 379 | 4 |

Experimental Procedures In Vitro Assay (Assay 1a and 1b)

Reagents.

PRMT5-MEP50 enzyme was purchased from Charles River (Argenta). The enzyme complex was produced in insect cells (Sf9) infected simultaneously with two baculoviruses. One virus expresses full length human PRMT5 with Flag-tag at N-terminus, the second virus expresses full length MEP50 with His6-TEV cleavage at N-terminus. The protein was affinity purified using anti-Flag (M2) beads eluted with 3×FLAG peptide, followed by His-Select eluted with 0.5M imidazole. Eluted protein was then dialysed against tris-buffered saline (TBS) (pH 8.0) containing 20% glycerol and 3 mM dithiothreitol (DTT).

Full-length untagged human recombinant histone H2A (residues 1-130, Genbank Accession #NM_021052, MW=14.1 kDa) expressed in *E. coli* was purchased from Reaction Biology Corporation, Cat #HMT-11-146. Reagents used for making reaction buffer or stopping reaction were purchased including Tris base (Sigma Cat #T-1503), NaCl (Sigma Cat #RGF-3270), MgCl$_2$ (Sigma Cat #M0250), DTT (Invitrogen Cat #15508-013) and Formic Acid (Riedel deHaen, Cat #33015)

High Throughput Mass Spectrometer Assay

PRMT5 catalyzes the sequential methylations of the terminal nitrogen atoms on the guanidine groups of arginine residues within proteins using co-substrate S-adenosyl-L-methionine (AdoMet, SAM), forming mono-methyl (MMA), syrmmetric-dimethyl arginine (sDMA) and S-adenosyl-L-homocysteine (AdoHcy, SAH). The enzyme activity was determined by following the product SAH formation using high throughput mass spectrometry (Agilent Rapidfire 300 System coupled to a Sciex 4000 series QTrap® triple-quad MS/MS). The reaction buffer was 20 mM Tris-HCl, pH 8.5, 50 mM NaCl, 5 mM MgCl$_2$ and 1 mM DTT. The reaction activity was stopped using 1% formic acid (final concentration).

Inhibition Studies.

The IC$_{50}$ Studies were performed using eleven point dosing series made for each compound by serially diluted 1:2 in dimethyl sulfoxide (DMSO), with point 12 being a DMSO control. Compounds were first spotted to plates, and followed by addition of 2 µM SAM and 0.6 µM H2A (histone H2A) solution mixture. The same volume of enzyme solution was added to initiate the enzymatic reactions. The final concentrations of the reaction are at 1 µM SAM, 0.3 µM H2A and 10 nM enzyme (assay 1a) or or 1.25 nM enzyme (assay 1b). The reaction was incubated at 30° C. for 60 minutes (min) when 10 nM enzyme was used and for 120 min when 1.25 nM enzyme was used. Subsequently, the reaction was quenched by addition of formic acid to a final concentration of 1%. The inhibitions of SAH formation in the presence of compounds were calculated as a percentage of the control relative to the uninhibited reaction as a function of inhibitor concentration. The data were fit as follows:

$$Y = \text{Bottom} + (\text{Top} - \text{Bottom})/(1 + 10^{((\log IC_{50} - X) * h)})$$

where IC$_{50}$ is the inhibitor concentration (same unit as X) at 50% inhibition and h is the Hill slope. Y is percent of inhibition, X is log of compound concentration. Bottom and Top are the plateaus in same units as Y.

Experimental Procedure PD Assay (Assay 2)

Reagents

A549 cells (ATCC, Cat #CCL-185) were cultured in Dulbecco's Modified Eagle's Medium (DMEM) (Sigma, Cat #D5796), supplemented with 10% Fetal Calf Serum (FCS) (HyClone™, Cat #SV30160.03), 100 mM Sodium Pyruvate (Sigma, Cat #S8636), 200 mM L-Glutamine (Sigma, Cat #G7513) and 50 mg/mL Gentamycing (Gibco, Cat #15750-037).

Reagents used for buffers were purchased: Dulbecco's phosphate buffered saline (DPBS) without Ca/Mg (Sigma, Cat #D8537), phosphate buffered saline (PBS) 10× (Roche, Cat #11 666 789 001), Formalin solution 10% (Sigma, HT50-1-128-4L), Methanol 100% (Sigma, Cat #32213-2.5L), Triton X-100 (Acros, Cat #215680010), Bovine Serum Albumin (BSA) (Sigma, Cat #A2153), Alexa fluor 488 goat anti-rabbit antibody (Life Technologies, Cat #A11034), HCS CellMask Deep Red Stain (Life Technologies, Cat #H32721), Hoechst Stain (Life Technologies, Cat #33258), Anti-dimethyl-Arginine, sym (SYM10) antibody (Millipore, 07-412).

Immunohistochemistry Procedure

Cells were plated at 400 cells/40 µL/well in 384 well black µplates clear bottom (Perkin Elmer) and overnight incubated at 37° C., 5% CO$_2$. The IC$_{50}$ Studies were performed using nine point dosing series ranging from 10 µM to 1 µM for each compound. 80 nL of the respective dilution of the compounds was added using the Labcyte POD 810 (Labcyte) reaching a final DMSO concentration of 0.2% in cell culture. After an incubation period of 48 h at 37° C. in 5% CO$_2$, cells were fixed in 10% formalin solution for 15 min at room temperature and 20 min in ice-cold methanol, after which they were washed 3× in DPBS. Subsequently, the cells were blocked for 1 h in blocking buffer (PBS+1% BSA and 0.5% Triton X-100) and incubated overnight at 4° C. with the SYM10 antibody diluted ½000 in blocking buffer. The cells were washed 3× with washing buffer (PBS+0.1% Triton X-100) and incubated with the Alexa fluor 488 goat anti-rabbit antibody diluted ½00 in blocking buffer for 1 h at room temperature. Subsequently, they were washed 3× with washing buffer and incubated for 30 min at room temperature with PBS containing a ⅕000 dilution of Hoechst Stain and a ⅕000 dilution of the HCS CellMask Deep Red Stain. After a final wash with PBS, the plates were imaged using the 10×W lens of the Opera® system (Perkin Elmer Life Sciences) using following settings (values in nm):

| laser | Filter camera | Primary dichrome | Detect dichrome |
|---|---|---|---|
| 488 | 540/75 | 405/488/561/635 | 510 |
| 405 | 450/50 | 405/488/561/635 | 510 |
| 635 | 690/50 | 405/488/561/635 | 510 |

Analyses:

The inhibition of nuclear symmetric Arginine dimethylation in the presence of compounds (% effect) was calculated as the "median nuclear SYM10 intensity"/"median cytoplasmic SYM10 intensity", normalized by below equation:

$$\text{normalized} = 100 - \frac{\text{raw} - \text{lowMedian}}{\text{highMedian} - \text{lowMedian}} * 100$$

In the above equations, the following variable names are used:

| | |
|---|---|
| normalized | The normalized feature value |
| raw | The raw feature value |
| lowMedian | The median of the raw values of the low control wells |
| highMedian | The median of the raw values of the high control wells |

In the above equations, the following controls were used for normalization:

Low control: minimum level of symmetrically dimethylated Arginines (cells treated with reference compound at 10 µM).

High control: maximum level of symmetrically dimethylated Arginines (DMSO treated cells).

IC$_{50}$ and pIC$_{50}$ (−log IC$_{50}$) values were calculated using the appropriate software.

The pIC$_{50}$ values in the Table below are averaged values (Co. No. means compound number; n.d. means not determined).

| Co. No. | pIC$_{50}$ Assay 1a | pIC$_{50}$ Assay 1b | pIC$_{50}$ Assay 2 | Co. No. | pIC$_{50}$ Assay 1a | pIC$_{50}$ Assay 1b | pIC$_{50}$ Assay 2 |
|---|---|---|---|---|---|---|---|
| 25 | 6.9 | n.d. | 5.7 | 2 | n.d. | 9.8 | 8.2 |
| 24 | 7.5 | n.d. | 5.8 | 11 | n.d. | >9.7 | 8.4 |
| 3 | 8.7 | n.d. | 7.7 | 9 | n.d. | 8.4 | 7.2 |
| 4 | 7.9 | n.d. | 7.5 | 10 | n.d. | 8.0 | 6.7 |
| 5 | 7.9 | n.d. | 5.4 | 12 | n.d. | 9.5 | 8.7 |
| 18 | 7.4 | n.d. | 6.9 | 21 | n.d. | 8.4 | 7.8 |
| 19 | 5.9 | n.d. | 5.3 | 27 | n.d. | 8.3 | 8.2 |
| 17 | 7.4 | n.d. | 6.0 | 28 | n.d. | 6.8 | 6.2 |
| 6 | 8.7 | n.d. | 7.8 | 29 | n.d. | 6.4 | 5.7 |
| 1 | 9.1 | n.d. | 8.9 | 30 | n.d. | 7.2 | 6.3 |
| 7 | 8.2 | n.d. | 7.6 | 20 | n.d. | n.d. | n.d. |
| 13 | 8.7 | 8.9 | 7.7 | 22 | n.d. | n.d. | n.d. |
| 14 | 8.9 | 8.8 | 7.9 | 16 | n.d. | n.d. | n.d. |
| 15 | n.d. | 9.0 | 8.2 | 26 | n.d. | n.d. | n.d. |
| 8 | n.d. | 8.6 | 7.6 | 23 | n.d. | 7.4 | n.d. |
| 31 | n.d. | 7.2 | n.d. | 55 | n.d. | 9.4 | n.d. |
| 32 | n.d. | n.d. | n.d. | 63 | n.d. | 5.7 | n.d. |
| 33 | n.d. | 8.3 | n.d. | 67 | n.d. | 6.3 | n.d. |
| 34 | n.d. | n.d. | n.d. | 56 | n.d. | 8.1 | n.d. |
| 35 | n.d. | n.d. | n.d. | 54 | n.d. | 7.0 | n.d. |
| 36 | n.d. | 5.7 | n.d. | 49 | n.d. | <5.6 | n.d. |
| 37 | n.d. | 6.1 | n.d. | 64 | n.d. | 7.0 | n.d. |
| 71 | n.d. | 7.0 | n.d. | 46 | n.d. | <5.6 | n.d. |
| 39 | n.d. | 5.7 | n.d. | 48 | n.d. | 7.5 | n.d. |
| 38 | n.d. | 6.1 | n.d. | 59 | n.d. | 5.7 | n.d. |
| 41 | n.d. | 6.4 | n.d. | 68 | n.d. | 5.9 | n.d. |
| 44 | n.d. | 5.8 | n.d. | 50 | n.d. | 7.5 | n.d. |
| 43 | n.d. | 6.6 | n.d. | 65 | n.d. | 8.0 | n.d. |
| 40 | n.d. | 7.1 | n.d. | 53 | n.d. | 8.7 | n.d. |
| 45 | n.d. | 6.3 | n.d. | 66 | n.d. | 7.4 | n.d. |
| 42 | n.d. | 6.5 | n.d. | 60 | n.d. | 6.6 | n.d. |
| 73 | n.d. | 7.6 | n.d. | 52 | n.d. | <5.6 | n.d. |
| 61 | n.d. | 8.1 | n.d. | 51 | n.d. | 6.5 | n.d. |
| 72 | n.d. | 7.9 | n.d. | 75 | n.d. | 6.6 | n.d. |
| 58 | n.d. | <5.6 | n.d. | 69 | n.d. | 5.7 | n.d. |
| 62 | n.d. | 6.1 | n.d. | 70 | n.d. | 6.3 | n.d. |
| 57 | n.d. | 7.1 | n.d. | 74 | n.d. | n.d. | n.d. |
| 47 | n.d. | 5.8 | n.d. | | | | |

Composition Examples

"Active ingredient" (a.i.) as used throughout these examples relates to compounds of Formula (I), and pharmaceutically acceptable addition salts, and solvates thereof, in particular to any one of the exemplified compounds.

Typical examples of recipes for the formulation of the invention are as follows:

1. Tablets

| | |
|---|---|
| Active ingredient | 5 to 50 mg |
| Di-calcium phosphate | 20 mg |
| Lactose | 30 mg |
| Talcum | 10 mg |
| Magnesium stearate | 5 mg |
| Potato starch | ad 200 mg |

2. Suspension

An aqueous suspension is prepared for oral administration so that each milliliter contains 1 to 5 mg of active ingredient, 50 mg of sodium carboxymethyl cellulose, 1 mg of sodium benzoate, 500 mg of sorbitol and water ad 1 ml.

3. Injectable

A parenteral composition is prepared by stirring 1.5% (weight/volume) of active ingredient in 0.9% NaCl solution or in 10% by volume propylene glycol in water.

4. Ointment

| | |
|---|---|
| Active ingredient | 5 to 1000 mg |
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

The invention claimed is:

1. A compound of Formula (I)

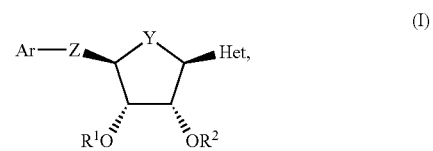

(I)

wherein
R$^1$ represents hydrogen;
R$^2$ represents hydrogen;
Y represents —CH$_2$—;
Z represents —X—CR$^{5a}$R$^{5b}$—, —CR$^{5c}$=CR$^{5d}$—, or —CR$^{5e}$R$^{5g}$—CR$^{5f}$R$^{5h}$—;
R$^{5a}$, R$^{5b}$, R$^{5c}$, R$^{5d}$, R$^{5e}$, R$^{5f}$, R$^{5g}$, and R$^{5h}$, represent hydrogen;
X represents —O—;
Ar represents a monocyclic aromatic ring selected from pyridinyl and imidazolyl: or a 9-membered bicyclic aromatic ring system consisting of a 6-membered ring fused with a 5-membered ring, wherein said 9-membered bicyclic aromatic ring system contains one, two or three heteroatoms each independently selected from O, S, and N, and said 9-membered bicyclic aromatic ring is attached to the remainder of the molecule via a ring carbon atom of the 5- or 6-membered ring;
Ar is optionally substituted on its carbon atoms with one, two, three or four substituents each independently selected from the group consisting of halo, —NH$_2$, —NH—C$_{1-4}$alkyl, —CF$_3$, C$_{3-6}$cycloalkyl, and C$_{1-4}$alkyl; and Ar is optionally substituted on one N-atom with one C$_{1-4}$alkyl;
Het is

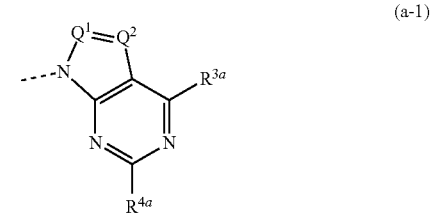

(a-1)

R$^{3a}$a represents halo, —NR$^{7a}$R$^{7b}$, or —O—C$_{1-4}$alkyl;
R$^{7a}$ represents hydrogen;
R$^{7b}$ represents hydrogen or C$_{1-4}$alkyl;
R$^{4a}$ represents hydrogen;
Q$^1$ represents CR$^{6a}$;
Q$^2$ represents CR$^{6b}$;
R$^{6a}$ and R$^{6b}$ each independently represent hydrogen or halogen; or a pharmaceutically acceptable addition salt or a solvate thereof.

2. The compound according to claim 1, wherein Ar represents a monocyclic aromatic ring selected from pyridinyl and imidazolyl.

3. The compound according to claim 1, wherein Ar represents a 9-membered bicyclic aromatic ring system consisting of a 6-membered ring fused with a 5-membered ring, containing one, two or three heteroatoms each independently selected from O, S, and N, said 9-membered bicyclic aromatic ring being attached to the remainder of the molecule via a ring carbon atom of the 5- or 6-membered ring.

4. The compound according to claim 1, wherein Ar represents a monocyclic aromatic ring selected from pyridinyl and imidazolyl; or a 9-membered bicyclic aromatic ring system selected from the group consisting of

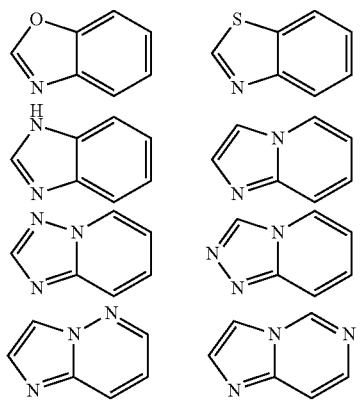

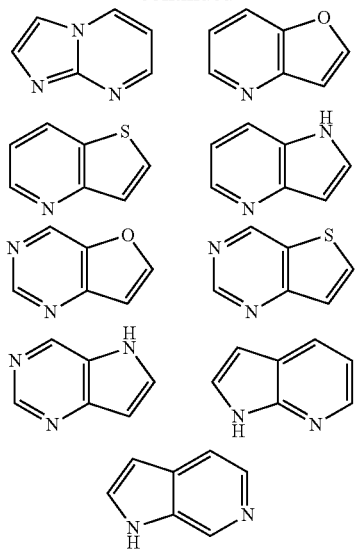

said 9-membered bicyclic aromatic ring being attached to the remainder of the molecule via a ring carbon atom of the 5- or 6-membered ring.

5. The compound according to claim 1, wherein $R^{3a}$ represents —$NR^{7a}R^{7b}$; and $R^{7a}$ and $R^{7b}$ represent hydrogen.

6. A pharmaceutical composition comprising a pharmaceutically acceptable carrier and, as active ingredient, a compound according to claim 1.

* * * * *